US010508284B2

(12) United States Patent
Christensen et al.

(10) Patent No.: US 10,508,284 B2
(45) Date of Patent: Dec. 17, 2019

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: Ceres, Inc., Thousands Oaks, CA (US)

(72) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: CERES, INC., Thousand Oaks, CA (US)

( * ) Notice: Subject to any disclaimer, the term of this patent is extended or adjusted under 35 U.S.C. 154(b) by 0 days.

(21) Appl. No.: 16/275,629

(22) Filed: Feb. 14, 2019

(65) Prior Publication Data

US 2019/0276836 A1    Sep. 12, 2019

Related U.S. Application Data

(60) Division of application No. 15/362,633, filed on Nov. 28, 2016, now Pat. No. 10,240,166, which is a division of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879.

(51) Int. Cl.
| | | |
|---|---|---|
| *C12N 15/82* | (2006.01) | |
| *A01H 1/02* | (2006.01) | |
| *C07K 14/415* | (2006.01) | |
| *C12Q 1/6895* | (2018.01) | |

(52) U.S. Cl.
CPC .......... *C12N 15/8273* (2013.01); *A01H 1/02* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,990,387 A | 11/1999 | Tomes et al. |
| 2006/0107345 A1 | 5/2006 | Alexandrov et al. |
| 2006/0150283 A1 | 7/2006 | Alexandrov et al. |
| 2009/0094717 A1 | 4/2009 | Troukhan et al. |
| 2009/0265275 A1 | 10/2009 | Alexandrov et al. |
| 2010/0083407 A1 | 4/2010 | Feldmann et al. |
| 2016/0369294 A9 | 12/2016 | Nadzan et al. |
| 2018/0223303 A1 | 8/2018 | Alexandrov et al. |
| 2019/0241902 A1 | 8/2019 | Christensen et al. |

FOREIGN PATENT DOCUMENTS

| | | | |
|---|---|---|---|
| EP | 1033405 | 9/2000 | |
| EP | 1033405 A2 * | 9/2000 | ........... C07K 14/415 |

OTHER PUBLICATIONS

Kim et al., "Molecular cloning of low temperature-inducible ribosomal proteins from soybean," *Journal of Experimental Botany* 55:1153-1155, 2004.
Lu et al., "Arabidopsis Mutants Deficient in Diacylglycerol Acyltransferase Display Increased Sensitivity to Abscisic Acid, Sugards, and Osmotic Stress during Germination and Seedling Development," *Plant Physiology* 129:1352-1358, 2002.
Ngo et al., "Computational Complexity, Protein Structure Prediction, and the Levinthal Pradox," *The Protein Folding Problem and Tertiary Structure Prediction*, K. Merz and S. Le Grand (eds.), pp. 492-495, 1994.
Guo et al., "Protein tolerance to random amino acid change," *PNAS* 101:9205-9210, 2004.
GenBank Accession No. AY117196, dated Sep. 18, 2002.
Keskin et al., "A new, structurally nonredundant, diverse data set of protein-protein interfaces and its implications," *Protein Science* 13:1043-1055, 2004.
Thornton et al., "From structure to function: Approaches and limitations," *Nature Structural Biology, Structural Gemonics Supplement*, Nov. 2000.
Wells, "Additivity of Mutational Effects in Proteins," *Biochemistry* 29:8509-8517, 1990.

* cited by examiner

*Primary Examiner* — Vinod Kumar
(74) *Attorney, Agent, or Firm* — Dentons US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased levels of cold tolerance and plant products produced from plants having increased cold tolerance levels.

12 Claims, 8 Drawing Sheets

Specification includes a Sequence Listing.

| SEQ ID | 1-47 | | | | | |
|---|---|---|---|---|---|---|
| SEQ-ID-NO-17-CLONE-839727 | MSAAE--- | -GA | VVFSEEKEAL | VLKSWAIMKK | DSANLGLRFF | LKIFEIAPSA | 47 |
| SEQ-ID-NO-16-CLONE-1554560 | MALAEADDGA | | VVFGEEEQEAL | VLKSWAVMKK | DAANLGLRFF | LKVFEIAPSA | 50 |
| SEQ-ID-NO-60-CLONE-1802327 | MALAE--- | -GN | VIFGEEEQEAL | VLKSWALMKK | DSADLGLRFF | LKIFEIAPSA | 47 |
| SEQ-ID-NO-9-CLONE-30469-FL | -MESE--- | -GK | VFTEEEQEAL | VVKSWSVMKK | NSAELGLKLF | IKIFEIAPTI | 46 |
| SEQ-ID-NO-10-GI-30909306 | -MESE--- | -GK | VFTEEEQEAL | VVKSWNVMKK | NSADLGLKLF | LKIFEIAPTA | 46 |
| SEQ-ID-NO-13-CLONE-546001 | -MTTLERG- | -- | -FSEEEQEAL | VVKSWNVMKK | NSGELGLKFF | LKIFEIAPSA | 46 |
| SEQ-ID-NO-70-CLONE-1916866 | MATYE--- | -GK | VFTEEEQEAL | VVKSWTVMKK | NAAELGLKFF | LKIFEIAPSA | 46 |

| | 48-97 | | | | | |
|---|---|---|---|---|---|---|
| SEQ-ID-NO-17-CLONE-839727 | RQMFPFLRDS | DVPLETNPKL | KTHAVSVFVM | TCEAAAQLRK | AGKTVRETT | 97 |
| SEQ-ID-NO-16-CLONE-1554560 | KQMFSFLRDS | DVPLEKNPKL | KTHAMSVFVM | TCEAAAQLRK | AGKVTVRETT | 100 |
| SEQ-ID-NO-60-CLONE-1802327 | KQMFSFLRDS | DVPLEKNPKL | KNHAMSVFVM | TCEAAAQLRK | AGKVTVRETT | 97 |
| SEQ-ID-NO-9-CLONE-30469-FL | KKMFSFLRDS | PIPAEQNPKL | KPHAMSVFVM | CCESAAQLRK | TGKVTVRETT | 96 |
| SEQ-ID-NO-10-GI-30909306 | KKLFSFLRDS | PIPAEONPKL | KPHAVSVFVM | CCESAVQLRK | TGKVTVKETT | 96 |
| SEQ-ID-NO-13-CLONE-546001 | QKLFSFLRDS | TVPLEQNPKL | KPHAMSVFVM | TCDSAVQLRK | AGKVTVRESN | 96 |
| SEQ-ID-NO-70-CLONE-1916866 | KKLFSFLRDS | NVPLEQNTKL | KPHAMSVFVM | TCESAVQLRK | AGKVTVRESN | 96 |

| | 98-147 | | | | | |
|---|---|---|---|---|---|---|
| SEQ-ID-NO-17-CLONE-839727 | LKRLGGTHLK | YGVADCHFEV | TRFALLETIK | EALPADMWGP | EMRNAWGEAY | 147 |
| SEQ-ID-NO-16-CLONE-1554560 | LKRLGATHLR | YGVADGHFEV | TGFALLETIK | EALPADMWSL | EMKKAWAEAY | 150 |
| SEQ-ID-NO-60-CLONE-1802327 | LKRLGATHFK | YGVADGHFEV | TRFALLETIK | EALPADMWSL | EMKNAWSEAY | 147 |
| SEQ-ID-NO-9-CLONE-30469-FL | LKRLGASHSK | YGVDEHFEV | AKYALLETIK | EAVP-EMWSP | EMKVAWGQAY | 145 |
| SEQ-ID-NO-10-GI-30909306 | LKRLGANHSK | YGVMDEHFEV | KYALLETIK | EAVP-EMWSP | EMKSAWGQAY | 145 |
| SEQ-ID-NO-13-CLONE-546001 | LKRLGATHFR | TGVANEHFEV | TKFALLETIK | EAVP-EMWSP | AMKNAWGEAY | 145 |
| SEQ-ID-NO-70-CLONE-1916866 | LKKLGATHFK | GVWDEHFEV | TKFALLETIK | EAVP-DMWSD | EMKNAWGEAY | 145 |

| | 148-163 | | |
|---|---|---|---|
| SEQ-ID-NO-17-CLONE-839727 | DQLVAAIKQE | MKPSE--- | 162 |
| SEQ-ID-NO-16-CLONE-1554560 | SQLVAAIKRE | MKPDA--- | 165 |
| SEQ-ID-NO-60-CLONE-1802327 | NQLVAAIKQE | MKPAA--- | 162 |
| SEQ-ID-NO-9-CLONE-30469-FL | DHLVAAIKAE | MNLSN--- | 160 |
| SEQ-ID-NO-10-GI-30909306 | DHLVAAIKAE | MKPSH--- | 160 |
| SEQ-ID-NO-13-CLONE-546001 | DQLVDAIKSE | MKPPSS--- | 161 |
| SEQ-ID-NO-70-CLONE-1916866 | DRLVAAIKIE | MKACSQAA | 163 |

FIGURE 3

| | | | | | | |
|---|---|---|---|---|---|---|
| SEQ-ID-NO-221-CLONE-839727-T | MSAAE----GA | VVFSEEKEAL | VLKSWAIMKK | DSANLGLRFF | LKIFEIAPSA | 47 |
| SEQ-ID-NO-207-CLONE-1554560-T | MALAEADDGA | VVFGEEQEAL | VLKSWAVMKK | DAANLGLRFF | LKVFEIAPSA | 50 |
| SEQ-ID-NO-208-CLONE-1802327-T | MALAE----GN | VIFGEEQEAL | VLKSWALMKK | DSADLGLRFF | LKIFEIAPTA | 47 |
| SEQ-ID-NO-7-CLONE-30469 | MESE----CK | LVFTEEQEAL | VVKSWSVMKK | NSAELGLKLF | LKIFEIAPTT | 46 |
| SEQ-ID-NO-227-GI-309093306-T | MESE----GK | LVFTEEQEAL | VVKSWSVMKK | NSADLGLKLF | LKIFEIAPTA | 46 |
| SEQ-ID-NO-219-CLONE-546001-T | MTTT----LE | RGFSEEQEAL | VVKSWNVMKK | NSCELGLKFF | LKIFEIAPSA | 46 |
| SEQ-ID-NO-212-CLONE-1916866-T | MATY----EG | KMFTEEQEAL | VVKSWTVMKK | NAAELGLKFF | LKIFEIAPSA | 46 |

| | | | | | |
|---|---|---|---|---|---|
| SEQ-ID-NO-221-CLONE-839727-T | RQMFPFLRDS | DVPLEINPKL | KTHAVSVFVM | --- | 77 |
| SEQ-ID-NO-207-CLONE-1554560-T | KQMFSFLRDS | DVPLEKNPKL | KTHAMSVFVM | --- | 80 |
| SEQ-ID-NO-208-CLONE-1802327-T | KQMFSFLRDS | DVPLEKNPKL | KNHAMSVFVM | --- | 77 |
| SEQ-ID-NO-7-CLONE-30469 | KKMFSFLRDS | PIPAEQNPKL | KPHAMSVFVM | YN | 78 |
| SEQ-ID-NO-227-GI-309093306-T | KKLFSFLRDS | PIPAEQNPKL | KPHAVSVFVM | --- | 76 |
| SEQ-ID-NO-219-CLONE-546001-T | QKLFSFLRDS | TVPLEQNPKL | KPHAVSVFVM | --- | 76 |
| SEQ-ID-NO-212-CLONE-1916866-T | KKLFSFLRDS | NVPLEQNTKL | KPHAMSVFVM | --- | 76 |

FIGURE 4

| SEQ-ID-NO-20-CLONE-271922  | MAKRTKKMGI | VGKYGTRYGA | SLRKQIKKME | VSQHSKYFCE | FCGKYGVKRK | 50 |
|---|---|---|---|---|---|---|
| SEQ-ID-NO-54-CLONE-1627907 | MTKRTKKAGI | VGKYGTRYGA | SLRKQIKKME | VSQHAKYFCE | FCGKYAVKRQ | 50 |
| SEQ-ID-NO-25-CLONE-664936  | MTKRTKKAGI | VGKYGTRYGA | SLRKQIKKME | VSQHSKFFCE | FCGKYAVKRK | 50 |
| SEQ-ID-NO-28-CLONE-632613  | MTKRTKKAGI | VGKYGTRYGA | SLRKQIKKME | VSQHSKYFCE | FCGKFAVKRK | 50 |
| SEQ-ID-NO-29-CLONE-1390976 | MTKRTKKAGI | VGKYGTRYGA | SLRKQIKKME | VSQHSKYFCE | FCGKFAVKRK | 50 |
| SEQ-ID-NO-58-CLONE-1783890 | MTKRTKKAGI | VGKYGTRYGA | SLRKQIKKME | VSQHSKYFCE | FCGKFAVKRK | 50 |

| SEQ-ID-NO-20-CLONE-271922  | AVGIWGCKDC | GKVKAGGAYT | MNTASAVTVR | STIRRLREQI | EIG | 92 |
|---|---|---|---|---|---|---|
| SEQ-ID-NO-54-CLONE-1627907 | AVGIWGCKDC | GKVKAGGAYT | LNTASAVTVR | STIRRLREQT | ESI | 92 |
| SEQ-ID-NO-25-CLONE-664936  | AVGIWGCKDC | GKVKAGGAYT | LNTASAVTVR | STIRRLREQT | EIG | 92 |
| SEQ-ID-NO-28-CLONE-632613  | AVGIWGCKDC | GKVKAGGAYT | MNTASAVTVR | STIRRLREQT | EA | 92 |
| SEQ-ID-NO-29-CLONE-1390976 | AVGIWGCKDC | GKVKAGGAYT | MNTASAVTVR | STIRRLREQT | EA | 92 |
| SEQ-ID-NO-58-CLONE-1783890 | AVGIWGCKDC | GKVKAGGAYT | MNTASAVTVR | STIRRLREQT | EA | 92 |

FIGURE 5

```
SEQ-ID-NO-34-CLONE-2403-FL       MQIFVKTLTG KTITLEVESS DTIDNVKAKI QDKEGIPPDQ QRLIFAGKQL  50
SEQ-ID-NO-35-CLONE-1482731       MQIFVKTLTG KTITLEVESS DTIDNVKSKI QDKEGIPPDQ QRLIFAGKQL  50
SEQ-ID-NO-36-CLONE-522921        MQIFVKTLTG KTITLEVESS DTIDNVKAKI QDKEGIPPDQ QRLIFAGKQL  50
SEQ-ID-NO-37-CLONE-1036726       MQIFVKTLTG KTITLEVESS DTIDNVKAKI QDKEGIPPDQ QRLIFAGKQL  50
SEQ-ID-NO-68-CLONE-1884696       MQIFVKTLTG KTITLEVESS DTIDNVKAKI QDKEGIPPDQ QRLIFAGKQL  50
SEQ-ID-NO-80-CLONE-2034916       MQIFVKTLTG KTITLEVESS DTIDNVKAKI QDKEGIPPDQ QRLIFAGKQL  50

SEQ-ID-NO-34-CLONE-2403-FL       EDGRTLADYN QKESTLHLV LRLRGGTMIK VKTLTGKEIE DIEPTDTID  100
SEQ-ID-NO-35-CLONE-1482731       EDGRTLADYN QKESTLHLV LRLRGGTMIK VKTLTGKEIE DIEPTDTID  100
SEQ-ID-NO-36-CLONE-522921        EDGRTLADYN QKESTLHLV LRLRGGTMIK VKTLTGKEIE DIEPTDTID  100
SEQ-ID-NO-37-CLONE-1036726       EDGRTLADYN QKESTLHLV LRLRGGTMIK VKTLTGKEIE DIEPTDTID  100
SEQ-ID-NO-68-CLONE-1884696       EDGRTLADYN QKESTLHLV LRLGGMQF  VKTLTGKTIT LEVESSDTID  100
SEQ-ID-NO-80-CLONE-2034916       EDGRTLADYN QKESTLHLV LRLRGGMQLF VKTLTGKTIT LEVESSDTID  100

SEQ-ID-NO-34-CLONE-2403-FL       RIKERVEEKE GIPPVQQRLI YAGKQLADDK TAKDYAIEGG SVLHLVLALR  150
SEQ-ID-NO-35-CLONE-1482731       RIKERVEEKE GIPPVQQRLI YAGKQLADDK TAKDYNIEGG SVLHLVLALR  150
SEQ-ID-NO-36-CLONE-522921        RIKERVEEKE GIPPVQQRLI YAGKQLADDK TAKEYNIEGG SVLHLVLALR  150
SEQ-ID-NO-37-CLONE-1036726       RIKERVEEKE GIPPDQQRLI YAGKQLEDGR IKDYNIEGG  SVSA        144
SEQ-ID-NO-68-CLONE-1884696       NVKAKIQDKE GIPPDQQRLI FAGKQLEDGR TLADYNIQKD STLHLVLRLR  150
SEQ-ID-NO-80-CLONE-2034916       NVKVKIQDKE GIPPDQQRLI FAGKQLEDGR TLADYNIQKE STLHLVLRLR  150

SEQ-ID-NO-34-CLONE-2403-FL       GGL          153
SEQ-ID-NO-35-CLONE-1482731       GGS          153
SEQ-ID-NO-36-CLONE-522921        GGT          153
SEQ-ID-NO-37-CLONE-1036726       -SG          146
SEQ-ID-NO-68-CLONE-1884696       GG-          152
SEQ-ID-NO-80-CLONE-2034916       GGMQIFVKTL QLEDGRTLAD YNI  200

SEQ-ID-NO-34-CLONE-2403-FL       ---------- ---------- ---------- -L   154
SEQ-ID-NO-35-CLONE-1482731       ---------- ---------- ---------- -D   154
SEQ-ID-NO-36-CLONE-522921        ---------- ---------- ---------- -Y   154
SEQ-ID-NO-37-CLONE-1036726       ---------- ---------- ---------- -S   147
SEQ-ID-NO-68-CLONE-1884696       ---------- ---------- ---------- -F   153
SEQ-ID-NO-80-CLONE-2034916       QLEDGRTLAD YNI TGKTITLEVE SSDTIDNVKA KIQDKEGIPP DQQRLIFAGK  213
```

FIGURE 6

| | | | | | |
|---|---|---|---|---|---|
| SEQ-ID-NO-40-CLONE-2403 | MQIFVKTLTG | KTITLEVESS | DTIDNVKAKI | QDK | 33 |
| SEQ-ID-NO-205-CLONE-1036726-T | MQIFVKTLTG | KTITLEVESS | DTIDNVKAKI | QDK | 33 |
| SEQ-ID-NO-211-CLONE-1884696-T | MQIFVKTLTG | KTITLEVESS | DTIDNVKAKI | QDK | 33 |
| SEQ-ID-NO-213-CLONE-1950105-T | MQIFVKTLTG | KTITLEVESS | DTIDNVKAKI | QDK | 33 |
| SEQ-ID-NO-218-CLONE-522921-T | MQIFVKTLTG | KTITLEVESS | DTIDNVKAKI | QDK | 33 |
| SEQ-ID-NO-206-CLONE-1482731-T | MQIFVKTLTG | KTITLEVESS | DTIDNVKSKI | QDK | 33 |

FIGURE 7

| SEQ ID | Sequence | | | | | |
|---|---|---|---|---|---|---|
| SEQ-ID-NO-46-CLONE-1055099 | MRKARPPQPQ | P-------QPSQQ | SP-------- | ---------- | ELRYGRVKR | PSGRYAAEIR | 38 |
| SEQ-ID-NO-56-CLONE-1761125 | MRDTAAVAV- | ----------A- | ---------- | ---------- | APRYRGVRKR | PWGRFAAEIR | 31 |
| SEQ-ID-NO-83-GI-125550159 | MCEAAA---- | ---------- | ---------- | ---------- | -PRYRGVRKR | PWGRFAAEIR | 25 |
| SEQ-ID-NO-45-CLONE-273307 | MRRRGVAAAP | ----------A- | ---------- | -------V | ELRFRGVRKR | PWGRFAAEIR | 35 |
| SEQ-ID-NO-62-CLONE-1838364 | MRKRGRGAAA | NAVARRPALQ | ---------- | ---------- | EPRYRGVRKR | PWGRFAAEIR | 46 |
| SEQ-ID-NO-50-CLONE-1240330 | MRRGRGRGGAS | A--AAVDVN | GD-------- | ---------- | EPRYRGVRKR | PWGRFAAEIR | 42 |
| SEQ-ID-NO-42-CLONE-674166 | MGRGCT-AAA | A-EVAEPGLR | PS-------- | -----GSI | EQRYRGVRKR | PWGRFAAEIR | 44 |
| SEQ-ID-NO-86-GI-56384582 | MGRGCATTAA | ----AVE-- | PV-------- | -----ILK | EPRYRGVRKR | PWGRFAAEIR | 39 |
| SEQ-ID-NO-48-ANNOT-1441430 | MGRITIITKQ | ATQNMLVIAK | PV-------- | -----YFK | EPRYRGVRKR | PWGRFAAEIR | 47 |
| SEQ-ID-NO-87-GI-57012880 | MRRGRAAAP | A-VDFPNGS | GG-------- | ------SK | EPRYRGVRKR | PWGRFAAEIR | 44 |
| SEQ-ID-NO-44-CLONE-975672 | MRKGRCSSAV | APVTGEPNGS | -PALP---- | ------VK | ELRFRGVRKR | PWGRFAAEIR | 39 |
| SEQ-ID-NO-84-GI-15223609 | MRRGRCSSAV | AGPTVVAAI-N | ---------- | ------GS | ELRFRGVRKR | PWGRFAAEIR | 44 |

| SEQ-ID-NO-46-CLONE-1055099 | DPAKKTPIWL | GTFDCAEDAA | RAYDSAARSL | RGPTARTNFP | PSSATQPPPR | 88 |
| SEQ-ID-NO-56-CLONE-1761125 | DPAKRARVWL | GTFDSAEDAA | RAYDVAARNL | RGPLARTNFP | CASSRLPLPS | 81 |
| SEQ-ID-NO-83-GI-125550159 | DPAKKARVWL | GTYDSAEDAA | RAYDAAARNL | RGPKARTNFP | LMSSLPLPSP | 75 |
| SEQ-ID-NO-45-CLONE-273307 | DPAKKARVWL | GTFDSAEEAA | RAYDAAARTL | RGPKAKTNFP | LPAAAALHHP | 85 |
| SEQ-ID-NO-62-CLONE-1838364 | DPLKKARVWL | GTFDSAEDAA | RAYDAAARTL | RGPKAKTNFP | INSSNIPAFP | 96 |
| SEQ-ID-NO-50-CLONE-1240330 | DPLKKARVWL | GTFDTAEEAA | RAYDTAARTL | RGPKAKTNFP | P---LSPFC | 88 |
| SEQ-ID-NO-42-CLONE-674166 | DPWKKTRVWL | GTFDSAEEAA | RAYDIAARTL | RGPKAKTNFP | ----SPPFY | 90 |
| SEQ-ID-NO-86-GI-56384582 | DPLKKARVWL | GTFDSAEEAA | RAYDIAARNL | RGPKAKTNFP | -----AQPFY | 85 |
| SEQ-ID-NO-48-ANNOT-1441430 | DPWKKTRVWL | GTFDSAEEAA | RAYDAAARAL | RGPAKTNFP | SITNQLFNH | 97 |
| SEQ-ID-NO-87-GI-57012880 | DPLKSRVWL | GTFDSAEEAA | RAYDAAARNL | RGPKAKTNFP | PYAHHQFN | 94 |
| SEQ-ID-NO-44-CLONE-975672 | DPWKKARVWL | GTFDSAEEAA | RAYDSAARNL | RGPKAKTNFQ | DCSPSSPLQ | 89 |
| SEQ-ID-NO-84-GI-15223609 | DPWKKARVWL | GTFDSAEEAA | RAYDSAARNL | RGPKAKTNFP | DSSPPPPN | 94 |

| SEQ-ID-NO-46-CLONE-1055099 | ---------- | ---------- | ---------- | ---------- | AAATSSQSST | 106 |
| SEQ-ID-NO-56-CLONE-1761125 | ---------- | ---PPPP--- | EHQGGC | ----GGGLVAPPPA | APTCSS-SST | 106 |
| SEQ-ID-NO-83-GI-125550159 | ---------- | ---------- | -HYHLPG | KAAAAAPPVA | GPACSA-SST | 100 |
| SEQ-ID-NO-45-CLONE-273307 | HMPAAA---- | AAAAPPY--- | -TYPTA | TGVVSTPPVA | RPACSSLSST | 124 |
| SEQ-ID-NO-62-CLONE-1838364 | FETN------ | ECF------- | IDORR-LYPMG | EFHDPEVNPQ | RPTSSMSSL SST | 137 |
| SEQ-ID-NO-50-CLONE-1240330 | -YP------ | HPTTDPFFYT | GFH-DOHHHH | NNNNL--NNPQ | RPTSSGMSST | 128 |
| SEQ-ID-NO-42-CLONE-674166 | ---------- | -HPDPF---- | SDH-RHFA-N | TGEDF-HDHR | RPTSSGMSST | 122 |
| SEQ-ID-NO-86-GI-56384582 | ----QN---- | PEAGNPF--- | GEL-RFYAGG | AGEGF-QDHR | RPTSSGMSST | 122 |
| SEQ-ID-NO-48-ANNOT-1441430 | ----QNQN--- | QSPTDPF--- | LDHHSINP- | -QDNP-IISQ | RPTSSLSST | 127 |
| SEQ-ID-NO-87-GI-57012880 | ----QGHN--- | PNN-DPF--- | VDS-RFYP-- | -GEQEVVILS | RPTSSMSST | 129 |
| SEQ-ID-NO-44-CLONE-975672 | ----PLHH-- | RNQIDPF--- | MDH-RLYG-- | ---QQF-PIVN | RPASSSMSST | 126 |
| SEQ-ID-NO-84-GI-15223609 | LRFNQIRNQN | QNQVDPF--- | MDH-RLFT-D | HQQQF-PIVN | RPTSSSMSST | 138 |

FIGURE 7 (cont)

| SEQ-ID | Sequence | Pos |
|---|---|---|
| SEQ-ID-NO-46-CLONE:1055099 | VESWSGGGP---------RAPARARSA ARAGTAKEGE EDCRSYCGSS | 144 |
| SEQ-ID-NO-56-CLONE:1761125 | VESSSGPRGA PRAAAA----------RAPRI RRRS VKKPRPAAFD LDCHSDCASS | 151 |
| SEQ-ID-NO-83-GI:125550159 | VESSSGPRGP RPAAA--------TAAAVPRRR VPRPAPPAPD AGCHSDCASS | 143 |
| SEQ-ID-NO-45-CLONE:273307 | VESFSGARP-----------RPVLPP---R FPC--PPST PD GDCRSDCGSS | 158 |
| SEQ-ID-NO-62-CLONE:1838364 | VESFSGPRPA QPPQKSAD---FAVVSTRKY YPRPPPVPE ---DCHSDCDSS | 183 |
| SEQ-ID-NO-50-CLONE:1240330 | VESFSGPRPA TTTTTTTT---ATPFLTATRR YPRTPPLVPE ---DCRSDCDSS | 177 |
| SEQ-ID-NO-42-CLONE:674166 | VESFSGPRAA VPA--------TAPVATGRR YPRTPPVIPE ---DCRSDCDSS | 163 |
| SEQ-ID-NO-86-GI:56384582 | VESFCGPRPV RPPM-------PPSAVTGRR HPRTPPVAPG ---DCHSDCDSS | 164 |
| SEQ-ID-NO-48-ANNOT:1441430 | VESFSGPRPP QPTTTT-----KSNGPRRS YTRSPPVVPD ---DCHSDCDSS | 171 |
| SEQ-ID-NO-87-GI:57012880 | VKSGSGVRPA PAPR-------QQTTASSRK YPRTPPVAPE ---DCRSDCDSS | 171 |
| SEQ-ID-NO-44-CLONE:975672 | VESFSGPRPT SS---------SVAKAATKR YPRTPPVVPE ---DCHSDCDSS | 166 |
| SEQ-ID-NO-84-GI:15223609 | | 176 |

| SEQ-ID | Sequence | Pos |
|---|---|---|
| SEQ-ID-NO-46-CLONE:1055099 | SSVLE----EGADDA AAS------ RSPLPFDLNM PPPQEGAL--- | 177 |
| SEQ-ID-NO-56-CLONE:1761125 | ASV-VD----DGDDAS TV------- RSRAPFDLNV PAPVDGDH--- | 182 |
| SEQ-ID-NO-83-GI:125550159 | ASV-VD----DADDAS TVR------ SRVAAFDLNL PPLDRDH--- | 175 |
| SEQ-ID-NO-45-CLONE:273307 | SSV-VD----DGDAL AAS------ PFFPLPFDLNL PPGGGAGV--- | 194 |
| SEQ-ID-NO-62-CLONE:1838364 | SSV-VD----DGDAL SSC----ASC RKITLPFDLNA LPLDEDG--- | 214 |
| SEQ-ID-NO-50-CLONE:1240330 | SSV-VD----DGDDNL VSS---SF REPLPFDLNA LPLDEDAA--- | 210 |
| SEQ-ID-NO-42-CLONE:674166 | SSV-VD----DADNDN VAS---SF P RQPLPFDLNA LPLDEDAD--- | 197 |
| SEQ-ID-NO-86-GI:56384582 | SSV-VD----DADNDN AASSTMLSFK RKPLPFDLNA PPLEEECD--- | 202 |
| SEQ-ID-NO-48-ANNOT:1441430 | SSV-VDHGDC EKENDNDN AAS---SLC RKPLPFDLNF PPLDQVD--- | 205 |
| SEQ-ID-NO-87-GI:57012880 | SSV-VE----DGXDIA JAS---SSF KPPFEFDLNF PPPMDDAG--- | 214 |
| SEQ-ID-NO-44-CLONE:975672 | SSV-D-----DDDI A SSS---SRR NPPFCFDLNF XPLDGVD--- | 200 |
| SEQ-ID-NO-84-GI:15223609 | | 210 |

| SEQ-ID | Sequence | Pos |
|---|---|---|
| SEQ-ID-NO-46-CLONE:1055099 | ---DAEADQM TCRYDITL RL ---------- ---------- | 194 |
| SEQ-ID-NO-56-CLONE:1761125 | ----ALDL-----C--- TELRL ---------- ---------- | 192 |
| SEQ-ID-NO-83-GI:125550159 | ----VDL------C--- TDLRL ---------- ---------- | 184 |
| SEQ-ID-NO-45-CLONE:273307 | GFYADEEDEL RL---TALRL ---------- ---------- | 211 |
| SEQ-ID-NO-62-CLONE:1838364 | ----RSPV YC---FMSL AM PVMNDDDRLL DLFFFFKKC | 246 |
| SEQ-ID-NO-50-CLONE:1240330 | ----ADDDL RR---TALCL ---------- ---------- | 222 |
| SEQ-ID-NO-42-CLONE:674166 | ---VATDDL FC---TALCL ---------- ---------- | 210 |
| SEQ-ID-NO-86-GI:56384582 | ---VANGLGEDL HC---TLLCL ---------- ---------- | 218 |
| SEQ-ID-NO-48-ANNOT:1441430 | ---LGSG--ADDL HC---TALCL ---------- ---------- | 219 |
| SEQ-ID-NO-87-GI:57012880 | ---LFVGA-DDX XC---TDLXL ---------- ---------- | 225 |
| SEQ-ID-NO-44-CLONE:975672 | ---LFNGA-DDL HC---TDLRL ---------- ---------- | 215 |
| SEQ-ID-NO-84-GI:15223609 | | 225 |

NUCLEOTIDE SEQUENCES AND POLYPEPTIDES ENCODED THEREBY USEFUL FOR MODIFYING PLANT CHARACTERISTICS IN RESPONSE TO COLD

This application is a divisional of copending application Ser. No. 15/362,633 filed on Nov. 28, 2016, which application is a divisional of application Ser. No. 11/779,266 filed on Jul. 17, 2007 (abandoned), which application is a Continuation-In-Part of application Ser. No. 11/778,060 filed on Jul. 15, 2007 (abandoned), which is a Continuation-In-Part of application Ser. No. 11/248,547 filed on Oct. 12, 2005 (now U.S. Pat. No. 7,244,879), the entire contents of which are hereby incorporated by reference and for which priority is claimed under 35 U.S.C. § 120.

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., TT Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1 is an alignment of ME01451. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE (Edgar (2004) Nuc. Acids Res. 32(5):1792-1797).

FIG. 2 is an alignment of ME02779.

FIG. 3 is an alignment of truncated mutant of ME02779.

FIG. 4 is an alignment of ME03944.

FIG. 5 is an alignment of ME05304.

FIG. 6 is an alignment of truncated mutant of ME05304.

FIG. 7 is an alignment of ME03186.

DETAILED DESCRIPTION OF THE INVENTION

1. Definitions

The following terms are utilized throughout this application:

Amino acid: As used herein, "amino acid" refers to one of the twenty biological occurring amino acids and to synthetic amino acids, including D/L optical isomers.

Cell type-preferential promoter or Tissue-preferential promoter: As used herein, these phrases refer to a promoter that drives expression preferentially in a target cell type or tissue, respectively, but may also lead to some transcription in other cell types or tissues as well.

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Control Plant: "Control plant" refers to a plant that does not contain the exogenous nucleic acid present in the transgenic plant of interest, but otherwise has the same of similar genetic background as such a transgenic plant. A suitable control plant can be a non-transgenic segregant from a transformation experiment, or a transgenic plant that contains an exogenous nucleic acid other than the exogenous nucleic acid of interest.

Domain: "Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Down-regulation: "Down-regulation" refers to regulation that decreases production of expression products (mRNA, polypeptide, or both) relative to basal or native states.

Endogenous: The term "endogenous," within the context of the current invention refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is catalyzed by an enzyme, RNA polymerase, and into protein, through translation of mRNA on ribosomes.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous polypeptide: "Heterologous polypeptide" as used herein refers to a polypeptide that is not a naturally occurring polypeptide in a plant cell, e.g., a transgenic

*Panicum* plant transformed with and expressing the coding sequence for a nitrogen transporter from a *Zea* plant.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an *Arabidopsis* gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Isolated nucleic acid: "Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Masterpool: The "master pools" discussed in these experiments are a pool of seeds from five independent transformation events of the same exogenous nucleotide sequence.

Modulation: As used herein, "Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Nucleic acid and polynucleotide: "Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked: As used herein, "operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math.* 2:482, by the homology alignment algorithm of Needleman and Wunsch (1970) *J Mol. Biol.* 48:443), by the search for similarity method of Pearson and Lipman (1988) *Proc. Natl. Acad. Sci.* (USA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Polypeptide: "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny: As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Regulatory region: As used herein, "regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell,* 1:977-984 (1989).

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30:321-9.); RCc2 and RCc3, promoters that direct root-specific gene transcription in rice (Xu et al. (1995) *Plant Mol. Biol.* 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$—5° C. to $T_m$—10° C. Medium or moderate stringency conditions are those providing $T_m$—20° C. to $T_m$—29° C. Low stringency conditions are those providing a condition of $T_m$—40° C. to $T_m$—48° C. The relationship of hybridization conditions to $T_m$ (in ° C.) is expressed in the mathematical equation $$T_m = 81.5 - 16.6(\log_{10}[Na^+]) + 0.41(\% \ G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^+])\} + 0.41(\% \ G+C) - 500/L \ 0.63(\% \ \text{formamide}) \quad (2)$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Up-regulation: "Up-regulation" refers to regulation that increases the level of an expression product (mRNA, polypeptide, or both) relative to basal or native states.

Vector: "Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

2. Important Characteristics of the Polynucleotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the farmer and, better yield under low temperatures.

3. The Polynucleotides and Polypeptides of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., *Molecular Cloning: A Laboratory Manual*, Second Edition, Cold Spring Harbor Laboratory Press, 1989, New York) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;

(b) YAC: Burke et al. (1987) *Science* 236:806-812;

(c) PAC: Sternberg N. et al. (1990) *Proc Natl Acad Sci USA*. January; 87:103-7;

(d) Bacteria-Yeast Shuttle Vectors: Bradshaw et al. (1995) *Nucl Acids Res* 23: 4850-4856;

(e) Lambda Phage Vectors: Replacement Vector, e.g., Frischauf et al. (1983) *J. Mol Biol* 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol Cell Biol* 1: 175-194; and (g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica*, v. 85, n. 1-3:13-27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2-5, 7, 9-18, 20-32, 34-38, 40 and 42-46 due to the fact that the different nucleic acid sequence encodes a protein having one or more conservative amino acid changes.

Polypeptides

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 20, as described in more detail herein. In some embodiments, cold tolerance-modulating polypeptides have greater than 80% identity to SEQ ID NOs: 2, 7, 9, 20, 34, 40, and 42, as described in more detail herein.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the cold tolerance-modulating activity of a truncated polypeptide. In some embodiments, a truncated polypeptide is a dominant negative polypeptide. SEQ ID NOs 7 and 40 set forth the amino sequences of cold tolerance-modulating polypeptides that are truncated at the 3' end relative to the naturally occurring polypeptides SEQ ID NOs 9 and 34, respectively. Expression in a plant of such a truncated polypeptide confers a difference in the level of cold tolerance in a tissue of the plant as compared to the corresponding level in tissue of a control plant that does not comprise the truncation.

A. Functional Homologs Identified by Reciprocal BLAST

In some embodiments, one or more functional homologs of a reference cold tolerance-modulating polypeptide defined by one or more of the pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at the Wellcome Trust Sanger Institute and HMMI janelia farm research campus. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
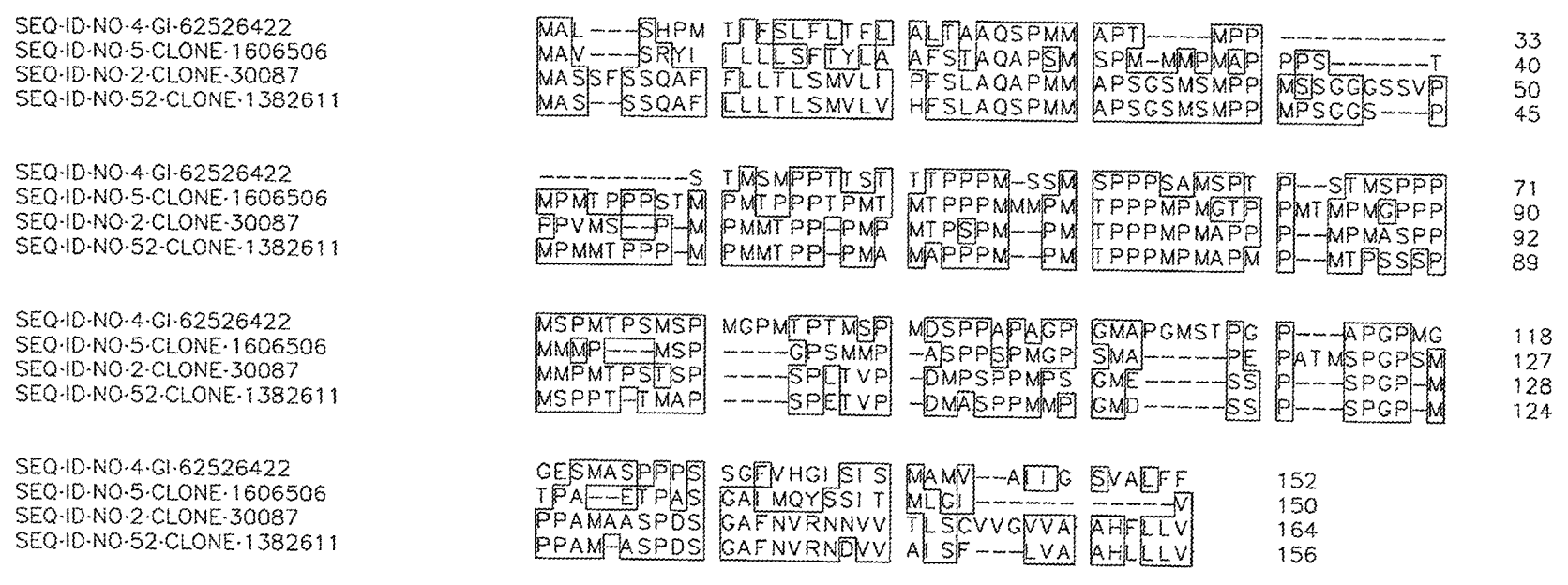

Amino acid sequences of functional homologs of the polypeptide set forth in SEQ ID NOs 2, 7, 9, 20, 34, 40 and 42 are provided in FIGS. 1-7, respectively. In some cases, a functional homolog of SEQ ID NOs 2, 7, 9, 20, 34, 40 and 42 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in the Sequence Listing.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in any one of FIGS. 1-7. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

B. Functional Homologs Identified by HMMER

In some embodiments, useful cold tolerance-modulating polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: —c, —consistency REPS of 2; —ir, —iterative-refinement REPS of 100; —pre, —pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as the HMMER page on the HHMI janelia farm research campus website; the Eddy Lab Home page on the HHMI janelia farm research campus website; and HMMER 2.3.2 download available on the Fish & Richardson website. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in one of Table 7. In some embodiments, a cold tolerance-modulating polypeptide discussed below fits the indicated HMM with an HMM bit score greater than 20, and has a domain indicative of an cold tolerance-modulating polypeptide. In some embodiments, a cold tolerance-modulating polypeptide discussed below fits the indicated HMM with an HMM bit score greater than 20, and has 80% or greater sequence identity (e.g., 75%, 80%, 85%, 90%, 95%, or 100% sequence identity) to an amino acid sequence shown in any one of FIGS. 1-7.

Polypeptides are shown in Table 7 that have HMM bit scores greater than 20 when fitted to an HMM generated from the amino acid sequences set forth in FIGS. 1-7, respectively.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a cold tolerance-modulating polypeptide, and the other strand of the stem portion of the double stranded RNA comprises a sequence that is similar or identical to the sequence that is complementary to the 3' or 5' untranslated region, respectively, of the mRNA encoding the cold tolerance-modulating polypeptide. In other embodiments, one strand of the stem portion of a double stranded RNA comprises a sequence that is similar or identical to the sequence of an intron in the pre-mRNA encoding a cold tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a cold tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

In some embodiments, nucleic acid based inhibition of gene expression does not require transcription of the nucleic acid.

Identification of Useful Nucleotide Sequences

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5×MS Media is prepared and the pH adjusted to 5.7 using 10N KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 µEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

REFERENCES

Levitt (1980) Chilling injury and resistance. In TT Kozlowsky, ed, Chilling, Freezing, and High Temperature Stresses: Responses of Plant to Environmental Stresses, Vol 1. Academic Press, New York, pp 23-64.

Graham and Patterson (1982) *Annu Rev Plant Physiol* 33: 347-372.

Guy (1990) *Annu Rev Plant Physiol Plant Mol Biol* 41: 187-223.

Nishida and Murata (1996) *Annu Rev Plant Physiol Plant Mol Biol* 47: 541-568.

EXAMPLES

Summary

| | |
|---|---|
| Trait area(s) | Cold |
| Sub-trait Area | Cold - germination and vigor |
| Coding sequence/ Species of Origin | 1. Vector Construct Sequence Identifier 14298746 corresponding to Clone 30087 - ME01451; encodes a 164 amino acid protein of unknown function from *Arabidopsis*. 2. Vector Construct Sequence Identifier 14298770 corresponding to Clone 30469 - ME02779 encodes a 78 amino acid protein with identity to the N-terminal half of an *Arabidopsis* class I nonsymbiotic hemoglobin. 3. Vector Construct Sequence Identifier 14301197 corresponding to Clone 271922 - ME03944 encodes a 92 amino acid 60s ribosomal protein L37a protein from *Arabidopsis*. 4. Vector Construct Sequence Identifier 14296769 corresponding to Clone 2403 - ME05304 encodes a truncated ubiquitin-like protein from *Arabidopsis*. 5. Vector Construct Sequence Identifier 14301334 corresponding to Clone 674166 - ME03186 from *Glycine max* encodes a 210 amino acid protein with similarity to the ethylene-responsive element binding protein (ERF) family. |
| Species in which Clone was Tested | *Arabidopsis thaliana* |
| Promoter | 35S, a strong constitutive promoter |
| Insert DNA type | cDNA |

Introduction

How plants respond to stress in the environment dictates their ability to survive and reproduce. There are probably many mechanisms by which plants regulate the temperatures under which they will germinate (Lu and Hills, 2003). Finding genes that result in stress tolerance when overexpressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods:

Generation and Phenotypic Evaluation of $T_1$ Events.

Wild-type *Arabidopsis* Wassilewskija (Ws) plants were transformed with a Ti plasmid containing different Clones in the sense orientation relative to the 35S promoter, by *Agrobacterium*-Mediated Transformation. The Ti plasmid vector used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:

Procedure for 1) identifying the candidate from a cold germination superpool screen, 2) confirming the phenotype in the second and third generations and 3) determining the lack of significant negative phenotypes.

1. Superpools screened for Cold Germination
2. Cold tolerant candidates identified
3. Independent events tested for Cold Germination and Finale™ resistance in two generations
4. For all candidates, at least 2 Events were significantly tolerant to cold in 2 generations
5. Tested positive events for negative phenotypes Growth Conditions and Planting Schema Under Cold Germination.

Up to five independent $T_2$ transformation events were evaluated for each line under cold conditions. Subsequently, $T_3$ generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5×MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

Results:

Example 1: ME01451

TABLE 1-1

| Construct | Event/Generation | Plant Stage | Assay | Result |
|---|---|---|---|---|
| 35S::30087 | -01/$T_2$ Finale resistant plants | Seedling | Cold Germination | Significant at $p \leq .05$ |
| 35S::30087 | -05/$T_2$ Finale resistant plants | Seedling | Cold Germination | Significant at $p \leq .05$ |
| 35S::30087 | -01/$T_3$ Finale resistant plants | Seedling | Cold Germination | Significant at $p \leq .05$ |
| 35S::30087 | -05/$T_3$ Finale resistant plants | Seedling | Cold Germination | Significant at $p \leq .05$ |

Ectopic expression of Clone 30087 under the control of the 35S promoter induces the following phenotypes:
  Early germination at 8° C. resulting in larger seedlings after 10 days of growth in the cold.
Plants from Events −01 and −05 which are heterozygous or homozygous for Clone 30087 do not show any negative phenotypes under long-day conditions.
The gene corresponding to Clone 30087 is up-regulated in developing seedlings, seeds and siliques and down-regulated in drought, heat and ABA.

Two Events of ME01451 Showed Significant Early Germination Under Cold Conditions in Both Generations.

All five events of ME01451 were sown as described in the Cold Germination Assay in both the $T_2$ and the $T_3$ generations. Two events, −01 and −05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |

TABLE 1-2-continued

T-test comparison of seedling area between transgenic seedlings
and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two Events of ME01451 Show 3:1 and 15:1 Segregation for Finale™ Resistance.

Events −01 and −05 segregated 15:1 and 3:1 (R:S), respectively, for Finale™ resistance in the $T_2$ generation (data not shown).

Qualitative Analysis of the $T_1$ Plants:
The physical appearance of all ten $T_1$ plants was identical to the controls.

Qualitative and Quantitative Analysis of the $T_2$ Plants:
Events −01 and −05 of ME01451 exhibited no statistically relevant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
    No observable or statistical differences between experimentals and controls.
  Fertility (silique number and seed fill)
    No observable or statistical differences between experimentals and controls

Example 2: ME02779

TABLE 2-1

| Construct | Event/Generation | Plant Stage | Assay | Result |
|---|---|---|---|---|
| 35S::30469 | −01/$T_2$ Finale resistant plants | Seedling | Cold Germination | Significant at $p \leq .05$ |

TABLE 2-1-continued

| Construct | Event/Generation | Plant Stage | Assay | Result |
|---|---|---|---|---|
| 35S::30469 | −03/$T_2$ Finale resistant plants | Seedling | Cold Germination | Significant at $p \leq .05$ |
| 35S::30469 | −01/$T_3$ Finale resistant plants | Seedling | Cold Germination | Significant at $p \leq .05$ |
| 35S::30469 | −03/$T_3$ Finale resistant plants | Seedling | Cold Germination | Significant at $p \leq .05$ |

Ectopic expression of Clone 30469 under the control of the 35S promoter induces the following phenotypes:
  Early germination at 8° C. resulting in larger seedlings after 10 days at 8° C.
  Plants from Events −01 and −03 which are heterozygous or homozygous for Clone 30469 do not show any negative phenotypes under long-day conditions.
  The gene corresponding to Clone 30469 is down-regulated in ABA, heat, and germinating seeds and up-regulated in high nitrogen and most cold and drought treatments.
  Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.

Two Events of ME02779 Showed Significant Early Germination Under Cold Conditions in Both Generations.

Five events of ME02779 were sown as described in the Cold Germination Assay in both the $T_2$ and the $T_3$ generations. Two events, −01 and −03 were significant in both generations at p=0.05 using a one-tailed t-test assuming unequal variance (Table 2-2). ME02779 transgenic seedlings were significantly larger than the pooled non-transgenic segregants.

TABLE 2-2

T-test comparison of seedling area between transgenic seedlings and
pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two Events of ME02779 Show 3:1 Segregation for Finale™ Resistance.

Events −01 and −03 segregated 3:1 (R:S) for Finale™ resistance in the $T_2$ generation (data not shown).

Qualitative Analysis of the $T_1$ Plants:

The physical appearance of nine of the ten $T_1$ plants was identical to the controls except for Event −09, which exhibited small rosettes and reduced fertility.

Qualitative and Quantitative Analysis of the $T_2$ Plants:

Events −01 and −03 of ME02779 exhibited no statistically relevant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting
  No observable or statistical differences between experimentals and controls.
Fertility (silique number and seed fill)
  No observable or statistical differences between experimentals and controls

Example 3: ME03944

TABLE 3-1

| Construct | Event/Generation | Plant Stage | Assay | Result |
|---|---|---|---|---|
| 35S::271922 | -02/$T_2$ Finale resistant plants | Seedling | Cold Germination | Significant at p ≤ .05 |
| 35S::271922 | -06/$T_2$ Finale resistant plants | Seedling | Cold Germination | Significant at p ≤ .05 |
| 35S::271922 | -02/$T_3$ Finale resistant plants | Seedling | Cold Germination | Significant at p ≤ .05 |
| 35S::271922 | -06/$T_3$ Finale resistant plants | Seedling | Cold Germination | Significant at p ≤ .05 |

Ectopic expression of Clone 271922 under the control of the 35S promoter induces the following phenotypes:
  Early germination at 8° C. resulting in larger seedlings after 10 days at 8° C.
Plants from Events −02 and −06 which are heterozygous or homozygous for Clone 271922 do not show any negative phenotypes under long-day conditions.
The gene corresponding to Clone 271922 shows little differential regulation in transcription profiling experiments on wildtype.
Clone 271922 encodes a 60s ribosomal protein L37a.

Two Events of ME03944 Showed Significant Early Germination Under Cold Conditions in Both Generations.

Four events of ME03944 were sown as described in the Cold Germination Assay in both the $T_2$ and the $T_3$ generations. Two events, −02 and −06, were significant in both generations at p≤0.05 using a one-tailed t-test assuming unequal variance (Table 3-2). The $T_3$ lines are indicated as −99 which indicates that the seeds are the bulked progeny from several $T_2$ plants. ME03944 transgenic seedlings were significantly larger than the pooled non-transgenic segregants.

TABLE 3-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME03944 | ME03944-02 | 0.0115 | 0.0004 | 23 | 0.0069 | 0.0006 | 35 | 3.4023E−08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E−05 |
| ME03944 | ME03944-06-99 | 0.0077 | 0.0007 | 21 | 0.0051 | 0.0004 | 29 | 0.0011 |

Two Events of ME03944 Show 3:1 Segregation for Finale™ Resistance.

Events −02 and −06 segregated 3:1 (R:S) for Finale™ resistance in the $T_2$ generation (data not shown).

Qualitative Analysis of the $T_1$ Plants:

The physical appearance of five of the six $T_1$ plants was identical to the controls. Event −03 exhibited a small rosette and curled leaves.

Other Characteristics:

Seedlings from ME03944-06 exhibited elongated hypocotyls. This phenotype co-segregated with Finale™ resistance.

Qualitative and Quantitative Analysis of the $T_2$ Plants:

Events −02 and −06 of ME03944 exhibited no statistically relevant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting
  No observable or statistical differences between experimentals and controls.
Fertility (silique number and seed fill)
  No observable or statistical differences between experimentals and controls

Example 4: ME05304

TABLE 4-1

| Construct | Event/Generation | Plant Stage | Assay | Result |
|---|---|---|---|---|
| 35S::2403 | -01/$T_2$ Finale resistant plants | Seedling | Cold Germination | Significant at p ≤ .05 |
| 35S::2403 | -04/$T_2$ Finale resistant plants | Seedling | Cold Germination | Significant at p ≤ .05 |
| 35S::2403 | -01/$T_3$ Finale resistant plants | Seedling | Cold Germination | Significant at p ≤ .05 |

TABLE 4-1-continued

| Construct | Event/Generation | Plant Stage | Assay | Result |
|---|---|---|---|---|
| 35S::2403 | -04/$T_3$ Finale resistant plants | Seedling | Cold Germination | Significant at $p \leq .05$ |

Ectopic expression of Clone 2403 under the control of the 35S promoter induces the following phenotypes:
  Early germination at 8° C. resulting in larger seedlings after 10 days at 8° C.
  Plants from Events –01 and –04 which are heterozygous or homozygous for Clone 2403 do not show any negative phenotypes under long-day conditions.
  The gene corresponding to Clone 2403 shows little differential regulation in transcript profiling experiments on wildtype.
  Clone 2403 encodes a truncated ubiquitin-like protein.

Two Events of ME05304 Showed Significant Early Germination Under Cold Conditions in Both Generations.

Four events of ME05304 were sown as described in the Cold Germination Assay in both the $T_2$ and the $T_3$ generations. Two events, –01 and –04 were significant in both generations at p≤0.05 using a one-tailed t-test assuming unequal variance (Table 4-2). The $T_3$ lines are indicated as –99 which indicates that the seeds are the bulked progeny from several $T_2$ plants.

TABLE 4-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two Events of ME05304 Show 3:1 Segregation for Finale™ Resistance.

Events –01 and –04 segregated 3:1 (R:S) for Finale™ resistance in the $T_2$ generation (data not shown).
Qualitative Analysis of the $T_1$ Plants:
  The physical appearance of seven of the ten $T_1$ plants was identical to the controls. The other three events exhibited the following phenotypes: late flowering (Events –01, –02 and –08), dark green rosette leaves (Events –01 and –08) and shorter petioles (Events –02 and –08). Event –01 did not reproduce the late-flowering phenotype in the $T_2$ generation.
Qualitative and Quantitative Analysis of the $T_2$ Plants:
Events –01 and –04 of ME05304 exhibited no statistically relevant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
    No observable or statistical differences between experimentals and controls.
  Fertility (silique number and seed fill)
    No observable or statistical differences between experimentals and controls.

Example 5: ME03186

TABLE 5-1

| Construct | Event/Generation | Plant Stage | Assay | Result |
|---|---|---|---|---|
| 35S::674166 | -04/$T_3$ Finale resistant plants | Seedling | Cold Germination | Significant at $p \leq .05$ |
| 35S::674166 | -04/$T_4$ Finale resistant plants | Seedling | Cold Germination | Significant at $p \leq .05$ |
| 35S::674166 | -05/$T_2$ Finale resistant plants | Seedling | Cold Germination | Significant at $p \leq .05$ |
| 35S::674166 | -05/$T_3$ Finale resistant plants | Seedling | Cold Germination | Significant at $p \leq .05$ |

Ectopic expression of Clone 674166 under the control of the 35S promoter results in early germination at 8° C. resulting in larger seedlings after 10 days at 8° C.

Plants from Events –04 and –05 which are hemizygous or homozygous for Clone 674166 do not show any negative phenotypes under long-day conditions.

Two Events of ME03186 Showed Significant Early Germination Under Cold Conditions in Both Generations.

Two events, –04 and –05 were significant in two generations at p≤0.05 using a one-tailed t-test assuming unequal variance (Table 5-2). '-99' signifies that seeds were pooled from several plants.

TABLE 5-2

T-test comparison of seedling area between transgenic seedlings and control non-transgenic segregants after 10 days at 8° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME03186-04-99[b] | 04-T3 | 0.0045 | 0.0003 | 35 | 0.0030 | 0.0002 | 31 | 1.37E−05 |
| ME03186-04-99 | 04-T3 | 0.0092 | 0.0003 | 48 | 0.0051 | 0.0005 | 12 | 3.72E−10 |
| ME03186-04-99-03 | 04-T4 | 0.0107 | 0.0002 | 70 | 0.0083 | 0.0005 | 34 | 2.72E−05 |
| ME03186-04-99-04 | 04-T4 | 0.0120 | 0.0004 | 62 | 0.0083 | 0.0005 | 34 | 3.61E−08 |
| ME03186-04-99-07 | 04-T4 | 0.0107 | 0.0003 | 69 | 0.0083 | 0.0005 | 34 | 4.91E−05 |
| ME03186-04-99-08 | 04-T4 | 0.0110 | 0.0003 | 69 | 0.0083 | 0.0005 | 34 | 5.53E−06 |
| ME03186-05[b] | 05-T2 | 0.0051 | 0.0005 | 22 | 0.0038 | 0.0005 | 6 | 0.0332 |
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a]Transgenic seedlings were compared to non-transgenic segregants within a seed line except for the T4 generation of Event-04. Since these seed lines were homozygous, they were compared to pooled non-transgenic segregants from another T4 generation event that was grown in the same flat as the T4 generation of Event-04.
[b]These events were sown twice. The first time was to identify ME03186 as a hit. They were repeated the second time with two generations to identify ME03186 as a candidate.

Two Events of ME03186 Show 3:1 Segregation for Finale™ Resistance.

Event −05 segregated 3:1 (R:S) for Finale™ resistance in the $T_2$ generation. $T_2$ generation seed was not available for Event −04. However, the $T_3$ generation seeds that were pooled from several $T_2$ plants segregated approximately 2:1 in a manner consistent with a single insert (see Table 5-2).

Qualitative and Quantitative Analysis of the $T_2$ Plants (Screening for Negative Phenotypes):

Events −04 and −05 of ME03186 exhibited no statistically significant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting

REFERENCES

Hunt et ak, (2001) *Plant Mol Biol* 47: 677-692.
Lu and Hills (2002) *Plant Physiol.* 129:1352-8

Example 6: Clone 1055099 (SEQ ID NO: 46)—ME 24967

In the same manner as Example 5, transgenics made with a construct of 35S—Clone 1055099 were screened for cold tolerance. Clone 1055099 (SEQ ID NO: 46) is a wheat functional homolog of clone 674166 (SEQ ID NO: 42), and showed the following results in the seedling cold tolerance assay.

TABLE 6-1

Cold Germination Assay results for ME24967.

| Event | p-values Internal[a] | p-values Pooled[b] | Avg. Seedling Area Transgenic | Avg. Seedling Area Internal | Avg. Seedling Area Pooled | Sample No. Transgenic | Sample No. Internal | Sample No. Pooled |
|---|---|---|---|---|---|---|---|---|
| ME03186-04-99[c] | 0.00224438 | 0.00224438 | 0.0032 | 0.0017 | 0.0017 | 30 | 40 | 40 |
| ME24967-02 | 0.12660455 | 0.45511103 | 0.0053 | 0.0071 | 0.0054 | 29 | 5 | 83 |
| ME24967-03[d] | 0.01488322 | 0.04610112 | 0.0069 | 0.0031 | 0.0054 | 31 | 3 | 83 |
| ME24967-05[d] | 0.08783497 | 3.0406E−08 | 0.0115 | 0.0092 | 0.0054 | 23 | 12 | 83 |
| ME24967-10 | 0.40686041 | 0.25206736 | 0.0049 | 0.0053 | 0.0054 | 28 | 6 | 83 |
| ME24967-11 | 0.19290195 | 0.40123421 | 0.0051 | 0.0038 | 0.0054 | 5 | 25 | 83 |
| ME24967-12 | 0.3021565 | 0.00329335 | 0.0032 | 0.0050 | 0.0054 | 27 | 2 | 83 |
| ME24967-13 | 0.24672812 | 0.31347649 | 0.0060 | 0.0077 | 0.0054 | 23 | 7 | 83 |
| ME24967-14 | 0.17548824 | 0.29369895 | 0.0050 | 0.0032 | 0.0054 | 26 | 5 | 83 |
| ME24967-15 | 0.29278326 | 0.38586196 | 0.0057 | 0.0048 | 0.0054 | 22 | 11 | 83 |
| ME24967-16 |  | 0.05451794 | 0.0041 | 0.0018 | 0.0054 | 34 | 1 | 83 |

TABLE 6-1-continued

Cold Germination Assay results for ME24967.

| Event | p-values | | Avg. Seedling Area | | | Sample No. | | |
|---|---|---|---|---|---|---|---|---|
| | Internal[a] | Pooled[b] | Transgenic | Internal | Pooled | Transgenic | Internal | Pooled |
| ME24967-17 | 0.27484717 | 0.13660585 | 0.0044 | 0.0058 | 0.0054 | 26 | 6 | 83 |

[a]Internal controls are segregating non-transgenic seedlings within an Event.
[b]Pooled controls are all of the segregating non-transgenic seedlings from all of the Events within a line.
[c]ME03186 is a positive control to verify that the experimental conditions were appropriate.
[d]These events show significantly improved seedling area for at least internal or pooled controls.

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the –postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 7, 9, 20, 34, 40 and 42 are shown in FIGS. 1-7, respectively. The BLAST percent identities and E-values of functional homologs to SEQ ID NOs: 2, 7, 9, 20, 34, 40 and 42 are shown in the Sequence Listing. The BLAST sequence identities and E-values given in the Sequence Listing were taken from the forward search round of the Reciprocal BLAST process.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in each of FIGS. 1-7 as input. Additional sequences were input into the model, and the HMM bit scores for the additional sequences are shown in the Sequence Listing. The results indicate that these additional sequences are functional homologs of SEQ ID NOs: 2, 7, 9, 20, 34, 40 and 42, respectively. The bit score results are provided in Table 7.

TABLE 7

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| Ceres CLONE ID no. 30087 | Ceres CLONE ID no. 30087 | DNA | *Arabidopsis thaliana* | 1 | 828 | | | | | | | | |
| Ceres Clone ID no. 30087 | Ceres CLONE ID no. 30087 | PRT | *Arabidopsis thaliana* | 2 | 164 | | | | | Y | | | |
| Ceres Clone ID no. 30087 | Ceres CLONE ID no. 947579 | PRT | *Brassica napus* | 3 | 155 | | | | | Y | | | |
| Ceres Clone ID no. 30087 | Public GI no. 62526422 | PRT | *Brassica napus* | 4 | 152 | | | | | | | | |
| Ceres Clone ID no. 30087 | Ceres CLONE ID no. 1606506 | PRT | *Parthenium argentatum* | 5 | 150 | | | | | Y | | | |
| Ceres CLONE ID no. 30469 | Ceres CLONE ID no. 30469 | DNA | Artificial Sequence | 6 | 586 | | | | | | | | |
| Ceres Clone ID no. 30469 | Ceres CLONE ID no. 30469 | PRT | Artificial Sequence | 7 | 78 | | | | | | | | 66 |
| Ceres Clone ID no. 30469 | Ceres CLONE ID no. 30469_FL | DNA | *Arabidopsis thaliana* | 8 | 483 | | | | | | | | |
| Ceres Clone ID no. 30469 | Ceres CLONE ID no. 30469_FL | PRT | *Arabidopsis thaliana* | 9 | 160 | Globin | Globin | 13 | 152 | Y | 184.6 | Y | 404.9 |
| Ceres Clone ID no. 30469 | Public GI no. 30909306 | PRT | *Raphanus sativus* | 10 | 160 | Globin | Globin | 13 | 152 | | 185.7 | Y | 410.4 |
| Ceres Clone ID no. 30469 | Public GI no. 37903656 | PRT | *Arabidopsis thaliana* | 11 | 158 | Globin | Globin | 10 | 149 | | 172.6 | | 387.2 |
| Ceres Clone ID no. 30469 | Public GI no. 15824736 | PRT | *Arabidopsis thaliana* | 12 | 163 | Globin | Globin | 13 | 152 | | 184.2 | | 405.4 |
| Ceres Clone ID no. 30469 | Ceres CLONE ID no. 546001 | PRT | *Glycine max* | 13 | 161 | Globin | Globin | 13 | 152 | | 182.8 | Y | 402.3 |
| Ceres Clone ID no. 30469 | Public GI no. 11095158 | PRT | *Glycine max* | 14 | 160 | Globin | Globin | 13 | 152 | | 167.8 | | 387.2 |
| Ceres Clone ID no. 30469 | Public GI no. 12963875 | PRT | *Glycine max* | 15 | 152 | Globin | Globin | 8 | 147 | | 145.8 | | 337.1 |
| Ceres Clone ID no. 30469 | Ceres CLONE ID no. 1554560 | PRT | *Zea mays* | 16 | 165 | Globin | Globin | 17 | 157 | | 185.7 | Y | 404.5 |
| Ceres Clone ID no. 30469 | Ceres CLONE ID no. 839727 | PRT | *Triticum aestivum* | 17 | 162 | Globin | Globin | 14 | 154 | | 187.8 | Y | 415.2 |
| Ceres Clone ID no. 30469 | Public GI no. 14701800 | PRT | *Triticum aestivum* | 18 | 169 | Globin | Globin | 21 | 161 | | 170.1 | | 386.9 |
| Ceres CLONE ID no. 271922 | Ceres CLONE ID no. 271922 | DNA | *Arabidopsis thaliana* | 19 | 416 | | | | | | | | |
| Ceres CLONE ID no. 271922 | Ceres CLONE ID no. 271922 | PRT | *Arabidopsis thaliana* | 20 | 92 | Ribosomal_L37ae; | Ribosomal L37ae protein family | 2 | 91 | Y | 266.3 | | |
| Ceres Clone ID no. 271922 | Public GI no. 4090257 | PRT | *Arabidopsis thaliana* | 21 | 92 | Ribosomal_L37ae | Ribosomal L37ae protein family | 2 | 91 | | 265.8 | | |
| Ceres Clone ID no. 271922 | Public GI no. 4741896 | PRT | *Arabidopsis thaliana* | 22 | 92 | Ribosomal_L37ae | Ribosomal L37ae protein family | 2 | 91 | | 264 | | |
| Ceres Clone ID no. 271922 | Ceres CLONE ID no. 36046 | PRT | *Arabidopsis thaliana* | 23 | 92 | Ribosomal_L37ae | Ribosomal L37ae protein family | 2 | 91 | | 257.8 | | |
| Ceres Clone ID no. 271922 | Public GI no. 6016699 | PRT | *Arabidopsis thaliana* | 24 | 92 | Ribosomal_L37ae | Ribosomal L37ae protein family | 2 | 91 | Y | 257.4 | | |
| Ceres Clone ID no. 271922 | Ceres CLONE ID no. 664936 | PRT | *Glycine max* | 25 | 92 | Ribosomal_L37ae | Ribosomal L37ae protein family | 2 | 91 | | 268.8 | | |
| Ceres Clone ID no. 271922 | Ceres CLONE ID no. 658438 | PRT | *Glycine max* | 26 | 92 | Ribosomal_L37ae | Ribosomal L37ae protein family | 2 | 91 | | 269 | | |
| Ceres Clone ID no. 271922 | Ceres CLONE ID no. 1049262 | PRT | *Glycine max* | 27 | 92 | Ribosomal_L37ae | Ribosomal L37ae protein family | 2 | 91 | | 268.9 | | |

TABLE 7-continued

| Query Identifier | Functional Homolog | Sequence Type | Species | Seq Id No | Length | Pfam | Pfam Description | Start | End | Profile | HMM Bit Score | FL Profile | FL Score |
|---|---|---|---|---|---|---|---|---|---|---|---|---|---|
| Ceres Clone ID no. 271922 | Ceres CLONE ID no. 632613 | PRT | Triticum aestivum | 28 | 92 | Ribosomal_L37ae | Ribosomal L37ae protein family | 2 | 91 | Y | 269 | | |
| Ceres Clone ID no. 271922 | Ceres CLONE ID no. 1390976 | PRT | Zea mays | 29 | 92 | Ribosomal_L37ae | Ribosomal L37ae protein family | 2 | 91 | Y | 269 | | |
| Ceres Clone ID no. 271922 | Ceres CLONE ID no. 1457185 | PRT | Zea mays | 30 | 92 | Ribosomal_L37ae | Ribosomal L37ae protein family | 2 | 91 | | 269 | | |
| Ceres Clone ID no. 271922 | Public GI no. 56202147 | PRT | Zea mays | 31 | 92 | Ribosomal_L37ae | Ribosomal L37ae protein family | 2 | 91 | | 269 | | |
| Ceres Clone ID no. 271922 | Public GI no. 58578274 | PRT | Zea mays | 32 | 92 | Ribosomal_L37ae | Ribosomal L37ae protein family | 2 | 91 | | 267.7 | | |
| Ceres Clone ID no. 2403 | Ceres CLONE ID no. 2403_FL | DNA | Arabidopsis thaliana | 33 | 632 | | | | | | | | |
| Ceres Clone ID no. 2403 | Ceres CLONE ID no. 2403_FL | PRT | Arabidopsis thaliana | 34 | 154 | ubiquitin; | Ubiquitin family | 1 | 74 | | 118.7 | | 416.2 |
| Ceres Clone ID no. 2403 | Ceres CLONE ID no. 2403_FL | PRT | Arabidopsis thaliana | 34 | 154 | ubiquitin; | Ubiquitin family | 77 | 150 | | 118.7 | | 416.2 |
| Ceres Clone ID no. 2403 | Ceres CLONE ID no. 1482731 | PRT | Zea mays | 35 | 169 | ubiquitin | Ubiquitin family | 1 | 74 | | 118.3 | | 417 |
| Ceres Clone ID no. 2403 | Ceres CLONE ID no. 1482731 | PRT | Zea mays | 35 | 169 | ubiquitin | Ubiquitin family | 77 | 150 | | 118.3 | | 417 |
| Ceres Clone ID no. 2403 | Ceres CLONE ID no. 522921 | PRT | Glycine max | 36 | 154 | ubiquitin | Ubiquitin family | 1 | 74 | | 118.7 | Y | 418.4 |
| Ceres Clone ID no. 2403 | Ceres CLONE ID no. 522921 | PRT | Glycine max | 36 | 154 | ubiquitin | Ubiquitin family | 77 | 150 | | 118.7 | Y | 418.4 |
| Ceres Clone ID no. 2403 | Ceres CLONE ID no. 1036726 | PRT | Brassica napus | 38 | 160 | ubiquitin | Ubiquitin family | 1 | 74 | | 118.7 | Y | 384.4 |
| Ceres Clone ID no. 2403 | Ceres CLONE ID no. 1036726 | PRT | Brassica napus | 37 | 160 | ubiquitin | Ubiquitin family | 77 | 142 | | 118.7 | Y | 384.4 |
| Ceres Clone ID no. 2403 | Ceres CLONE ID no. 513071 | PRT | Glycine max | 38 | 188 | ubiquitin | Ubiquitin family | 1 | 74 | | 114.3 | Y | 408.6 |
| Ceres Clone ID no. 2403 | Ceres CLONE ID no. 513071 | PRT | Glycine max | 38 | 188 | ubiquitin | Ubiquitin family | 77 | 150 | | 114.3 | Y | 408.6 |
| Ceres Clone ID no. 2403 | Ceres CLONE ID no. 2403 | DNA | Artificial Sequence | 39 | 620 | | | | | | | | |
| Ceres Clone ID no. 2403 | Ceres CLONE ID no. 2403 | PRT | Artificial Sequence | 40 | 33 | ubiquitin; | Ubiquitin family | 1 | 33 | Y | 87.6 | | −83.1 |
| Ceres CLONE ID no. 674166 | Ceres CLONE ID no. 674166 | DNA | Glycine max | 41 | 1106 | | | | | | | | |
| Ceres CLONE ID no. 674166 | Ceres CLONE ID no. 674166 | PRT | Glycine max | 42 | 210 | AP2; | AP2 domain | 26 | 89 | Y | 491.8 | | |
| Ceres CLONE ID no. 674166 | Public GI no. 12332345 | PRT | Glycine max | 43 | 225 | AP2 | AP2 domain | 26 | 89 | | 522.4 | | |
| Ceres CLONE ID no. 674166 | Ceres CLONE ID no. 975672 | PRT | Brassica napus | 44 | 215 | AP2 | AP2 domain | 21 | 84 | Y | 481.7 | | |
| Ceres CLONE ID no. 674166 | Ceres CLONE IO no. 273307 | PRT | Zea mays | 45 | 211 | AP2 | AP2 domain | 17 | 80 | Y | 419.7 | | |
| Ceres CLONE ID no. 674166 | Ceres CLONE ID no. 1055099 | PRT | Triticum aestivum | 46 | 194 | AP2 | AP2 domain | 20 | 83 | Y | 358.4 | | |
| Ceres CLONE ID no. 674166 | Ceres ANNOT ID no. 1441430 | DNA | Populus balsamifera subsp. trichocarpa | 47 | 660 | | | | | | | | |
| Ceres CLONE ID no. 674166 | Ceres ANNOT ID no. 1441430 | PRT | Populus balsamifera subsp. trichocarpa | 48 | 219 | AP2 | AP2 domain | 29 | 92 | Y | 504.4 | | |
| Ceres CLONE ID no. 674166 | Ceres CLONE ID no. 1240330 | DNA | Glycine max | 49 | 985 | | | | | | | | |
| Ceres CLONE ID no. 674166 | Ceres CLONE ID no. 1240330 | PRT | Glycine max | 50 | 222 | AP2 | AP2 domain | 24 | 87 | | 483.3 | | |
| Ceres CLONE ID no. 30087 | Ceres CLONE ID no. 1382611 | DNA | Zea mays | 51 | 726 | | | | | | | | |
| Ceres CLONE ID no. 30087 | Ceres CLONE ID no. 1382811 | PRT | Zea mays | 52 | 156 | | | | | Y | | | |
| Ceres Clone ID no. 271922 | Ceres CLONE ID no. 1627907 | DNA | Papaver somniferum | 53 | 580 | | | | | | | | |
| Ceres Clone ID no. 271922 | Ceres CLONE ID no. 1627907 | PRT | Papaver somniferum | 54 | 92 | Ribosomal_L37ae | Ribosomal L37ae protein family | 2 | 91 | Y | 288.1 | | |
| Ceres Clone ID no. 271922 | Ceres CLONE ID no. 1761125 | DNA | Panicum virgatum | 55 | 983 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| Ceres CLONE ID no. 674166 | Ceres CLONE ID no. 1761125 | PRT | Panicum virgatum | 56 | 192 | AP2 | AP2 domain | 13 | 76 | Y | 363 | | |
| Ceres CLONE ID no. 271922 | Ceres CLONE ID no. 1783890 | DNA | Panicum virgatum | 57 | 594 | | | | | | | | |
| Ceres CLONE ID no. 271922 | Ceres CLONE ID no. 1783890 | PRT | Panicum virgatum | 58 | 92 | Ribosomal L37ae | Ribosomal L37ae protein family | 2 | 91 | Y | 269 | | |
| Ceres CLONE ID no. 30469 | Ceres CLONE ID no. 1802327 | DNA | Panicum virgatum | 59 | 880 | | | | | | | | |
| Ceres CLONE ID no. 30469 | Ceres CLONE ID no. 1802327 | PRT | Panicum virgatum | 60 | 162 | Globin | Globin | 14 | 154 | | 191.4 | Y | 417.9 |
| Ceres CLONE ID no. 874166 | Ceres CLONE ID no. 1838364 | DNA | Gossypium hirsutum | 61 | 1017 | | | | | | | | |
| Ceres CLONE ID no. 874166 | Ceres CLONE ID no. 1838384 | PRT | Gossypium hirsutum | 62 | 248 | AP2 | AP2 domain | 28 | 91 | Y | 484.1 | | |
| Ceres CLONE ID no. 874166 | Ceres CLONE ID no. 1878458 | DNA | Gossypium hirsutum | 63 | 708 | | | | | | | | |
| Ceres CLONE ID no. 30469 | Ceres CLONE ID no. 1876458 | PRT | Panicum virgatum | 64 | 162 | Globin | Globin | 14 | 154 | | 191.9 | | 415.3 |
| Ceres Clone ID no. 30469 | Ceres CLONE ID no. 1879148 | DNA | Panicum virgatum | 65 | 712 | | | | | | | | |
| Ceres CLONE ID no. 30469 | Ceres CLONE ID no. 1879148 | PRT | Panicum virgatum | 66 | 164 | Globin | Globin | 16 | 156 | | 185.7 | | 411.2 |
| | Ceres CLONE ID no. 1884696 | DNA | Gossypium hirsutum | 87 | 1129 | | | | | | | | |
| Ceres CLONE ID no. 2403 | Ceres CLONE ID no. 1884696 | PRT | Gossypium hirsutum | 68 | 153 | ubiquitin | Ubiquitin family | 1 | 74 | | 175.2 | Y | 408 |
| Ceres CLONE ID no. 2403 | Ceres CLONE ID no. 1884896 | PRT | Gossypium hirsutum | 68 | 153 | ubiquitin | Ubiquitin family | 77 | 150 | | 175.2 | Y | 408 |
| Ceres CLONE ID no. 30469 | Ceres CLONE ID no. 1916866 | DNA | Gossypium hirsutum | 69 | 679 | | | | | | | | |
| Ceres Clone ID no. 30469 | Ceres CLONE ID no. 1916866 | PRT | Gossypium hirsutum | 70 | 163 | Globin | Globin | 13 | 152 | | 188.3 | Y | 409.8 |
| Ceres Clone ID no. 30469 | Ceres CLONE ID no. 1950105 | DMA | Panicum virgatum | 71 | 1003 | | | | | | | | |
| Ceres CLONE ID no. 2403 | Ceres CLONE IO no. 1950105 | PRT | Panicum virgatum | 72 | 229 | ubiquitin | Ubiquitin family | 1 | 74 | | 262.8 | | 504.1 |
| Ceres CLONE ID no. 2403 | Ceres CLONE ID no. 1950105 | PRT | Panicum virgatum | 72 | 229 | ubiquitin | Ubiquitin family | 77 | 150 | | 262.8 | | 504.1 |
| Ceres CLONE ID no. 2403 | Ceres CLONE IO no. 1950105 | PRT | Panicum virgatum | 72 | 229 | ubiquitin | Ubiquitin family | 153 | 226 | | 262.8 | | 504.1 |
| | Ceres CLONE ID no. 1990746 | DNA | Panicum virgatum | 73 | 724 | | | | | | | | |
| Ceres Clone ID no. 30469 | Ceres CLONE ID no. 1990746 | PRT | Panicum virgatum | 74 | 164 | Globin | Globin | 16 | 156 | | 184.9 | | 405.6 |
| | Ceres CLONE ID no. 2007485 | DNA | Panicum virgatum | 75 | 696 | | | | | | | | 369.2 |
| Ceres CLONE ID no. 674166 | Ceres CLONE ID no. 2007485 | PRT | Panicum virgatum | 76 | 201 | AP2 | AP2 domain | 17 | 80 | | 271.2 | | |
| | Ceres CLONE ID no. 2033803 | DNA | Panicum virgatum | 77 | 698 | | | | | | | | |
| Ceres Clone ID no. 30469 | Ceres CLONE ID no. 2033803 | PRT | Panicum virgatum | 78 | 156 | Globin | Globin | 16 | 148 | | 184.9 | | |
| Ceres Clone ID no. 30469 | Ceres CLONE ID no. 2034916 | DNA | Panicum virgatum | 79 | 724 | | | | | | | | |
| Ceres CLONE ID no. 2403 | Ceres CLONE ID no. 2034916 | PRT | Panicum virgatum | 80 | 213 | ubiquitin | Ubiquitin family | 1 | 74 | | 259.2 | Y | 460.4 |
| Ceres CLONE ID no. 2403 | Ceres CLONE ID no. 2034916 | PRT | Panicum virgatum | 80 | 213 | ubiquitin | Ubiquitin family | 77 | 150 | | 259.2 | Y | 460.4 |
| Ceres CLONE ID no. 2403 | Ceres CLONE ID no. 2034916 | PRT | Panicum virgatum | 80 | 213 | ubiquitin | Ubiquitin family | 153 | 213 | | 259.2 | Y | 460.4 |
| Ceres CLONE ID no. 674166 | Ceres CLONE ID no. 651581 | DNA | Glycine max | 81 | 1194 | | | | | | | | |
| Ceres CLONE ID no. 674166 | Ceres CLONE ID no. 651581 | PRT | Glycine max | 82 | 224 | AP2 | AP2 domain | 24 | 87 | | 469.5 | | |
| | Public GI no. 125550159 | PRT | Oryza sativa subsp. indica | 83 | 184 | AP2 | AP2 domain | 7 | 70 | Y | 344 | | |
| Ceres CLONE ID no. 874166 | Public GI no. 15223809 | PRT | Arabidopsis thaliana | 84 | 225 | AP2 | AP2 domain | 26 | 89 | Y | 522.4 | | |
| Ceres CLONE ID no. 30087 | Public GI no. 30683885 | PRT | Arabidopsis thaliana | 85 | 164 | | | | | | | | |
| Ceres CLONE ID no. 874166 | Public GI no. 56384582 | PRT | Pisum sativum | 86 | 218 | AP2 | AP2 domain | 21 | 84 | Y | 484.2 | | |
| Ceres CLONE ID no. 874166 | Public GI no. 57012880 | PRT | Nicotiana tabacum | 87 | 225 | AP2 | AP2 domain | 26 | 89 | Y | 521.4 | | |
| Ceres Clone ID no. 30489 | Public GI no. 62548111 | PRT | Gossypium hirsutum | 88 | 163 | Globin | Globin | 13 | 152 | | 188.3 | | 409.8 |
| Ceres CLONE ID no. 2403 | Ceres CLONE ID no. 100021733 | PRT | Gossypium hirsutum | 89 | 153 | ubiquitin | Ubiquitin family | 1 | 74 | | 173.2 | | 410.3 |
| Ceres CLONE ID no. 2403 | Ceres CLONE ID no. 100021733 | PRT | Gossypium hirsutum | 89 | 153 | ubiquitin | Ubiquitin family | 77 | 150 | | 175.2 | | 410.5 |
| | Ceres CLONE ID no. 947579 | DNA | Brassica napus | 90 | 775 | | | | | | | | |
| | Ceres CLONE ID no. 36046 | PRT | Arabidopsis thaliana | 91 | 1032 | | | | | | | | |
| | Ceres CLONE ID no. 1606506 | DNA | Parthenium argentatum | 92 | 492 | | | | | | | | |
| | Ceres CLONE ID no. 546001 | DNA | Glycine max | 93 | 970 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| | Ceres CLONE ID no. 1554560 | DNA | Zea mays | 94 | 604 | | | | | | | | |
| | Ceres CLONE ID no. 639727 | DNA | Triticum aestivum | 95 | 848 | | | | | | | | |
| | Ceres CLONE ID no. 664936 | DNA | Glycine max | 96 | 440 | | | | | | | | |
| | Ceres CLONE ID no. 658438 | DNA | Glycine max | 97 | 463 | | | | | | | | |
| | Ceres CLONE ID no. 1049262 | DNA | Glycine max | 98 | 458 | | | | | | | | |
| | Ceres CLONE ID no. 632813 | DNA | Triticum aestivum | 99 | 600 | | | | | | | | |
| | Ceres CLONE IO no. 1390976 | DNA | Zea mays | 100 | 546 | | | | | | | | |
| | Ceres CLONE ID no. 1457185 | DNA | Zea mays | 101 | 550 | | | | | | | | |
| | Ceres CLONE ID no. 1482731 | DNA | Zea mays | 102 | 668 | | | | | | | | |
| | Ceres CLONE ID no. 522921 | DNA | Glycine max | 103 | 752 | | | | | | | | |
| | Ceres CLONE ID no. 1036726 | DNA | Brassica napus | 104 | 484 | | | | | | | | |
| | Ceres CLONE ID no. 513071 | DNA | Glycine max | 105 | 580 | | | | | | | | |
| | Ceres CLONE ID no. 975672 | DNA | Brassica napus | 106 | 987 | | | | | | | | |
| | Ceres CLONE ID no. 273307 | DNA | Zea mays | 107 | 1034 | | | | | | | | |
| | Ceres CLONE ID no. 1055099 | DNA | Triticum aestivum | 108 | 911 | | | | | | | | |
| Ceres Clone ID no. 30469 | Ceres GI ID no. GI_15226675 | PRT | Arabidopsis thaliana | 109 | 160 | Globin | Globin | 13 | 152 | | 184.4 | | 404.9 |
| | Ceres Promoter 21876 | DNA | Arabidopsis thaliana | 110 | 1823 | | | | | | | | |
| | Ceres Promoter PT0668 | DNA | Arabidopsis thaliana | 111 | 1000 | | | | | | | | |
| | Ceres Promoter PT0535 | DNA | Arabidopsis thaliana | 112 | 1000 | | | | | | | | |
| | Ceres Promoter PT0585 | DNA | Arabidopsis thaliana | 113 | 999 | | | | | | | | |
| | Ceres Promoter PT0613 | DNA | Arabidopsis thaliana | 114 | 1000 | | | | | | | | |
| | Ceres Promoter PT0625 | DNA | Arabidopsis thaliana | 115 | 351 | | | | | | | | |
| | Ceres Promoter PT0633 | DNA | Arabidopsis thaliana | 116 | 1022 | | | | | | | | |
| | Ceres Promoter PTD650 | DNA | Arabidopsis thaliana | 117 | 1000 | | | | | | | | |
| | Ceres Promoter PT0660 | DNA | Arabidopsis thaliana | 118 | 998 | | | | | | | | |
| | Ceres Promoter PT0665 | DNA | Arabidopsis thaliana | 119 | 1000 | | | | | | | | |
| | Ceres Promoter PT0672 | DNA | Arabidopsis thaliana | 120 | 999 | | | | | | | | |
| | Ceres Promoter PT0676 | DNA | Arabidopsis thaliana | 121 | 1000 | | | | | | | | |
| | Ceres Promoter PT0678 | DNA | Arabidopsis thaliana | 122 | 998 | | | | | | | | |
| | Ceres Promoter PT0683 | DNA | Arabidopsis thaliana | 123 | 1000 | | | | | | | | |
| | Ceres Promoter PT0688 | DNA | Arabidopsis thaliana | 124 | 1000 | | | | | | | | |
| | Ceres Promoter PT0695 | DNA | Arabidopsis thaliana | 125 | 1000 | | | | | | | | |
| | Ceres Promoter PT0708 | DNA | Arabidopsis thaliana | 126 | 1000 | | | | | | | | |
| | Ceres Promoter PT0710 | DNA | Arabidopsis thaliana | 127 | 1000 | | | | | | | | |
| | Ceres Promoter PT0723 | DNA | Arabidopsis thaliana | 128 | 1002 | | | | | | | | |
| | Ceres Promoter PT0740 | DNA | Arabidopsis thaliana | 129 | 1000 | | | | | | | | |
| | Ceres Promoter PT0743 | DNA | Arabidopsis thaliana | 130 | 1024 | | | | | | | | |
| | Ceres Promoter PT0758 | DNA | Arabidopsis thaliana | 131 | 1000 | | | | | | | | |
| | Ceres Promoter PT0829 | DNA | Arabidopsis thaliana | 132 | 921 | | | | | | | | |
| | Ceres Promoter PT0837 | DNA | Arabidopsis thaliana | 133 | 763 | | | | | | | | |
| | Ceres Promoter PT0838 | DNA | Arabidopsis thaliana | 134 | 751 | | | | | | | | |
| | Ceres Promoter PT0848 | DNA | Arabidopsis thaliana | 135 | 669 | | | | | | | | |
| | Ceres Promoter PT0863 | DNA | Arabidopsis thaliana | 136 | 702 | | | | | | | | |
| | Ceres Promoter PT0879 | DNA | Arabidopsis thaliana | 137 | 435 | | | | | | | | |
| | Ceres Promoter PT0886 | DNA | Arabidopsis thaliana | 138 | 397 | | | | | | | | |
| | Ceres Promoter YP0007 | DNA | Arabidopsis thaliana | 139 | 1024 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| | Ceres Promoter YP0008 | DNA | Arabidopsis thaliana | 140 | 1000 | | | | | | | | |
| | Ceres Promoter YP0019 | DNA | Arabidopsis thaliana | 141 | 999 | | | | | | | | |
| | Ceres Promoter YP0028 | DNA | Arabidopsis thaliana | 142 | 1024 | | | | | | | | |
| | Ceres Promoter YP0039 | DNA | Arabidopsis thaliana | 143 | 1024 | | | | | | | | |
| | Ceres Promoter YP0050 | DNA | Arabidopsis thaliana | 144 | 1024 | | | | | | | | |
| | Ceres Promoter YP0086 | DNA | Arabidopsis thaliana | 145 | 999 | | | | | | | | |
| | Ceres Promoter YP0088 | DNA | Arabidopsis thaliana | 146 | 1024 | | | | | | | | |
| | Ceres Promoter YP0092 | DNA | Arabidopsis thaliana | 147 | 1024 | | | | | | | | |
| | Ceres Promoter YP0096 | DNA | Arabidopsis thaliana | 148 | 1020 | | | | | | | | |
| | Ceres Promoter YP0097 | DNA | Arabidopsis thaliana | 149 | 1000 | | | | | | | | |
| | Ceres Promoter YP0101 | DNA | Arabidopsis thaliana | 150 | 1004 | | | | | | | | |
| | Ceres Promoter YP0102 | DNA | Arabidopsis thaliana | 151 | 1000 | | | | | | | | |
| | Ceres Promoter YP0103 | DNA | Arabidopsis thaliana | 152 | 1004 | | | | | | | | |
| | Ceres Promoter YP0107 | DNA | Arabidopsis thaliana | 153 | 1003 | | | | | | | | |
| | Ceres Promoter YP0110 | DNA | Arabidopsis thaliana | 154 | 1024 | | | | | | | | |
| | Ceres Promoter YP0111 | DNA | Arabidopsis thaliana | 155 | 1024 | | | | | | | | |
| | Ceres Promoter YP0115 | DNA | Arabidopsis thaliana | 156 | 996 | | | | | | | | |
| | Ceres Promoter YP0117 | DNA | Arabidopsis thaliana | 157 | 1024 | | | | | | | | |
| | Ceres Promoter YP0119 | DNA | Arabidopsis thaliana | 158 | 1000 | | | | | | | | |
| | Ceres Promoter YP0120 | DNA | Arabidopsis thaliana | 159 | 999 | | | | | | | | |
| | Ceres Promoter YP0121 | DNA | Arabidopsis thaliana | 160 | 999 | | | | | | | | |
| | Ceres Promoter YP0128 | DNA | Arabidopsis thaliana | 161 | 1004 | | | | | | | | |
| | Ceres Promoter YP0137 | DNA | Arabidopsis thaliana | 162 | 1001 | | | | | | | | |
| | Ceres Promoter YP0143 | DNA | Arabidopsis thaliana | 163 | 1001 | | | | | | | | |
| | Ceres Promoter YP0144 | DNA | Arabidopsis thaliana | 164 | 1003 | | | | | | | | |
| | Ceres Promoter YP0156 | DNA | Arabidopsis thaliana | 165 | 1004 | | | | | | | | |
| | Ceres Promoter YP0158 | DNA | Arabidopsis thaliana | 166 | 1000 | | | | | | | | |
| | Ceres Promoter YP0188 | DNA | Arabidopsis thaliana | 167 | 1005 | | | | | | | | |
| | Ceres Promoter YP0190 | DNA | Arabidopsis thaliana | 168 | 1002 | | | | | | | | |
| | Ceres Promoter YP0212 | DNA | Arabidopsis thaliana | 169 | 995 | | | | | | | | |
| | Ceres Promoter YP0214 | DNA | Arabidopsis thaliana | 170 | 1024 | | | | | | | | |
| | Ceres Promoter YP0263 | DNA | Arabidopsis thaliana | 171 | 911 | | | | | | | | |
| | Ceres Promoter YP0275 | DNA | Arabidopsis thaliana | 172 | 999 | | | | | | | | |
| | Ceres Promoter YP0285 | DNA | Arabidopsis thaliana | 173 | 981 | | | | | | | | |
| | Ceres Promoter YP0286 | DNA | Arabidopsis thaliana | 174 | 996 | | | | | | | | |
| | Ceres Promoter YP0337 | DNA | Arabidopsis thaliana | 175 | 1000 | | | | | | | | |
| | Ceres Promoter YP0356 | DNA | Arabidopsis thaliana | 176 | 1000 | | | | | | | | |
| | Ceres Promoter YP0374 | DNA | Arabidopsis thaliana | 177 | 1000 | | | | | | | | |
| | Ceres Promoter YP0377 | DNA | Arabidopsis thaliana | 178 | 998 | | | | | | | | |
| | Ceres Promoter YP0380 | DNA | Arabidopsis thaliana | 179 | 999 | | | | | | | | |
| | Ceres Promoter YP0381 | DNA | Arabidopsis thaliana | 180 | 1000 | | | | | | | | |
| | Ceres Promoter YP0384 | DNA | Arabidopsis thaliana | 181 | 999 | | | | | | | | |
| | Ceres Promoter YP0385 | DNA | Arabidopsis thaliana | 182 | 998 | | | | | | | | |
| | Ceres Promoter YP0396 | DNA | Arabidopsis thaliana | 183 | 1000 | | | | | | | | |
| | Ceres Promoter p13879 | DNA | Arabidopsis thaliana | 184 | 1514 | | | | | | | | |
| | Ceres Promoter p326 | DNA | Arabidopsis thaliana | 185 | 1954 | | | | | | | | |
| | Ceres Promoter p32449 | DNA | Arabidopsis thaliana | 186 | 2016 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| | Ceres Promoter PD1367 | DNA | Arabidopsis thaliana | 187 | 667 | | | | | | | | |
| | Ceres Promoter p530c10 | DNA | Oryza sativa | 188 | 1836 | | | | | | | | |
| | Ceres Promoter pOsFIE2-2 | DNA | Oryza sativa | 189 | 3000 | | | | | | | | |
| | Ceres Promoter pOsMEA | DNA | Oryza sativa | 190 | 2023 | | | | | | | | |
| | Ceres Promoter pOsYp102 | DNA | Oryza sativa | 191 | 2034 | | | | | | | | |
| | Ceres Promoter pOsYp285 | DNA | Oryza sativa | 192 | 1877 | | | | | | | | |
| | Ceres Promoter PT0565 | DNA | Arabidopsis thaliana | 193 | 1000 | | | | | | | | |
| | Ceres Promoter YP0015 | DNA | Arabidopsis thaliana | 194 | 999 | | | | | | | | |
| | Ceres Promoter YP0087 | DNA | Arabidopsis thaliana | 195 | 999 | | | | | | | | |
| | Ceres Promoter YP0093 | DNA | Arabidopsis thaliana | 196 | 1000 | | | | | | | | |
| | Ceres Promoter YP0108 | DNA | Arabidopsis thaliana | 197 | 999 | | | | | | | | |
| | Ceres Promoter YP0022 | DNA | Arabidopsis thaliana | 198 | 999 | | | | | | | | |
| | Ceres Promoter YP0080 | DNA | Arabidopsis thaliana | 199 | 999 | | | | | | | | |
| | Ceres Promoter PR0924 | DNA | Arabidopsis thaliana | 200 | 3000 | | | | | | | | |
| | Ceres Promoter YP0388 | DNA | Arabidopsis thaliana | 201 | 1000 | | | | | | | | |
| | Ceres Promoter PD0901 | DNA | Arabidopsis thaliana | 202 | 283 | | | | | | | | |
| | Ceres Promoter PT0623 | DNA | Arabidopsis thaliana | 203 | 1000 | | | | | | | | |
| Ceres Clone ID no. 2403 | Truncated version of Ceres CLONE ID no. 100021733 | PRT | Artificial Sequence | 204 | 33 | ubiquitin | Ubiquitin family | 1 | 33 | | 87.6 | | -83.1 |
| Ceres Clone ID no. 2403 | Truncated version of Ceres CLONE ID no. 1036726 | PRT | Artificial Sequence | 205 | 33 | ubiquitin | Ubiquitin family | 1 | 33 | | 87.6 | | -83.1 |
| Ceres Clone ID no. 2403 | Truncated Version of Ceres CLONE ID no. 1482731 | PRT | Artificial Sequence | 206 | 33 | ubiquitin | Ubiquitin family | 1 | 33 | Y | 87.1 | | -85 |
| Ceres Clone ID no. 30469 | Truncated Version of Ceres CLONE ID no. 1554560 | PRT | Artificial Sequence | 207 | 80 | Globin | Globin | 17 | 78 | Y | 185.7 | | 61.3 |
| Ceres Clone ID no. 30469 | Truncated Version of Ceres CLONE ID no. 1802327 | PRT | Artificial Sequence | 208 | 77 | Globin | Globin | 14 | 75 | Y | 191.4 | | 67.2 |
| Ceres Clone ID no. 30469 | Truncated Version of Ceres CLONE ID no. 1876458 | PRT | Artificial Sequence | 209 | 77 | Globin | Globin | 14 | 75 | | 191.9 | | 67.7 |
| Ceres Clone ID no. 30469 | Truncated Version of Ceres CLONE ID no. 1879148 | PRT | Artificial Sequence | 210 | 79 | Globin | Globin | 16 | 77 | | 185.7 | | 61.3 |
| Ceres Clone ID no. 30469 | Truncated Version of Ceres CLONE ID no. 1884696 | PRT | Artificial Sequence | 211 | 33 | ubiquitin | Ubiquitin family | 1 | 33 | Y | 87.6 | | 65 |
| Ceres Clone ID no. 30469 | Truncated Version of Ceres CLONE ID no. 1916866 | PRT | Artificial Sequence | 212 | 76 | Globin | Globin | 13 | 74 | Y | 188.3 | | 65 |
| Ceres Clone ID no. 30469 | Truncated version of Ceres CLONE ID no. 1950105 | PRT | Artificial Sequence | 213 | 33 | ubiquitin | Ubiquitin family | 1 | 33 | Y | 87.6 | | 60.7 |
| Ceres Clone ID no. 30469 | Truncated Version of Ceres CLONE ID no. 1990746 | PRT | Artificial Sequence | 214 | 79 | Globin | Globin | 16 | 77 | | 184.9 | | 60.7 |
| Ceres Clone ID no. 2403 | Truncated Version of Ceres CLONE ID no. 2033803 | PRT | Artificial Sequence | 215 | 79 | Globin | Globin | 16 | 77 | | 184.9 | | 60.7 |
| Ceres Clone ID no. 2403 | Truncated Version of Ceres CLONE ID no. 2034916 | PRT | Artificial Sequence | 216 | 33 | ubiquitin | Ubiquitin family | 1 | 33 | | 87.6 | | 63.3 |
| Ceres Clone ID no. 2403 | Truncated version of Ceres CLONE ID no. 513071 | PRT | Artificial Sequence | 217 | 33 | ubiquitin | Ubiquitin family | 1 | 33 | | 85.9 | | 44.7 |
| Ceres Clone ID no. 2403 | Truncated version of Ceres CLONE ID no. 522921 | PRT | Artificial Sequence | 218 | 33 | ubiquitin | Ubiquitin family | 1 | 33 | Y | 87.6 | | 22.4 |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| Ceres Clone ID no. 30469 | Truncated Version of Ceres CLONE ID no. 546001 | PRT | Artificial Sequence | 219 | 76 | Globin | Globin | 13 | 74 | Y | 182.8 | | 59.6 |
| Ceres Clone ID no. 30469 | Truncated Version of Ceres CLONE ID no. 651581 | PRT | Artificial Sequence | 220 | 76 | Globin | Globin | 13 | 74 | | 185.7 | | 63.9 |
| Ceres Clone ID no. 30469 | Truncated Version of Ceres CLONE ID no. 839727 | PRT | Artificial Sequence | 221 | 77 | Globin | Globin | 14 | 75 | Y | 187.8 | | 63.3 |
| Ceres Clone ID no. 30469 | Truncated Version of Public GI ID no. 11095158 | PRT | Artificial Sequence | 222 | 76 | Globin | Globin | 13 | 76 | | 167.8 | | 44.7 |
| Ceres Clone ID no. 30469 | Truncated Version of Public GI ID no. 12963875 | PRT | Artificial Sequence | 223 | 71 | Globin | Globin | 8 | 69 | | 145.8 | | 22.4 |
| Ceres Clone ID no. 30489 | Truncated Version of Public GI ID no. 14701800 | PRT | Artificial Sequence | 224 | 84 | Globin | Globin | 21 | 82 | | 170.1 | | 45.8 |
| Ceres Clone ID no. 30469 | Truncated Version of Public GI ID no. 15226675 | PRT | Artificial Sequence | 225 | 76 | Globin | Globin | 13 | 74 | | 184.6 | | 63 |
| Ceres Clone ID no. 30469 | Truncated Version of Public GI ID no. 15824736 | PRT | Artificial Sequence | 226 | 76 | Globin | Globin | 13 | 74 | | 184.2 | | 60.9 |
| Ceres Clone ID no. 30469 | Truncated Version of Public GI ID no. 30909306 | PRT | Artificial Sequence | 227 | 76 | Globin | Globin | 13 | 74 | Y | 185.7 | | 63.9 |
| Ceres Clone ID no. 30469 | Truncated Version of Public GI ID no. 37903656 | PRT | Artificial Sequence | 228 | 73 | Globin | Globin | 10 | 71 | | 172.6 | | 49.6 |
| Ceres Clone ID no. 30469 | Truncated Version of Public GI ID no. 62548111 | PRT | Artificial Sequence | 229 | 76 | Globin | Globin | 13 | 74 | | 188.3 | | 65 |

The invention claimed is:

1. A plant cell transformed with an exogenous nucleic acid, wherein said exogenous nucleic acid comprises a polynucleotide operably linked to a heterologous promoter, wherein said polynucleotide comprises a nucleotide sequence encoding a polypeptide having 95 percent or greater amino acid sequence identity to the amino acid sequence of SEQ ID NO: 2, wherein a transgenic plant produced from said transformed plant cell is selected for increased level of cold tolerance as compared to a control plant of the same plant species that does not comprise said exogenous nucleic acid.

2. A transgenic plant comprising the transformed plant cell of claim 1.

3. The transgenic plant of claim 2, wherein said transgenic plant is a member of a plant species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

4. A transgenic plant comprising the transformed plant cell of claim 1, wherein said transgenic plant exhibits an increased level of cold tolerance as compared to a control plant of the same plant species that does not comprise said exogenous nucleic acid.

5. A vegetative plant product comprising a plant tissue from the transgenic plant according to claim 2, wherein the vegetative plant product and the plant tissue comprise the exogenous nucleic acid.

6. The transformed plant cell of claim 1, wherein said polynucleotide encoding said polypeptide has 95 percent or greater sequence identity to the nucleotide sequence of SEQ ID NO: 1.

7. The transformed plant cell of claim 1, wherein said polynucleotide encoding said polypeptide comprises the nucleotide sequence of SEQ ID NO:1.

8. The transformed plant cell of claim 1, wherein said polypeptide comprises the amino acid sequence of SEQ ID NO:2.

9. The transgenic plant of claim 2, wherein said polynucleotide encoding said polypeptide has 95 percent or greater sequence identity to the nucleotide sequence of SEQ ID NO: 1.

10. The transgenic plant of claim 2, wherein said polynucleotide encoding said polypeptide comprises the nucleotide sequence of SEQ ID NO:1.

11. The transgenic plant of claim 2, wherein said polypeptide comprises the amino acid sequence of SEQ ID NO:2.

12. A seed produced by the transgenic plant of claim 2, wherein the seed comprises the exogenous nucleic acid.

* * * * *

SEQUENCE LISTING

<160> NUMBER OF SEQ ID NOS: 229

<210> SEQ ID NO 1
<211> LENGTH: 828
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451
<220> FEATURE:
<221> NAME/KEY: misc_feature
<223> OTHER INFORMATION: Encodes the protein at SEQ ID NO: 2

<400> SEQUENCE: 1 aactttctc tcccactctt tcttttacta ctctcacaca tatctctgtc tatatatcac     60
tttacataaa ccactattcc acacacaaac acacatagcc atggcctctt ctttctcttc    120
acaagccttc ttcttgctca cattgtctat ggttttaatt cctttctctt tagctcaagc    180
tcccatgatg gctccttctg gctcaatgtc catgccgcct atgtctagcg gcggtggaag    240
ctcggttcct cctccagtga tgtctccgat gccaatgatg actccaccac ctatgcctat    300
gactccatca cccatgccca tgactccacc acctatgcct atggctccac caccaatgcc    360
catggcttca ccaccaatga tgccaatgac tccatctaca agcccaagcc cattaacagt    420
tccggatatg ccttcgccgc cgatgccatc cggaatggaa tcttcacctt ctccaggacc    480
catgccaccg gcaatggcgg cttcgccgga ttcgggagct tcaatgttga aacaacgt      540 cgtaacactt tcatgcgttg ttggagttgt tgcagctcat tttctcctcg tttgaaatga    600
ttattgaatt ggtcagcctc gatcgttttc ttgtaattta ctttcatatt ttttttccct    660
caaattatta gtggtcatca ttttataata tttgagtttg tgtttgatgt acgattcaga    720
catttgtttg cattatgtgc ttaataagtt tatcgttgac tctacttgaa gagagacttt    780
gtgtgtgatg taaattctt ctatctatgg aacattgcat tcgtagcc                  828

<210> SEQ ID NO 2
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451

<400> SEQUENCE: 2

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Pro Val Met Ser Pro Met Pro Met Met Thr Pro Pro Pro
    50                  55                  60

Met Pro Met Thr Pro Ser Pro Met Pro Met Thr Pro Pro Pro Met Pro
65                  70                  75                  80

Met Ala Pro Pro Pro Met Pro Met Ala Ser Pro Pro Met Met Pro Met
                85                  90                  95

```
Thr Pro Ser Thr Ser Pro Ser Pro Leu Thr Val Pro Asp Met Pro Ser
                100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
130                 135                 140

Asn Asn Val Val Thr Leu Ser Cys Val Val Gly Val Val Ala Ala His
145                 150                 155                 160

Phe Leu Leu Val

<210> SEQ ID NO 3
<211> LENGTH: 155
<212> TYPE: PRT
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 3

Met Ala Ala Ser Gln Ala Phe Leu Leu Leu Thr Leu Ser Met Ala Leu
1               5                   10                  15

Val His Phe Ser Leu Ala Gln Ser Pro Met Met Ala Pro Ser Gly Ser
                20                  25                  30

Met Ser Met Pro Pro Met Pro Ser Gly Gly Ser Pro Met Pro Met Met
            35                  40                  45

Thr Pro Pro Pro Met Pro Met Met Thr Pro Pro Pro Met Ala Met Ala
    50                  55                  60

Pro Pro Pro Met Pro Met Thr Pro Pro Pro Met Ala Pro Met
65                  70                  75                  80

Pro Met Thr Pro Ser Ser Ser Pro Met Ser Pro Pro Thr Thr Met Ala
                85                  90                  95

Pro Ser Pro Glu Thr Val Pro Asp Met Ala Ser Pro Pro Met Met Pro
                100                 105                 110

Gly Met Glu Ser Ser Pro Ser Pro Gly Pro Met Pro Pro Ala Met Ala
        115                 120                 125

Ser Pro Asp Ser Gly Ala Phe Asn Val Arg Asn Asp Val Val Ala Ile
    130                 135                 140

Ser Phe Leu Val Ala Ala His Leu Leu Leu Val
145                 150                 155

<210> SEQ ID NO 4
<211> LENGTH: 152
<212> TYPE: PRT
<213> ORGANISM: Brassica napus
<220> FEATURE:
<221> NAME/KEY: misc_feature
<223> OTHER INFORMATION: Public GI no. 62526422
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 4

Met Ala Leu Ser His Pro Met Thr Ile Phe Ser Leu Phe Leu Thr Phe
1               5                   10                  15

Leu Ala Leu Thr Ala Ala Gln Ser Pro Met Met Ala Pro Thr Met Pro
                20                  25                  30
```

Pro Ser Thr Met Ser Met Pro Pro Thr Thr Ser Thr Thr Pro Pro
            35                  40                  45

Pro Met Ser Ser Met Ser Pro Pro Ser Ala Met Ser Pro Thr Pro
 50                  55                  60

Ser Thr Met Ser Pro Pro Met Ser Pro Met Thr Pro Ser Met Ser
 65                  70                  75                  80

Pro Met Gly Pro Met Thr Pro Thr Met Ser Pro Met Asp Ser Pro Pro
                 85                  90                  95

Ala Pro Ala Gly Pro Gly Met Ala Pro Gly Met Ser Thr Pro Gly Pro
            100                 105                 110

Ala Pro Gly Pro Met Gly Gly Glu Ser Met Ala Ser Pro Pro Ser
            115                 120                 125

Ser Gly Phe Val His Gly Ile Ser Ile Ser Met Ala Met Val Ala Ile
            130                 135                 140

Ile Gly Ser Val Ala Leu Phe Phe
145                 150

<210> SEQ ID NO 5
<211> LENGTH: 150
<212> TYPE: PRT
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 5

Met Ala Val Ser Arg Tyr Ile Ile Leu Leu Leu Ser Phe Thr Tyr Leu
 1               5                   10                  15

Ala Ala Phe Ser Thr Ala Gln Ala Pro Ser Met Ser Pro Met Met Met
                 20                  25                  30

Pro Met Ala Pro Pro Ser Thr Met Pro Met Thr Pro Pro Pro Ser
            35                  40                  45

Thr Met Pro Met Thr Pro Pro Thr Pro Met Thr Met Thr Pro Pro
 50                  55                  60

Pro Met Met Met Pro Met Thr Pro Pro Met Pro Met Gly Thr Pro
 65                  70                  75                  80

Pro Met Thr Met Pro Met Gly Pro Pro Met Met Met Pro Met Ser
                 85                  90                  95

Pro Gly Pro Ser Met Met Pro Ala Ser Pro Pro Ser Pro Met Gly Pro
            100                 105                 110

Ser Met Ala Pro Glu Pro Ala Thr Met Ser Pro Gly Pro Ser Met Thr
            115                 120                 125

Pro Ala Glu Thr Pro Ala Ser Gly Ala Ile Met Gln Tyr Ser Ser Ile
            130                 135                 140

Thr Met Leu Gly Ile Val
145                 150

<210> SEQ ID NO 6
<211> LENGTH: 586
<212> TYPE: DNA
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779

```
<220> FEATURE:
<221> NAME/KEY: misc_feature
<223> OTHER INFORMATION: Encodes the protein at SEQ ID NO: 7

<400> SEQUENCE: 6
aaaagatcta caaaacagag agttgtatac tttaaatcat ttagaggttg tgaaatatta      60
tggagagtga aggaaagatt gtgttcacag aagagcaaga ggctcttgta gtgaagtctt     120
ggagtgtcat gaagaaaaac tcagctgaat taggtctcaa actcttcatc aagatctttg     180
agattgcacc aacaacgaag aagatgttct ctttcttgag agactcacca attcctgctg     240
agcaaaatcc aaagctcaag cctcacgcaa tgtctgtttt tgtcatgtac aactgaggaa     300
aacagggaaa gttacggtga gggagactac tttgaagaga cttggagcca gccattctaa     360
atacggtgtc gttgacgaac actttgaggt ggccaagtat gcattgttgg agacgataaa     420
ggaggcagtg ccggagatgt ggtcaccgga gatgaaggtg gcttggggtc aggcttatga     480
tcaccttgtt gctgccatta aagctgaaat gaatctttcc aactaaaaaa tcatatacta     540
ttatatagtt gtaaacttgt aataaatatt tcattttgaa ttgttc                    586

<210> SEQ ID NO 7
<211> LENGTH: 78
<212> TYPE: PRT
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<222> LOCATION: (13)..(74)
<223> OTHER INFORMATION: Pfam Name: Globin
      Pfam Description: Globin

<400> SEQUENCE: 7

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Tyr Asn
65                  70                  75

<210> SEQ ID NO 8
<211> LENGTH: 483
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<223> OTHER INFORMATION: Encodes the protein at SEQ ID NO: 9

<400> SEQUENCE: 8
atggagagtg aaggaaagat tgtgttcaca gaagagcaag aggctcttgt agtgaagtct      60
tggagtgtca tgaagaaaaa ctcagctgaa ttaggtctca aactcttcat caagatcttt     120
gagattgcac caacaacgaa gaagatgttc tctttcttga gagactcacc aattcctgct     180
```

```
gagcaaaatc caaagctcaa gcctcacgca atgtctgttt ttgtcatgtg ttgtgaatca      240
gcagtacaac tgaggaaaac agggaaagtt acggtgaggg agactacttt gaagagactt      300
ggagccagcc attctaaata cggtgtcgtt gacgaacact ttgaggtggc caagtatgca      360
ttgttggaga cgataaagga ggcagtgccg gagatgtggt caccggagat gaaggtggct      420
tggggtcagg cttatgatca ccttgttgct gccattaaag ctgaaatgaa tctttccaac      480
taa                                                                    483
```

```
<210> SEQ ID NO 9
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 9
```

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
                20                  25                  30

Leu Lys Leu Phe Ile Lys Ile Phe Glu Ile Ala Pro Thr Thr Lys Lys
            35                  40                  45

Met Phe Ser Phe Leu Arg Asp Ser Pro Ile Pro Ala Glu Gln Asn Pro
        50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160

```
<210> SEQ ID NO 10
<211> LENGTH: 160
<212> TYPE: PRT
<213> ORGANISM: Raphanus sativus
<220> FEATURE:
<221> NAME/KEY: misc_feature
<223> OTHER INFORMATION: Public GI no. 30909306
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

```
<400> SEQUENCE: 10

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
                20                  25                  30

Leu Lys Leu Phe Ile Lys Ile Phe Glu Ile Ala Pro Thr Ala Lys Lys
            35                  40                  45

Leu Phe Ser Phe Leu Arg Asp Ser Pro Ile Pro Ala Glu Gln Asn Pro
        50                  55                  60

Lys Leu Lys Pro His Ala Met Ser Val Phe Val Met Cys Cys Glu Ser
65                  70                  75                  80

Ala Ala Gln Leu Arg Lys Thr Gly Lys Val Thr Val Lys Glu Thr Thr
                85                  90                  95

Leu Lys Arg Leu Gly Ala Asn His Ser Lys Tyr Gly Val Val Asp Glu
            100                 105                 110

His Phe Glu Val Thr Lys Tyr Ala Leu Leu Glu Thr Ile Lys Glu Ala
        115                 120                 125

Val Pro Glu Met Trp Ser Pro Glu Met Lys Ser Ala Trp Gly Gln Ala
    130                 135                 140

Tyr Asp His Leu Val Ala Ala Ile Lys Ala Glu Met Lys Pro Ser His
145                 150                 155                 160

<210> SEQ ID NO 11
<211> LENGTH: 158
<212> TYPE: PRT
<213> ORGANISM: Arabidopsis thaliana
<220> FEATURE:
<221> NAME/KEY: misc_feature
<223> OTHER INFORMATION: Public GI no. 37903656
<220> FEATURE:
<221> NAME/KEY: misc_feature
<222> LOCATION: (10)..(149)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
                20                  25                  30

Phe Leu Lys Ile Phe Glu Ile Ala Pro Ser Ala Gln Lys Leu Phe Ser
            35                  40                  45

Phe Leu Arg Asp Ser Asp Ile Pro Leu Glu Lys Asn Pro Lys Leu Lys
        50                  55                  60

Pro His Ala Met Ser Val Phe Val Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
            100                 105                 110

Val Thr Lys Phe Ala Leu Leu Glu Thr Ile Lys Glu Ala Leu Pro Glu
        115                 120                 125

Met Trp Ser Pro Glu Met Lys Asn Ala Trp Gly Glu Ala Tyr Asp Gln
    130                 135                 140
```

```
Leu Val Ala Ala Ile Lys Ser Glu Met Lys Pro Pro Leu Asn
145                 150                 155
```

<210> SEQ ID NO 12
<211> LENGTH: 163
<212> TYPE: PRT
<213> ORGANISM: Arabidopsis thaliana
<220> FEATURE:
<221> NAME/KEY: misc_feature
<223> OTHER INFORMATION: Public GI no. 15824736
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 12

```
Met Ala Thr Tyr Glu Gly Lys Val Phe Thr Glu Glu Gln Ala Leu
1               5                   10                  15

Val Val Lys Ser Trp Thr Val Met Lys Lys Thr Ala Glu Leu Gly
                20                  25                  30

Leu Lys Phe Phe Leu Lys Ile Phe Glu Ile Ala Pro Ser Ala Lys Lys
                35                  40                  45

Leu Phe Ser Phe Leu Arg Asp Ser Asn Val Pro Leu Glu Gln Asn Thr
50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
                100                 105                 110

His Phe Glu Val Thr Lys Phe Ala Leu Leu Glu Thr Ile Lys Glu Ala
            115                 120                 125

Val Pro Asp Met Trp Ser Asp Glu Met Lys Asn Ala Trp Gly Glu Ala
            130                 135                 140

Tyr Asp Arg Leu Val Ala Ala Ile Lys Ile Glu Met Lys Ala Cys Ser
145                 150                 155                 160

Gln Ala Ala
```

<210> SEQ ID NO 13
<211> LENGTH: 161
<212> TYPE: PRT
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 13

```
Met Thr Thr Thr Leu Glu Arg Gly Phe Ser Glu Glu Gln Ala Leu
1               5                   10                  15

Val Val Lys Ser Trp Asn Val Met Lys Lys Asn Ser Gly Glu Leu Gly
                20                  25                  30
```

```
                    20                  25                  30
Leu Lys Phe Phe Leu Lys Ile Phe Glu Ile Ala Pro Ser Ala Gln Lys
            35                  40                  45

Leu Phe Ser Phe Leu Arg Asp Ser Thr Val Pro Leu Glu Gln Asn Pro
 50                  55                  60

Lys Leu Lys Pro His Ala Val Ser Val Phe Val Met Thr Cys Asp Ser
 65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
                100                 105                 110

His Phe Glu Val Thr Lys Phe Ala Leu Leu Glu Thr Ile Lys Glu Ala
                115                 120                 125

Val Pro Glu Met Trp Ser Pro Ala Met Lys Asn Ala Trp Gly Glu Ala
                130                 135                 140

Tyr Asp Gln Leu Val Asp Ala Ile Lys Ser Glu Met Lys Pro Pro Ser
145                 150                 155                 160

Ser

<210> SEQ ID NO 14
<211> LENGTH: 160
<212> TYPE: PRT
<213> ORGANISM: Glycine max
<220> FEATURE:
<221> NAME/KEY: misc_feature
<223> OTHER INFORMATION: Public GI no. 11095158
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 14

Met Gly Thr Leu Asp Thr Lys Gly Phe Thr Glu Glu Gln Glu Ala Leu
 1               5                  10                  15

Val Val Lys Ser Trp Asn Ala Met Lys Lys Asn Ser Ala Glu Leu Gly
                20                  25                  30

Leu Lys Leu Phe Leu Lys Ile Phe Glu Ile Ala Pro Ser Ala Gln Lys
            35                  40                  45

Leu Phe Ser Phe Leu Lys Asp Ser Lys Val Pro Leu Glu Gln Asn Thr
 50                  55                  60

Lys Leu Lys Pro His Ala Met Ser Val Phe Leu Met Thr Cys Glu Ser
 65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
                100                 105                 110

His Phe Glu Val Thr Lys Phe Ala Leu Leu Glu Thr Ile Lys Glu Ala
                115                 120                 125

Val Pro Glu Met Trp Ser Pro Ala Met Lys Asn Ala Trp Gly Glu Ala
                130                 135                 140

Tyr Asp Gln Leu Val Asn Ala Ile Lys Ser Glu Met Lys Pro Ser Ser
145                 150                 155                 160
```

```
<210> SEQ ID NO 15
<211> LENGTH: 152
<212> TYPE: PRT
<213> ORGANISM: Glycine max
<220> FEATURE:
<221> NAME/KEY: misc_feature
<223> OTHER INFORMATION: Public GI no. 12963875
<220> FEATURE:
<221> NAME/KEY: misc_feature
<222> LOCATION: (8)..(147)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 15

Met Ser Ser Phe Ser Glu Glu Gln Ala Leu Val Val Lys Ser Trp
1               5                   10                  15

Gly Ser Met Lys Lys Asp Ala Gly Glu Trp Gly Leu Lys Phe Phe Leu
                20                  25                  30

Lys Ile Phe Glu Ile Ala Pro Ser Ala Lys Lys Met Phe Ser Phe Leu
            35                  40                  45

Lys Asp Ser Asn Val Pro Leu Asp Gln Asn Pro Lys Leu Lys Ile His
50                  55                  60

Ala Lys Ser Val Leu Val Met Thr Cys Glu Ala Ala Val Gln Leu Arg
65                  70                  75                  80

Lys Ala Gly Lys Val Val Val Arg Asp Ser Thr Leu Lys Lys Ile Gly
                85                  90                  95

Ala Thr His Phe Lys Tyr Gly Val Val Asp Glu His Phe Glu Val Thr
            100                 105                 110

Lys Tyr Ala Leu Leu Glu Thr Ile Lys Glu Ala Ser Gln Glu Met Trp
        115                 120                 125

Ser Val Glu Met Lys Asn Ala Trp Gly Glu Ala Tyr Asp Gln Leu Val
    130                 135                 140

Ser Ala Ile Lys Thr Glu Met Lys
145                 150

<210> SEQ ID NO 16
<211> LENGTH: 165
<212> TYPE: PRT
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<222> LOCATION: (17)..(157)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 16

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
                20                  25                  30

Ala Asn Leu Gly Leu Arg Phe Phe Leu Lys Val Phe Glu Ile Ala Pro
            35                  40                  45

Ser Ala Lys Gln Met Phe Ser Phe Leu Arg Asp Ser Asp Val Pro Leu
```

```
                    50                  55                  60
Glu Lys Asn Pro Lys Leu Lys Thr His Ala Met Ser Val Phe Val Met
 65                  70                  75                  80

Thr Cys Glu Ala Ala Ala Gln Leu Arg Lys Ala Gly Lys Val Thr Val
                 85                  90                  95

Arg Glu Thr Thr Leu Lys Arg Leu Gly Ala Thr His Leu Arg Tyr Gly
                100                 105                 110

Val Ala Asp Gly His Phe Glu Val Thr Gly Phe Ala Leu Leu Glu Thr
                115                 120                 125

Ile Lys Glu Ala Leu Pro Ala Asp Met Trp Ser Leu Glu Met Lys Lys
130                 135                 140

Ala Trp Ala Glu Ala Tyr Ser Gln Leu Val Ala Ile Lys Arg Glu
145                 150                 155                 160

Met Lys Pro Asp Ala
                165

<210> SEQ ID NO 17
<211> LENGTH: 162
<212> TYPE: PRT
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 17

Met Ser Ala Ala Glu Gly Ala Val Val Phe Ser Glu Glu Lys Glu Ala
 1                5                  10                  15

Leu Val Leu Lys Ser Trp Ala Ile Met Lys Lys Asp Ser Ala Asn Leu
                 20                  25                  30

Gly Leu Arg Phe Phe Leu Lys Ile Phe Glu Ile Ala Pro Ser Ala Arg
             35                  40                  45

Gln Met Phe Pro Phe Leu Arg Asp Ser Asp Val Pro Leu Glu Thr Asn
 50                  55                  60

Pro Lys Leu Lys Thr His Ala Val Ser Val Phe Val Met Thr Cys Glu
 65                  70                  75                  80

Ala Ala Ala Gln Leu Arg Lys Ala Gly Lys Ile Thr Val Arg Glu Thr
                 85                  90                  95

Thr Leu Lys Arg Leu Gly Gly Thr His Leu Lys Tyr Gly Val Ala Asp
                100                 105                 110

Gly His Phe Glu Val Thr Arg Phe Ala Leu Leu Glu Thr Ile Lys Glu
             115                 120                 125

Ala Leu Pro Ala Asp Met Trp Gly Pro Glu Met Arg Asn Ala Trp Gly
130                 135                 140

Glu Ala Tyr Asp Gln Leu Val Ala Ala Ile Lys Gln Glu Met Lys Pro
145                 150                 155                 160

Ser Glu

<210> SEQ ID NO 18
<211> LENGTH: 169
<212> TYPE: PRT
```

```
<213> ORGANISM: Triticum aestivum
<220> FEATURE:
<221> NAME/KEY: misc_feature
<223> OTHER INFORMATION: Public GI no. 14701800
<220> FEATURE:
<221> NAME/KEY: misc_feature
<222> LOCATION: (21)..(161)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 18
```

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met Thr Cys Glu Ala Ala Ala Gln Leu Arg Lys Ala Gly
                85                  90                  95

Lys Val Thr Val Arg Asp Thr Thr Leu Lys Arg Leu Gly Ala Thr His
            100                 105                 110

Phe Lys Tyr Gly Val Gly Asp Ala His Phe Glu Val Thr Arg Phe Ala
        115                 120                 125

Leu Leu Glu Thr Ile Lys Glu Ala Val Pro Val Asp Met Trp Ser Pro
130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165

```
<210> SEQ ID NO 19
<211> LENGTH: 416
<212> TYPE: DNA
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<223> OTHER INFORMATION: Encodes the protein at SEQ ID NO: 20

<400> SEQUENCE: 19
gctcattagg gtttctcatc tacgacggcg tggtgttcct ccttcctgct ctgaaaaatg      60
gcgaagagaa cgaagaaggt tggaatcgtc ggcaaatacg aacacgttta tggtgcgagt     120
atcaggaagc agattaagaa gatggaggtc agccagcaca gcaagtactt ctgtgagttc     180
tgtggcaagt acggagtgaa gcgaaaggct gttggtatct ggggttgcaa ggattgtggc     240
aaggtcaagg caggtggtgc ttacacaatg aacaccgcca gtgcggtcac tgttagaagc     300
acgatcagaa ggttgaggga gcagatcgag ggttaaaagt ctgctggctt tttatatttg     360
gtttccttgt tttgacaatt taagttttgc atcaacagtg agaacatgtt ttgatt         416
```

<210> SEQ ID NO 20
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<222> LOCATION: (2)..(91)
<223> OTHER INFORMATION: Pfam Name: Ribosomal_L37ae;
      Pfam Description: Ribosomal L37ae protein family

<400> SEQUENCE: 20

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
            20                  25                  30

Gln His Ser Lys Tyr Phe Cys Glu Phe Cys Gly Lys Tyr Gly Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 21
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4090257
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 21

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Pro Ser Ala Val Thr Val Arg
65                  70                  75                  80

Ser Thr Ile Arg Arg Leu Arg Glu Gln Thr Glu Gly
                85                  90

<210> SEQ ID NO 22
<211> LENGTH: 92

```
<212> TYPE: PRT
<213> ORGANISM: Arabidopsis thaliana
<220> FEATURE:
<221> NAME/KEY: misc_feature
<223> OTHER INFORMATION: Public GI no. 4741896
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 22

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Tyr Ala Val Lys
            35                  40                  45

Arg Lys Ala Val Gly Ile Trp Gly Cys Lys Ala Cys Gly Lys Val Lys
        50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 23
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 23

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
                20                  25                  30

Gln His Ser Lys Tyr Phe Cys Glu Phe Cys Gly Lys Xaa Gly Val Lys
            35                  40                  45

Xaa Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90
```

85                  90

<210> SEQ ID NO 24
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 6016699
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 24

Met Thr Lys Arg Thr Lys Lys Ala Arg Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Asn Lys Tyr Phe Cys Glu Phe Cys Gly Lys Tyr Ser Val Lys
            35                  40                  45

Arg Lys Val Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 25
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 25

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Phe Phe Cys Glu Phe Cys Gly Lys Tyr Ala Val Lys
            35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Gly
                85                  90

```
<210> SEQ ID NO 26
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 26

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 27
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 27

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 28
<211> LENGTH: 92
<212> TYPE: PRT
```

```
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 28

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 29
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 29

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 30
<211> LENGTH: 92
<212> TYPE: PRT
<213> ORGANISM: Zea mays
<220> FEATURE:
<221> NAME/KEY: misc_feature
```

<223> OTHER INFORMATION: Ceres CLONE ID no. 1457185
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional homolog of Ceres Clone ID no. 271922
    given in SEQ ID NO: 20

<400> SEQUENCE: 30

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 31
<211> LENGTH: 92
<212> TYPE: PRT
<213> ORGANISM: Zea mays
<220> FEATURE:
<221> NAME/KEY: misc_feature
<223> OTHER INFORMATION: Public GI no. 56202147
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional homolog of Ceres Clone ID no. 271922
    given in SEQ ID NO: 20

<400> SEQUENCE: 31

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 32
<211> LENGTH: 92
<212> TYPE: PRT
<213> ORGANISM: Zea mays
<220> FEATURE:
<221> NAME/KEY: misc_feature
<223> OTHER INFORMATION: Public GI no. 58578274
<220> FEATURE:
<221> NAME/KEY: misc_feature

```
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 32

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
            20                  25                  30

Gln His Ser Glu Tyr Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 33
<211> LENGTH: 632
<212> TYPE: DNA
<213> ORGANISM: Arabidopsis thaliana
<220> FEATURE:
<221> NAME/KEY: misc_feature
<223> OTHER INFORMATION: Ceres CLONE ID no. 2403_FL
<220> FEATURE:
<221> NAME/KEY: misc_feature
<223> OTHER INFORMATION: Encodes the protein at SEQ ID NO: 34

<400> SEQUENCE: 33
attccccatc gcacagaccc gcctaagaat ccgagagaga agaagagata atgcagatct    60
tcgtcaaaac cctcaccggc aaaactataa ccctagaggt tgagagcagc gacaccatcg   120
acaatgttaa agccaaaatc caggacaaat agggcatacc acctgatcaa cagaggctga   180 ttttttgctgg taagcaattg gaagatggcc ggaccttagc tgactacaac atccagaaag   240
agtctactct tcatcttgtc ctcaggctca gaggtggaac catgatcaag gtgaagacac   300
tcactggaaa agaaatcgag attgatatcg aaccaaccga cactattgat cggatcaaag   360
aacgtgttga agagaaagaa ggcatccctc ctgttcaaca aaggctcatc tatgccggaa   420
aacagcttgc tgatgacaaa acggccaaag attatgcgat agagggaggc tctgttcttc   480
atttggttct tgctcttagg ggtggtcttc tctgatctga ataaataagc ttttcaacaa   540
acatctttcc cctcactatt gtcctccttt tgtggaattc atgacacaca aaaattgcta   600
tgggaaattg gaatattatg atgttttttc tc                                 632

<210> SEQ ID NO 34
<211> LENGTH: 154
<212> TYPE: PRT
<213> ORGANISM: Arabidopsis thaliana
      220>
<221> NAME/KEY: misc_feature
<223> OTHER INFORMATION: Ceres CLONE ID no. 2403_FL
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
```

```
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 34

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Ala Ile Glu Gly Gly Ser Val Leu His
    130                 135                 140

Leu Val Leu Ala Leu Arg Gly Gly Leu Leu
145                 150

<210> SEQ ID NO 35
<211> LENGTH: 154
<212> TYPE: PRT
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 35

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80
```

```
Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Lys Glu Gly Ile
            100                 105                 110

Pro Pro Val Gln Gln Arg Leu Ile Tyr Ala Gly Lys Gln Leu Ala Asp
            115                 120                 125

Asp Lys Thr Ala Lys Asp Tyr Asn Ile Glu Gly Gly Ser Val Leu His
            130                 135                 140

Leu Val Leu Ala Leu Arg Gly Gly Ser Asp
145                 150

<210> SEQ ID NO 36
<211> LENGTH: 154
<212> TYPE: PRT
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 36

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Lys Glu Gly Ile
            100                 105                 110

Pro Pro Val Gln Gln Arg Leu Ile Tyr Ala Gly Lys Gln Leu Ala Asp
            115                 120                 125

Asp Lys Thr Ala Lys Glu Tyr Asn Ile Glu Gly Gly Ser Val Leu His
            130                 135                 140

Leu Val Leu Ala Leu Arg Gly Gly Thr Tyr
145                 150

<210> SEQ ID NO 37
<211> LENGTH: 147
<212> TYPE: PRT
<213> ORGANISM: Brassica napus
<220> FEATURE:
<221> NAME/KEY: misc_feature
<223> OTHER INFORMATION: Ceres CLONE ID no. 1036726
```

```
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(142)
<223> OTHER INFORMATION: Pfam Name: ubiquitin
      Pfam Description: Ubiquitin family
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 37

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Xaa Lys Asp Tyr Asn Ile Glu Gly Gly Ser Val Ser Ala
    130                 135                 140

Ser Gly Ser
145

<210> SEQ ID NO 38
<211> LENGTH: 153
<212> TYPE: PRT
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 38
```

```
Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Ser Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Xaa Leu Ala Leu Arg Gly Gly Tyr
145                 150
```

<210> SEQ ID NO 39
<211> LENGTH: 620
<212> TYPE: DNA
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<223> OTHER INFORMATION: Encodes the protein at SEQ ID NO: 40

<400> SEQUENCE: 39
attccccatc gcacagaccc ccctaagaat ccgagagaga agaagagata atgcagatct      60
tcgtcaaaac cctcaccggc aaaactataa ccctagaagt tgagagcagc gacaccatcg     120
acaatgttaa agccaaaatc caggacaaag agggcatacc acctgatcaa cagaggctga     180
tttttgctgg taagcaattg gaagatggcc ggaccttagc tgattacaac atccagaaag     240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcata tatgccggaa     420
aacagcttgc tgatgacaaa acggccaaag attatgcgat agagggaggc tctgttcttc     480
atttggttct tgctcttagg ggtggtcttc tctgatctta ataataagc ttttcaacaa      540 acatcttttc cctcactatt gtcctcctta tgtggaattc atgacacacc aaaattgcta     600
tgggaaattg gaatattatg                                                 620

<210> SEQ ID NO 40
<211> LENGTH: 33
<212> TYPE: PRT
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304

```
<220> FEATURE:
<221> NAME/KEY: misc_feature
<222> LOCATION: (1)..(33)
<223> OTHER INFORMATION: Pfam Name: ubiquitin
      Pfam Description: Ubiquitin family

<400> SEQUENCE: 40
```

| Met | Gln | Ile | Phe | Val | Lys | Thr | Leu | Thr | Gly | Lys | Thr | Ile | Thr | Leu | Glu |
|---|---|---|---|---|---|---|---|---|---|---|---|---|---|---|---|
| 1 | | | | 5 | | | | | 10 | | | | | 15 | |

| Val | Glu | Ser | Ser | Asp | Thr | Ile | Asp | Asn | Val | Lys | Ala | Lys | Ile | Gln | Asp |
|---|---|---|---|---|---|---|---|---|---|---|---|---|---|---|---|
| | | | 20 | | | | | 25 | | | | | 30 | | |

Lys

```
<210> SEQ ID NO 41
<211> LENGTH: 1106
<212> TYPE: DNA
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<223> OTHER INFORMATION: Encodes the protein at SEQ ID NO: 42

<400> SEQUENCE: 41 atattttttgt gtagatgaag atcaacaaga gaaggtgttg ttgtgagttg tgttgttatg      60
gtaccttcct tcaaccacaa aacctctctc cctctaccac ccattctctt ctctctctct     120
ctctcccgtc ctccatctct caccttctca atctcttcac caccaccatc atcatcatta     180
tcttctccaa tctctataac ctcgaaatcc ctcaaaacct ctccctcaaa ccaaatgaaa     240
tgaccctttt gtgagaacat ttttttcccc ttaagaaaag gtcaaaggct gcaactttttt    300 cttaaccaat ctcacatttt tttattttttc aacgtatttt ggccaggttt ggttttctgg   360
gttgtcttgg aattcaaaaa agattccaac tttgaagatg ggtagggggtg gaaccgccgc   420 ggcggcggcg gaggtcgccg aacccggttt aaggccggtt tatttcaaag aacagcgata    480
taggggcgtc agaaaaagac cgtggggccg gttcgctgcc gaaatcagag acccttttgaa   540 gaaagccagg gtttggctcg gaacctttga caccgccgag gaggcggcgc gtgcctacga    600
cacggcggcg agaaccctcc ggggacccaaa ggcgaagacc aatttccctc tttctccgcc   660
gttctaccat cccgatccat tttccgatca ccggcacttc gccaacaccg gcgaagattt    720
ccacgatcac cggcgaccaa catccagtgg catgagcagc accgtagagt ccttcagcgg    780
cccccgtgct gccgtgccgg cgacagcgcc ggtggccacc ggccggagat atccccggac    840 gccaccgtt atccccgagg actgccgcag cgactgcgat tcgtcgtcct ccgtcgttga     900
cgacggcgaa ggcgacaacg tggcgtcgtc gttcccgcga gaaccgttgc cgtttgatct    960
aaacgcgttg ccgttagacg atgctgacgt ggcaaccgat gatctgttct gcaccgttct   1020
ttgcctctga tgagaaaaaa tgaaaaaacg gaacgaaatg atgtatttgg ttcgttgacg    1080
gaattattat tattttttttc tttctt                                        1106

<210> SEQ ID NO 42
<211> LENGTH: 210
<212> TYPE: PRT
<213> ORGANISM: Glycine max
<220> FEATURE:
<221> NAME/KEY: misc_feature
<223> OTHER INFORMATION: Ceres CLONE ID no. 674166
```

```
<220> FEATURE:
<221> NAME/KEY: misc_feature
<223> OTHER INFORMATION: Ceres SEED LINE ID no. ME03186
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<222> LOCATION: (26)..(89)
<223> OTHER INFORMATION: Pfam Name: AP2;
      Pfam Description: AP2 domain

<400> SEQUENCE: 42

Met Gly Arg Gly Gly Thr Ala Ala Ala Ala Glu Val Ala Glu Pro
 1               5                  10                  15

Gly Leu Arg Pro Val Tyr Phe Lys Glu Gln Arg Tyr Arg Gly Val Arg
                20                  25                  30

Lys Arg Pro Trp Gly Arg Phe Ala Ala Glu Ile Arg Asp Pro Leu Lys
            35                  40                  45

Lys Ala Arg Val Trp Leu Gly Thr Phe Asp Thr Ala Glu Glu Ala Ala
50                  55                  60

Arg Ala Tyr Asp Thr Ala Ala Arg Thr Leu Arg Gly Pro Lys Ala Lys
65                  70                  75                  80

Thr Asn Phe Pro Leu Ser Pro Pro Phe Tyr His Pro Asp Pro Phe Ser
                85                  90                  95

Asp His Arg His Phe Ala Asn Thr Gly Glu Asp Phe His Asp His Arg
            100                 105                 110

Arg Pro Thr Ser Ser Gly Met Ser Ser Thr Val Glu Ser Phe Ser Gly
        115                 120                 125

Pro Arg Ala Ala Val Pro Ala Thr Ala Pro Val Ala Thr Gly Arg Arg
    130                 135                 140

Tyr Pro Arg Thr Pro Pro Val Ile Pro Glu Asp Cys Arg Ser Asp Cys
145                 150                 155                 160

Asp Ser Ser Ser Val Val Asp Asp Gly Glu Gly Asp Asn Val Ala
                165                 170                 175

Ser Ser Phe Pro Arg Glu Pro Leu Pro Phe Asp Leu Asn Ala Leu Pro
            180                 185                 190

Leu Asp Asp Ala Asp Val Ala Thr Asp Asp Leu Phe Cys Thr Val Leu
        195                 200                 205

Cys Leu
    210

<210> SEQ ID NO 43
<211> LENGTH: 225
<212> TYPE: PRT
<213> ORGANISM: Glycine max
<220> FEATURE:
<221> NAME/KEY: misc_feature
<223> OTHER INFORMATION: Public GI no. 12322345
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 43

Met Arg Arg Gly Arg Gly Ser Ser Ala Val Ala Gly Pro Thr Val Val
```

-continued

```
1               5                   10                  15
Ala Ala Ile Asn Gly Ser Val Lys Glu Ile Arg Phe Arg Gly Val Arg
            20                  25                  30
Lys Arg Pro Trp Gly Arg Phe Ala Ala Glu Ile Arg Asp Pro Trp Lys
            35                  40                  45
Lys Ala Arg Val Trp Leu Gly Thr Phe Asp Ser Ala Glu Glu Ala Ala
            50                  55                  60
Arg Ala Tyr Asp Ser Ala Ala Arg Asn Leu Arg Gly Pro Lys Ala Lys
65                  70                  75                  80
Thr Asn Phe Pro Ile Asp Ser Ser Pro Pro Pro Asn Leu Arg
                    85                  90                  95
Phe Asn Gln Ile Arg Asn Gln Asn Gln Asn Gln Val Asp Pro Phe Met
                    100                 105                 110
Asp His Arg Leu Phe Thr Asp His Gln Gln Gln Phe Pro Ile Val Asn
                    115                 120                 125
Arg Pro Thr Ser Ser Ser Met Ser Ser Thr Val Glu Ser Phe Ser Gly
            130                 135                 140
Pro Arg Pro Thr Thr Met Lys Pro Ala Thr Thr Lys Arg Tyr Pro Arg
145                 150                 155                 160
Thr Pro Pro Val Val Pro Glu Asp Cys His Ser Asp Cys Asp Ser Ser
                    165                 170                 175
Ser Ser Val Ile Asp Asp Asp Asp Ile Ala Ser Ser Ser Arg Arg
            180                 185                 190
Arg Asn Pro Pro Phe Gln Phe Asp Leu Asn Phe Pro Pro Leu Asp Cys
            195                 200                 205
Val Asp Leu Phe Asn Gly Ala Asp Asp Leu His Cys Thr Asp Leu Arg
210                 215                 220
Leu
225
```

```
<210> SEQ ID NO 44
<211> LENGTH: 215
<212> TYPE: PRT
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other
<220> FEATURE:
<221> NAME/KEY: misc_feature
```

<223> OTHER INFORMATION: Functional homolog of Ceres Clone ID no. 674166
      given in SEQ ID NO: 42

<400> SEQUENCE: 44

Met Arg Lys Gly Arg Gly Ser Ser Ala Val Pro Pro Ala Leu Pro Gly
1               5                   10                  15

Ser Val Lys Glu Pro Arg Tyr Arg Gly Val Arg Lys Arg Pro Trp Gly
                20                  25                  30

Arg Phe Ala Ala Glu Ile Arg Asp Pro Leu Lys Lys Ser Arg Val Trp
            35                  40                  45

Leu Gly Thr Phe Asp Ser Ala Glu Glu Ala Ala Arg Ala Tyr Asp Ala
        50                  55                  60

Ala Ala Arg Asn Leu Arg Gly Pro Lys Ala Lys Thr Asn Phe Gln Ile
65                  70                  75                  80

Asp Cys Ser Pro Ser Pro Leu Gln Pro Leu His His Arg Asn Gln
                85                  90                  95

Ile Asp Pro Phe Met Asp His Arg Leu Tyr Gly Gly Glu Gln Glu Val
            100                 105                 110

Val Ile Ile Ser Arg Pro Ala Ser Ser Met Ser Ser Thr Val Lys
        115                 120                 125

Ser Cys Ser Gly Val Arg Pro Ala Ser Ser Val Ala Lys Ala Ala
130                 135                 140

Thr Lys Arg Tyr Pro Arg Thr Pro Pro Val Ala Pro Glu Asp Cys Arg
145                 150                 155                 160

Ser Asp Cys Asp Ser Ser Ser Val Val Glu Asp Gly Xaa Asp Ile
                165                 170                 175

Ala Ser Ser Ser Ser Arg Arg Lys Pro Pro Phe Glu Phe Asp Leu Asn
            180                 185                 190

Phe Xaa Pro Leu Asp Gly Val Asp Leu Phe Val Gly Ala Asp Asp Xaa
        195                 200                 205

Xaa Cys Thr Asp Leu Xaa Leu
        210             215

<210> SEQ ID NO 45
<211> LENGTH: 211
<212> TYPE: PRT
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 45

Met Arg Arg Arg Gly Val Ala Ala Ala Asp Ala Asp Gly Asp Val Glu
1               5                   10                  15

Leu Arg Phe Arg Gly Val Arg Lys Arg Pro Trp Gly Arg Tyr Ala Ala
                20                  25                  30

Glu Ile Arg Asp Pro Ala Lys Lys Ala Arg Val Trp Leu Gly Thr Phe
            35                  40                  45

Asp Ser Ala Glu Asp Ala Ala Arg Ala Tyr Asp Ala Ala Ala Arg Met
        50                  55                  60

```
Leu Arg Gly Pro Lys Ala Arg Thr Asn Phe Pro Leu Pro Ala Ala Ala
 65                  70                  75                  80

Ala Leu His His Pro His Met Pro Ala Ala Ala Ala Ala Ala Ala Pro
                 85                  90                  95

Pro Tyr Thr Thr Tyr Pro Thr Ala Thr Gly Val Val Ser Thr Pro Pro
            100                 105                 110

Val Ala Arg Pro Ala Cys Ser Ser Leu Ser Ser Thr Val Glu Ser Phe
        115                 120                 125

Ser Gly Ala Arg Pro Arg Pro Val Leu Pro Pro Arg Phe Pro Pro Pro
    130                 135                 140

Ser Ile Pro Asp Gly Asp Cys Arg Ser Asp Cys Gly Ser Ser Ala Ser
145                 150                 155                 160

Val Val Asp Asp Asp Cys Thr Asp Ala Ala Ala Ser Ala Ser Cys Pro
                165                 170                 175

Phe Pro Leu Pro Phe Asp Leu Asn Leu Pro Pro Gly Gly Gly Gly Ala
            180                 185                 190

Gly Val Gly Phe Tyr Ala Asp Glu Glu Asp Glu Leu Arg Leu Thr Ala
        195                 200                 205

Leu Arg Leu
    210

<210> SEQ ID NO 46
<211> LENGTH: 194
<212> TYPE: PRT
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<222> LOCATION: (20)..(83)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 46

Met Arg Lys Ala Arg Pro Pro Gln Pro Gln Pro Gln Pro Ser Gln Gln
  1               5                  10                  15

Ser Pro Glu Ile Arg Tyr Arg Gly Val Arg Lys Arg Pro Ser Gly Arg
                 20                  25                  30

Tyr Ala Ala Glu Ile Arg Asp Pro Ala Lys Lys Thr Pro Ile Trp Leu
             35                  40                  45

Gly Thr Phe Asp Cys Ala Glu Asp Ala Ala Arg Ala Tyr Asp Ser Ala
 50                  55                  60

Ala Arg Ser Leu Arg Gly Pro Thr Ala Arg Thr Asn Phe Pro Pro Ser
 65                  70                  75                  80

Ser Ala Thr Gln Pro Pro Pro Arg Pro Pro Pro Ala Ala Ala Ala Ala
                 85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Ala Arg Ser Ala Ala Arg Ala Gly
        115                 120                 125

Thr Ala Lys Glu Gly Glu Glu Asp Cys Arg Ser Tyr Cys Gly Ser Ser
    130                 135                 140

Ser Ser Val Leu Leu Glu Glu Gly Ala Asp Asp Ala Ala Ala Ser Arg
145                 150                 155                 160
```

Ser Pro Leu Pro Phe Asp Leu Asn Met Pro Pro Gln Glu Gly Ala
            165                 170                 175

Leu Asp Ala Glu Ala Asp Gln Met Thr Cys Arg Tyr Asp Thr Leu Leu
        180                 185                 190

Arg Leu

<210> SEQ ID NO 47
<211> LENGTH: 660
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1441430
<220> FEATURE:
<221> NAME/KEY: misc_feature
<223> OTHER INFORMATION: Encodes the protein at SEQ ID NO: 48

<400> SEQUENCE: 47

```
atggggagaa caagaacaac aacaaaacag gctgttgacc caaatggatc tgcaacccaa      60
aatatgttag taattgcaaa agagcccaga tacagaggag tacgaaagag accatgggga     120
agattcgctg cggagattag agatccctgg aaaaagacca gagtttggct gggcaccttc     180
gactctgcag aggatgcagc gcgtgcctac gatgcggctg ctcgcaccct ccgcggagca     240
aaggccaaga caaactttcc tatctccaca acgaaccagt tattcaatca tcaaaatcaa     300
aaccaaagcc caaccgatcc cttcttggat caccacagta taaatcccca agacccaca     360 tctagcagtt tgagcagtac agtggagtct ttcagcggtc ctaggcctcc gcagccaaca     420
acaacaacaa aatcgggaaa tgggccgagg agatctcatc cacggatccc accggttgtt     480
ccagaagatt gtcatagcga ttgcgattca tcttcttcgg tggttgatga cagagatgtc     540
gcatccgctg cttcttcttt gtgccgcaag cctttgcctt tcgatctaaa tttcccaccg     600
ttggaccagg ttgacttggg ctctggtgat gatctccact gcactgcttt atgcctttga     660
```

<210> SEQ ID NO 48
<211> LENGTH: 219
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no. 1441430
<220> FEATURE:
<221> NAME/KEY: misc_feature
<222> LOCATION: (29)..(92)
<223> OTHER INFORMATION: Pfam Name: AP2
     Pfam Description: AP2 domain
<220> FEATURE:
<221> NAME/KEY: misc_feature
<223> OTHER INFORMATION: Functional Homolog of Ceres CLONE ID no. 674166
     Given in SEQ ID NO: 42

<400> SEQUENCE: 48

Met Gly Arg Thr Arg Thr Thr Thr Lys Gln Ala Val Asp Pro Asn Gly
1               5                   10                  15

Ser Ala Thr Gln Asn Met Leu Val Ile Ala Lys Glu Pro Arg Tyr Arg
            20                  25                  30

Gly Val Arg Lys Arg Pro Trp Gly Arg Phe Ala Ala Glu Ile Arg Asp
        35                  40                  45

Pro Trp Lys Lys Thr Arg Val Trp Leu Gly Thr Phe Asp Ser Ala Glu
    50                  55                  60

Asp Ala Ala Arg Ala Tyr Asp Ala Ala Ala Arg Thr Leu Arg Gly Ala
65                  70                  75                  80

Lys Ala Lys Thr Asn Phe Pro Ile Ser Thr Thr Asn Gln Leu Phe Asn
                85                  90                  95

His Gln Asn Gln Asn Gln Ser Pro Thr Asp Pro Phe Leu Asp His His
            100                 105                 110

Ser Ile Asn Pro Gln Arg Pro Thr Ser Ser Ser Leu Ser Ser Thr Val
        115                 120                 125

Glu Ser Phe Ser Gly Pro Arg Pro Pro Gln Pro Thr Thr Thr Thr Lys
    130                 135                 140

Ser Gly Asn Gly Pro Arg Arg Ser His Pro Arg Ile Pro Pro Val Val
145                 150                 155                 160

Pro Glu Asp Cys His Ser Asp Cys Asp Ser Ser Ser Val Val Asp
                165                 170                 175

Asp Arg Asp Val Ala Ser Ala Ala Ser Ser Leu Cys Arg Lys Pro Leu
            180                 185                 190

Pro Phe Asp Leu Asn Phe Pro Pro Leu Asp Gln Val Asp Leu Gly Ser
        195                 200                 205

Gly Asp Asp Leu His Cys Thr Ala Leu Cys Leu
    210                 215

<210> SEQ ID NO 49
<211> LENGTH: 985
<212> TYPE: DNA
<213> ORGANISM: Glycine max
<220> FEATURE:
<221> NAME/KEY: misc_feature
<223> OTHER INFORMATION: Ceres CLONE ID no.1240330
<220> FEATURE:
<221> NAME/KEY: misc_feature
<223> OTHER INFORMATION: Encodes the protein at SEQ ID NO: 50

<400> SEQUENCE: 49

```
attattcctc ttccatctct attctccata acacccacca caccacttgt gaaaaacctc     60
attaatatca cacactgaca tgtatctctg agctccaatc caatacaaga ccacaccttg    120
tcgtgtcgga cgaaccttgg tgtctgtttt tttttttttt tcattatttt ctccgaagag    180
atgaggaagg gcagaggtgg aggcgcctcg gcggcggcgg tggatgtgaa cggatccatt    240
ttaaaggagc ctcggtaccg gggcgtgagg aagagaccgt gggggagatt cgccgcggag    300
atcagagacc cgttgaagaa agccagggtt tggttgggaa ccttcgattc tgccgaggat    360
gctgctcgtg cctacgacgc cgccgctcgg actctccgag gtcccaaggc caaaacaaat    420
ttccccccctc tctcacctttt tgctatcca caccccacca ccgatccttt cttctacact    480
ggtttccacg atcaacacca ccaccacaac aacaacaacc ttaacaaccc tcaaagaccc    540
acttcaagtg gcatgagtag caccgttgag tccttcagtg ggccccgccc tccaccacc     600
accactacca ccacaaccac aactgcgacg ccgttttga ctgctacgcg gagatacccg    660
cgcactcccc ctcttgtccc tgaagactgc cacagtgact gcgactcttc ctcctccgtc    720
gttgacgacg gcgacgacaa catcgtttcg tcgtcgtttc gacctccctt gccgtttgat    780
ctcaacgcgc tgccgtttga tgatgctgcc gcggatgatg atctacgccg caccgcgctt    840
tgtctctgat gatgattatc gtgcgatgat gattttaat ttctcatttt tttacttgat    900
tttttttgtta ttgctatgca gaagaaatat atatttaaaa tgatgatcag atgtaagatt    960
atggtaatat gatcttaatt ctgtg                                          985
```

<210> SEQ ID NO 50
<211> LENGTH: 222

<212> TYPE: PRT
<213> ORGANISM: Glycine max
<220> FEATURE:
<221> NAME/KEY: misc_feature
<223> OTHER INFORMATION: Ceres CLONE ID no. 1240330
<220> FEATURE:
<221> NAME/KEY: misc_feature
<222> LOCATION: (24)..(87)
<223> OTHER INFORMATION: Pfam Name: AP2
    Pfam Description: AP2 domain
<220> FEATURE:
<221> NAME/KEY: misc_feature
<223> OTHER INFORMATION: Functional Homolog of Ceres CLONE ID no. 674166
    Given in SEQ ID NO: 42

<400> SEQUENCE: 50

Met Arg Lys Gly Arg Gly Gly Ala Ser Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asp Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Pro Pro Thr Thr Thr Thr Thr Thr
    130                 135                 140

Thr Thr Thr Thr Ala Thr Pro Phe Leu Thr Ala Thr Arg Arg Tyr Pro
145                 150                 155                 160

Arg Thr Pro Pro Leu Val Pro Glu Asp Cys His Ser Asp Cys Asp Ser
                165                 170                 175

Ser Ser Ser Val Val Asp Asp Gly Asp Asp Asn Ile Val Ser Ser Ser
            180                 185                 190

Phe Arg Pro Pro Leu Pro Phe Asp Leu Asn Ala Leu Pro Phe Asp Asp
        195                 200                 205

Ala Ala Ala Asp Asp Asp Leu Arg Arg Thr Ala Leu Cys Leu
    210                 215                 220

<210> SEQ ID NO 51
<211> LENGTH: 726
<212> TYPE: DNA
<213> ORGANISM: Zea mays
<220> FEATURE:
<221> NAME/KEY: misc_feature
<223> OTHER INFORMATION: Ceres CLONE ID no.1382611
<220> FEATURE:
<221> NAME/KEY: misc_feature
<223> OTHER INFORMATION: Encodes the protein at SEQ ID NO: 52

<400> SEQUENCE: 51
acttttctct cccattcttt tacaactcac gttgcacagc cttttctct atatattact        60 tgacataaac tactattcac aacacaaaca cacacataac catggcctct tcttcacaag     120
ctttcctttt gctcacattg tctatggttt tagttcattt ctctttagct caatctccca     180

-continued

```
tgatggctcc ttctggctcc atgtccatgc cgccaatgcc tagcggcggc tctccaatgc    240
caatgatgac tccaccacct atgccaatga tgactccacc acctatggct atggctccac    300
cacctatgcc tatgactcca ccaccaatgc ccatggctcc gatgccaatg actccatctt    360
caagtccaat gagcccacca actactatgg ccccaagtcc agaaacagtc cctgatatgg    420
cttcgccacc gatgatgcca ggaatggatt cttctccttc tccgggaccc atgccaccgg    480
caatggcctc tccagattcc ggagcattca atgtaagaaa cgacgtcgta gcaatttcgt    540
tccttgttgc agctcatttg ctcctagttt gagattatta ttaaattggc cagcgtcgtg    600
tttgtgtaat ttactttcat ttttttctcg agccattaat tttcatgttt tatcatatat    660
ttgggtttgt gtttgatatg gtacgattca gacatttgtt tgcttaataa gtttatcgtt    720
gactct                                                               726
```

<210> SEQ ID NO 52
<211> LENGTH: 156
<212> TYPE: PRT
<213> ORGANISM: Zea mays
<220> FEATURE:
<221> NAME/KEY: misc_feature
<223> OTHER INFORMATION: Ceres CLONE ID no. 1382611
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 52

```
Met Ala Ser Ser Ser Gln Ala Phe Leu Leu Leu Thr Leu Ser Met Val
1               5                   10                  15

Leu Val His Phe Ser Leu Ala Gln Ser Pro Met Met Ala Pro Ser Gly
                20                  25                  30

Ser Met Ser Met Pro Pro Met Pro Ser Gly Gly Ser Pro Met Pro Met
            35                  40                  45

Met Thr Pro Pro Pro Met Pro Met Met Thr Pro Pro Pro Met Ala Met
        50                  55                  60

Ala Pro Pro Pro Met Pro Met Thr Pro Pro Pro Met Pro Met Ala Pro
65                  70                  75                  80

Met Pro Met Thr Pro Ser Ser Ser Pro Met Ser Pro Pro Thr Thr Met
                85                  90                  95

Ala Pro Ser Pro Glu Thr Val Pro Asp Met Ala Ser Pro Pro Met Met
                100                 105                 110

Pro Gly Met Asp Ser Ser Pro Ser Pro Gly Pro Met Pro Pro Ala Met
            115                 120                 125

Ala Ser Pro Asp Ser Gly Ala Phe Asn Val Arg Asn Asp Val Val Ala
        130                 135                 140

Ile Ser Phe Leu Val Ala Ala His Leu Leu Leu Val
145                 150                 155
```

<210> SEQ ID NO 53
<211> LENGTH: 580
<212> TYPE: DNA
<213> ORGANISM: Papaver somniferum
<220> FEATURE:
<221> NAME/KEY: misc_feature
<223> OTHER INFORMATION: Ceres CLONE ID no.1627907
<220> FEATURE:
<221> NAME/KEY: misc_feature
<223> OTHER INFORMATION: Encodes the protein at SEQ ID NO: 54

<400> SEQUENCE: 53

-continued

```
gcagaagcac aaggtaagat tgaaggagga gaccggaact cttcttcgcc aaaaccctag    60
ttcgagctca ccaacaacaa tctttcgcaa tgactaagcg taccaagaag gccggaattg   120
tgggtaaata tggtaccaga tatggagctt cattaaggaa acagattaag aagatggaag   180
tgagtcagca tgcaaagtac ttctgtgagt tctgcggaaa gtacgctgtg aagagacagg   240
ctgttggaat ctggggatgc aaggattgtg gcaaagttaa agctggtggt gcttacactt   300
tgaacaccgc cagtgccgtg acagttagaa gcaccattag aaggttgagg gagcaaactg   360
aatcttagat tgatctcgtt atctatattt tgtattttgg tactgggtga gaggtaccat   420
cagagctaat ttagtgttta tcaccttttc tggtcttcaa gaactagtta gtcattttgt   480
tattcagaga tttttgataa tgtctagtat cttacatttg tgagcagact atttctttgt   540
ttcaaattat ggagttctga tgaatcttat atttattctc                         580
```

<210> SEQ ID NO 54
<211> LENGTH: 92
<212> TYPE: PRT
<213> ORGANISM: Papaver somniferum
<220> FEATURE:
<221> NAME/KEY: misc_feature
<223> OTHER INFORMATION: Ceres CLONE ID no. 1627907
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional Homolog of Ceres CLONE ID no. 271922
    Given in SEQ ID NO: 20

<400> SEQUENCE: 54

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ala Lys Tyr Phe Cys Glu Phe Cys Gly Lys Tyr Ala Val Lys
        35                  40                  45

Arg Gln Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 55
<211> LENGTH: 983
<212> TYPE: DNA
<213> ORGANISM: Panicum virgatum
<220> FEATURE:
<221> NAME/KEY: misc_feature
<223> OTHER INFORMATION: Ceres CLONE ID no.1761125
<220> FEATURE:
<221> NAME/KEY: misc_feature
<223> OTHER INFORMATION: Encodes the protein at SEQ ID NO: 56

<400> SEQUENCE: 55

```
accagaccac accacaccac accgcgtcca catcctcccg cgcttctccg ctcagcccgc    60
gcgtttccgc tgaggaggga tagccgcgcg gcgcgtcgag gggtttgtct ttgatcgggt   120
agctgaggct gagcgggcgg ggcaggatga tgcgcgacac ggcggccgtg gccgtggcgg   180
cgccgcggta caggggcgtg cggaagcggc cgtggggccg gttcgcggcg gagatccgcg   240
```

-continued

```
acccggcgaa gcgcgcgcgc gtctggctcg gcaccttcga ctccgccgag gccgcggcgc    300
gcgcctacga cgtcgccgcg cggaccctgc gcggcccgct cgccaggacc aacttccccc    360
gcgcctcctc ccgcctcccg ctgccctccc gccaccaagg cggctgtggc ggcggcctcg    420
tcgcgccgcc gcccgccgcg ccgacgtgca gctccagctc caccgtcgag tcctccagcg    480
gaccccgagg ggcgcccagg gctgctgcgg cggcggcgcc tcgaattcgg aggcggtcgg    540
tgaaaaagcc gcggccggca gcgcccgaca tcgactgcca cagcgactgc gcctcgtcgg    600
cctccgtcgt ggacgacggc gacgacgcct ccacggtccg gtcgcgcgcg ccgttcgacc    660
tcaacgtccc ggctccggtg gacggtgacc acgcccctcga cctctgcacg gagctgcggc    720
tctgagcaat atgatcctcg aacaacaaca acagcaaaac attgaaggcg attttttcccc  780 ggtcttcttt tcctgactaa attctgatat gatcaatatg ctcgagagtt ctcgttttct    840
ttaacgcctc ttgtatttgg atctgctacc atcttctctg cccattctat ttgtacacca    900
gataacatgt aagatgttca cgaattaaca catatctttt cttaaaaaaa tgaattaaca    960
cggaaaaaaa aaaaaaaaaa aaa                                            983
```

```
<210> SEQ ID NO 56
<211> LENGTH: 192
<212> TYPE: PRT
<213> ORGANISM: Panicum virgatum
<220> FEATURE:
<221> NAME/KEY: misc_feature
<223> OTHER INFORMATION: Ceres CLONE ID no. 1761125
<220> FEATURE:
<221> NAME/KEY: misc_feature
<222> LOCATION: (13)..(76)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 56

Met Met Arg Asp Thr Ala Ala Val Ala Val Ala Ala Pro Arg Tyr Arg
1               5                   10                  15

Gly Val Arg Lys Arg Pro Trp Gly Arg Phe Ala Ala Glu Ile Arg Asp
                20                  25                  30

Pro Ala Lys Arg Ala Arg Val Trp Leu Gly Thr Phe Asp Ser Ala Glu
            35                  40                  45

Ala Ala Ala Arg Ala Tyr Asp Val Ala Ala Arg Thr Leu Arg Gly Pro
        50                  55                  60

Leu Ala Arg Thr Asn Phe Pro Cys Ala Ser Ser Arg Leu Pro Leu Pro
65                  70                  75                  80

Ser Arg His Gln Gly Gly Cys Gly Gly Leu Val Ala Pro Pro
                85                  90                  95

Ala Ala Pro Thr Cys Ser Ser Ser Thr Val Glu Ser Ser Ser Gly
            100                 105                 110

Pro Arg Gly Ala Pro Arg Ala Ala Ala Ala Ala Pro Arg Ile Arg
        115                 120                 125

Arg Arg Ser Val Lys Lys Pro Arg Pro Ala Ala Pro Asp Ile Asp Cys
130                 135                 140

His Ser Asp Cys Ala Ser Ser Ala Ser Val Val Asp Gly Asp Asp
145                 150                 155                 160

Ala Ser Thr Val Arg Ser Arg Ala Pro Phe Asp Leu Asn Val Pro Ala
                165                 170                 175
```

Pro Val Asp Gly Asp His Ala Leu Asp Leu Cys Thr Glu Leu Arg Leu
          180                 185                 190

<210> SEQ ID NO 57
<211> LENGTH: 594
<212> TYPE: DNA
<213> ORGANISM: Panicum virgatum
<220> FEATURE:
<221> NAME/KEY: misc_feature
<223> OTHER INFORMATION: Ceres CLONE ID no.1783890
<220> FEATURE:
<221> NAME/KEY: misc_feature
<223> OTHER INFORMATION: Encodes the protein at SEQ ID NO: 58

<400> SEQUENCE: 57
gagccctacc cgcacccgcg ccgccgccgc cccgcgcccc gtcgccgcag acgactccgc     60
cccgtcgccg cgatgacgaa gcgcaccaag aaggccggaa tcgtcggcaa atatggaact    120
aggtatggtg ctagcttgcg taagcaaatc aagaagatgg aggtgtctca gcactccaag    180
tacttctgcg agttctgtgg aaagtttgct gtgaaaagga aagcagttgg aatctgggga    240
tgcaaggact gcgggaaggt taaggctggt ggtgcttaca ccatgaacac tgctagtgca    300
gtcaccgtca ggagcacaat ccgtcgcttg agggagcaga ctgaagcata atcggagctc    360
ttctctgcag tagtcctgtg cttttttgtac cgtctaagac atatggctgt ttggcctaag    420
aacattcatg aatattctgg ttatgcttaa ggatatcaaa aattatggtg ctaaaatttg    480
tacttcgttg ctgttgcaaa gttgacctgt cttgatccat tcataatgta gaatttcctc    540
atggttctta tctccagttt gctactcttt ggccaaaaaa aaaaaaaaaa aaaa          594

<210> SEQ ID NO 58
<211> LENGTH: 92
<212> TYPE: PRT
<213> ORGANISM: Panicum virgatum
<220> FEATURE:
<221> NAME/KEY: misc_feature
<223> OTHER INFORMATION: Ceres CLONE ID no. 1783890
<220> FEATURE:
<221> NAME/KEY: misc_feature
<222> LOCATION: (2)..(91)
<223> OTHER INFORMATION: Pfam Name: Ribosomal_L37ae
       Pfam Description: Ribosomal L37ae protein family
<220> FEATURE:
<221> NAME/KEY: misc_feature
<223> OTHER INFORMATION: Functional Homolog of Ceres CLONE ID no. 271922
       Given in SEQ ID NO: 20

<400> SEQUENCE: 58

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 59
<211> LENGTH: 880

```
<212> TYPE: DNA
<213> ORGANISM: Panicum virgatum
<220> FEATURE:
<221> NAME/KEY: misc_feature
<223> OTHER INFORMATION: Ceres CLONE ID no.1802327
<220> FEATURE:
<221> NAME/KEY: misc_feature
<223> OTHER INFORMATION: Encodes the protein at SEQ ID NO: 60

<400> SEQUENCE: 59
acacagatac attcgtcgat ccaccactgt ccagtgcttg gcggttacgc acgcacgcac      60
acagatagga ttatctttta ctacaccaac tcaccaagat actagcaagc cgaatcgaca     120
aacaagcagc aggaagagga ggcatggcgc tcgcggaggg gaacgtcatc ttcggcgagg     180
agcaggaggc gctggtgctc aagtcgtggg ccctcatgaa gaaggactcg gccgacctcg     240
gcctccgctt cttcctcaag atcttcgaga tcgcgccgtc ggcgaagcag atgttctcgt     300
tcctgcgcga ctccgacgtg ccgctcgaga agaaccccaa gctcaagaac cacgccatgt     360
ccgtcttcgt catgacctgc gaggcggcgg cgcagctacg gaaggccggg aaggtcaccg     420
tcagggagac gacgctcaag cggctgggcg ccacgcactt caagtacggc gtcgccgacg     480
gccacttcga ggtgacgagg ttcgcgctgc tggagacgat aaaggaggcg cttcccgccg     540
acatgtggag cctggagatg aagaacgcct ggagcgaggc ttacaaccag ctggtggcgg     600
ccatcaagca ggagatgaag cctgccgcat gatgctgctg ctgctactga gatgaagcct     660
gcccgcatga tgctgctgct gctactcggc ctccgcgctg agttccccct acgatgcacc     720
accatctcca aattcttcat cgctgttttt ttttttttgc tgttttgact tgtattgtgc     780
attttccaaa tctctcgatg gagacaagtg tgatgactaa tttttgagag catgtatata     840
tgttgtgatg agcattgaat aaaaaaaaaa aaaaaaaaa                             880

<210> SEQ ID NO 60
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1802327
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 60
```

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

```
Thr Leu Lys Arg Leu Gly Ala Thr His Phe Lys Tyr Gly Val Ala Asp
            100                 105                 110
Gly His Phe Glu Val Thr Arg Phe Ala Leu Leu Glu Thr Ile Lys Glu
        115                 120                 125
Ala Leu Pro Ala Asp Met Trp Ser Leu Glu Met Lys Asn Ala Trp Ser
    130                 135                 140
Glu Ala Tyr Asn Gln Leu Val Ala Ala Ile Lys Gln Glu Met Lys Pro
145                 150                 155                 160
Ala Ala

<210> SEQ ID NO 61
<211> LENGTH: 1017
<212> TYPE: DNA
<213> ORGANISM: Gossypium hirsutum
<220> FEATURE:
<221> NAME/KEY: misc_feature
<223> OTHER INFORMATION: Ceres CLONE ID no.1838364
<220> FEATURE:
<221> NAME/KEY: misc_feature
<223> OTHER INFORMATION: Encodes the protein at SEQ ID NO: 62

<400> SEQUENCE: 61
cctgcccatt tccatcttcc ttctttcctt cctctttcct ttgtcttctt gctttatctt      60 cccttatct tcaatctttt ctgttctgtt tttttcttag attcataggt aagttcgttt     120
tggttggctt gattatttcc tcacttccct tcttttttgg ttcatcgtga tcttttcatc     180 aaccccttt gattgttata tagattgtta ctattctttt aatctttta atattttttt     240 tccatgagga gagggagagg tgccgcagct gcaaacgccg tagctaggag accggcactg     300
caacccagcg gatctattaa agagccgaga tacagaggtg ttagaaaaag gccatggggc     360
agattcgcgg ccgagattcg agacccttgg aagaagacca gggtctggtt agggacgttc     420
gactcggccg aagaagccgc tcgagcctac gatacggcgg cgaggacgct ccgtggaccc     480
aaagctaaaa caaatttccc cataaattct tcaaatatcc cggcttttcc tttcgaaacc     540
aatcatcacc acaacgaagg gttcatcgac caacgccggt tatatccgat gggcgaattt     600
catgaccccg aagtgaatcc acagagaccc acgaggagta gcatgagtag cacggtggag     660
tcgtttagtg gacccagacc ggcccaacca ccgcaaaagt cggcggactt cgcggtggtt     720
tcgactagga agtactatcc gaggccgccg ccagtagagc cagaggattg tcatagtgac     780
tgtgattcat catcgtcggt ggttgatgat ggggatatcg cgttgtcttc ttgtcggaaa     840
actttgcctt tcgatctcaa ttttccaccc ttggatgaag atggaagatc tccagtgtac     900
tgctttatgt ctttgatcgc gatgccggtg atgaatgatg atgatcgatt attggatctc     960 ttttctttt ttaaaaaatg ttagcttttt taagcggaaa aaaaaaaaaa aaaaaaa        1017

<210> SEQ ID NO 62
<211> LENGTH: 246
<212> TYPE: PRT
<213> ORGANISM: Gossypium hirsutum
<220> FEATURE:
<221> NAME/KEY: misc_feature
<223> OTHER INFORMATION: Ceres CLONE ID no. 1838364
<220> FEATURE:
<221> NAME/KEY: misc_feature
<222> LOCATION: (28)..(91)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
```

<400> SEQUENCE: 62

Met Arg Arg Gly Arg Gly Ala Ala Ala Asn Ala Val Ala Arg Arg
1               5                   10                  15

Pro Ala Leu Gln Pro Ser Gly Ser Ile Lys Glu Pro Arg Tyr Arg Gly
            20                  25                  30

Val Arg Lys Arg Pro Trp Gly Arg Phe Ala Ala Glu Ile Arg Asp Pro
            35                  40                  45

Trp Lys Lys Thr Arg Val Trp Leu Gly Thr Phe Asp Ser Ala Glu Glu
        50                  55                  60

Ala Ala Arg Ala Tyr Asp Thr Ala Ala Arg Thr Leu Arg Gly Pro Lys
65              70                  75                  80

Ala Lys Thr Asn Phe Pro Ile Asn Ser Ser Asn Ile Pro Ala Phe Pro
                85                  90                  95

Phe Glu Thr Asn His His His Asn Glu Gly Phe Ile Asp Gln Arg Arg
            100                 105                 110

Leu Tyr Pro Met Gly Glu Phe His Asp Pro Glu Val Asn Pro Gln Arg
            115                 120                 125

Pro Thr Arg Ser Ser Met Ser Ser Thr Val Glu Ser Phe Ser Gly Pro
        130                 135                 140

Arg Pro Ala Gln Pro Pro Gln Lys Ser Ala Asp Phe Ala Val Val Ser
145                 150                 155                 160

Thr Arg Lys Tyr Tyr Pro Arg Pro Pro Val Glu Pro Glu Asp Cys
                165                 170                 175

His Ser Asp Cys Asp Ser Ser Ser Val Val Asp Asp Gly Asp Ile
            180                 185                 190

Ala Leu Ser Ser Cys Arg Lys Thr Leu Pro Phe Asp Leu Asn Phe Pro
        195                 200                 205

Pro Leu Asp Glu Asp Gly Arg Ser Pro Val Tyr Cys Phe Met Ser Leu
        210                 215                 220

Ile Ala Met Pro Val Met Asn Asp Asp Asp Arg Leu Leu Asp Leu Phe
225                 230                 235                 240

Phe Phe Phe Lys Lys Cys
                245

<210> SEQ ID NO 63
<211> LENGTH: 708
<212> TYPE: DNA
<213> ORGANISM: Panicum virgatum
<220> FEATURE:
<221> NAME/KEY: misc_feature
<223> OTHER INFORMATION: Ceres CLONE ID no.1876458
<220> FEATURE:
<221> NAME/KEY: misc_feature
<223> OTHER INFORMATION: Encodes the protein at SEQ ID NO: 64

<400> SEQUENCE: 63
acacagatac attcgtcgat ccaccactgt ccagtgcttg gcggttacgc acgcacgcac    60
acagatagga ttatctttta ctacaccaac tcaccaagat actagcaagc cgaatcgaca   120
aacaagcagc aggaagagga ggcatggcgc tcgcggaggg gaacgtcatc ttcggcgagg   180
agcaggaggc gctggtgctc aagtcgtggg ccctcatgaa gaaggactcg ccgacctcg   240 gcctccgctt cttcctcaag atcttcgaga tcgcgccgtc ggcgaagcag atgttctcgt   300
tcctgcgcga ctccgacgtg ccgctcgaga agaaccccaa gctcaagacc acgccatgt   360 ccgtcttcgt catgacctgc gaggcggcgg cgcagctacg gaaggccggg aaggtcaccg   420

```
tcagggagac gacgctcaag cggctgggcg ccacgcactt caagtacggc gtcgccgacg    480
gccacttcga ggtgacgagg ttcgcgctgc tggagacgat aaaggaggcg cttcccgccg    540
acatgtggag cctggagatg aagtacgcct ggagcgaggc ttacaaccag cttgtggcgg    600
ccatcaagca ggagatgaag cctgccgcat gatgctgctg ctgctactcg gcctccgcgc    660
tgagttcccc ctacgatgca ccaccatctc caaattcttc atcgctgt                708
```

<210> SEQ ID NO 64
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1876458
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 64

Met Ala Leu Ala Glu Gly Asn Val Ile Phe Gly Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Tyr Ala Trp Ser
    130                 135                 140

Glu Ala Tyr Asn Gln Leu Val Ala Ala Ile Lys Gln Glu Met Lys Pro
145                 150                 155                 160

Ala Ala

<210> SEQ ID NO 65
<211> LENGTH: 712
<212> TYPE: DNA
<213> ORGANISM: Panicum virgatum
<220> FEATURE:
<221> NAME/KEY: misc_feature
<223> OTHER INFORMATION: Ceres CLONE ID no.1879148
<220> FEATURE:
<221> NAME/KEY: misc_feature
<223> OTHER INFORMATION: Encodes the protein at SEQ ID NO: 66

<400> SEQUENCE: 65

```
acacagatac attcgtcgat ccaccactgt ccagtgctcg gctcggttac gcacgcacgc    60
acacaaattg tagtacctgt gttttacacc accaaagata ctagcaagcc gagtcgacaa    120
```

```
acaaagcagc aggaagaggc atggcgctcg ctgacgggaa cggcgcggcc atcttcggcg    180
aggagcagga ggcgctggtg ctcaagtcgt gggccctcat gaagaaggac tcggccgacc    240
tcggcctccg cttcttcctc aagatcttcg agatcgcgcc gtcggcgaag cagatgttct    300
cgttcctgcg cgactccgac gtgccgctgg agaagaaccc caagctcaag acccacgcca    360
tgtccgtctt cgtcatgacc tgcgaggcgg cagcgcagct acggaaggcc gggaaggtca    420
ccgtcaggga gacgacgctc aagcggctgg gcgcaacgca cttcaagtac ggcgtcgccg    480
acggccactt cgaggtgaca aggttcgcgc tgctggagac gataaaggag gcgcttcccg    540
ccgacatgtg gagcctggag atgaagaacg cctggagcga ggcttacaac cagctcgtgg    600
cggccatcaa gcaggagatg aagcctgctg catgatgctg catgctgcta catactcggc    660
ctccgagttc cccctacgat gcaccaccat ctccaagttc ttcatcgcta tt            712
```

<210> SEQ ID NO 66
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1879148
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 66

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
                20                  25                  30

Asp Leu Gly Leu Arg Phe Phe Leu Lys Ile Phe Glu Ile Ala Pro Ser
            35                  40                  45

Ala Lys Gln Met Phe Ser Phe Leu Arg Asp Ser Asp Val Pro Leu Glu
        50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
                100                 105                 110

Ala Asp Gly His Phe Glu Val Thr Arg Phe Ala Leu Leu Glu Thr Ile
            115                 120                 125

Lys Glu Ala Leu Pro Ala Asp Met Trp Ser Leu Glu Met Lys Asn Ala
        130                 135                 140

Trp Ser Glu Ala Tyr Asn Gln Leu Val Ala Ile Lys Gln Glu Met
145                 150                 155                 160

Lys Pro Ala Ala

<210> SEQ ID NO 67
<211> LENGTH: 1129
<212> TYPE: DNA
<213> ORGANISM: Gossypium hirsutum
<220> FEATURE:

<221> NAME/KEY: misc_feature
<223> OTHER INFORMATION: Ceres CLONE ID no.1884696
<220> FEATURE:
<221> NAME/KEY: misc_feature
<223> OTHER INFORMATION: Encodes the protein at SEQ ID NO: 68

<400> SEQUENCE: 67

```
atccgccccc atttgttcgc tctgtatatt gaacttttct ttctcgattt tctctttgaa      60
caaaaatgat gaagatcttc aaccagactc tcaccggcaa gactatcacg ctcgaggtcg     120
agagctccga caccatcgaa ggcgccaaca ccattctcca agatggaggg agcctccctc     180
cttaccgaac ccgactgatc ttcgccggac aacagcttga ggacggactg accttgtgcg     240
attacaacat cttaaaggag gtcaactctc cacctcttcc tccggttgcg cggtgggatg     300
cttaccttcc ggaggacctt gaccggcaat accatcactc tccaggtcta aagcgccgac     360
tcgatcaagt tcgttcacgc taacatccaa gactaggaag gcgtccccccc ataccaacta     420
cgactctgct tcgaccgaaa acaacttgaa gacggccgta ccttggccga ctacaacatc     480
cagaaggagt caacgctcca tcttgtcctt cgtttgcgtg gcgggatgca aatcttcgtt     540
aagacgctta cgggaaagac gatcactctc gaggtcgaga gctctgacac gatcgacaac     600
gtgaaagcca aaatccaaga caaggaaggc atcccgccag accagcaacg tctcatcttc     660
gccggaaagc aactcgagga cgggcggact ttagccgatt acaatatcca gaaggaatcg     720
actcttcatc tggtcctgcg tcttggaggt gggatgcaga tcttcgtcaa gactttgacc     780
ggtaagacga ttactttaga agtggagagc tcggatacga ttgataacgt gaaagcgaag     840
attcaggaca agaaggaat tccaccagat cagcaaaggt tgattttttgc tgggaaacaa     900
ctggaagacg gaaggacttt ggctgattac aatattcaaa aggattccac tcttcacctt     960
gttcttcgtc ttcgtggtgg gttctaagcc ttaaggtctc ccttaatgtg ggttttctgg    1020
ttttacgtga aggactgtgc cctgtaatgg ccttttaaat aatttctagt ctttgtttac    1080
cggttgcatc tatgtatggt ttctcttaga atggaattag catatttac                1129
```

<210> SEQ ID NO 68
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 1884696
<220> FEATURE:
<221> NAME/KEY: misc_feature
<222> LOCATION: (1)..(74)
<223> OTHER INFORMATION: Pfam Name: ubiquitin
    Pfam Description: Ubiquitin family
<220> FEATURE:
<221> NAME/KEY: misc_feature
<222> LOCATION: (77)..(150)
<223> OTHER INFORMATION: Pfam Name: ubiquitin
    Pfam Description: Ubiquitin family
<220> FEATURE:
<221> NAME/KEY: misc_feature
<223> OTHER INFORMATION: Functional Homolog of Ceres CLONE ID no. 2403
    Given in SEQ ID NO: 40

<400> SEQUENCE: 68

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

Gln Leu Glu Asp Gly Arg Thr Leu Ala Asp Tyr Asn Ile Gln Lys Glu
 50                  55                  60

Ser Thr Leu His Leu Val Leu Arg Leu Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
                100                 105                 110

Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Asp Ser Thr Leu His
        130                 135                 140

Leu Val Leu Arg Leu Arg Gly Gly Phe
145                 150

<210> SEQ ID NO 69
<211> LENGTH: 679
<212> TYPE: DNA
<213> ORGANISM: Gossypium hirsutum
<220> FEATURE:
<221> NAME/KEY: misc_feature
<223> OTHER INFORMATION: Ceres CLONE ID no.1916866
<220> FEATURE:
<221> NAME/KEY: misc_feature
<223> OTHER INFORMATION: Encodes the protein at SEQ ID NO: 70

<400> SEQUENCE: 69

```
aaatcaaata cctactgcaa ttaaaatccc ggaattactt aaacaacaat ggctacctat      60
gaaggtaaag ttttcactga agaacaagaa gctttggtgg tcaagtcatg gactgtaatg     120
aagaagaacg cagctgaatt gggtcttaaa ttcttcttga agatatttga gattgcacca     180
tcagccaaga aactattctc attcttgaga gactccaatg ttccattgga gcaaaacaca     240
aagctgaagc cccatgccat gtctgtcttt gtcatgacat gtgaatctgc agtgcaactg     300
cgtaaagcag gcaaagttac agtgagggaa tcaaatttga agaaattagg agctacccat     360
tttaagtatg gggtagttga tgaacatttt gaggtaacaa aatttgctct tttggagacc     420
ataaaagaag cagtaccaga tatgtggtca gatgagatga agaatgcatg gggtgaagcc     480
tatgatcgtt tggtcgcagc cattaaaata gaaatgaagg catgctcaca agctgcatga     540
tttcacaagt tccctacatt attgcttgtt aattttgggt ccaataagat tgaaagtttt     600
caatcattta aacatgtaat gtaacatagc tattgctcat cactactgtt ttttcccct      660
agtttgtttg ctcctgttc                                                  679
```

<210> SEQ ID NO 70
<211> LENGTH: 163
<212> TYPE: PRT
<213> ORGANISM: Gossypium hirsutum
<220> FEATURE:
<221> NAME/KEY: misc_feature
<223> OTHER INFORMATION: Ceres CLONE ID no. 1916866
<220> FEATURE:
<221> NAME/KEY: misc_feature
<222> LOCATION: (13)..(152)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 70

```
Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala

<210> SEQ ID NO 71
<211> LENGTH: 1003
<212> TYPE: DNA
<213> ORGANISM: Panicum virgatum
<220> FEATURE:
<221> NAME/KEY: misc_feature
<223> OTHER INFORMATION: Ceres CLONE ID no.1950105
<220> FEATURE:
<221> NAME/KEY: misc_feature
<223> OTHER INFORMATION: Encodes the protein at SEQ ID NO: 72

<400> SEQUENCE: 71
atcgccacaa gttcgcgatc tctcgatttc acaaatcgcc gagaagaccc gagcagagaa    60
gttccctccg atcgccttgc caagatgcag atctttgtga agacactcac tggcaagact   120
atcacccttg aggtggagtc ttctgacaca attgacaatg tcaaggcaaa gatccaggac   180
aaggaaggga ttcctccaga ccagcagcgc cttatcttcg ctggcaagca gcttgaggat   240
ggccgtacac ttgcagatta caacattcag aaggagtcca cactgcacct tgtcctcagg   300
ctgcgtggag gcatgcagat tttcgtgaag accctcactg caagacgat cacccctggag    360 gtggagtcat ctgacaccat cgacaatgtg aaggcaaaga tccaggacaa ggagggcatc   420
ccccctgacc agcagcgcct catctttgca ggcaagcagt tggaggatgg gcgaactctg   480
gctgactaya atatccagaa agaatcmacc ctgcacctsg tsctccgcct gcgtggtgga   540
atgcagatct tgtgaagac gcttaccggc aagaccatca ccttggaggt ggagtcttcg   600
gacaccatcg acaatgtgaa ggcgaagatt caggacaagg agggcattcc tccggaccag   660
crgcgcctca tctttgctgg caagcagcta gaggacgggc gtaccctggc ggattacaac   720
atccagaagg agtccaccct ccaccttgtc ctgcgcctcc gtggtggttt ctgagcctag   780
tgctcctgag ttgccttttg tcgttatggt caacctctgg tttaagtcgt gtgaactctc   840
tgcattgcgt tgctagtgtc tggttgtggt tgtaataaga acatgaagaa catgttgctg   900
tggatcacat gactttttt ttttgaaccg gaagatcaca tgactttcat ggctttaagt   960
```

-continued

```
tcctgaactc tgaaatctgg accccctttt aagctctgaa ctc             1003
```

```
<210> SEQ ID NO 72
<211> LENGTH: 229
<212> TYPE: PRT
<213> ORGANISM: Panicum virgatum
<220> FEATURE:
<221> NAME/KEY: misc_feature
<223> OTHER INFORMATION: Ceres CLONE ID no. 1950105
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(226)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40
<220> FEATURE:
<221> NAME/KEY: misc_feature
<222> LOCATION: (135)..(135)
<223> OTHER INFORMATION: Xaa is any aa, unknown, or other
<220> FEATURE:
<221> NAME/KEY: misc_feature
<222> LOCATION: (141)..(141)
<223> OTHER INFORMATION: Xaa is any aa, unknown, or other
<220> FEATURE:
<221> NAME/KEY: misc_feature
<222> LOCATION: (145)..(145)
<223> OTHER INFORMATION: Xaa is any aa, unknown, or other
<220> FEATURE:
<221> NAME/KEY: misc_feature
<222> LOCATION: (146)..(146)
<223> OTHER INFORMATION: Xaa is any aa, unknown, or other
<220> FEATURE:
<221> NAME/KEY: misc_feature
<222> LOCATION: (193)..(193)
<223> OTHER INFORMATION: Xaa is any aa, unknown, or other

<400> SEQUENCE: 72

Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Xaa Asn Ile Gln Lys Glu Xaa Thr Leu His
    130                 135                 140
```

Xaa Xaa Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Xaa Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225

<210> SEQ ID NO 73
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.1990746
<220> FEATURE:
<221> NAME/KEY: misc_feature
<222> LOCATION: (623)..(623)
<223> OTHER INFORMATION: n is a, c, t, g, unknown, or other
<220> FEATURE:
<221> NAME/KEY: misc_feature
<222> LOCATION: (624)..(624)
<223> OTHER INFORMATION: n is a, c, t, g, unknown, or other
<220> FEATURE:
<221> NAME/KEY: misc_feature
<222> LOCATION: (625)..(625)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 74

<400> SEQUENCE: 73
acacagatac actcgtcgat ccaccagacc accactgtcc agtgctcggc tcggttacgc     60
acgcacgcac acaaatagga gtacctgttt tacaccacca agatactagc aagcccaagc    120
cgagtcgaca acaagcagc aggaagaggc atggcgctcg cggaggggaa cggcgcggcc     180
atcttcggcg aggaacagga ggcgctggtg ctcaagtcgt gggccctcat gaagaaggac    240
tcggccgacc tcggcctccg cttcttcctc aagatcttcg agatcgcgcc gtcggcgaag    300
cagatgttct cgttcctgcg cgactccgac gtgccgctgg agaagaaccc caagctcaag    360
acccacgcca tgtccgtctt cgtcatgacc tgcgaggcgg cagtgcagct acggaaggcc    420
gggaaggtca ccgtcaggga gacgacgctc aagcggctgg gcgcaacgca cttcaagtac    480
ggcgtcgccg acggccactt cgaggtgaca aggttcgcgc tgctggagac gataaaggag    540
gcgcttcccg ccgacatgtg gagcctggag atgaagaacg cctggagcga ggcttacaac    600
cagctcgtgg cggccatcaa gcnnnagatg aagcctgccg catgatgctg catgctgcta    660
catactcggc ctccgagtcc ccctacgat gcaccaccat ctcccagttc ttcatcgcta    720
tttt                                                                 724

<210> SEQ ID NO 74
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1990746
<220> FEATURE:

-continued

```
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
<220> FEATURE:
<221> NAME/KEY: misc_feature
<222> LOCATION: (158)..(158)
<223> OTHER INFORMATION: Xaa is any aa, unknown, or other
<220> FEATURE:
<221> NAME/KEY: misc_feature
<222> LOCATION: (159)..(159)
<223> OTHER INFORMATION: Xaa is any aa, unknown, or other

<400> SEQUENCE: 74

Met Ala Leu Ala Glu Gly Asn Gly Ala Ala Ile Phe Gly Glu Gln
1               5                   10                  15

Glu Ala Leu Val Leu Lys Ser Trp Ala Leu Met Lys Lys Asp Ser Ala
                20                  25                  30

Asp Leu Gly Leu Arg Phe Phe Leu Lys Ile Phe Glu Ile Ala Pro Ser
            35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Val Gln Leu Arg Lys Ala Gly Lys Val Thr Val Arg
                85                  90                  95

Glu Thr Thr Leu Lys Arg Leu Gly Ala Thr His Phe Lys Tyr Gly Val
                100                 105                 110

Ala Asp Gly His Phe Glu Val Thr Arg Phe Ala Leu Leu Glu Thr Ile
            115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Xaa Xaa Met
145                 150                 155                 160

Lys Pro Ala Ala

<210> SEQ ID NO 75
<211> LENGTH: 696
<212> TYPE: DNA
<213> ORGANISM: Panicum virgatum
<220> FEATURE:
<221> NAME/KEY: misc_feature
<223> OTHER INFORMATION: Ceres CLONE ID no.2007485
<220> FEATURE:
<221> NAME/KEY: misc_feature
<223> OTHER INFORMATION: Encodes the protein at SEQ ID NO: 76

<400> SEQUENCE: 75
agagcagggg gatggaagaa aataaactac tggccaaacc ctagccgagc cccgggtccg      60
ctcaccgcct tcccaccccc ccacccaccc acctgccccc cccccccccc cgccctcgcc     120
gtccgcgatg cgccgggcga agccgccgca gccgcagccg tcgccgtcgc cggagatccg     180
gtaccgcggc gtgcggaggc ggccatcggg gcgctacgcc gccgagatcc gggacccggc     240
caagaagacc ccgatctggc tcggcaccct cgactccgcc gaggccgccg cgcgcgccta     300
cgacgccgcc gccgatccc tccgcgggcc caccgcccgc accaacttcc ccagcgccgc     360
ggcccccgcg ccgcggcaca gcaggccccc cgccccctcc gccgccgcgc aggcggctgc     420
```

```
cgcggcggca gcggccacgt ccagccacag cagcaccata gagtcgtgga gcgacggcgc    480
gacccgcgcc gcgctggcgc gtagcgctgc ctccgtcctg gcgcgcagcg ccgctccgac    540
ggaggaggaa gacgaggact gccgcagcta ctgcggatcc tcgtcgtccg tcctctgcga    600
agacactggg ggcgacgatg cggccgcctc ccgcgcgccc ctgccgttcg atctgaacct    660
gccgccgcct catgacgcgg cctccgagac cgatca                              696
```

<210> SEQ ID NO 76
<211> LENGTH: 201
<212> TYPE: PRT
<213> ORGANISM: Panicum virgatum
<220> FEATURE:
<221> NAME/KEY: misc_feature
<223> OTHER INFORMATION: Ceres CLONE ID no. 2007485
<220> FEATURE:
<221> NAME/KEY: misc_feature
<222> LOCATION: (17)..(80)
<223> OTHER INFORMATION: Pfam Name: AP2
     Pfam Description: AP2 domain
<220> FEATURE:
<221> NAME/KEY: misc_feature
<223> OTHER INFORMATION: Functional Homolog of Ceres CLONE ID no. 674166
     Given in SEQ ID NO: 42

<400> SEQUENCE: 76

```
Met Arg Arg Ala Lys Pro Pro Gln Pro Gln Pro Ser Pro Ser Pro Glu
1               5                   10                  15

Ile Arg Tyr Arg Gly Val Arg Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

Asp Ser Ala Glu Ala Ala Ala Arg Ala Tyr Asp Ala Ala Ala Arg Ser
    50                  55                  60

Leu Arg Gly Pro Thr Ala Arg Thr Asn Phe Pro Ser Ala Ala Ala Pro
65                  70                  75                  80

Ala Pro Arg His Ser Arg Pro Pro Ala Pro Ser Ala Ala Ala Gln Ala
                85                  90                  95

Ala Ala Ala Ala Ala Ala Ala Thr Ser Ser His Ser Ser Thr Ile Glu
            100                 105                 110

Ser Trp Ser Asp Gly Ala Thr Arg Ala Ala Leu Ala Arg Ser Ala Ala
        115                 120                 125

Ser Val Leu Ala Arg Ser Ala Ala Pro Thr Glu Glu Glu Asp Glu Asp
    130                 135                 140

Cys Arg Ser Tyr Cys Gly Ser Ser Ser Val Leu Cys Glu Asp Thr
145                 150                 155                 160

Gly Gly Asp Asp Ala Ala Ala Ser Arg Ala Pro Leu Pro Phe Asp Leu
                165                 170                 175

Asn Leu Pro Pro Pro His Asp Ala Ala Ser Glu Thr Asp Gln Met Gly
            180                 185                 190

Ala Arg Tyr Asp Thr Leu Leu Arg Leu
        195                 200
```

<210> SEQ ID NO 77
<211> LENGTH: 698
<212> TYPE: DNA
<213> ORGANISM: Panicum virgatum
<220> FEATURE:
<221> NAME/KEY: misc_feature
<223> OTHER INFORMATION: Ceres CLONE ID no.2033803
<220> FEATURE:
<221> NAME/KEY: misc_feature
<223> OTHER INFORMATION: Encodes the protein at SEQ ID NO: 78

<400> SEQUENCE: 77

```
acacagatac attcgtcgat ccaccagacc accactgtcc agtgctcggc tcggttacgc      60
acgcacgcac acaaatagga gtacctgttt tacaccaaga tactagcaag cccaagccga    120
gtcgacaaac aagcagcagg aagaggcatg gcgctcgcgg aggggaacgg cgcggccatc    180
ttcggcgagg agcaggaggc gctggtgctc aagtcgtggg ccctcatgaa gaaggactcg    240
gccgacctcg gcctccgctt cttcctcaag atcttcgaga tcgcgccgtc ggcgaagcag    300
atgttctcgt tcctgcgcga ctccgacgtg ccgctggaga gaacccccaa gctcaagacc    360
cacgccatgt ccgtcttcgt catgacctgc gaggcggcag cgcagctacg gaaggccggg    420
aaggtcaccg tcagggagac gacgctcaag cggctgggcg caacgcactt caagtacggc    480
gtcgccgacg gccacttcga ggtgacaagg ttcgcgcttc ccgccgactt gtggagcctg    540
gagatgaaga acgcctggag cgaggcttac aaccagctcg tggcggccat caagcaggag    600
atgaagcctg ccgcatgatg ctgcatgctg ctacatactc ggcctccgag ttccccctac    660
gatgcaccac catctccaag ttctttcatt gtcttgtg                             698
```

<210> SEQ ID NO 78
<211> LENGTH: 156
<212> TYPE: PRT
<213> ORGANISM: Panicum virgatum
<220> FEATURE:
<221> NAME/KEY: misc_feature
<223> OTHER INFORMATION: Ceres CLONE ID no. 2033803
<220> FEATURE:
<221> NAME/KEY: misc_feature
<222> LOCATION: (16)..(148)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 78

```
Met Ala Leu Ala Glu Gly Asn Gly Ala Ala Ile Phe Gly Glu Gln
1               5                  10                  15

Glu Ala Leu Val Leu Lys Ser Trp Ala Leu Met Lys Lys Asp Ser Ala
                20                  25                  30

Asp Leu Gly Leu Arg Phe Phe Leu Lys Ile Phe Glu Ile Ala Pro Ser
            35                  40                  45

Ala Lys Gln Met Phe Ser Phe Leu Arg Asp Ser Asp Val Pro Leu Glu
        50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
                100                 105                 110

Ala Asp Gly His Phe Glu Val Thr Arg Phe Ala Leu Pro Ala Asp Leu
            115                 120                 125

Trp Ser Leu Glu Met Lys Asn Ala Trp Ser Glu Ala Tyr Asn Gln Leu
        130                 135                 140

Val Ala Ala Ile Lys Gln Glu Met Lys Pro Ala Ala
145                 150                 155
```

```
<210> SEQ ID NO 79
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.2034916
<220> FEATURE:
<221> NAME/KEY: misc_feature
<223> OTHER INFORMATION: Encodes the protein at SEQ ID NO: 80

<400> SEQUENCE: 79
aatccaatct cccccgatcc ccaatcgcga attcccctct ccggcaggcg aagcaatcga      60
ggggcaccct ttcatctcgt caagatgcag atctttgtga agaccctcac tggtaagacc     120
atcaccctcg aggttgagtc ctcggatacc attgacaacg tcaaggctaa aatccaggac     180
aaggagggga tccctccgga ccagcagcgc ctcatctttg ccggcaagca gctcgaagat     240
gggaggacgc ttgctgacta acatccagaa aggagtccca cctccacct cgtgctcagg      300
ctcaggggtg gtatgcagat ctttgtcaag actctcaccg gcaagacgat tactcttgag     360
gttgagtcct cggacacgat cgacaatgta aaggtgaaga tccaagacaa ggaggggatc     420
ccaccggacc agcagcgcct catctttgcc ggcaagcagc tcgaggatgg ccgcactctg     480
gctgactaca acattcagaa agagtcgacc cttcaccttg tgctcaggct gaggggaggc     540
atgcaaatat ttgtcaagac tctgactggc aagaccatca cgcttgaggt ggagtcgtct     600
gacaccattg ataatgtgaa ggcgaagatc caagacaagg agggcatccc gccggaccag     660
cagcgcctga tctttgccgg taagcagctg gaggatggtc gtaccctggc agactataat     720
attc                                                                  724

<210> SEQ ID NO 80
<211> LENGTH: 213
<212> TYPE: PRT
<213> ORGANISM: Panicum virgatum
<220> FEATURE:
<221> NAME/KEY: misc_feature
<223> OTHER INFORMATION: Ceres CLONE ID no. 2034916
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(213)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 80

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
```

```
          50                  55                  60
Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
                 85                  90                  95

Asp Thr Ile Asp Asn Val Lys Val Ile Gln Asp Lys Glu Gly Ile
                100                 105                 110

Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Glu Ser Thr Leu His
        130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile
        210
```

<210> SEQ ID NO 81
<211> LENGTH: 1194
<212> TYPE: DNA
<213> ORGANISM: Glycine max
<220> FEATURE:
<221> NAME/KEY: misc_feature
<223> OTHER INFORMATION: Ceres CLONE ID no.651581
<220> FEATURE:
<221> NAME/KEY: misc_feature
<222> LOCATION: (678)..(678)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 82

<400> SEQUENCE: 81

```
gtgtagttga aggagcagaa gaagaagaag agaaggtggt accgccttca attctctttt      60
tctctctcca tttctcatcc tcatcatctt attattcctc ttccatctct attctccata    120
acacccacca caccacttgt gaaaaacctc attaatatca cacactgaca tgtatctctg    180
agctccaatc caatacaaga ccacaccttg tcgtgtcgga cgaaccttgg tgtctgtttt    240
tttttttttt tttcattatt ttctccgaag agatgaggaa gggcaraggt ggaggcgcct    300
cggcggcggc ggtggatgtg aacggatcca ttttaaagga gcctcggtac cggggcgtga    360
ggaagagacc gtgggggaga ttcgccgcgg agatcagaga cccgttgaag aaagccaggg    420
tttggttggg aaccttcaat tctgccgagg atgctgctcg tgcctacrac gccgccgctc    480
ggactctccg aggtcccaag gccaaaacaa atttccccc tctctcacct ttttgctatc     540 cacacccac caccgatcct tcttstaca ctggtttcca cgatcaacac caccaccaca      600
acaacaacaa ccttaacaac cctcaaagac ccacttcaag tggcatgagt agcmccgttg    660
agtccttcag tgggccnnc ccttttttccc ccaccaccac cmctaccacc acaaccacaa    720
ctgcgacgcc gttttgact gctacgcgga gatacccgcg cactccccct cttgtccctg     780
```

```
aagactgcca cagtgactgc gactcttcct cctccgtcgt tgacgacggc gacgacaaca    840
tcgtttcgtc gtcgtttcga cctcccttgc cgtttgatct caacgcgctg ccgtttgatg    900
atgctgccgc ggatgatgat ctacgccgca ccgcgctttg tctctgatga tgattatcgt    960
gcgatgatga tttttaattt ctcatttttt tacttgattt ttttgttatt gctatgcaga   1020
agaaatatat atttaaaatg atgatcagat gtaagattat ggtaatatga tcttaattct   1080
gtgagaggaa gattccgtgt tggttatatt ttcttctttt tattatttt ttaaacattt    1140 ttatttagaa ggaaatattg aatgaaaaga aaaagagaa agtaattatg atcg          1194
```

<210> SEQ ID NO 82
<211> LENGTH: 224
<212> TYPE: PRT
<213> ORGANISM: Glycine max
<220> FEATURE:
<221> NAME/KEY: misc_feature
<223> OTHER INFORMATION: Ceres CLONE ID no. 651581
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
<220> FEATURE:
<221> NAME/KEY: misc_feature
<222> LOCATION: (137)..(137)
<223> OTHER INFORMATION: Xaa is any aa, unknown, or other

<400> SEQUENCE: 82

Met Arg Lys Gly Arg Gly Gly Ala Ser Ala Ala Ala Val Asp Val
1               5                  10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asn Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Xaa Phe Ser Pro Thr Thr Thr Thr
    130                 135                 140

Thr Thr Thr Thr Thr Thr Ala Thr Pro Phe Leu Thr Ala Thr Arg Arg
145                 150                 155                 160

Tyr Pro Arg Thr Pro Pro Leu Val Pro Glu Asp Cys His Ser Asp Cys
                165                 170                 175

Asp Ser Ser Ser Ser Val Val Asp Asp Gly Asp Asp Asn Ile Val Ser
            180                 185                 190

Ser Ser Phe Arg Pro Pro Leu Pro Phe Asp Leu Asn Ala Leu Pro Phe
        195                 200                 205

Asp Asp Ala Ala Ala Asp Asp Asp Leu Arg Arg Thr Ala Leu Cys Leu

-continued

```
                210               215               220

<210> SEQ ID NO 83
<211> LENGTH: 184
<212> TYPE: PRT
<213> ORGANISM: Oryza sativa subsp. indica
<220> FEATURE:
<221> NAME/KEY: misc_feature
<223> OTHER INFORMATION: Public GI ID no. 125550159
<220> FEATURE:
<221> NAME/KEY: misc_feature
<222> LOCATION: (7)..(70)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 83

Met Cys Glu Ala Ala Ala Pro Arg Tyr Arg Gly Val Arg Lys Arg Pro
1               5                   10                  15

Trp Gly Arg Phe Ala Ala Glu Ile Arg Asp Pro Ala Lys Arg Ala Arg
            20                  25                  30

Val Trp Leu Gly Thr Tyr Asp Ser Ala Glu Ala Ala Arg Ala Tyr
        35                  40                  45

Asp Val Ala Ala Arg Asn Leu Arg Gly Pro Leu Ala Arg Thr Asn Phe
    50                  55                  60

Pro Leu Val Ser Ser Leu Pro Leu Pro Ser Pro His Tyr His Leu Pro
65                  70                  75                  80

Gly Lys Ala Ala Ala Ala Ala Pro Pro Val Ala Gly Pro Ala Cys Ser
                85                  90                  95

Ala Ser Ser Thr Val Glu Ser Ser Gly Pro Arg Gly Pro Arg Pro
            100                 105                 110

Ala Ala Thr Ala Ala Ala Val Pro Arg Arg Val Pro Arg Pro Ala
        115                 120                 125

Pro Pro Ala Pro Asp Ala Gly Cys His Ser Asp Cys Ala Ser Ser Ala
    130                 135                 140

Ser Val Val Asp Asp Ala Asp Ala Ser Thr Val Arg Ser Arg Val
145                 150                 155                 160

Ala Ala Phe Asp Leu Asn Leu Pro Pro Pro Leu Asp Arg Asp His Val
                165                 170                 175

Asp Leu Cys Thr Asp Leu Arg Leu
            180

<210> SEQ ID NO 84
<211> LENGTH: 225
<212> TYPE: PRT
<213> ORGANISM: Arabidopsis thaliana
<220> FEATURE:
<221> NAME/KEY: misc_feature
<223> OTHER INFORMATION: Public GI ID no. 15223609
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 84

Met Arg Arg Gly Arg Gly Ser Ser Ala Val Ala Gly Pro Thr Val Val
```

```
                1               5                   10                  15
            Ala Ala Ile Asn Gly Ser Val Lys Glu Ile Arg Phe Arg Gly Val Arg
                            20                  25                  30

Lys Arg Pro Trp Gly Arg Phe Ala Ala Glu Ile Arg Asp Pro Trp Lys
                        35                  40                  45

Lys Ala Arg Val Trp Leu Gly Thr Phe Asp Ser Ala Glu Glu Ala Ala
                    50                  55                  60

Arg Ala Tyr Asp Ser Ala Ala Arg Asn Leu Arg Gly Pro Lys Ala Lys
                65                  70                  75                  80

Thr Asn Phe Pro Ile Asp Ser Ser Pro Pro Pro Asn Leu Arg
                            85                  90                  95

Phe Asn Gln Ile Arg Asn Gln Asn Gln Asn Gln Val Asp Pro Phe Met
                            100                 105                 110

Asp His Arg Leu Phe Thr Asp His Gln Gln Phe Pro Ile Val Asn
                            115                 120                 125

Arg Pro Thr Ser Ser Ser Met Ser Ser Thr Val Glu Ser Phe Ser Gly
                    130                 135                 140

Pro Arg Pro Thr Thr Met Lys Pro Ala Thr Thr Lys Arg Tyr Pro Arg
            145                 150                 155                 160

Thr Pro Pro Val Val Pro Glu Asp Cys His Ser Asp Cys Asp Ser Ser
                            165                 170                 175

Ser Ser Val Ile Asp Asp Asp Asp Ile Ala Ser Ser Arg Arg
                            180                 185                 190

Arg Asn Pro Pro Phe Gln Phe Asp Leu Asn Phe Pro Pro Leu Asp Cys
                        195                 200                 205

Val Asp Leu Phe Asn Gly Ala Asp Asp Leu His Cys Thr Asp Leu Arg
                    210                 215                 220
            Leu
            225

<210> SEQ ID NO 85
<211> LENGTH: 164
<212> TYPE: PRT
<213> ORGANISM: Arabidopsis thaliana
<220> FEATURE:
<221> NAME/KEY: misc_feature
<223> OTHER INFORMATION: Public GI ID no. 30683885
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 85

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
                20                  25                  30

Ser Gly Ser Met Ser Met Pro Pro Met Ser Ser Gly Gly Ser Ser
            35                  40                  45

Val Pro Pro Val Met Ser Pro Met Pro Met Met Thr Pro Pro Pro
        50                  55                  60

Met Pro Met Thr Pro Pro Pro Met Pro Thr Pro Pro Met Pro
65                  70                  75                  80

Met Ala Pro Pro Met Pro Met Ala Ser Pro Met Met Pro Met
                85                  90                  95

Thr Pro Ser Thr Ser Pro Ser Pro Leu Thr Val Pro Asp Met Pro Ser
                100                 105                 110
```

```
Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 86
<211> LENGTH: 218
<212> TYPE: PRT
<213> ORGANISM: Pisum sativum
<220> FEATURE:
<221> NAME/KEY: misc_feature
<223> OTHER INFORMATION: Public GI ID no. 56384582
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 86

Met Gly Arg Gly Gly Ala Thr Thr Ala Ala Ala Val Glu Pro Val
1               5                   10                  15

Phe Phe Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ala Arg Val Trp
        35                  40                  45

Leu Gly Thr Phe Asp Thr Ala Glu Glu Ala Ala Arg Ala Tyr Asp Thr
    50                  55                  60

Ala Ala Arg Asn Leu Arg Gly Pro Lys Ala Lys Thr Asn Phe Pro Leu
65                  70                  75                  80

Ala Gln Pro Phe Tyr Gln Asn Pro Glu Ala Gly Asn Pro Phe Gly Glu
            85                  90                  95

Leu Arg Phe Tyr Ala Gly Gly Ala Gly Glu Gly Phe Gln Asp His Arg
        100                 105                 110

Arg Pro Thr Ser Ser Gly Met Ser Ser Thr Val Glu Ser Phe Gly Gly
    115                 120                 125

Pro Arg Pro Val Arg Pro Pro Met Pro Pro Ser Ala Val Thr Gly Arg
130                 135                 140

Arg Tyr Pro Arg Thr Pro Val Ala Pro Gly Asp Cys Arg Ser Asp
145                 150                 155                 160

Cys Asp Ser Ser Ser Val Val Asp Ala Asp Asn Asp Asn Ala
            165                 170                 175

Ala Ser Ser Thr Met Leu Ser Phe Lys Arg Gln Pro Leu Pro Phe Asp
        180                 185                 190

Leu Asn Ala Pro Pro Leu Glu Glu Gly Asp Val Ala Asn Gly Leu Gly
    195                 200                 205

Glu Asp Leu His Cys Thr Leu Leu Cys Leu
    210                 215

<210> SEQ ID NO 87
<211> LENGTH: 225
<212> TYPE: PRT
<213> ORGANISM: Nicotiana tabacum
```

-continued

```
<220> FEATURE:
<221> NAME/KEY: misc_feature
<223> OTHER INFORMATION: Public GI ID no. 57012880
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 87
```

Met Arg Arg Gly Arg Ala Ala Ala Pro Ala Val Thr Gly Glu
1               5                   10                  15

Pro Asn Gly Ser Gly Gly Ser Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Thr Arg Val Trp Leu Gly Thr Phe Asp Ser Ala Glu Asp Ala Ala
    50                  55                  60

Arg Ala Tyr Asp Ala Ala Ala Arg Ala Leu Arg Gly Pro Lys Ala Lys
65                  70                  75                  80

Thr Asn Phe Pro Leu Pro Tyr Ala His His His Gln Phe Asn Gln Gly
                85                  90                  95

His Asn Pro Asn Asn Asp Pro Phe Val Asp Ser Arg Phe Tyr Pro Gln
            100                 105                 110

Asp Asn Pro Ile Ile Ser Gln Arg Pro Thr Ser Ser Ser Met Ser Ser
        115                 120                 125

Thr Val Glu Ser Phe Ser Gly Pro Arg Pro Pro Ala Pro Arg Gln
130                 135                 140

Gln Thr Thr Ala Ser Ser Arg Lys Tyr Thr Arg Ser Pro Pro Val Val
145                 150                 155                 160

Pro Asp Asp Cys His Ser Asp Cys Asp Ser Ser Ser Val Val Asp
                165                 170                 175

His Gly Asp Cys Glu Lys Glu Asn Asp Asn Asp Asn Asp Asn Ile Ala
            180                 185                 190

Ser Ser Ser Phe Arg Lys Pro Leu Leu Phe Asp Leu Asn Leu Pro Pro
        195                 200                 205

Pro Met Asp Asp Ala Gly Ala Asp Leu His Cys Thr Ala Leu Cys
    210                 215                 220

Leu
225

```
<210> SEQ ID NO 88
<211> LENGTH: 163
<212> TYPE: PRT
<213> ORGANISM: Gossypium hirsutum
<220> FEATURE:
<221> NAME/KEY: misc_feature
<223> OTHER INFORMATION: Public GI ID no. 62548111
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 88
```

```
Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Leu Ala Ala

<210> SEQ ID NO 89
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 100021733
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 89

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110
```

```
Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Glu Ser Thr Leu His
    130                 135                 140

Leu Val Leu Arg Leu Arg Gly Gly Phe
145                 150

<210> SEQ ID NO 90
<211> LENGTH: 775
<212> TYPE: DNA
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Encodes the protein at SEQ ID NO: 3

<400> SEQUENCE: 90
ctctctagat cttggatcac tcggacgaca tgtgttggat cccagtgcac tggccctgcc      60
agcctactca aaaaaacswt samttttckc tcccattstt tkacractca tcgttggcac     120
wtcctwcttt ctstatatat tacttgacat wawcyrctmt ycacmwcaca wacacacacw     180
taaccatggc cagcttcaca wgctttcctt ttgctcacat tgyctatggc tttagytcat     240
ytctctttag ctcwatctcc catgatggcc ccttctggct ccatgtccat gscgckchat     300
gccatagcgg cggctctcca atgccaatga tgactccacc acctatgcca atgatgactc     360
cmccgcctat ggctatggct ccaccaccta tgcctatgac tccaccacca atgcccatgg     420
ctccgatgcc aatgactcca tcttcaagtc caatgagccc accaactact atggccccaa     480
gtccagaaac agtccctgat atggcttcgc caccgatgat gccgggaatg gagtcttctc     540
cttctccggg acccatgcca ccggcaatgg cctctccaga ttccggagca ttcaatgtaa     600
gaaacgacgt cgtagcaatt tcgttccttg ttgcagctca tttgctccta gtttgagatt     660
attattaaat tggccagcgt cgtgttgtgt aatttacttt cattttttct cgagccatta     720
gttttcatgt tttatcatat atttgggttt gtgtttgata tggtacgatt cagmc          775

<210> SEQ ID NO 91
<211> LENGTH: 1032
<212> TYPE: DNA
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<223> OTHER INFORMATION: Encodes the protein at SEQ ID NO: 23

<400> SEQUENCE: 91
gctcattagg gtttctcatc tacggcgtgg tgttcctcct tcctgctctg aaaaatggcg      60
aagagaacga agaaggttgg aatcgtcggc aaatacggaa cacgttatgg tgcgagtatc     120
aggaagcaga ttaagaagat ggaggtcagc cagcacagca agtacttctg tgagttctgt     180
ggcaagtacg gagtgaagcg aaaggctgtt ggtatctggg gttgcaagga ttgtggcaag     240
gtcaaggcag gtggtgctta cacaatgaac accgccagtg cggtcactgt tagaagcacg     300
atcagaaggt tgagggagca gatcgagggt taaaagtctg ctgaggaaga tgctgagaca     360
gtatacgctt gtatcgactt ggtatcaacg ataatacaga ggaagctgag gaagatcaag     420
gagaaggact cagaccatgg aaggcacatg aaaggtttca acagattgaa ggtaagggaa     480
```

| ccagtgattg agccggttgt ggaggatgtt gaggacagta ctgactcgag cgtaggagaa | 540 |
| gaagaagaag aggatgattt gatcaaggag attgtccgta ccaagacttt cgagatgcca | 600 |
| ccattgactg tcgctgaggc agtcgagcag ctggaactag tcagtcacga cttctatggc | 660 |
| ttccaaaatg aaaactggtg agataaacat agtgtacaag agaaaagaag gaggttacgg | 720 |
| tctgataatc ccaaagaaag acgggaaggc cgagaaggtt gagccgcttc caaccgagca | 780 |
| attgaatgaa cactctttcg ccgagtagac tgcctctgca cacaccaaaa ccgataagct | 840 |
| catctctcct tacagtttac ctgtgtagga gttagggttc ttgaataaac aatgcaacaa | 900 |
| agattgtaga agtcagtgta cataaaaaaa tggccaacca ctctttgtta cttttgtggt | 960 |
| gaaaaggaag atcttaattc tctttccatc agatgatagc aatacatttt ttcataaaca | 1020 |
| agaatgttac at | 1032 |

```
<210> SEQ ID NO 92
<211> LENGTH: 492
<212> TYPE: DNA
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Encodes the protein at SEQ ID NO: 5

<400> SEQUENCE: 92
```

| atctagcttc aaccttttt tcctctcact actcaattca atatggctgt ctcacgttac | 60 |
| attatcctac tcttatcctt cacctacttg gctgccttct ccaccgctca agctccatca | 120 |
| atgtcaccaa tgatgatgcc catggcacca ccaccatcga cgatgcccat gacaccacca | 180 |
| ccatcgacga tgcccatgac accaccacca acgcccatga ccatgacacc accaccaatg | 240 |
| atgatgccca tgacaccacc accaatgccc atggggacac caccaatgac aatgcccatg | 300 |
| ggaccgccac caatgatgat gcccatgagc ccaggaccat ccatgatgcc agcctccccg | 360 |
| ccatcaccca tgggaccgtc catggcacct gaaccagcta ccatgtcgcc tggaccctcc | 420 |
| atgacgcctg ctgagacacc agccagtggc gctatcatgc agtattctag catcactatg | 480 |
| ttgggcattg tg | 492 |

```
<210> SEQ ID NO 93
<211> LENGTH: 970
<212> TYPE: DNA
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<223> OTHER INFORMATION: Encodes the protein at SEQ ID NO: 13

<400> SEQUENCE: 93
```

| agatataatc gaaaaaaatt actgtttgga tatattccac tatttagaaa gcaaatgga | 60 |
| ctacgaaaac ttgagtaaca aggtaagcca cacaaatggg aatgactccc cattacaatg | 120 |
| aagggccaac ttcattttca atgaatccca ctataaaaac tttagcaatg caaaagctaa | 180 |
| aacatcaacc atttcctcat ccactttcac tggaatcaca atcctgaaac aaaaacatct | 240 |
| tagcatttaa catactacta gacaacatga ccaccacatt ggaaagaggt ttctcggaag | 300 |
| agcaagaagc tctggtggtg aagtcatgga atgtcatgaa gaagaattct ggagagttgg | 360 |
| gtctcaagtt tttcttgaaa atatttgaga ttgctccatc agctcagaaa ttgttctcat | 420 |

```
tcttgagaga ttcaacggtt cctttggagc aaaatcccaa gctcaagccc catgccgtgt      480
ctgtctttgt aatgacctgt gattcagcag ttcagctgcg gaaggccggg aaagtcactg      540
tcagagaatc aaacttgaaa aaattaggtg ctacccattt tagaaccggc gtagcaaacg      600
agcatttcga ggtgacaaag tttgcactgt tggagaccat aaaagaagct gtaccagaaa      660
tgtggtcacc ggctatgaag aatgcatggg gagaagctta tgatcagctg gtcgatgcca      720
ttaaatctga aatgaaacca ccctcctctt agactccagt ttaagcagtt cctttccttc      780
cctctcaatt ctcaaattgt tatattaata aaagtgagaa agtttaggct tgtgctttta      840
ttttgtgtga atgtaatata ctttgtgtac gtagacttgg ctattgggag ttgctaggtt      900
gggaagtgtt tcgcattcaa caattctgta gttgaaggtg attaaatgaa ttatagctat      960
ttgtttcttc                                                            970
```

<210> SEQ ID NO 94
<211> LENGTH: 604
<212> TYPE: DNA
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<223> OTHER INFORMATION: Encodes the protein at SEQ ID NO: 16

<400> SEQUENCE: 94

```
tcgtatccac ccaacctccc actgtaaaaa agagcagcgg aacgtgcgtg catccatcca       60
attccaatcc cagtcccaat cccaccagtg tccagtgctc ggggaaccga cacagctcct      120
cagcagagaa gccagcccga tcagcagaca gcaggcatgg cgctcgcgga ggccgacgac      180
ggcgcggtgg tcttcggcga ggagcaggag gcgctggtgc tcaagtcgtg ggccgtcatg      240
aagaaggacg ccgccaacct gggcctccgc ttcttcctca aggtcttcga gatcgcgccg      300
tcggcgaagc agatgttctc gttcctgcgc gactccgacg tgccgctaga gaagaacccc      360
aagctcaaga cgcacgccat gtccgtcttc gtcatgacct gcgaggcggc ggcgcagctc      420
cgcaaggccg ggaaggtcac cgtgagggag accacgctca agaggctggg cgccacgcac      480
ttgaggtacg gcgtcgcaga tggacacttc gaggtgacgg ggttcgcgct gcttgagacg      540
atcaaggagg cgctccccgc tgacatgtgg agcctcgaga tgaagaaagc ctgggccgag      600
gcct                                                                  604
```

<210> SEQ ID NO 95
<211> LENGTH: 846
<212> TYPE: DNA
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<223> OTHER INFORMATION: Encodes the protein at SEQ ID NO: 17

<400> SEQUENCE: 95

```
acgccgtccg tttctggctc atcaggaggt ccaaaggccg cgcaagtcga cctatataag       60
cgcctccgct ccagcttggg atcaaatcac gaccaacacg taccggatct tgaccgaccg      120
aaccattcag tgctcgcgct cactcacgca tcataggcca gttaagcggg aaggaaggaa      180
ggaaggaagc catgtctgcc gcggagggag ccgtcgtgtt cagcgaggag aaggaggcgc      240
```

```
tggtgctcaa gtcatgggcc atcatgaaga aggattccgc caaccttggg ctccgcttct      300
tcctcaagat cttcgagatc gcgccgtcgg cgaggcagat gttcccgttc ctgcgcgact      360
ccgacgtgcc gctggagacc aaccccaagc tcaagaccca cgccgtgtcc gtcttcgtca      420
tgacgtgcga ggctgctgcg cagctgcgga aagccgggaa gatcaccgtc agggagacca      480
ccctgaagag gctgggcggc acgcacttga aatacggcgt ggcagatggc cactttgagg      540
tgacgcggtt cgctctgctc gagacgatca aggaggcgct tccggcggac atgtgggggc      600
cggagatgag gaacgcgtgg ggcgaggcct acgaccaact ggtcgcggcc atcaagcaag      660
agatgaagcc ctctgagtag ctcatccatt gtactcatat catatgccac gcaacttccg      720
tccatatccg tccaactttc gttgcttgac cggttcactc atgtcaccat attgtgtttg      780
tattgtgtgt ttacgtgtac taacgcatat tgtaaaatgg gcattcaata aaggaacaaa      840
ttgtgc                                                                846
```

<210> SEQ ID NO 96
<211> LENGTH: 440
<212> TYPE: DNA
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<223> OTHER INFORMATION: Encodes the protein at SEQ ID NO: 25

<400> SEQUENCE: 96

```
ctcttgtctt agtctaataa acaacacgga cgcagagcct tcgatccaga aaccatgact       60
aagagaacga agaaggcagg cattgtcgga aaatatggta cccgatatgg tgctagtttg      120
cggaagcaga ttaagaagat ggaagttagt cagcatagca aattcttttg tgaattttgt      180
gggaagtatg ctgtgaagag gaaggctgtg ggaatatggg gatgcaagga ttgtggtaaa      240
gtgaaagctg gcggtgccta cactttgaat actgcaagtg ctgtcactgt gcgcagcacc      300
atccggaggt tgagggaaca aaccgagggt tgagctttt ggttgatgtt agattttgag       360
caaattaact ggagaaatga ttcgtttttg tttaggaagc tgtattgttt caacttacaa      420
tgcagtgtga attgctttcg                                                  440
```

<210> SEQ ID NO 97
<211> LENGTH: 463
<212> TYPE: DNA
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<223> OTHER INFORMATION: Encodes the protein at SEQ ID NO: 26

<400> SEQUENCE: 97

```
atatawcttg actctccgca attccctgtc tcckccgccg cagcttccgt ctcccggatt       60
tcgccgcctg ccgcakccgc agcagctcgc cgsccacgcs tcctayccgt cgacgagatg      120
acgaascgca ccaagaaggc tggaattgtc ggcaaatatg gtacccgtta tggtgccagt      180
ttgcgtaagc agatcargaa gatggaggtg tctcagcact ccaagtactt ckgtgagttc      240
tgtgggaagt ttgctgtgaa gaggaaagsa gttggaattt ggggatgcaa tggactgtgg      300
gaaggwsaag gaaaccttcg ccwkaaaccg tgagctcgaa gtgmggtcca ctccaggwgg      360
gccatgctcg gggccttggg swgcagtctt ccccgaagct attgtyccgc aacggggtca      420
```

```
agtttggaga agctgtgtgg ttcaaggccg ggtcccagat ctt                      463
```

<210> SEQ ID NO 98
<211> LENGTH: 458
<212> TYPE: DNA
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<223> OTHER INFORMATION: Encodes the protein at SEQ ID NO: 27
<220> FEATURE:
<221> NAME/KEY: misc_feature
<222> LOCATION: (224)..(224)
<223> OTHER INFORMATION: n is a, c, t, g, unknown, or other

<400> SEQUENCE: 98

```
aacaaaccct cgttcacggt tcaacttcag cagccgcgcc tctaacttgt agcagcgata     60
cctcttctct tatcactaaa aaatgaccaa gagaaccaag aaggccggta ttgttggaaa    120
atacggcacc cgatatggtg ctagtttaag gaagcaaatc aagaagatgg aagttagtca    180
gcacagtaaa ttcttttgtg agttctgtgg aaagtacgct gttnagagga aggccgtggg    240
tatttggggc tgcaaagatt gtggaaaagt gaaggctgga ggtgcttaca cattgaatac    300
tgcgagtgct gtcactgtcc ggagcaccat tcggaggctg agagagcaga ctgagagttg    360
aaagcagttt acacttttca tttgtttcca aagcttattt taaaattatc atacaatttt    420
ggcaggtcta tgttaggaat attagtaatg tgctactt                            458
```

<210> SEQ ID NO 99
<211> LENGTH: 600
<212> TYPE: DNA
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<223> OTHER INFORMATION: Encodes the protein at SEQ ID NO: 28

<400> SEQUENCE: 99

```
ctcaaaaccc taggcttcca tatataactt gactctccac aattccctgt ctccgccgcc     60
gcagctttcg tctcccggat ttcgccgccg cagccgctca ccgcccacgc tcctacccg    120
tcgacgagat gacgaagcgc accaagaagg ctggtattgt cggcaaatat ggtacccgtt    180
atggtgccag tttgcgtaag cagatcaaga agatggaggt gtctcagcac tccaagtact    240
tctgtgagtt ctgtgggaag tttgctgtga agaggaaagc agttggaatt tggggatgca    300
aggactgtgg gaaggtgaag gctggcggtg cttacactat gaacactgcc agtgcggtca    360
ctgtcaggag cactatccgt cgtttgaggg agcagactga agcataagtt gctactagtg    420
ttttgtccta gtgaatcatc tgggatttcg cagtttagac gatactttgg attcagttcc    480
attggctgtt tagtcaagga ttatctttgt acttggtgcg atgatgttct gttatgttat    540
tctcccaccc ttttgttgcc tgattccact ctgatttact gtggattctg atttgccttc    600
```

<210> SEQ ID NO 100
<211> LENGTH: 546
<212> TYPE: DNA
<213> ORGANISM: Zea mays
<220> FEATURE:
<221> NAME/KEY: misc_feature
<223> OTHER INFORMATION: Ceres CLONE ID no. 1390976

```
<220> FEATURE:
<221> NAME/KEY: misc_feature
<223> OTHER INFORMATION: Encodes the protein at SEQ ID NO: 29

<400> SEQUENCE: 100
aagcatccac aattccacat aacctcgccc gcgccgcctc ccccacgaga cgccttcttg      60
ctctcgcttc cggtgacgcc cgccacttcc tccccgacga gatgacgaaa cgcaccaaga     120
aggcaggaat cgttggcaaa tatggtacca ggtatggtgc cagtttacgt aaacagatca     180
agaagatgga ggtctcgcag cactccaaat acttctgtga gttctgtggc aagtttgccg     240
tgaagaggaa agcagttggt atctggggat gcaaggactg tgggaaggtt aaggccggtg     300
gcgcctacac aatgaacact gctagtgcgg tcactgtgag aagcacaatc cggcgcctgc     360
gggagcagac cgaagcatga ttgcgggcag cttgaaaagg agtacctgga tttttgtagt     420
tcagccaaga gccgtgaacc attttgcctt tttagctaaa tgaacaagaa atgtttatct     480
atctgtagtg accactttgt actcatggtt tgtcatgcta aattgatggt atgcactatg     540
caatgc                                                                546

<210> SEQ ID NO 101
<211> LENGTH: 550
<212> TYPE: DNA
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<223> OTHER INFORMATION: Encodes the protein at SEQ ID NO: 30

<400> SEQUENCE: 101
atatataact tgactctccg caattccctg tctccgccgc cgcagcttcc gtctcccgga      60
tttcgccgcc gccgcagccg cagcagctcg ccgcccacgc ctcctacccg tcgacgagat     120
gacgaagcgc accaagaagg ctggaattgt cggcaaatat ggtacccgtt atggtgccag     180
tttgcgtaag cagatcaaga agatggaggt gtctcagcac tccaagtact tctgtgagtt     240
ctgtgggaag tttgctgtga agaggaaagc agttggaatt tggggatgca aggactgtgg     300
gaaggtgaag gctggcggtg cttacaccat gaacactgcc agtgcggtca ctgtcaggag     360
cactatccgt cgcttgaggg agcagactga agcataagtt gctactagtg ttttgtccta     420
gtgaatcatc tgggattttg cagtttagac gatactttgg attcagttct gttggctgtt     480
tagtcaagga ttatctttgt acttggtgcg atgatgttct gttatgttat tctctcaccc     540
tttttttgcc                                                            550

<210> SEQ ID NO 102
<211> LENGTH: 668
<212> TYPE: DNA
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<223> OTHER INFORMATION: Encodes the protein at SEQ ID NO: 35

<400> SEQUENCE: 102
aaaaattcat tgatcgaaaa aagaaaaaaa gaaagaaaag aaaagatgca gatcttcgtg      60
aaaaccttga ccggcaaaac cataacccta gaggttgaaa gcagcgacac catcgacaat     120
gtcaaatcca aaatccagga caaagagggg ataccacctg atcaacagag gctcatcttt     180
```

```
gctgggaaac aacttgagga tggtcgaacg ctagctgact acaacattca gaaagagtcc    240
actcttcact tggttctgag gcttaggggt gggaccatga tcaaggtcaa gactctcact    300
ggtaaagaaa tcgaaattga tatcgaacct accgatacta ttgaccggat caaggaacgt    360
gttgaggaga aagaaggcat ccctcctgtt caacaaaggc tcatctatgc tgggaaacag    420
ctagctgatg acaaaacggc aaaggactac aacatagagg gaggctctgt tcttcatctg    480
gtccttgctc tcaggggtgg ttctgactaa ataactattt gctctagagt tcctttcaat    540
ggctttggtt ggttgaatcc atgagacaaa gtgaatacaa tttggatttc gtgctttggt    600
tactatgatg ctatttcagc tggtttggat caatttacca aaaaaaaaa aaaaaaaaa    660 aaaaaaag                                                              668
```

```
<210> SEQ ID NO 103
<211> LENGTH: 752
<212> TYPE: DNA
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<223> OTHER INFORMATION: Encodes the protein at SEQ ID NO: 36
<220> FEATURE:
<221> NAME/KEY: misc_feature
<222> LOCATION: (639)..(639)
<223> OTHER INFORMATION: n is a, c, t, g, unknown, or other
<220> FEATURE:
<221> NAME/KEY: misc_feature
<222> LOCATION: (674)..(674)
<223> OTHER INFORMATION: n is a, c, t, g, unknown, or other
<220> FEATURE:
<221> NAME/KEY: misc_feature
<222> LOCATION: (690)..(690)
<223> OTHER INFORMATION: n is a, c, t, g, unknown, or other
<220> FEATURE:
<221> NAME/KEY: misc_feature
<222> LOCATION: (697)..(697)
<223> OTHER INFORMATION: n is a, c, t, g, unknown, or other
<220> FEATURE:
<221> NAME/KEY: misc_feature
<222> LOCATION: (700)..(700)
<223> OTHER INFORMATION: n is a, c, t, g, unknown, or other
<220> FEATURE:
<221> NAME/KEY: misc_feature
<222> LOCATION: (714)..(714)
<223> OTHER INFORMATION: n is a, c, t, g, unknown, or other

<400> SEQUENCE: 103
aattacaaat acaaatacga ataccttct ctctcacaca aaacactagt ccctcccttc     60
ttccttgtct ctttctcttc tcaacaacat gcagatcttc gtcaagactt tgactggcaa    120
gaccatcacc ctcgaggtcg agagtagcga caccatcgac aacgtcaagg ccaagatcca    180
ggacaaggaa ggtatccctc ctgaccagca gagtttgatt tttgctggta agcagctgga    240
agatggtcgc actcttgctg attataacat acaaaaggaa tcaacacttc acttggtctt    300
gaggctcagg ggaggaacca tgattaaagt gaagactcta actggaaaag aaattgaaat    360
tgacattgag ccaactgata caatcgaccg gatcaaggaa cgcgttgaag aaaaagaggg    420
aattccacct gtgcagcaga gactcatata tgcaggtaaa cagcttgctg atgacaaaac    480
agctaaagag tacaacattg agggtggttc tgtacttcac ttggtgcttg cattgagggg    540
tggtacttat tagtgtagat gccatatcag aacccaaaga catgaaagga agctctattc    600
ctgccccgtc tctctgaaga catcattgtt cttttatgng cttggttttt gtaattgtgg    660
```

```
ctactattgg tggncagtaa ctcagtatcn ttttagntgn atgctattta aaanccctaa      720
ggtgggcctt tatatgaata tctgaaccaa tg                                    752

<210> SEQ ID NO 104
<211> LENGTH: 484
<212> TYPE: DNA
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<223> OTHER INFORMATION: Encodes the protein at SEQ ID NO: 37

<400> SEQUENCE: 104
gaaatcaaat aaaaaaatct ttaagcaaga aagaaagaa aatgcagatc ttcgtcaaaa       60
ccctgacggg gaaaaccata accctggagg ttgaaagcag cgacaccatc gacaatgtca     120
aagccaaaat ccaggacaaa gaaggaatac cgccggatca gcagaggctg atcttcgctg    180
ggaagcaact agaagacggt agaacccttg cggactacaa catccagaaa gagtccactc    240
ttcacttggt cttgaggctt aggggtggca ccatgatcaa ggtcaagact ctcactggca    300
aagaaatcga gattgacatc gaacctaccg acaccattga tcgcatcaag gagcgtgttg    360
aggagaaaga aggcatccct cctgttcaac agaggctcat ctacgctgga aaacagctag    420
ctgatgacaa gacggcmaaa gactacaaca tcgaggagg ctctgtttct gcatctggtt    480
cttg                                                                  484

<210> SEQ ID NO 105
<211> LENGTH: 580
<212> TYPE: DNA
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<223> OTHER INFORMATION: Encodes the protein at SEQ ID NO: 38
<220> FEATURE:
<221> NAME/KEY: misc_feature
<222> LOCATION: (543)..(543)
<223> OTHER INFORMATION: n is a, c, t, g, unknown, or other

<400> SEQUENCE: 105
aagaaaaagg aaattttctt gggcgttctt cggcttcgtt gtcacaaggt tcgagttcgt      60
caccgtctag tacgactgtg cgagggagga agaggcgagg agaagatgca gatcttcgtg    120
aagaccctga cggggaagac catcacctc gaggtggaga gcagcgacac cgtcgacaac    180
gtcaaagcca aaatccagga caaggaaggg attcccccag atcaacagcg actgatattc    240
gctggcaagc agctggagga tggacgcacg ctggctgact acaacatcca aaaggagtca    300
actcttcatt tggtcctcag gcttaggggt ggaaccatga tcaaggtcaa aactctcact    360
gggaaagaga tcgagatcga cattgaaccc actgactcga ttgacaggat caaggagcgt    420
gttgaagaga agaaggcat tcctcccgtg cagcaaaggc tcatctatgc tggtaagcag    480
cttgctgatg acaagaccgc aaaggactac aacatcgagg gtggatctgt cctccatctt    540
gtncttgctc tgaggggtgg ttactagtct aaacctgatg                           580

<210> SEQ ID NO 106
<211> LENGTH: 987
<212> TYPE: DNA
<213> ORGANISM: Brassica napus
```

```
<220> FEATURE:
<221> NAME/KEY: misc_feature
<223> OTHER INFORMATION: Ceres CLONE ID no. 975672
<220> FEATURE:
<221> NAME/KEY: misc_feature
<223> OTHER INFORMATION: Encodes the protein at SEQ ID NO: 44

<400> SEQUENCE: 106
attccatcaa cttcagacac acagatctct tctcaatcac attacttctg gttctcccac      60
catgaggaaa gggagaggct cttccgccgt tccacccgcc cttcccggat ctgtgaagga     120
gccgaggtac agaggcgtta ggaagagacc ttggggccgt ttcgccgccg agatccgtga     180 cccettgaaa aaatcccgag tctggctcgg cacgttcgac tccgcggagg aagccgcacg     240
cgcctacgac gcagccgctc gtaacctccg cggtccaaag gccaagacca acttccaaat     300
cgactgttct ccttcctctc ctctccaacc actccatcat cggaaccaga tcgatccctt     360
tatggaccac cggttatacg gcggagagca ggaggttgtt atcatcagcc ggccggcgag     420
tagcagcatg agcagcaccg ttaagtcgtg cagcggagtg agaccagcgt cttcttccgt     480
ggcgaaggcg gcgacgaaga gatatccacg gactccgccg gtggcgccgg aggattgccg     540
cagcgactgc gattcgtcgt cgtcggtggt tgaagacgga aacgacatag cttcgtcgtc     600
ttcgcggcgg aaaccgccgt tgagtttga  tcttaatttt ccsccgttgg atggcgttga     660
cttattcgta ggcgcggacg atctccactg caccgatctg cgtctttgat ctttgagcac     720
aatgacaaca aagatgatga agaagtgata gggagagaga gtttgtgtta agatctgttg     780
ttgtaagaac cagatctgtg tttcattcac ttgtctgttt cttataaaga tcaaaccttt     840
gttacatgta acacttatat agctgctgat gattcttaat tattcaaaat ccaaagtctg     900
tagaatttat acagtatcta tcactgatgt gcttatggat ggtttggagt atgaggctac     960
attttcataa atacattcaa tgtgtgt                                         987

<210> SEQ ID NO 107
<211> LENGTH: 1034
<212> TYPE: DNA
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<223> OTHER INFORMATION: Encodes the protein at SEQ ID NO: 45

<400> SEQUENCE: 107
ctctccttcc ttcacggatt cccaaatact cgcttccaat accaattctc cgatccacgt      60
tcgttcccgc accctcgcgc tccgctgatc cggcggcatg cggcgccgcg gcgtggcggc     120
ggctgatgcg gacggtgacg tggagttgcg gttccgcggg gtgcggaaga ggccgtgggg     180
ccggtacgca gcggagatcc gggacccggc gaagaaggcg cgcgtctggc tcggcacatt     240
cgactccgcc gaggacgccg cccgcgccta cgacgccgca gcgcggatgc tgcgcgggcc     300
caaggccagg accaacttcc cgctccccgc cgcagccgcc ctccaccacc cccacatgcc     360
cgctgctgcc gccgcagcag ctccaccata cacaacatat cccaccgcca cgggcgtcgt     420
ctcgacgccg ccggtcgcca gaccggcttg cagcagcctc agctccaccg tggagtcctt     480
cagcggcgcg cggccgcggc ctgtgctccc gccgcggttc cctccgccgt cgattcctga     540
tggcgactgc cgcagcgact gtggttcctc ggcctcggtc gtggacgacg actgcacgga     600
cgcggccgcc tctgcgtcgt gccccttccc gctcccgttc gacctcaacc tgcccccagg     660
```

-continued

```
cggcggcgga gccggcgtcg ggttttacgc cgatgaggag gatgagctca ggctcacggc    720
gctgcggctg tgacgtcgag ctcaatcgag ccgctgctta gaaagaggaa aaggagaaaa    780
atatttggtt cttcccttct cttgtagccg acacgaactc tccatccact acgatgttgt    840
tgtttacttg atctgattat gatatttgcc tgaatcctag tcaacttacc tgcatgcatg    900
cctgcttgtt ttctggcgat tgaggattat cgccaaacgc caaatcttgc agcagctgtt    960
gtactgtaat atatcaacat tttacttcct tcctcttatg aggaaagaga cagataaagt    1020
aacttatttc aatc    1034
```

<210> SEQ ID NO 108
<211> LENGTH: 911
<212> TYPE: DNA
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<223> OTHER INFORMATION: Encodes the protein at SEQ ID NO: 46

<400> SEQUENCE: 108

```
aaacaaaaaa ccaccagggg aagaagggaa agacacacgc cactgtgacc aaaccctagg     60
ccggccgcga tgcgcaaggc gaggccgccg cagccccagc cgcagccgtc gcagcagtcg    120
ccggagatcc ggtaccgcgg cgtgcggaag cgccctcgg gccgctacgc cgccgagatc    180
cgggaccccg ccaagaagac gccgatctgg ctcggcacct tcgactgcgc cgaggacgcc    240
gcccgcgcct acgactccgc cgcccgatcc ctccgcgggc ccaccgcccg caccaacttc    300
ccgccctcct ccgccacgca gccgccgccg aggccccctc ccccgcggc gcgggccgcg    360 gccgccacgt ccagccagag cagcaccgtc gagtcctgga gcggcggcgg gccccgcgcc    420
cccgccaggg cccgcagcgc cgcccgagcg ggcacggcca aggaggggga ggaggactgc    480
cgcagctact gcggctcctc gtcctccgtc ctcctcgagg agggcgcgga cgacgcggcc    540
gcctcccgct ccccgctgcc cttcgatctg aacatgccgc cccgcagga ggggcgctt    600 gacgccgagg ccgatcagat gacctgccgg tacgacacgc tgctccgcct ctagctccac    660
gacgacgaga gcaaggattc gtgggagggg aactgggaaa aggaacgaga aaagcgcttg    720 ccccgctcc gctccggtcc gtcttccgat gatctcgtgg tgttctctct tgttagaaa    780 tggataattc ttgccatttt ttttcttac tttctttcct tcttcttttt tttttcttct    840
taccactttg attcgatatg tgaataattg agtcatgtaa gctgcgagca aggaaatctg    900
agcttttcct t    911
```

<210> SEQ ID NO 109
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres GI ID no. GI_15226675
<220> FEATURE:
<221> NAME/KEY: misc_feature
<222> LOCATION: (13)..(152)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 109

```
Met Glu Ser Glu Gly Lys Ile Val Phe Thr Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
            35                  40                  45

Met Phe Ser Phe Leu Arg Asp Ser Pro Ile Pro Ala Glu Gln Asn Pro
50                      55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
130                 135                 140

Tyr Asp His Leu Val Ala Ala Ile Lys Ala Glu Met Asn Leu Ser Asn
145                 150                 155                 160

<210> SEQ ID NO 110
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 28176

<400> SEQUENCE: 110
gtctcttaaa aaggatgaac aaacacgaaa ctggtggatt atacaaatgt cgccttatac      60
atatatcggt tattggccaa aagagctatt ttaccttatg gataatgtg ctactatggt     120
tggagttgga ggtgtagttc aggcttcacc ttctggttta agccctccaa tgggtaatgg     180
taaatttccg gcaaaaggtc ctttgagatc agccatgttt ccaatgttg aggtcttata     240
ttccaagtat gagaaaggta aaataaatgc gtttcctata gtggagttgc tagatagtag     300
tagatgttat gggctacgaa ttggtaagag agttcgattt tggactagtc cactcggata     360
ctttttcaat tatggtggtc ctggaggaat ctcttgtgga gtttgatatt tgcgagtata     420
atctttgaac ttgtgtagat tgtacccaaa accgaaaaca tatcctatat aaatttcatt     480
atgagagtaa aattgtttgt tttatgtatc atttctcaac tgtgattgag ttgactattg     540
aaaacatatc ttagataagt ttcgttatga gagttaatga tgattgatga catacacact     600
cctttatgat ggtgattcaa cgtttttggag aaaatttatt tataatctct cataaattct     660
ccgttattag ttgaataaaa tcttaaatgt ctcctttaac catagcaaac caacttaaaa     720
atttagattt taaagttaag atggatattg tgattcaacg attaattatc gtaatgcata     780
ttgattatgt aaaataaaat ctaactaccg gaatttattc aataactcca ttgtgtgact     840
gcatttaaat atatgtttta tgtcccatta attaggctgt aatttcgatt tatcaattta     900
tatactagta ttaatttaat tccatagatt tatcaaagcc aactcatgac ggctagggtt     960
ttccgtcacc ttttcgatca tcaagagagt ttttttataa aaaatttat acaattatac    1020
aatttcttaa ccaaacaaca cataattata agctatttaa catttcaaat tgaaaaaaaa    1080
aatgtatgag aatttttgtgg atccatttttt gtaattcttt gttgggtaaa ttcacaacca    1140
```

-continued

```
aaaaaataga aaggcccaaa acgcgtaagg gcaaattagt aaaagtagaa ccacaaagag    1200
aaagcgaaaa ccctagacac ctcgtagcta taagtaccct cgagtcgacc aggattaggg    1260
tgcgctctca tatttctcac attttcgtag ccgcaagact cctttcagat tcttacttgc    1320
aggttagata ttttctctct ttagtgtctc cgatcttcat cttcttatga ttattgtagc    1380
tgtttagggt ttagattctt agttttagct ctatattgac tgtgattatc gcttattctt    1440
tgctgttgtt atactgcttt tgattctcta gctttagatc cgtttactcg tcgatcaata    1500
ttgttcctat tgagtctgat gtataatcct ctgattaatt gatagcgttt agttttgata    1560
tcgtcttcgc atgtttttta tcatgtcgat ctgtatctgc tctggttata gttgattctg    1620
atgtatttgg ttggtgatgt tccttagatt tgatatacct gttgtctcgt ggtttgatat    1680
gatagctcaa ctggtgatat gtggttttgt ttcagtggat ctgtgtttga ttatattgtt    1740
gacgttttgg ttgttgtatg gttgatggtt gatgtatttt tgttgattct gatgtttcga    1800
tttttgtttt tgttttgaca gct                                            1823

<210> SEQ ID NO 111
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 111
atagagtttt actatgcttt tggaatcttt cttctaatgt gccaactaca gagaaataca     60
tgtattacca ctaggaatcg gaccatatca tagatatcag gattagataa ctagttctcg    120
tcgctatcac ttcgcattaa gttctagtaa ttgttaaaga ttctaatttt ttactaaaca    180
aaaactaaat caacatcaaa tatgcaaagt gtgtgttgtc cacacaagtg actcaaagta    240
tacgcaggtg ggattggacc atattattgc aaatcgtttc cgaaccactc atatttcttt    300
ttttctctcc tttttttatc cggagaatta tggaaccact tcatttcaac ttcaaaacta    360
attttttggt tcagtgatca aatacaaaaa aaaaaaaaaa gttatagata ttaaatagaa    420
aactattcca atcttaaaaa tacaaatgaa accataattt taatttatac aaaactattt    480
aattagctaa gggttgtctt aacgtttaga aaataaaaaa ttatgattgt ctgtttaaaa    540
ttacaatgaa tgaataaaaa aaatatgcaa tgaatgaaag aataaatttt gtacatccga    600
tagaatgaga aaatgaattt tgtacaaacc actcaagaat tcaaaacaat tgtcaaagtt    660
ttcttctcag ccgtgtgtcc tcctctccta gccgccacat ctcacacact aatgctaacc    720
acgcgatgta accgtaagcg ctgagttttt gcatttcaga tttcacttcc accaaacaaa    780
actcgccacg tcatcaatac gaatcattcc gtataaacgt ctagattctt tacagcctac    840
aatgttctct tctttggtcg gccattattt aacgctttga acctaaatct agcccagcca    900
acgaagaaga cgaagcaaat ccaaaccaaa gttctccatt ttcgtagctt ctttaagctt    960
tttcagtatc atagagacac ttttttttttt ttgattagaa                         1000

<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535
```

```
<400> SEQUENCE: 112
ttagtgaaat tatgacatta agtaaggttt tcttagttag ctaatgtatg gctattcaat      60
tgttatgtta ggctatttta gttagtatat gaatttaggc agtctatgca aatgatttcg     120
ttttcatttt ttcatatgta aacatcaaga tcaagtaacg ccattcgagt tgatattttt     180
tttttaaatt agtgtgtgta aattttggac cgcttatttg agtttgctaa tgaagttgca     240
tatatattac gttaaaccat aggcaaacta atttgaaaca tccgattcga tttcctgtaa     300
tttttcttgg ttaattgacc aaaatcaaga tcttcagaaa taaaataaaa gacgaaagaa     360
agctgtcgca aagcagattg tgttaaaaaa aagtggattg ggctcaaacg caacttgtcc     420
agcccgtgac aattacccta tacgcaagta agagtaacgt atcactggca aaagttggta     480
ttagttacga tatctttgtc atgggggcat gcatgggcat ggcttaagag ttaagcctta     540
agaagagtcc cacactcgtg actctcatga tcacttgttg tttcttacgg gcaaatacat     600
ttaactttat tcttcattta ttcacctata ttcttttgga taataacttt tctctatata     660
aaataacaaa catcgtacgt ttcatttatt tacaacaagc gatgagaatt aaaaggagac     720
cttaattgat gatactcttc ttttctctcg gttacaacgg gattattaca gataatgata     780
atctatatgg atgctgacgt ggaaaaacaa aatttggtga aacacgtcaa ttaagcacga     840
cttttccatg gctagtggct aagatcgttt catcacatgg ctatatcata taatacttgg     900
atgaattcaa aataaacgac tgagaaaatg tccacgtcac ggcgcaccgc tttggactta     960
agtctcctat aataaataca acaccaaaca ttgcattcca                          1000

<210> SEQ ID NO 113
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 113
tgaagtcatt taatatgagt ttgacattag gtaaacctaa tctatgagat tatagaatgt      60
agcaaaacta tcaatgtttc ttttccaaaa tattttgtgg ttttttcttt tggttcatta     120
tgttttgtta tttgtgaatt atttttaatat gaagtaatta tattgatttt atatgatata     180
catattattt tgatataaaa tttaacactt atccattaaa atagcatggg cataatcaaa     240
atcgggacta ttacgatgaa aaagatagtt aaattgtatg ataaaataaa atgtgtaaga     300
ttaaaatttt gggttttaga aaattactaa acaaaatata gacaaagtat gttgactatt     360
atttaaaatt taaatatcat caataagata tagttaaagt cattaagtgt atagcaaaat     420
gaaaattcta agattaaaat tcgattaaaa tttttttttac taaattaaat atttaaaaat     480
agggattatc atttactatt tacaattcta atatcatggg taaaaattga taacttttt      540 taaacccgcc tatctaggtg ggcctaacct agtttactaa ttactatatg attaacttat     600
taccactttt acttcttctt ttttggtcaa attactttat tgttttttat aaagtcaaat     660
tactctttgc attgtaaaata atagtagtaa ctaaaatctt aaaacaaaat attcaacctt     720
tcccattatt ggaatggtaa tgtcttcaac accattgacc aacgttaagg aatgtctttt     780 aatattttg gaacctaaat gctaatactg tataccacaa tcacttatga gtattgaagt     840
tgagatagag gaggtacaag gagacccttat ctgcagaaga caaaaagcca ttttttagcaa     900 aactaaagaa agaaaaaaga ttgaaacaca aatatgcgcc actcgtagtc caccccctatc     960
```
tctttggcaa aagccacttc actctttttc cctttttat            999

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 114
ttaatactaa cattgtagaa agccacaaaa aagaaattga aatgtgagta gatgctgagt     60
cagaggtttg gtcaatacac aacagctaat tgagataata ttatacacgt cacgatgact    120
tgttttttct cctcccaact tgttaatttc tttattctta aaattaaacc atcgcaaaaa    180
cagaagaaca cagctgtttt tctcgactcc caatttctat tttgctgcta aggacatttc    240
atttcattat ttcccaattc aggactcctt agattttcct aaatttgttt tcctaacttg    300
ctctctctca ttctaacatt ttctcatttt tttagattat cttgtacttt ttagtagatt    360
attttatcag gttttacaaa catacattga cattctaaaa agggcttcta aaaattcagt    420
gtggaatgct gatatactaa aaaaaggtca tgcaaaatta tctacgattt atctaaaatt    480
agataatttg ccatatataa ctattaacta ataatcgatc ctttgatttt ttgtttagat    540
aaaacgaaac agctatatct tttttttttg ttatcggatt ttaatcgaat aaaagctgaa    600
aaataacagt tatatcttct tctttttttaa ctaatgaaac agttatatct taaacaaaca    660
acagaaacag taaatatta atgcaaatcc gcgtcaagag ataaattta acaaactaat     720
aacaattgag ataagattag cgcaaaagaa actctaattt tagagcgtgt aaacacaaac    780
acgtcttgaa agtaaacgtg aattacacgc ttctaaaacg agcgtgagtt ttggttataa    840
cgaagatacg gtgaagtgtg acacctttct acgttaattt cagtttgagg acacaactca    900
agttatgttt gatatctaag gacttgcact gtctccaaat ctgcaggaag gactttttga    960
ttggatcaat ataaatacca tctccattct cgtctccttc                        1000

<210> SEQ ID NO 115
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 115
gatcatgatc agtttcaact cgctgtgccc acgtgtcgag agatcggcac gtgcctgagc     60
tctcagccgc tcataaatac acttgtttag tagcaacagt atactatagt agtcctctcc    120
tgtttggctt ttagcttgca tcgatggatg gatggatgga tcgcatgaga gggcttcgcg    180
aaggtacgga accttacaca acgcgtgtcc tttctacgtg gccatcgtgt aggcgtctcg    240
ccatgctacg tgtcccggag gatgtctcga tgccaaccct tataaatact gttccattcc    300
aatcccatcg ccacagccag tgcaaatctg atcgatcaag ataatcgagc a            351

<210> SEQ ID NO 116
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

```
<400> SEQUENCE: 116
cccgatcggc cttaatctga gtcctaaaaa ctgttatact taacagttaa cgcatgattt      60
gatggaggag ccatagatgc aattcaatca aactgaaatt tctgcaagaa tctcaaacac     120
ggagatctca aagtttgaaa gaaaatttat ttcttcgact caaaacaaac ttacgaaatt     180
taggtagaac ttatatacat tatattgtaa ttttttgtaa caaaatgttt ttattattat     240
tatagaattt tactggttaa attaaaaatg aatagaaaag gtgaattaag aggagagagg     300
aggtaaacat tttcttctat tttttcatat tttcaggata aattattgta aaagtttaca     360
agatttccat ttgactagtg taaatgagga atattctcta gtaagatcat tatttcatct     420
acttctttta tcttctacca gtagaggaat aaacaatatt tagctccttt gtaaatacaa     480
attaattttc gttcttgaca tcattcaatt ttaattttac gtataaaata aaagatcata     540
cctattagaa cgattaagga gaaatacaat tcgaatgaga aggatgtgcc gtttgttata     600
ataaacagcc acacgacgta aacgtaaaat gaccacatga tgggccaata gacatggacc     660
gactactaat aatagtaagt tacattttag gatggaataa atatcatacc gacatcagtt     720
tgaaagaaaa gggaaaaaaa gaaaaaataa ataaaagata tactaccgac atgagttcca     780
aaaagcaaaa aaaagatca agccgacaca gacacgcgta gagagcaaaa tgactttgac     840
gtcacaccac gaaaacagac gcttcatacg tgtccctta tctctctcag tctctctata     900
aacttagtga gaccctcctc tgttttactc acaaatatgc aaactagaaa acaatcatca     960
ggaataaagg gtttgattac ttctattgga aagaaaaaaa tctttggaaa aggcctgcag    1020
gg                                                                   1022

<210> SEQ ID NO 117
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 117
catacttaat tctaaaaaaa caacacttat agtttataag cagctcttat gataaaaatc       60
tttctgagtt atagctctgt taaacttgta ttcaccccaa aaacggatgt ttcatttctt     120 atttttact tggagtattt tattgtaatt tgtaaaaaaa aatgtaaagt gggggatatc      180
atgaaaaaca acgtcacttt gtttggtcac aatatacatt tgataaaata atggtcgtcg    240
cgtgatttag ttgattttg ttttatcaac cacgtgtttc acttgatgag tagtttatat     300
agttaacatg attcggccac ttcagatttg ggtttgccca catatgacat accgacatag   360
aaggttaaat ccacgtggga aatgccaata ttcaatgttt ggttttcaaa agagaatcat    420
ttctttatat gatctcaaaa gtatggaatt gaaatgacta atgagcacat gcaattggtg   480
ctatcttaaa aaccgaacgt ctttgaattt aatttgtttt tcaccaaagg tacctaatga    540 aacccttca ttaaaaaata aggtaacaa acaaaatttt gtattggaaa aacatttt      600 tggaatatat aatttggtaa tagaattatg agcaaaaaag aaaaagaaaa gaaagaataa   660
tgagcataat aaagccttta cagtattact aattgggccg agcagttttg ggctcttgat   720
catgtctagt aatcttaaac agacgataaa gttaactgca atttagttgg ttcaggtgag   780
ctaccaaatc caaaaatacg cagattaggt tcaccgtacc ggaacaaacc ggatttatca   840
aaatccttaa gttatacgaa atcacgcttt tccttcgatt tctccgctct tctccactct   900
```

| | |
|---|---|
| tcttctctgt tctatcgcag acattttgt ttatatgcat acataataat aatacactct | 960 |
| tgtcaggatt tttgattctc tctttggttt tctcggaaaa | 1000 |

<210> SEQ ID NO 118
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 118

| | |
|---|---|
| caagtcaagt tccaatattc taaggagaaa taatagtata ctaaacatac attagagagg | 60 |
| ttaaacttct ttttggattt aagtgtgtat gcataggcta tttattctta agtataacta | 120 |
| ttaactgtag ctagatttat acaagaaata cataaaactt tatgcatgtg aggtagccat | 180 |
| gaatatacgt acatgttgca atcgattata catgttgtat ttggatttct ctatacatgt | 240 |
| tttaacttgt cattctctaa gtatatacat accattaata ctgtgggcat gagtttatga | 300 |
| taagactttt cttttggaga ccagttttgt tttccttttcc acctatattt gtctataggc | 360 |
| ttcacggtac actagtttac aagtgttttt atatgttcta ataaaattg agattttccg | 420 |
| gaacggtatg atctgtttgc aaataaggac gtatatataa cagtatcaaa tatatttgtt | 480 |
| gttataaggc aataatatat tttctgagat attgcgtgtt acaaaaaga aatatttgtt | 540 |
| aagaaaaaaa aagatggtcg aaaaagggga gtaggtgggg gcggtcggct tttgattagt | 600 |
| aataaaagaa accacacgag tgacctaccg attcgactca acgagtctac cgagctaaca | 660 |
| cagattcaac tcgctcgagc ttcgttttat gacaagttgg tttttttttt tttttttaat | 720 |
| ttttcatct tcttgggttt ggttgggtca ctcttcaggt caggtgtgta aaaaagaaag | 780 |
| aaagaaaaga gagattgttg tgttgtaacc cctttgacta aaatctaatg aacttttta | 840 |
| acacaacaaa actccttcag atctgaaagg gttcttcttc tctcttagtc tcttcgtcct | 900 |
| tttattctcc gtcgtcgttt catgatctga ctctctggtc ttctcttctt cttcttcttc | 960 |
| ttctatttt tcttacttcg tcactgttgt gtctgaac | 998 |

<210> SEQ ID NO 119
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 119

| | |
|---|---|
| aaaaaggatg ggtaatggga cctatttcc ccaacatccc acatgcacac ttccctctcc | 60 |
| attctctcac atttatttct ttcattctaa tttatccatt ccgtgtgtaa catattcact | 120 |
| aataatctca tctcactaac tcattcattg attgtgatat gtttatctag aattagtgtt | 180 |
| ttaacactgt gtctacatat gatttccttt tcattgtatg tgaacatgtt aactcactaa | 240 |
| tcattttgta ttttcgagtt aacatgagtc tccacttcgg tagactaaag taaagatagg | 300 |
| tttgagtata ataagttta aaatttgctt taaaatcaat atttataaat aagttttat | 360 |
| cataagtgat ttttgtatgt tatattggac cttgtataaa cagactacag aagaaaatta | 420 |
| tttatgagaa cttgtaatgt tagagtggac ctcgtataaa ctaattatgt gggcttttac | 480 |
| cataaactat ttatgaaaat tattatggcc cacaccacta taactaaagc ccacatattt | 540 |
| agcagcccag tttcattgta agagacatgt tcgctctgga actagaattt tctggttttt | 600 |

```
gggtatttgt tttcttatgt gtagagaaat gatggtaacg attaaatgtt gtgtattaca    660
atttacaatg gtaagacgat taatatattt acacacaatt ttgttgttgc tgtaacacgt    720
tagtgtgtgt gatgatagaa tttcataaag ctttaactac gaggggcaaa atgttaattc    780
taaatagttg acagcagaaa aagatatgta tacataatat aaggattaaa acgtaaataa    840
taataaataa ggcgagttaa attaaaaccc tgttaaaacc ctagcttgaa acacatgtat    900
aaaaacactt gcgagcgcag cttcatcgcc atcgccattc tctctctcat caaaagcttt    960
tctccttgat tttcgcattc tttagagtct taacgcaaag                          1000
```

<210> SEQ ID NO 120
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 120

```
cagccgtaaa tcctccataa atttattttg caagttttgc tcattatata atgagcggaa     60
tttatgatat aatcgtttgt aataatgtta tgttttgatc aaaatttgaa attaaaagta    120
ggtgagaact tgttatacag tgtagataag gtggatcttg aatataaaaa taaaatttat    180
aagatgtatt taaagcagaa aagcataaaa ctttagataa aataatgtaa aaatgtgtta    240
gcatcaatgt tgggatattg gccgacccga acttaatcaa tgtcggaagc cattacttct    300
ctcccaaaag acctttttcc ttcggagaac taggaacttc ctcactacct ttcgcttaac    360
gtgaaagcca taaatttcat atattcataa aaatcagaaa atctaaaact gtttagtatc    420
acctgttttt ggtatagact attggttttg tgttacttcc taaactatat gatttcgtac    480
ttcattggat cttatagaga tgaatattcg taaaaagata agttatctgg tgaaacgtta    540
cttcagtcat gttgggtcta gatttacata ctactatgaa acatttttaag ataataatta    600 tcctagccaa ctatatgttc tatattatgg gccaagaaga tatagaacta aaagttcaga    660
atttaacgat ataaattact agtatattct aatacttgaa tgattactgt tttagttgtt    720
tagaataaat agtagcgtgt tggttaagat accatctatc cacatctata tttgtgtggg    780
ttacataaaa tgtacataat attatataca tatatatgta tattttttgat aaagccatat    840 attactcctt gacctctgcc cccatttcct tttactataa ataggaatac tcatgatcct    900
ctaattcagc aatcaacacc aacgaacaca accttttcca aagccaataa taaaagaaca    960
aaagctttta gtttcatcaa agacgaagct gccttagaa                           999
```

<210> SEQ ID NO 121
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 121

```
aagatagtac agtttcagtg ttttgagaaa aaaagctgaa ctaaaactaa aatgtttaag     60
gacacaatat ttagtttcaa ttagataatt caacagtttg aacaattttt tttttttttt    120
tttgaagtca tttatttata caatgtttta aaacgcatta agcatttagg cagccgacaa    180
acgcctattg tctaactgta aataggcgct tccacttagg ttcatattgc atatttacta    240
```

```
tatgtgtata gtgacaaaaa ccaatatttc tcttattttg gatgaaggta tagtagttgt      300
taaatgttca atataattaa gcattaatga caaataaaat aaaattaatt tagttgataa      360
aaagataatc ttataaaaag atcgatgaat agatataatg gtttactgaa ttctatagct      420
cttaccttgc acgactatgt cccaaggaga ggaagtacct taactataat tctgaacata      480
attttgtcta tcttggtgag tattatatga cctaaaccct ttaataagaa aaagtataat      540
actggcgtaa cgtaataaat taacacaatc ataagttgtt gacaagcaaa aaaacataca      600
taatttgttt aatgagatat attagttata gttcttatgt caaagtacaa ttatgcctac      660
caaaattaat taatgatttc aacaggaagt ctgagatgat gggccgacgt gtagttacgt      720
ttcttgaatt gtgagagatg gtatttatta tactgaagaa aacattattt actaaataaa      780
ttttcatttc acatcttctg taatcaatgc gggtagatga agaagttgtt aatacgatgg      840
ccaaccatat ggatctcttt tttggcgttt ctatatatag taacctcgac tccaaaggca      900
ttacgtgact caataaaatc aagtcttttg ttttcctttta tccaaaaaaa aaaaaaagtc      960
ttgtgtttct cttaggttgg ttgagaatca tttcatttca                          1000
```

<210> SEQ ID NO 122
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 122

```
aattaaatga aaccgcccct aaattaggag ggatttgggt aagtggtaac acattcactg       60
gaaacatgtg aagaaaggag gatgtcaagt agctgaaaac tcagtatagt aaccaacggc      120
ttctcaccaa cctttcatta ataatttggt catccctata ttttattca acattttgtt      180 tttcaatagc ttagagcacc ttaataccct tcagtgtttt tttataaaaa aaacaaaaat      240
tgggattaat catcaatccc caaatgtaac gtttacttag attatgttca ttttctata      300 cacacaaatc atattctttt gttttaatct tcgaaaaacg agaggacatt aaataccct      360 aaaaaggag gggacattac taccaacgta cattaacatg tttgatagca aacgatttat      420
tttgttcgtt ttgaaaaggg gaaagtaatg tgtaaattat gtaaagatta ataaactttt      480
atggtatagt aacattttcg aataataaga gagggaaaac actcgccatt gtcggcaatt      540
tagaaccaat attagaaggg ttttttttaga gaaaaaggac ttaaaagttt agagaccta      600 acaacaactt atttagaaat agacatgctt aagttgacaa cagcgagttt attttctata      660
tcgaagaaaa atacgaactt tttcttaatt agatttcgaa tgcatgcact atcgagaatc      720
gaccgtcaca agaaaaaact aatatacata ctgtacatat ctatattcaa tattggtggg      780
gatgggttta atgtgtattt ataattcatg gataaattca cacaataagg tccatgaaac      840
tagaaggtac caaaaataag cattaatgac tctttgccac ttatatatat gattctctca      900
tagtaccatt ttattctccc aaacctatct tcttcttcct ctcttgtctc tctcgctctc      960
tctcttctac attgtttctt gaggtcaatc tattaaaa                            998
```

<210> SEQ ID NO 123
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 123

```
gattgaatga tgagtgtgca cccttgtatt actaataaaa aatttagcaa cagttataag      60
ctaacgtcat ccatgagtca ttcattagat tcactatttg cgttctcaaa aatcgaattg     120
ttaaaatttg agaagctcta atatacgagt caatgagatg tggcaaaagc atgtccttga     180
ccataaaatt tcgaggggtc aactcattag ataaggacaa gaatcaacca attgaaggcg     240
tcttctataa caagtttctt tattactaat attaaagtcc aatggggtga ggggagaag     300
aacttaaata aaaggaaata attggtaagt gaataaaatc taaatacgat actagatgat     360
tgatttgtgc tagtgcatgg tattagatca gatatgtgtt actattcgaa ttcaaattgg     420
catattccat gttgttgata agaaaattgt agaagtgtaa agctgagtt actatattca     480
aactagtggt ttacataaag tgagacaaca actgtttcac aaaaatgact ataaaatagt     540
aagtagtatt aggtcaattg attttaaaat tttaatcaaa ttcaaatttg tgatataatc     600
aaatttgttt atagaaaatg ttaagaaatc aattttggca gaactaattc agtgagaaac     660
aatcatttac aaaaacaatt ttaacattat ttaacagtaa gatttgacat ttaacccgtt     720
cgtgtgaacc catcatatct aacatggctc tacccatgac gcctccatgc catggacaat     780
tttgacagat cagaagttct gaacgtggac gaggtaagaa caccatgatg atacgattgg     840
agttagttat gtcgccaccg acatcactgc caatctcatt aataaaagtg gtactaaatc     900
tctaatctct attaactata aatataacaa agaaccaaaa gaaagtttct tatctctctt     960
atctttcata atttccaaga aacacaaacc ttttctacta                          1000
```

<210> SEQ ID NO 124
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 124

```
acgttcagag gcatcgcttt tgtacaaatt gaagcgggtt tgttcaatat ttaaaataac      60
acaggaaaca ttcaaatgta ttattgatgt tgcttaggtt tgtgaaatga tatgaaccat     120
atcgtatata ttactagatt tttcttatat gttttaaggg tagtggggct gacctatcat     180
tctgtttggc attaccaatc agactatcag agtattcacc attcaggatt ccataactag     240
aaaaagaagg ggtttacatt ttctcatact gtataatttt ctactatcag agattttatc     300
gattacatta atctcatagt gattattctg atttataaaa aagttgacaa ataattaaa     360
accagtattt tataacaaga ttgtctctct cccatggcca ttattttgac ctctgactta     420
tttaaatctt aattaacagc ataatactgt attaagcgta tttaaatgaa acaaaataaa     480
agaaaaaaag aacaaaacga aagagtggac cacatgcgtg tcaagaaagg ccggtcgtta     540
ccgttaaggt gtgtcgaact gtgattgggc cacgttaacg gcgtatccaa aagaaagaaa     600
gggcacgtgt atagatctag gaaaaagaa agaatggacg gtttagattg tatctaggta     660
ccaggaaatg gaacgtcaca ccaaacggta cgtgtcggat cctgcccgtt gatgctgacg     720
gtcagcaact tccccttatt catgcccccc tgcccgttaa ttacgtgtaa cccttccatg     780
cgaaaatcaa accctttttt ttttttgcgt tcttcttcaa cttttcttt taaatcaaac     840
cttttctttt taaaatcaca ttgcatttcc taacgctcaa caaaatctct ctctactaat     900
atctctctct ctctctctct attgttgaag aagactcata atcggagatt gtttgttttt     960
```

```
ggtttgctct gtaaattgga gaagttttgt tagagatcaa          1000
```

<210> SEQ ID NO 125
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 125

```
aacattttct ttaacttact cttaaatttt aatagtaagt tgatgcatgt tatgttgatc    60
cgtcttgatc acaaatattg ttttatggac gaattctttg acagtaaatg ctatagtga   120
ctcagcttgg agcatcccga tatgaaaaca aagtgcagta ttgtgtcgtg gtcatcacta   180
acgcactttc ctagaactat cgcgcgtgtt tgacctatgc aacacaccag atgtcatgaa   240
cgtatactta aatagaaaca atgatataga caattggcta tattctgtca tggaacgcaa   300
accggataac atgtctatta gattcatcgg acttgatcat ggttatgtct aatagacga   360
attctttgtt aacgattggt taaaacggct cacgttagag catcctacta tgacttcaaa   420
attgataaat attacatgga aatcacttta attttagtta gaaggtagtt aatttagata   480
ttcttattta ataaattaaa aaatagaaga aaaaagatg agaagagttt tgtttataa    540
aataagaaat atcttttatt gtaattttaa aattaaacaa atttaattta tattaaaatt   600
atctttgttt tattgttaag gcaataatta ttttttggt gggaattgtt aaaacaataa   660
ttagtatact gttaagtggt cctttaataa taagataacg tgatttaaaa aagaacgaga   720
caggctaata tagtagagag gaaaaaatac aatttaggcc caataaagcc caatatagag   780
ttgtgctcaa acacaggtct tcgccagatt tcctatgacg ccgtgtgtca atcatgacgc   840
caagtgtcat tcaagaccgt cacgtggcgt tgtttctaca cataggcgat ccatacaaat   900
cagtaacaaa cacgaaaaga gcattcatat gtacgaaagt agaaaagaag agactctttg   960
tgataaaact aagtaagaaa tagcataaaa gtaaaaggga                          1000
```

<210> SEQ ID NO 126
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 126

```
gtttccaaaa ctagtattct ttatttgctc tattcattat attttttatat ttgtaacgtc    60
ccgaccgtct ttattaggtt tcgacaatca cttctcggaa ggtcgtccat cctgaaatta   120
ctctatccta aacatgttta actataaaat tctctcgaaa cttttgtaac gtatataacc   180
acataaattc tcttaaactt atttgcatac accattatat ttctgaaatc gatatgttac   240
aatattattt aatatttaga ttacttttac tgaatcgaat taaatatcaa atcgaaacaa   300
atctaatcta ccaaaaataa ttttgttata aacatttctt gcctagttct acctcatata   360
cattttagtt aaagaaagaa atcacaacaa ttcccataat tcaataatta aatccacaaa   420
atcttggagt aagtaagaga aataaaaaga tagtatctta acataaacaa ttcaaagatg   480
ctctctcaca caattcacac acacttacaa aacaaaagac agaaacaatg ttttcattca   540
aatcaaaaga agttataaca ctagtacaaa aaaagctcaa attctaatag taactctttt   600
```

```
tatttcccaa ttacccaaag attctctctc acttcacaaa actagctttg agagtcgtgt      660
tccacaaaat ccattaaagc tgaaacggtt ttgctcacca ttcaaacaaa tacaaaattg      720 caaaaccccca aattataaca aataatata aaaattaaac cgctaaaaag agtgaaccaa     780
caaaaatcgc cgaatgtgtg tgtaatgaga aaaccgaccc atcatcccaa tcatctcttc      840
ccgtgtcact ctcttcctct cccacgtttc ttctctcttc cctttatggg ttttaacttc      900
tccttcttct tcttcttcaa tcttcagttt tcaaattcaa caacaattca cattttgatt      960
tcttcatcat ctctctctct ctcgcttctc tctcaaatcg                           1000
```

```
<210> SEQ ID NO 127
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 127
```

```
tagtgcgcgt ggggagaggg aatggtgaaa ccttagtggt taagttatga ggaaaatgat      60
aaaaggataa acaatcaaa tgcagcttga aacggccata acataaagta ccttatggtg      120
gtgcgaatat ttttgtgttt ctttcactct tttattgctg aaagctacga cacttgtctt     180
aatatattgt ttccgcaagt cacatgatct acttttttatt taacgtctag aaacgccgag    240
atatatgatg attagtatat cacgtctatg caaattgtta gttcgtgttt ggccaaaaga     300
tatcgagaca tgtctgaaga accgagtctg gttttgagat atttcttcaa gcattactat    360
acaatagaaa aaggagacac gcgaatatga taatagcaaa aggcataaaa aggcgaaaat    420
taaagaaaaa cgtaaagtga tttggcctca atcaacggga acgtatctta atttttagagg   480 ttcttctttt acttttgaga cgagagagtt tgcgtctttg cgagctgctt tggttgacta    540
aacattatca tattgaaaac caaaatacaa cggaggaata tttgtcacag tttcactttc    600
acattgtttc cttaacgttt aatcaaccttt gttcaaaatt tctatagttg taatcatcat   660
tgtttacaaa atttttcgttc aaagatgatt ttaaataaaa ttgtgaaaga aaaccttttc   720
tgaaataagg attggatgat agtgttaaaa gaaaatatg aactgaggca aaaagaggag    780
tggtccccgg aagattgtga aatgtgtcat ctaaaccagc cagacgtagt cacgtgttct    840
ctctagcttt atgaacttcc ttagccagca ccatcattgt gattgtagta tatatgtaac   900
cctaccttca tctctcccat tttccattct ccatatagac tcctttacaa tatacaaaac   960
ctatccaaaa gcgaagaagc caagcaaaca tattataaaa                         1000
```

```
<210> SEQ ID NO 128
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 128
```

```
gtcatatctt atcaacacgt caacgatcaa aacctttagc ctattaaatt caacggctta     60
gatcaaaacg aaactaggtg ggtcccactt ttaatatcgt ggctgcataa catttcctcg    120
ataactgaag ccgttgtggt ctttctcaga atctggtgct taaacactct ggtgagttct    180
agtacttctg ctatgatcga tctcattacc atttcttaaa tttctctccc taaatattcc    240
gagttcttga ttttttgataa cttcaggttt tctcttttttg ataaatctgg tctttccatt    300
```

```
tttttttttt tgtggttaat ttagtttcct atgttcttcg attgtattat gcatgatctg    360
tgtttggatt ctgttagatt atgttattgg tgaatatgta tgtgttttg catgtctggt    420 tttggtctta aaaatgttca aatctgatga tttgattgaa gcttttttag tgttggtttg    480
attcttctca aaactactgt taatttacta tcatgttttc caactttgat tcatgatgac    540
acttttgttc tgctttgtta taaaattttg gttggtttga ttttgtaatt atagtgtaat    600
tttgttagga atgaacatgt tttaatactc tgttttrcga tttgtcacac attcgaatta    660
ttaatcgata atttaactga aaattcatgg ttctagatct tgttgtcatc agattatttg    720
tttcgataat tcatcaaata tgtagtcctt tgctgatttt gcgactgttt catttttct    780 caaaattgtt ttttgttaag tttatctaac agttatcgtt gtcaaaagtc tctttcattt    840
tgcaaaatct tctttttttt tttgtttgta acttgttttt ttaagctaca catttagtct    900
gtaaaatagc atcgaggaac agttgtctta gtagacttgc atgttcttgt aacttctatt    960
tgtttcagtt tgttgatgac tgctttgatt ttgtaggtca aa                     1002

<210> SEQ ID NO 129
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 129
tgtggccact aaagatttac ccttaaccgg gcccatataa gcccacgtca agtggcgctt     60
atacgctctc cgtaagagag ccaacatttg gtatgtaatg ttgcaaatta ttcttcaaga    120
caataaattc aaatataatt caatattgtc caaatatagt gatgtacttc agttgtgcac    180
atagaaactc cactaaacca acttttagat agatgcattc acaaatttc aacaatgtcg    240 cgaaagtcta atccatcacc agattctaac attttaatta ttatatttaa ctatacatac    300
tctaatcagc atgagtcaaa cgtgtacaat agcccaagca tataataaga ccaaagtcaa    360
actcaaataa atgtctccaa actcaaaact tgaaaaagac ctaattatta catggtagat    420
atgactttgt cgacaagtaa accaactaat cctcgaagct accttctctt cccagttatt    480
atgtgtgatc gatttataaa tctcttcttc taataacacc tatatttttc ttatgatgtg    540
aataaatata aaacttttaa ctttaaaaca tatttatccg aaatattgca cttagatttc    600
aaatagataa ataatagtac tatctaactg atattgaaaa gacctaacac ggaaaacagt    660
tttataaaaa atcccaaatg tgggtaatta tcttgatttc ttggggggaaa cagaaaatgg    720 attaagatta atcggagtcg tgtcaagcag ctcgttaata actgtagcaa gttgactgag    780
taagcatcaa cgtgtcatct ccgtaaagcc cattatttct agtctcgccg cgtcttctct    840
tccacgtagc acttcacttt ttctctcctt tgtttccttt tggaacacaa acgtttctat    900
ttataggaat aattacgtcg tccgtatctg tgtcggaaca tagatccaaa ttaaaagcga    960
cttacttaat tacatatcgt tcgtgttttt ttcttcaaaa a                       1001

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743
```

<400> SEQUENCE: 130

```
tcgattggcc cgatcggccc caaaatcaag ctgagccgct tcaaacttca gcttttgaaa     60
tcaccccaa  actcatgtcc tcttatcatt ataactaaag gatctttcat tttatttaac    120
tcatcgtctt gcactaccca acccaaaggt tccaactata cccgaagctt tctaaaggtc    180
caaagacttt tttttcgag  ccagactatt caagccaaga aaagccaaac cccacaagcc    240
agtactttc  aattccatat tataaactta tctgtcttgt tttagtccca ctaaaaacaa    300
cagaatttaa tttaggttga gctaaaaccc ttgacaaaag tgtatagtcg tcgattcagt    360
agcacactca tcactcatca gatttgatag ttgacctaaa gtatgactac tccatttcaa    420
ctaacaaatg aaaataaaag agacctaagg gttagaggat tgaaactata ctctcaagtc    480
ttttatcact aggctactac cagctagtta acttgatgga tttaagcaag aaaacgtaga    540
atttatattc gagcagattg tttagctaaa aaagcttggg tttgaaattg ccttttctcc    600
catataagca cgtcggttcc taaataactc tttctagcgg agagtgtctt tccaataatt    660
taataaaaat ggtgtttgta tatcaaaaaa aaagaaaaaa agaaactgat cgagatagaa    720
cgtttgcagt tttataaaca atttaaaaaa caaaaaaaat taaactcaat gtattttta    780
ttaattcaca acaataata  aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

<210> SEQ ID NO 131
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 131

```
agctagccac atcagtgacc aaaaaagata attaacaaac caaataaaat aacaaatttt     60
gatcatttgg aataaaattt ataaaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
tacatgatat ttagttatta tagcgtaatt aactaagata agaaattaac taaagtgata    600
ttctgattat tattatttt  gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
taatcatttt ttcgtgaata attctctctc ccattccatt atttctcagt atctctcttt    900
```

```
ctttcccta ctttattgtt gcttttaaac cttcaatttg ctcataaacc aaatatataa    960
tatcaaaaca aacaaacaaa aaatcagaat tcccctaata                         1000
```

<210> SEQ ID NO 132
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 132

```
aaagttttga attattggga atcaatttcg aagttttgta attctttggg ggctaatagg    60
atattttatt ttcttggttt cgtctattgt tgttttttcta tttatggttg ggcttttaga   120
actctggaca ggcccatgtc atatgttttc ccttctcctt atattttca tttttcattt    180 tgttaaatta atgcataata tccaaaaaca atttaaattt ttgaaggaac cctttagtta   240
cggctccgaa gctttcacaa gtgagaatgt gagatcaaag aaggcaaatg gaggatttta   300
aaagttaaaa tcatctttta tctgcaaaag ttgacaattt ttttgtatca aatctaaatc    360
atcaaactct cttaaactac aagagcataa caacctctat gtaatccatg aaataatctg   420
cttgaaggac ataacataaa tcattatggc tagagtgact aacttcaatc aaatcctctt    480
aactctagct cccttacaat ggtatcgtaa aacattatgc attagggatt gttgtcctag    540
gaaaataaaa taaaatccc cacagaccaa ctaccatttt aacttaaaaa taagcttcgt    600
ccgcgacgaa ttgttttcca tcctaaaaat agaatggtgt aatctgctaa tggtttagtt    660
ccattaactt gcaagttcta ttgaaagcct aaatgtcaat aaagatatta aaattcggag    720
tcaaaagaca aatgaatcaa aagcaacaag acaagtcagc tccattcttc actacccatc    780
ttttacaata aatcatctct cttttcacaa atttcaaact actctcattg cccttttagct   840 ttgttataga gccaacacta cagagagact cacacacttg tttcaataat taaatctgaa    900
tttggctctt cttataaact a                                              921
```

<210> SEQ ID NO 133
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 133

```
aactacaagg gagacataat atcaccatct ggttcctgtt atcatctgaa gatttcttgt    60
tttaccttcc agtgataaaa tgatccttat aatacatata gatatattaa attgctgtat   120
tttaagatta tagatatata aggtacatga gagtgtttat ttaaaaaaat tcacttggaa    180
ttcatgtttt gtgatacgtt agattggaat ccatttggga aaagaagaat catctgttct    240
tatgtctcaa attttgactt cattcacttt tcttcttgtc ttttaagaaa gcttccacaa    300
tctaactgtt cgatgtgaaa actgagattc gagtaagaaa atgtgaactg tgttatactg    360
ttttttaatt agataattta gattgcactc agataaatta ataacattcc tcgaatactt    420
ttatgtgatt ggatatatta ggtatatctg ccaaccaacc aataaactgc tatgtttaaa    480
caaattaaat aaattagtat atgtttactc aagaataaag aagatagaaa agaaaattct    540
atatgagcta aatttgctgg aggaggcatc ggacgtgggt accagacctt tccaagcaca    600
cgagtagtgc ttagccatgt catgctaaca tacaccattt ggttcataca aaatccaaat    660
```

```
caaaatctat ttttaaaatc ttttgcacac gtctttgaaa aacacctctc atactatagc    720
tacggaagct tcaatttcaa ggtttgtcta aaagctaacg att                      763
```

<210> SEQ ID NO 134
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 134

```
atactggtat gcttaaggtt gaagccaaga tctctgtctt acccaagtaa ccactttcta     60
ttagaaggga tcaacactaa gaatatggag atttaagcct aagggctaag gcggttctca    120
acaatacatg atgtgaatac aatcacagac gatttactga ggtttgttga taagatcttg    180
atcagtctct gcatcatctg ttcaacaatc tcaatctttg actgtttgct ttcggagcca    240
taaacagagg aatcccttat tccctgttat aggagcaata caccaagtat tatttccatg    300
gctgaaattc tcttatggaa acctaattgt tccattgaag ctgtaaaatc gaatctggtg    360
aatattctcg agcaaagccg catgctaatt atgtcaattc agaagagttt gattaggaga    420
ctcgaagcga gtttgatgat cttttcttgat gttcaactcc gattgtaagg gtataattga    480
cttttcatgt attacggctc caccacctga cactaaggca ctctttgtcc atctcgttgg    540
tatcatcgga ttcggatggt aaaaataaaa agagcagagg aaacttgtta ctcatgcaag    600
cttctcaggt gccacgtcac tccattacgt gtcatcttca cacaccatct cgctcaaaac    660
cgatctcatt tttcaaacct taaggcaga agcaactgat taagttaaca ctcttgagaa    720
gctctcgatt aagcttgaac ttggaggatc a                                   751
```

<210> SEQ ID NO 135
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 135

```
tctctttaaa tcagttaact aaccgtttat atatttacga taaggtttga agagattatt     60
gataaaataa tacatttcat aatcccgcgt tcaaccgttt aaagtaacat ttaagttgac    120
tatatctaat ttttttttcca ttaaatatgg agctggtaaa ctttatcaac ttctaaaaag   180
tgtaacaaca aaaattaggt caatcacaat tctgtttttt ttattatttt ggattgactt    240
ccaattgcaa atagtcttag tgatcaccat tatcatacat atatacatca gtaggtttc    300 atcatgatat accacaaagt atttgacaag ccatatggtt ttggatcaaa aagtcggtcc    360
aaaattaatg tttatgtgc aagaaccgac ccattgtaca cacgtgttaa catcttcaag    420
actttcatct ctattttct tttggtcatt aagatacca ttgatccgaa tctgttacat     480
tcccacctac tttttttaatt tttactatcc actccaaatt aaacacaacc gatgatttta    540
ataattggaa gcttttaaaa atatttcaaa acaagcctct ttgtgtttgt ctatatatat    600
acacgtaata agaaggtgaa tgaatctcac agcttacttg ttctaaggct tccaataacg    660
aaaacagta                                                            669
```

<210> SEQ ID NO 136

```
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 136
cgggaaacga caatctgatc tctagtccag tcgattggcc cgatcggccg attataaact     60
tacatgagac aagtataaat aattattata aacttattaa gtttaagatc aaggcttttg    120
tgcaatgtat caatgaatgt tagatgtgat atgatgaaag caatgttttg aacacataca    180
tagtcattga tcggaatgtg tgttattaga aatgcatgcc taagccgata gggttatcta    240
tgtttggtct tggacattat agccaaattt cgaatctaat tcttccaata tatatttttt    300
tttttttgct tagggccact actagtattg cttatcaatt ttaagagctc atgaaaatgc    360
aacaatatag tagttgcaaa tccttgtttc aagagaaatc aaagggccac ttgtgaattg    420
aataataata atatttgcaa ataacctttc actaaaccat accaacaaaa ccacacagat    480
ttggcaaaga cataaccttt gggagacgtg aaaaggctca aaatttgaca attgtcctta    540
caaattcgct cattagtgca attgtgagat ttgtttgcat ccaaatccaa ttcataactc    600
acactcgtct caaattcgaa aaggcctgca gggccagtgc actgggatcc aacaatgtcc    660
tccgactcgt ccaagatcaa gaggaagcgg aaccgcaccg cg                       702

<210> SEQ ID NO 137
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 137
ttctaggaag actggtcaag ctaagctgtt tctgtttttt gtttttgtac tttacttttt     60
gtttgctagt gggaactggg tttattgggc cttgaagttg ataaaagatg aataaaagac    120
atatcgccta aagcccatat gagaagcaga agacaaaaac ctccaacttt gggcataaat    180
tttgattata gttaaaagtc cagacccaat ttggcacctg gcttagttac gattctaagg    240
catgacacct gcctaatatg tttattacag aaaataaaga gaatcagcta ggtgtccctt    300
attgaacaca ttaacaaact ccaacgacac tacgtgtctt cgtgactctt actatatcca    360
aaaacctata gctaaagctg aatttttccat gattagtata gtcccaacca aaaaaatact    420
gaagaaggca taagc                                                     435

<210> SEQ ID NO 138
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 138
agtgtatttg aaaacgacat tgaagaatta atatatttttt ttttaatttt agttttttat     60
agtacaaata ttaaaacaaa caatcctacc atatcataac atttgtaaat aacatttttaa    120 gttttgttttt gagttttaat taattttcta tgcaaaaaa atgaagtcaa tagactaagt    180
gaatcatata gtataaataa acacaattta aatagtttca aataaattta gaaagaataa    240
```

| | |
|---|---|
| aacaaataga atcagaagg tgtctgtttc ctcctcgcaa catacgatca aagagaaaca | 300 |
| acttgaccct ttacattgct caagagctca tctcttccct ctacaaaaat ggccgcacgt | 360 |
| ctccaacctt ctcccaactc cttcttccgc catcatc | 397 |

<210> SEQ ID NO 139
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 139

| | |
|---|---|
| agcagaacaa ctatatttat tgtgtcacat aaatctgaga tcatttataa ccaccaaaga | 60 |
| acctatacac agtaaatgac aaatgtatct ccctctatct ctattgccca tatgtagatg | 120 |
| ctaaagtaag atttctcttt tttttaatgt acttttttt gtataaagta tattccataa | 180 |
| gaaaaaggaa aagcttgttt atggatcaat tgaccccaaa aaaagttttt agatcaaagc | 240 |
| ccaatataaa aaaaaacac agtagtgaca caaaggaact taaataaacc atgaattgat | 300 |
| ctataaacag tagagatcga taaggcgaac atttttccatg tgaagtgtct tctttcatct | 360 |
| ataatatttt tgacatccaa taatttcctc tataatatca ttcacataat tgatagaaac | 420 |
| attatgttag aattgtccac atcatttgag ctgtaatata ttctgttta acaaattata | 480 |
| tggtagttgc ttaatcttat gtccatcttc ttctatgcat cgttttcgcg cctagttgtc | 540 |
| cagtccattt caactaccta cctctaattc ttatcttaaa acaacatttt ttaatttaag | 600 |
| tattatgctc aaagactaac tagatagaaa accgttatta acattaaac gaattaaaag | 660 |
| tcttacatgg aaaatgtagg tttataaacc acgagttatg attgacaata aaaaaaatgc | 720 |
| aaatcatcaa tcaaagaga cttgagtgcg actctatatc aaccattgca attaaaatta | 780 |
| tctatcacaa aaattttaga cagattaagt taatttagtc taaattcact aatttatttt | 840 |
| ctataattag taattaacta tatttattta tttacacatt ttctgataat ttagaaattt | 900 |
| gcatgaataa caaatataag attttggaaa ttagtagcaa attaattaa taattatttt | 960 |
| tgcctaaatg aaccaaacta taaaacctcc acatacacca gtcatcaaat ttacagagac | 1020 |
| aaca | 1024 |

<210> SEQ ID NO 140
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 140

| | |
|---|---|
| ctcgagagat gaagtcttag taatgtttga acaaacaata atcacgtttt ccatcaaatt | 60 |
| cgagcattta aagtttatat tactacatgc cccaagatga taccgtccat ctcatccgaa | 120 |
| aatatttctg aaattgcgct aagacaacaa tgtttgctca aattcgatca tttaaagttt | 180 |
| acaaatctct catcaatctt acaaacttct cacactaaac agaggtacat attttcttat | 240 |
| aaagacaaaa ggttcgaaca gctggcttct caactcgagt tgtttgtcag ggcctctctt | 300 |
| cactaactac aagttggtac ttcaaatatt ggtggctagc ttcacgtgat attgtctaca | 360 |
| aattaaaccc atgaaaaagc tgcattaatt gttccaagtg aaccctgagg agtgtcaata | 420 |
| gtctttgctt tagtgtgatc attaaaccaa atctctaaat tcctaatttg tactaacatt | 480 |

```
tggaacgtat ttcctactct tctccctgct ccaactccca aaaataagat tagttagatt    540
tctataacta atatacatgt atactcccaa aaacagtaaa accatattaa taaagctaat    600
tttgcataga tttatttcgg taaaccggcg gttcaagttg gggaaaaaaa agacaaacgg    660
tctaaagtca tccaaagaca aaaaaccaaa gacaagttga gagagacgag accaatcaca    720
acattgcttc gtagattgcg tgacatcatc cttgacggct actttcattt gtgtcttatt    780
tggataaaac gcacgtgttt aattcacgaa ccttcatagc aataagaaat ttccattact    840
ttcatatttt caactttttt tattacccat tacatgctta aaatattaat tcacaagtct    900
ttgtcaaaat tcaatatttt ccaggttcat gaaccctttt tatctcaatc tactctataa    960
tatctcccta taaattacaa caaaacctct ttattttca                          1000

<210> SEQ ID NO 141
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0019

<400> SEQUENCE: 141
gatataagta gaatcatttt ttgccgccgt ttctcgctaa cacaccgaaa actgaatcaa     60
atctcctagc tcttctacgc aaaatcgagt gcatcgacaa tggcggaacg tggtgtcgaa    120
cgtggtggag atcgcggcga tttcggacgt ggattcggtg gtcgcggcgg tggaagaggt    180
ggtccgagag gtcgtggtcg ccgtgcaggt cgtgctccag aggaggagaa atgggtgcca    240
gtgactaagc ttggtcgtct cgtaaaggaa ggtaagatca caaagattga gcagatctac    300
ctccattctc tcccagtcaa ggagtaccag atcatagatt tactcgtcgg tccttcattg    360
aaagacgaag tgatgaaaat catgccggtt caaaaacaaa ccagagccgg tcagagaacg    420
agattcaagg ccttcatcgt cgtcggagat agtaacggtc acgtcggatt aggagtcaaa    480
tgctccaagg aagttgcgac ggcgatcaga ggcgcgatca ttctcgcgaa attgtctgtg    540
gttccgatac gaagaggtta ttggggtaac aagattggaa aaccacatac ggttccgtgt    600
aaggtaaccg ggaaatgtgg atctgttact gtacgtatgg ttccagctcc gagaggttct    660
ggtattgtgg cggctagagt tcctaagaag gttcttcaat tcgctggaat tgatgatgtc    720
tttacttctt ctagaggatc caccaaaact cttggaaact tcgtcaaggt atgtactttc    780
acaatggctg ttttggtttg atgaactctg aattaggcag tgaaaaagta atcattacca    840
gttaagtgaa tttatattga agattaggat ttagctgatt gtattggttt gagcatgtga    900
gtttgtgttt aagattgctt gaattgaaat gctttaggtt gtttgattac gctaaattct    960
gactaatgta attcaaattg ttgttgtttt ttttggtc                            999

<210> SEQ ID NO 142
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 142
gtcagtgaag tcgattggta gtacttgaaa cacttggttg gtttcatgta tttggcctat     60
atataaacaa acatcgtaat tatatacgga ttttttttcgg aattttacgc catatctgta   120
```

```
agtatatata acatgcatgt cgttttcaaa ttcatatgat gaacgatcca cgtaagtgct      180
actactccta caatattgca tgagagagat atgtatttat aaattttatt ttgaagaaga      240
aataagaggg aaggttactt gggtggatcg atgtgaaaac aaaagaagaa aaagcgaaac      300
ccactaagcc attacatgat atcgaccttc ttatctttt  cctctttatt ttattttct       360 catcttcttt ttgtcaggac tttttctac ttaatgaaac ctccaaacta tctaactaat       420
acactcccat gtagaataaa gaaaattata aagatattg ttgatatttt gtaactagaa       480
aatatatttg ctctgtaatt tttcgtaagt taaatcaaca ttttaaagta gaaacaaata      540
ttactgcaaa aagtaggatc attatttttg tccaaaatct cagttagcta tagggttgta      600
gtaaaaacaa aacacattct tgatttgccc caaaaaataa agagagagaa gaatattgtt      660
caaaagtggt ctcttctctc tctaattatg ttttcactaa acccaattag attcaaacag      720
tctacaaagt ccaaaagata aacatgggac aacaattcga tgcaaaaaat cctcttttca      780
tgctcttttt ttattctcta gtcttttaaa ttactaataa aaactcacaa atccaccaaa      840
cccattctct acaactcacc ttcatctaga tttacccact cccaccgaga aacacaagaa      900
aaaaaatata catatataaa tatacaagac aacacatgat gctgatgcaa tatacacaac      960
aaagtattaa atcttagata ttgtgggtct ccctttcttc tattcatttt cttattcatt     1020
aaaa                                                                  1024

<210> SEQ ID NO 143
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 143
ccgttcgagt atttgaaaat ttcgggtaca cccgcctaaa taggcggacc ttatctagta       60
tatatataca tttgaactat attgtttact ttttagttga tttaggctat gtcatgacat      120
tgacataaat ctacctgtta tttatcacgt gtaattcgtg taaagtgtaa actagaaagt      180
tcaaatacgt atttgttttt gttctgttat ataggattgt catagttgta aatctacaat      240
ttattacaac atgaataagt acacaagcaa tgtaattgga tttaattgct aaactcttta      300
catggtcaat ctaaatttga taagaaatac gtcacatatt actaagactg atagtttttt      360
tgttgtcacc aattatttt gttaaattga cgaaaacaat tccaaaaact caaatgtaca       420
aaatcataca gtctcacaaa catctcatag agaaagatat aaatctccca tatgggaacg      480
ataacacgag gtcgaaatac tattcgtaaa actaaaacgc cttagttata aatcgttagt      540
tgtaaccgcg gtcgagaata catacagatc cacgaaacta ctactacaca tgctgctgaa      600
ttggaatttg gaaaagacca tcttctttag gaagagctca cccaatgagt gacaaaggtg      660
tcggtggctt gttttctacc catatgtata catcaaatgg tagtttcatt aacgtttggt      720
tttgagaaaa gtaagacttt ggctagtagc taggttcgta tataataaac tcttttgaga      780
aagttcatca ctggtggaaa atgttaaacc ggttttttct catttttttcc gccatgttaa     840 ccaccggttt aaaaagaccg taacacattg aaagattaat aagggtatat ttgtaattac      900
ggtttgctgg caattttaa ttattatttt aattagagaa aatagagaag ccctatcaat       960
gtacatggta tatatataaa aggcaaaacc ctagaaaacg atactattcg actcagccgt     1020
cctt                                                                  1024
```

<210> SEQ ID NO 144
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 144

| | | | | | |
|---|---|---|---|---|---|
| aatctgatct | ctagtccagt | cgattggtac | ttgagggaaa | catcatattt | ttaaaccttg | 60 |
| tctcagtaag | ctaacacaca | ccccttgtga | ttacttatcc | atgtttatcc | acaagaatgc | 120 |
| agttggattg | agatattttc | ttctttgttg | aaatcaggcc | tcaaggtgtt | catgtggtct | 180 |
| gcaaaaaaat | tcccaaaaat | aaagatagtg | acatctgaaa | tcgataatgg | attagacgaa | 240 |
| gagtttcgtg | ttattccttg | gtatgggcgg | gtttggggac | agatattttg | gcacagacga | 300 |
| ggactaggcc | actgtggtcc | tgcagcatta | ggtgtcccct | ccatgtcctg | cattacattt | 360 |
| tattgatgga | ttcatcaccc | tatctactac | aacggctaca | caaactatga | agagttttgt | 420 |
| ttactaataa | atgcccaagt | gagggggtcga | tcgaacccgg | gacacgtttt | tcagtttacc | 480 |
| atatagaatt | atccttggaa | cccttgatac | tccatagaac | atcaccacct | ctgttgtcat | 540 |
| ctcaggaatc | caggttcaaa | cctagtctct | ctctccctag | tgggaggtat | atggccactg | 600 |
| ggccaatgat | gacaaaatgc | aaaaaaaata | aaatacattt | gggttcatta | tctaaaatat | 660 |
| ctcttgtgtt | tgtaagtttt | ggttgcacac | tcgtgtggtt | gaagtgtgtg | tgagaggtac | 720 |
| tatacaatac | actctgcttt | tgttttgtac | ctatctcttt | ctcttctcca | catatccaag | 780 |
| actttgggga | taaagctgag | atcattggtt | gccatttggt | tgtgtagaag | caatcaccca | 840 |
| tttgctttat | ccgaggttga | taaatttcct | cgggttctcc | ttctgacacg | tatgacaaat | 900 |
| tctaatagta | tattcctcgt | agatattacc | tatatattct | caatagttgc | aggtacttaa | 960 |
| ggctttgtct | tggcatcctc | gtcctcttca | gcaaaactcg | tctctcttgc | actccaaaaa | 1020 |
| gcaa | | | | | | 1024 |

<210> SEQ ID NO 145
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 145

| | | | | | |
|---|---|---|---|---|---|
| cttatccttt | aacaatgaac | aggttttag | aggtagcttg | atgattcctg | cacatgtgat | 60 |
| cttggcttca | ggcttaattt | tccaggtaaa | gcattatgag | atactcttat | atctcttaca | 120 |
| tacttttgag | ataatgcaca | agaacttcat | aactatatgc | tttagtttct | gcatttgaca | 180 |
| ctgccaaatt | cattaatctc | taatatcttt | gttgttgatc | tttggtagac | atgggtacta | 240 |
| gaaaaagcaa | actacaccaa | ggtaaaatac | ttttgtacaa | acataaactc | gttatcacgg | 300 |
| aacatcaatg | gagtgtatat | ctaacggagt | gtagaaacat | ttgattattg | caggaagcta | 360 |
| tctcaggata | ttatcggttt | atatggaatc | tcttctacgc | agagtatctg | ttattcccct | 420 |
| tcctctagct | ttcaatttca | tggtgaggat | atgcagtttt | ctttgtatat | cattcttctt | 480 |
| cttctttgta | gcttggagtc | aaaatcggtt | ccttcatgta | catacatcaa | ggatatgtcc | 540 |
| ttctgaattt | ttatatcttg | caataaaaat | gcttgtacca | attgaaacac | cagctttttg | 600 |
| agttctatga | tcactgactt | ggttctaacc | aaaaaaaaaa | aaatgtttaa | tttacatatc | 660 |

```
taaaagtagg tttagggaaa cctaaacagt aaaatatttg tatattattc gaatttcact      720
catcataaaa acttaaattg caccataaaa ttttgtttta ctattaatga tgtaatttgt      780
gtaacttaag ataaaaataa tattccgtaa gttaaccggc taaaaccacg tataaaccag      840
ggaacctgtt aaaccggttc tttactggat aaagaaatga aagcccatgt agacagctcc      900
attagagccc aaaccctaaa tttctcatct atataaaagg agtgacatta gggttttgt       960 tcgtcctctt aaagcttctc gttttctctg ccgtctctc                             999

<210> SEQ ID NO 146
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 146
tcgattggga ttactacttc atctagtaag gttctgaaaa cgtttgttgt tgataaggaa       60
gattcgtctc aggttattac tgttgatctt caaggtttgt gattgtgacg cttatacatg      120
tgctgaaact gtggtgttta tttattgaaa acaaaaaaaa agtctctctt gtagtttcat      180
tgtactaaat agaaaacaag aaacgttttt tctttaatc ttctacattg ataatattgg       240
atcaaaggat tgtttctgca agacacaaca caaacatact tatactagtt tacttctact      300
aagtactaac tacataccca tacacacact tgcacctaga ctttacttct agacatcatt      360
accctaaggt agaaccaagc ttacaagcaa gttttaccga caactcttac attacaactc      420
tagtctgtag tctttaacgt agacttacta actagtcatt agtggtttaa ttttttaaat      480
tttcatccat atgttttgt tgtagatata aactaaagtc ggtcacattt ataattgtc        540 attatgtccg cgtaaaagtc aattcagcta ttggacattt atgaaatgta agattttctc      600
tctcatttcc ccgtgcgtga agacatgcat tggttttct gtaataatca acaaatccaa       660 acccctttc gatctttatt tggacattgt tagagacaaa atttctctat agtctttttc       720
ctaatttgat accatgtttt tgtttctgca caaatttact cactggttta actaactatc      780 cacttatta tgattttacc attaggcgtc agctagccct agtcaaattt gtaaacaagc       840
caagctatct acataaatcg agatgtcatt aacgttaatc gtcgttaatt cgaatttgaa      900
aacatagata gctttagcag tacaatgggc aatggtaaga agaatagcaa aaggcccaat      960
atttggtttg cagaaattaa agccttaaaa aaaagcccac agatatttgt caaagaaccc     1020
taat                                                                  1024

<210> SEQ ID NO 147
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 147
aaagattgag ttgagagaga tggtggagac gcagaacaga caaagggagt ttaccatata       60
gtgctctaaa gggcaatgag attgcagtga tgtggctatc cggggaatca tcgcaggtta      120
ttccttccca tgagcaacaa tcaatggatg ggttccaatt cagaggagaa acagaagaag      180
aaacgtttcc agagaaccac agtagggatt ctcgatcttg cgagttgcag agagcctctg      240
```

```
aaactgcaat agaaaggaca ctgatgaaaa gaacacactg aaggagtatg ccaatcatgt      300
gaaaactcag agcttgtatt ggtcttgtgg ttgatgaagt tctcacaaaa cctttggctt      360
tgaatctccc ctcattagtc atggtgagaa caagaacaag acgagaaaca gacaaagaag      420
atgaaaaaac ttgttggcca gtgttgacta aggggaata gccccagaca taacaaaatt       480
agacttgtcg tacatcttta atattttttt atctgtttct ttgtcctgac gctttcatta      540
ttcctgtgat caattttctc ataccattgg tccatcgtta atcctttctt aatttcattt      600
tctacgtaac atgagaggag accaagtcct atgagaacag ttgacgtaac agtggttgtt      660
aagttaagtt aaaagagga agctagtgag agtgaccgtt aggtagagaa gtgagatctt       720
taaccactct tctttctctc tctctctgct tttttcgtcg tctttcacat ctactgttcg      780
caaactctct tatgcttcca ataatggtga taccaattga gacttgcagg agaatctcct      840
cttctccaca ctctatcaac tggtcagcca tggaatggtc gtttcagttt caatattcct      900
ggattctttt taaggattcc tgtttctctt ctgttcctgg tatattctta acgacgaaat      960
tagtatcgga tcctggtaat acattttgaa gcttttaagt accattgcac tgggatccaa     1020
caat                                                                  1024

<210> SEQ ID NO 148
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 148
gaggtcagtg agtcgattgg tgcaaaattg aaaaattgaa gggtgaaaca aatttaaaga       60
taatatctat taaatcctct aattttaaaa atttagcaaa aattgtatt tcttatggat      120 ctgttagttc acacgtatct taattagtac caaatcatat ctaatgatta gtgataaaac     180
tagttagata tctatatgtg tctttaccat ttaacttgaa tccttcttct tttttttacg     240
taaacaactt gaatccttcg ttaatacata aatttaaagc attttttctt taattctatt      300
gatcggtata tatttactat aagttttagc tcatatgcaa tttcaaatga tatgctttta      360
aattttgtct aggtgtgata gttgtatctt taacataaat cttatagcaa aattatactt     420
gatattctaa atttatctat ttgctcttgt gaacctcata ttagtctaga gaaactttga     480
aatcctttca attagttgta tgtccaatac attttactaa acatttatta gtctttttaa      540
ttaagattat tgttagaaaa aaaaagattt tttaaaaata aataatatgt tttagataca      600
atgtgagtta ggcttcttat atttaaaaa ataaatttat ttcatactta aaaatagttt      660
ggaatttcaa tttatttggc tgaataccat aaaaatgtc aatttgaacc ttatacccat      720
tgactatttg gtgttagaaa ccctttaaca aaaaaaact atttggtgtt agatatcaaa     780
ataaaaaaag tttaaccatt ggtttcttat attgaattgg atattgttac atgtattaaa     840
gttttttggg tttaatttg aaacgttgat agaaactatt aagtttaagt ttggtagtat       900
atttatttgt ggaaaattta attgccatta aatataacgt caacttttt tggtttttt        960 tgagaagtta cgttgtgatt ttgatttcct atataaaagt tagattacgt cattttttaa     1020

<210> SEQ ID NO 149
<211> LENGTH: 1000
<212> TYPE: DNA
<213> ORGANISM: Arabidopsis thaliana
<220> FEATURE:
```

<221> NAME/KEY: misc_feature
<223> OTHER INFORMATION: Ceres Promoter YP0097

<400> SEQUENCE: 149

| | | | | | |
|---|---|---|---|---|---|
| ttcatcttta | tatttaagag | tttaaaaact | gcaacttttg | ttttctttc | actaagtctt | 60 |
| atggccacag | ttaattaaaa | gcagatgaaa | ggtggtccaa | tggaaaagga | gaatgtgatt | 120 |
| gggctagttg | ggagagttct | gatgtctagt | gttgggtaca | cgtgtccgtc | agttacacat | 180 |
| agcattaaat | cagacggcat | gtcattattc | aaatctagtt | cacatagtac | gactaatagc | 240 |
| tgataaatta | atgattatac | agcatatgaa | ttatgaattc | aaaaaaaaaa | aaaaattgaa | 300 |
| aatgttaagg | agatgctata | ttttacaaaa | ttcatcgcaa | tgctttctac | taatttgcta | 360 |
| agtggtcttc | tccagttagt | cttgtcgatt | ccaagcgata | ttattaaatc | ttgaagcatc | 420 |
| gctcaaagca | ttatagctta | agataaccaa | attgttatta | aaaacaccta | gtgaaatttt | 480 |
| taaattaaaa | caattttgat | atctttgtaa | tatctaatac | tactctttct | gtgtctaaaa | 540 |
| ggattaattt | tcaaaaattt | cacacatatt | aaaaaaaaaa | aaaaattact | agctaaacaa | 600 |
| ttttcaataa | tcataaaaca | atagtaactt | aataatttt | ttttattttc | aaaatagtcc | 660 |
| tcaagtttta | caattcatt | tagtattata | atcaacaaaa | tttgtattaa | aaagttggaa | 720 |
| aattaatctt | tgtggaacaa | aaaaatctag | aaatcattt | ttagaattag | agagaggttt | 780 |
| gataaaaaaa | aataaaaaaa | aatagagaga | ggtagtacat | actaaacgat | gtgatactac | 840 |
| tattgacaaa | atcttaattc | tcagtttagt | agaataaact | agaaggaatg | aatgaagtaa | 900 |
| atgcgaatcc | aactactaac | aaaccctact | tagtcatcat | attttcccat | atgaaatccc | 960 |
| tatataaacc | catcatcatc | tcccactttt | ttcatatcca | | | 1000 |

<210> SEQ ID NO 150
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 150

| | | | | | |
|---|---|---|---|---|---|
| ttctcgttct | ctagaatatt | gctggaccgg | attaggtcaa | tattattggg | ccagattaga | 60 |
| tattgaattg | tcgacgttgc | ttacgttacg | ttatatcttg | tttaagaatt | aaacctatcg | 120 |
| acttagtctt | aattaagaaa | acattgcctt | aaattctctg | gtctgcgacc | gttttttga | 180 |
| ccgttaaccc | ctaattaaag | aaacaaaata | attatagaaa | gagcactgaa | atgtgattat | 240 |
| tttaacagta | ctcttatgag | aaaattcgta | cttttagtt | ttttttttgt | acaaatctct | 300 |
| aagaaaaaca | ctactactaa | ttaagaaacg | tttcaaacaa | ttttattttc | gttggctcat | 360 |
| aatctttctt | tctcggtccg | ggactaaccg | ttggcaaaaa | aaaaaaaaaa | gttgacaata | 420 |
| attattaaag | cgtaaatcat | acctctcaaa | taaaaacttg | aatttggaaa | caaagacaac | 480 |
| taaaaaactc | gaatttaaga | gaattcctaa | aatcaagtga | agtatcatca | cttggtaaaa | 540 |
| tttcataacc | gttggcttct | atttctatgt | gtgccttggt | ttgcaggaga | taatatttca | 600 |
| tttccaacca | atgatattcg | tacacatagt | caaacaaatg | tttgtctttg | ttattatatt | 660 |
| gagaaagaaa | caagaaagag | agagagagat | agataagacg | aaggaagtga | agcttccaag | 720 |
| cgcccaccgt | taaaaatctc | gtgtgcaagt | ttcaaataca | agtggccggt | ggtctccata | 780 |
| atttgatcgt | catccaatta | aaaggaaga | aaaagcgtgt | tttatacaag | aaaactcatt | 840 |
| aaaatagcaa | gtctagaaat | atctcaacac | taatctacca | cgtctattac | acacacacac | 900 |

| | |
|---|---|
| acacacactt gatcttaatt tattttcaag attcaagaaa atacccattc cattaccaca | 960 |
| acttgaccac acgcctatat ataaaacata aaagccctttt cccc | 1004 |

<210> SEQ ID NO 151
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 151

| | |
|---|---|
| atttggttga taacgttttc actcgactaa ttatatactt cagaaggata gtaatagaat | 60 |
| accaaaataa ttaaatgatt ggttagtgcc ttagtggaga cttttttaacc gattctaata | 120 |
| gactaatgat gtagctaagc atttatttgg gatcatcact gtttgaaaac gtgaaatgtg | 180 |
| ataaagtta tgaaacgatt aaaatataaa ataaccgtac aaaacattat gtaccgtttt | 240 |
| tttctctgtt cttttggcga tttggtttag ttcgttacac tctaaatgtt attgcagata | 300 |
| tatatataat gatgcatttg catctgagga acatataatt ccggttaaca cttccaaatc | 360 |
| ttatatccgt ctaggtaggg atttttataaa tcatttgtgt catcatgcgt tatgcttgtc | 420 |
| ggctttgacc ataacgcaga gatatagaac tagctttttac ttaacttttta gatttattat | 480 |
| ttgatctaga gttaagtgga gatatatagt gtttttgtta gattattggt ggatgtgaga | 540 |
| gtttgtcttt agtttcaagt tgagaatata aggcaagagg agactctgag gcaatcagag | 600 |
| gttttgattg gcaaaatatc caaaaggccc aaaccaagtc gaagcccatc tcgtacaaaa | 660 |
| aaagaaagag atctgtaaga aaaaatattc tttgatattc ttacaaaaat aagtgtaaaa | 720 |
| cttttattag tcaaaatctt caatctttaa aaactctcat cactcctacg aaagcgcgtg | 780 |
| agagttatga gacattcctt aatagcatta ctcacaagtc acaagttcaa aacgtctgac | 840 |
| tgaaacagaa acaagccttt gttgaagtct tgaagaagag acattagtac tcgtcgtata | 900 |
| gccataaaag gtaatatacg aaatttcttc gctaatctct tcaccttcct ctacgcgttt | 960 |
| cactttcact ttataaatcc aaatctccct tcgaaaacat | 1000 |

<210> SEQ ID NO 152
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 152

| | |
|---|---|
| gttttgaaga acaatctgga tcgaaatcta acataaggtc atcgtattca agttacgcag | 60 |
| tcaaggactt gacatcatcc tactctggtc tgaggttacc acttccaaag atgggatttt | 120 |
| tcgactcggt atgcttccta agaaattcgt tttattgaac ctagcaaata tcttgtaatg | 180 |
| taagattcct gagatgatga agaaaaaaca aacttttgtt acagcaggag aacggagaga | 240 |
| aagaaaacag agaaccaaat gctcttgaag caaacagaag aagaagacac aaatccaaac | 300 |
| ttgagacttc ttctacacca gaaaccgca gcattctggg acaacgcaaa acacgaaagt | 360 |
| gaaacgggca atgatatata tgtcttgggt gcgttacaag gcatcgtttg caactgttga | 420 |
| gttggataag tcaactgtct tctttttcctt tggttgtagt agctgccttt tttttccttt | 480 |
| gttgctttaa gaaatagccc gaaaaaaaga atgttctaca tttcggagca gaaaactaac | 540 |

```
cgaatgagtt tttggtcgga tcatcggatc gatcagatat attttgagtt acgaactgtt    600
ataaaaaaag ccataatttt gtgttgagtt tgcaaaatac cttataactt gttatttgag    660
attgcacctc catatatatt aattcgtaag agtatttatt aagtaagctt tagtataaat    720
ccttttttcc tttaaagtaa gttaatgttc tactaaataa tagtaaagtt gaagaaccgc    780
tccgttttta caccatgcac gtgttatcta acaaagaaaa tatggtacac ctaatggcta    840
atgcaaagga caacacaatg aaactaactt gactctgtgt tatagaaacc catagacatc    900
tgcatacatc ctagtatttg tataaattgg actcaaattc ctgaggacaa tcatagcaaa    960
caatcacatc atcgcaatat acataaacaa aagaggaaga aaaa                    1004

<210> SEQ ID NO 153
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 153
taacaatcct tgggaacatt gcatccatag atatccggtt aagatcgatc tttgaactca     60
taaaaactag tagattggtt ggttggtttc catgtaccag aaggcttacc ctattagttg    120
aaagttgaaa ctttgttccc tactcaattc ctagttgtgt aaatgtatgt atatgtaatg    180
tgtataaaac gtagtactta aatgactagg agtggttctt gagaccgatg agagatggga    240
gcagaactaa agatgatgac ataattaaga acgaatttga aaggctctta ggtttgaatc    300
ctattcgaga atgtttttgt caaagatagt ggcgattttg aaccaaagaa acatttaaa    360 aaatcagtat ccggttacgt tcatgcaaat agaaagtggt ctaggatctg attgtaattt    420
tagacttaaa gagtctctta agattcaatc ctggctgtgt acaaaactac aaataatcta    480
ttttagacta tttgggcctt aactaaactt ccactccatt atttactgag gttagagaat    540
agacttgcga ataaacacat tccccgagaa atactcatga tcccataatt agtcggaggg    600
tatgccaatc agatctaaga acacacattc cctcaaattt taatgcacat gtaatcatag    660
tttagcacaa ttcaaaaata atgtagtatt aaagacagaa atttgtagac ttttttttgg    720
cgttaaaaga agactaagtt tatacgtaca ttttattta agtggaaaac cgaaattttc    780
catcgaaata tatgaattta gtatatatat ttctgcaatg tactattttg ctattttggc    840
aactttcagt ggactactac tttattacaa tgtgtatgga tgcatgagtt tgagtataca    900
catgtctaaa tgcatgcttt gtaaaacgta acggaccaca aaagaggatc catacaaata    960
catctcatag cttcctccat tattttccga cacaaacaga gca                    1003

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 154
gggatgcggt tccgcttcct cttgatcttg gacgagtcgg aggacattgt tggatcccag     60
tgcaatggta atataaaaca agaaaacaag agattttata ggacaatcac taaatgacat    120
ttaattgatt aaacatttat tcattaataa ttgtatgtta ctaacttcaa catttaataa    180
ttttgtttaa gatacgttta catcagagac tattaatatt tttacaggtt gtaactttaa    240
```

```
actttgtctt gaatcgaaca tgactataga ttttgggcaa acttaaagat aacaacattt      300 ccgtttttt  tcaaattatt acaaatcaaa ctgatatatt agacacaaca cgattacacg      360
taatgaaaaa agaaaagat  aaaaagataa agaagggat  cgattctgtt tggtctggtt      420
tagtgagatt caaagttaag ctcttccttt caagacatgc cttcttaaac cgggaatgtg      480
aacgtttgta atgtagtccg tccagttaat gcttccaaca tcaaatccaa attctctctt      540
ctcgtcctct gacatattct ccattaatct ctggggtatt gctgttatca aatctgtaaa      600
agaaaccaaa aaaaaagat  gaaaactttg cgggtaccgg ttttgtctgc tctaagaatt      660
agaatgttaa tgagttctgt cttaccttcc accatagaaa gtgtatggct cataaatagt      720
agcaaggtgt ttggcttgtt caacagattt cttgcatata aactttagct tctgcatcat      780
cttactatcc actgaactca taccactcat caacccactc cgttcttgag catctctcca      840
caaatgatcc gagaaatcat caacggaatt gaaaagtttc atcaaacgca ccataatagg      900 atcacctta  gagtccatgc atggagatgt tttgtagtgg ttataaagaa gctccgctaa      960
gtcttcgaaa accagcgggt ttatcgccga agaagcgatc tgatacacgt ttatttcagg     1020
ttcc                                                                  1024
```

<210> SEQ ID NO 155
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 155

```
cgattggatt tagtctatac attatagggc gcaagtttgt ggatttaaga attatataaa       60
aacttgaaat atatagtttt tatgcattct cctcttgtgt aatacataaa ccaaatatga      120
gataggttaa tctgtatttc agataatatt aaattccaaa caatattttt acttgttata      180
agaaggcaat taatatctct ctgttaatgg caagtggtac caagtagtat taaactatta      240
atgcaatgga agagtactgt tggaaattat aatcctctat cacacattca aacagatctc      300
ctgaaatctt ctcttccaaa cttgtacttc tctgatccaa atgtaggctc caaaatatag      360
acatttacca tttactaagt ccacaactcc tttcttgtct ccttcaaaaa tgactcttgt      420
gtaaccacca tatgactccg acagttcggc attgccatga tgagagctta aaaattcacc      480
ttcctgagca tttcaagtct tcactccctt agcttgacct gaaccaagat aaaatgcctt      540
tgtcgtcccg taatatccat cctgctttgg acggcatcat agttacattc gatccatcct      600
atttacaatg ttatttttagt attaaaaaca tgacaataaa tttgttgtta acatattca     660 aatacaatat gattggattt ataagtaatt gtaatatgaa atgtccttag taatatgtta      720
aaaaatacat agatacacac acgtactaaa agaggcaacg cgggagatgt cattagagga      780
agaactagga agcagagcgt tcatgcaaaa tgctaccaaa acgttaatg  caatatctca      840 actaatcagc acagtccatt tcatactgag aatgtaaaaa ccaatcagca tcgtccattt      900
tttcatctaa ttatttgtta actcttaatt ggccacaact tccaaccaca tgacgctctt      960
tctattccct ttatatattc ccatctcaaa tgttcttgga gacacaaaat atcataaaca     1020
tata                                                                  1024
```

<210> SEQ ID NO 156
<211> LENGTH: 996

```
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 156
gtcgattgga tgatgaacat tctacatata taattattat gtttaagcac ttagacagca     60
taaattcttt ctaattatat aaatctaacc ttgttacatt gtacatctat aaattacttg    120
aagaaataac gagttctatt tcttttaaa aattaaaaat actataccat atctcagtga     180
ttaagttgaa ccaaaaggta cggaggagaa acaagcattt gattcttcct tattttattt    240
tattcatctc tcactaatga tggtggagaa aaaagaaaa tacctaacaa acaaatatat     300
attgtcatac aaaatatttt ctatatttt agttaattag tttatattcc tcacttttca     360
gggcttatat aagaaagtga gcaaacacaa atcaaaatgc agcagcaaat actatcatca    420
cccatctcct tagttctatt ttataattcc tcttcttttt gttcatagct ttgtaattat    480
agtcttattt ctctttaagg ctcaataaga ggaggtacta ttactacact tctctctact    540
tttacttgta ttttagcatt aaaatcctaa aatccgtttt aaattcaaaa ataaacttag    600
agatgtttaa tctcgattcg ttttttcggc tttaggagaa taattatatg aaattagtat    660
ggatatcttt actagtttcc attcaaatga ttctgatttc aatctaatac tctcactctt    720
taattaaact atatgtagtg taatttcaca ctgttaaatt tctaccatgt catgtatatt    780
agagttgcat agaaaattgt aaaacatcca tttgaattcg aatgaaacaa aatgttttaa    840
aataaaattt tggttttaa aagaaaaatc taaaactgaa ttatatcgtt taaccaagtt    900
gtaaaagtca taaaacgtag tatcttgtaa atcgctcttc cacggtccaa atagacttct    960
agtaataaac aagtaaaact aattttggtt tcttac                              996

<210> SEQ ID NO 157
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 157
gtcagtgagt cgattggatc acagtccttt atgataaaac aaactcataa ttattccacc     60
gacaacatgc gttttaaatt atttttctt aaattatatt atattatatt gatatcaacc    120
tagctaaaat aattcggatg gcgaaatcgg acaattttta atagaaaaaa tgggtatgaa    180
gatagtctat gattccgttc ttagcgacta gagggacctg ctcaaatctc ccgggtgata    240
cgcgatgtca agctcaatag aaccccacaa ccgacgagac cgagaaatcc ttgatttggg    300
ctagaagatt ttgaaataaa tttaatatat tctaagtaac ttgcttaaat ttttttttcaa    360
actctaaaga cataactaac ataaagtaaa aaaaaaaag ttaatacatg ggaagaaaaa     420
aattaaacta atgattagct ctctaacgtg tttaatctcg tatcaagttt ttttttaaaa    480
attatattgc tattaaaaca ttgtactatt gtttctattt tgtttagcta ttattcttgt    540
gaaatgaaaa gttgtgttta ttcaattact aaatggcaat atttatcttg gaaaactata    600
cctctaattg gattaggccc tagacatcct ctttagctta ttgacgttaa aattattccc    660
aaaactatta aagtttagta gtttgaaaga tgcatcaaga cctactcaga taggtaaaag    720
tagaaaacta cagttagtgt gattatattt taaaatatat aaaacaatct tattaaacta    780
```

```
aatattcaag atatatactc aaatggaaga taaaaacatt tagtctgtta ccactaccag    840
cctagctagt cactaatagt cactttggaa ctgagtagat atttgcatct tgagttacca    900
tggactcaaa agtccaaaaa gagaccccga gtgaaaatgc taccaactta ataacaaaga    960
agcatttaca gcggtcaaaa agtatctata aatgtttaca caacagtagt cataagcacc   1020
attg                                                                1024

<210> SEQ ID NO 158
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 158
taccaaaaat aaggagtttc caaaagatgg ttctgatgag aaacagagcc catccctctc     60
cttttcccct tcccatgaaa gaaatcggat ggtcctcctt caatgtcctc cacctactct    120
tctcttcttt cttttttttct ttcttattat taaccattta attaatttcc ccttcaattt   180
cagtttctag ttctgtaaaa agaaaataca catctcactt atagatatcc atatctattt    240
atatgcatgt atagagaata aaaaagtgtg agtttctagg tatgttgagt atgtgctgtt    300
tggacaattg ttagatgatc tgtccatttt ttttcttttt cttctgtgta taaatatatt    360
tgagcacaaa gaaaaactaa taaccttctg ttttcagcaa gtagggtctt ataaccttca    420
aagaaatatt ccttcaattg aaaacccata aaccaaaata gatattacaa aaggaaagag    480
agatattttc aagaacaaca taattagaaa agcagaagca gcagttaagt ggtactgaga    540
taaatgatat agtttctctt caagaacagt ttctcattac ccaccttctc cttttttgctg   600 atctatcgta atcttgagaa ctcaggtaag gttgtgaata ttatgcacca ttcattaacc    660
ctaaaaataa gagatttaaa ataaatgttt cttcttttctc tgattcttgt gtaaccaatt   720
catgggtttg atatgtttct tggttattgc ttatcaacaa agagatttga tcattataaa    780
gtagattaat aactcttaaa cacacaaagt ttctttattt tttagttaca tcccctaattc   840 tagaccagaa catggatttg atctattttct tggttatgta ttcttgatca ggaaaaggga    900
tttgatcatc aagattagcc ttctctctct ctctctagat atctttcttg aatttagaaa    960
tctttattta attatttggt gatgtcatat ataggatcaa                         1000

<210> SEQ ID NO 159
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 159 tagttttga tttaatctac gttttctta atcataaatg ggtaattatt agttttgca       60 aaatcaaaat ccaaaaattg ttctaaacac tgcaaccatt taaggcctat atcactcaga    120
aaatttctgg tgggagaact aatcgtttgt cctttctaaa tctcacatat tagaatttag    180
aattagtgtg ctacataaga atattagttc agctcggaac aactatttttt tggtaaaaca   240 gagaacttaa acaaatgcat tatttttatca acatgcattt tgaattgaat ataaaatttc   300
ataattgtaa agacataaat tacataaaat tttacgtgaa aaaatagata tagaaagaaa    360
atgaaactaa ctgatgatat gctctctaaa tttttttaatc tcataacaag aattcaaatt   420
```

```
aattagttca tatttttggt taatataaca tttacctgtc taagttggaa ctttcatttt    480
tttctgtttt gtttagtcag tattcttaat gtgaaacgga aagttgaatt tattcaaact    540
taaattcaat agcattaatt aaaggcgaaa gctattatct ctacatgtgg ttcaaactag    600
acatccaatt taattagctt attgacgttg aaatgttttc caaaactact atagtttggc    660
aatttgaaag atgcatcaga actactcaga caggtaaaag tagaacctct agctgtgtga    720
attgtatgtt agtccataaa gaacatcttg taaacttcat acttaagata tatattacaa    780
tatatacttg aatggtagat aaaaacgatt agtctgattg ctagcatact cacaactatt    840
tggaaatgag taagatattg gcattctaga gttactacta tggagacaaa agtcgaataa    900
aagagacctc acgtgaaaat gttacgagct agtaaaaaaa gcatttacac taacggtaaa    960
aaaagtatct ataaatgttt acacaaggta gtagtcatt                           999
```

<210> SEQ ID NO 160
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 160

```
ttggattttt ttttgttga gtcagcagac catctaatct ctcttttcc accacagcct      60 gctttctatg aagcatttgg gcttacggtt gtggaatcaa tgacttgtgc actcccaacg   120
tttgctacct gtcatggtgg acccgcagag attatcgaaa acggagtttc tgggttccac   180
attgacccat atcatccaga ccaggttgca gctaccttgg tcagcttctt tgagacctgt   240
aacaccaatc caaatcattg ggttaaaatc tctgaaggag ggctcaagcg aatctatgaa   300
aggttggccc attctccttg acaggcttaa caatacaact tgtatcgctt caacaagatg   360
atggcttaat aaggattttt gcatgtatag gtacacatgg aagaagtact cagagagact   420
gcttaccctg gctggagtct atgcattctg gaaacatgtg tctaagctcg aaaggagaga   480
aacacgacgt tacctagaga tgttttactc attgaaattt cgtgatttgg ttagtgtaac   540
ccactgttat tcttttgatg tctacatcta ctttacttac attattcttt tcttcggttt   600
gcaggccaat tcaatcccgc tggcaacaga tgagaactga tcatgacagg gtaggatttt   660
atttcctgca ctttctttag atcttttgtt tgtgttatct tgaataaaaa ttgttgggtt   720
ttgtttcctt cagtggtttg attttggact tatttgtgtt aatgttgttt tggctgttct   780
cttaatatca ataacaaata aatttactgg ttggtatcta agatctaaca atagttacta   840
tttttagagg taaagacacc aaccttgtta tattggtcag agagctaaaa ccttgacttg   900
ttgggaaaac aaaactctaa tgacagaaaa tctgacatga tgccttataa ttcacagcct   960
catgttctac ataaatccta acaatagcac tttgtttct                          999
```

<210> SEQ ID NO 161
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 161

```
gataaactga taatggaaaa gaacaaagaa accagttttt aactatttgc atatgtaatt    60
```

```
tatttgttgc aaattatatt tagttaaaat gtttcctcta tttatatata tatatatcag    120
tcaagcacta tgtataagaa atgtcaattt ataaatttt acatgtcctt taacagaaag    180
aaaatgaatt tttacatgtc attcatagag agtcactcgt ttatttctta tatagagaat    240
aacacactca catgcatatg catgcaatat gatacattt atgacaaaga taatcaacgg    300
aaacggtcaa gacataattt gataaacaac ttgcacgatg cacagatctg atcaaatata    360
taactcttta acatatccaa aatattcaaa aagaaaaact cgatccaaac tagcaacatc    420
acgctcacgc ggtaggctaa aaatttatta atctccaaaa gtctttctta tgaacactgc    480
aaacacaaca acttgaaaag tcatataggt ttagatgatg acgcgtattg gctatcgctt    540
accggagtgg ctcataaata caataaacaa tacgtaaaag tcaaagtcaa atatatttag    600
tcaactataa ccattaatcg ggcaaaacct ttagctgtca aaacaacgtg aaaacgatat    660
ttgtatatat catcaagaat cagtagataa gagaatgatt taatcccctg actattacaa    720
ttttggtgta ataaacagtc tctattggtt tttattcttt gttttaattt ctcatgacct    780
atagagagaa ttaggtagtt tcgaaaattg gctaatcaac ttttgaaaac tactgtctac    840
tttgcttaaa ttctctacac ttagtttcgg ataagataat tgtcggacta atagttaatc    900
ccttgacaat ctttgatatt ataaaaggtt tagttaatct cttctctata taaatattca    960
tacaccagct ttcaaaaata tataatccaa acaccaaaaa caaa                    1004
```

<210> SEQ ID NO 162
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 162

```
gtggcacatg ctgaaacccc gagcatctct ccggaagaca cgcgtcgttc gctccaaaga     60
aaacagtcac agctgccgga gaatctccgc cgtcttcttc tgccaccgga aaaactctct    120
ccaccacttt cagtgcccac ctcgtgttat atccactgta tcctcgtagc accatatcag    180
cctaataaaa ttttatgtat caaattttaa gacatagccg aaactacact atactagaca    240
ataataatat gatttgtttc ctgaaaaatt atggtttcat gagaaacatt aatcatctat    300
aaaacaaatt agctatggca tcgaagagtt atcaatcaaa actgatgaat ctttacttaa    360
tatatacaac atatctttac cttgcggcgg agaagatcgg cgagagaagc accccagcca    420
ccgtcactaa aggattcttc agtgatggaa tcaccaaaga gaaaaccctt ccgtctcatc    480
atcttccaca caatcttctt gagaaaatct gagagataag aaaggtgtag tggttttgct    540
gaagtgatcg tgtttgattt agtaaagaaa tgctttattt attgttgggg gaaacataaa    600
taaataaagt aaaagtggat gcactaaatg ctttcaccca ctaatcaccg acctttcatg    660
gtttattgtg aaatacactc atagatagac atacaatacc ttatgtacgt aaataacatt    720
ttatttgtcg acacttatgt aagtaacgca tagattattt tctatgtgat tgccactctc    780
agactctcag tttcaaccaa taataacaat aactacaaca acattaatca taaacatatg    840
ctctggttta caattaaagc ttagattaag aaactgtaac aacgttacag aaaaaaaatg    900
ttatttacgt tttgtaagat tagtctctag aatcatcacc gttttttata tattaatgat    960
tctttcttat atataaaacc tttctcgaaa tacccatgaa a                        1001
```

<210> SEQ ID NO 163

```
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 163
atacaacaga tggcagatat cgagttaaat acgtgaatca gccgttacga tattttaaaa      60
ctagaaaatt atttaaaaat attgcaaaat accatttaat ttcattgttc ataaaaaaaa     120
gaaattcaaa aacttaaaaa ctgattcaaa aatttggatt aattctcatt aacagtcttc     180
aacactacaa caacatgttt ctaatttatt ttatatttta ataattaaac aatatatacg     240
tctgcacatt gttgctccga cataatctag tataaaaata gttgcagcat atgtgaaaag     300
caagcagcat ttatcactca atacttttaa ttttatctgt tgtatgtatt aaggttttgt     360
agctttaaga aaacgcttat aatataaaat aacttctaaa agatatttca tgcgtataca     420
ataaatattt gtgaaaaaac atttcgaaaa cgtgtacaat atataaacta ttgtgttatc     480
ttttgacatt caaacaaatg ttgacaatgt aattttatcc atgatatgat tggccaatta     540
gctgcgaggt aaaaatccgt atacgagtaa aagtaagata aaatttcgca agaagatttt     600
tagcaggaaa tctaagacaa gtgtcatgaa cgtgtcaatc aacaaacgaa aaggagaatt     660
atagaatcca gattcgacgt accacattaa taaatatcaa aacatttat gttattttat     720
ttttgctctg gcagttacac tctttttcat tgctccaata aaaaaatcac tcgcatgcat     780
gcatatatat acaccatagt aaactccgcc tcttcttcat tttaaaagta tcagtttaca     840
ctgacacaat ccttaactat tttcctttgt tcttcttcat ctttattaca cattttttc      900
aaggtaacaa ataatctttt taagtcactt ttatactctt taaatcttag attgatatat     960
gaatgcatgt taatatttca agatttatag gtctaccaaa c                        1001

<210> SEQ ID NO 164
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 164
aaacgttgca agattattga ttgtgagaaa gagtgctcaa ggtagtactg atttctgtaa      60
agctcacggt ggtgggaaac gatgttcttg gggagatggg aaatgtgaga aaatttgcta     120
gaggaaagaa gcggtttatg cgctgcgcat aacactatta tgtctcggga gaacaaagat     180
ggaagcaaga gcggtttgat tggaccggga ctctttagtg gccttgtttt tggctctact     240
tctgatcatt ctcagtctgg agctagcgct gtctctgatt gtactgattc tgttgaacga     300
atacagtttg agaataggca gaagaacaag aagatgatga taccgatgca ggttctagta     360
ccttcatcaa tgaaatctcc aagtaattca catgaaggag aaacaaacat ctatgacttc     420
atggttccgg aggagagagt tcacggcggt gggctagtaa tgtctttact tggtggctcc     480
attgatcgaa actgaaagcc atttatggta aaagtgtcac attctcagca aaaacctgtg     540
taaagctgta aaatgtgtgg gaatctccga atctgtttgt agccggttac gttatgctgg     600
atcaaaaact caagatttgt tggatattgt tatgctggat cggtggtgaa accacttccc     660
ggttgctaaa taaataaacg ttttgtttt ataatctttt tcactaaacg gcagtatggg     720
ccttagtgg gcttcctta agcgaccaat acaatcgtcg caccggaatc tactaccatt     780
```

```
tataggttta ttcatgtaaa acctcggaaa atttgagagc cacaacggtc aagagacaaa      840
aacaacttga agataaaggg ataaggaagg cttcctacat gatggacaac atttctttcc      900
acacaaattc tcataataaa atcttataa tacaaatact tacgtcataa tcattcaatc       960
tagtccccat gttttaaggt cctgtttctt gtctgataca aat                      1003
```

<210> SEQ ID NO 165
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 165

```
ttggtttgca ttgtgaagat ttgtattaac tatagaacat tgaattgatg gtgttaagtt       60
cttacacaag cgtgcttctc ggtttgaact gtttcttttg tatgttgaat cagagcttag      120
tttataggaa ccagagtatc tacttagtca ttctctgatg ctaagtgcta aggttctacc      180
tagttgccct ctaggccctt atgttattga taacttatga agctatttga acacttgatt      240
cttaggagac ctaagttggt acagccagat agagtgtatg ttcttgttct ctatgtgaca      300
ggatcaagct gccacacata gttcaagggt atgctctgtg tgggtttgct cagattgagg      360
acaaatctat acaaggaagt agagtctttg acattttgat gttgtatgat aagaagaaga      420
aaggagagta ataagaaag agaaagggga aacagaaaca cgtgggagaa catcccaaag       480
aggaagcaca cgcggatctt catgcaaagc tccccgattc tcccatgtgg tcccttctc      540 cctttgtccc cctcctcttt cttcttttct cattttactc cttttttac cattatacaa      600 cgaatctttt ttatcataat ttttggtt tggtttattt tccaataaca ctttcttggt       660
tacttcccat tctcactttt tcatataaga aactcacttt gggaaactta tgtttgagaa      720
tgacaagtct ttttagagaa agtgatgtaa caaatctaaa gtgattatat aataaccttg      780
cacaatgttt ttgattttt gtaagattcg aatattaggt ttattattcg tagggaataa       840
acttactttc aaaagcgttc ataagttaat actttcatat atgatcataa gtacggacac      900
tattgttttt tgtttgtttg tgtttattct aaaagaaagt agcttttaat tgaaatgtcc      960
tcggaggcac agtttaaagt tcgagtgtaa cagtttctaa ggca                      1004
```

<210> SEQ ID NO 166
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 166

```
ttattagatt aatagattgc attgcattgc ttgtgctttc aatttacaaa ttgtctccca       60
actccatcga cacatctctt tttgtgtata taagattcag acttgttata tttttttat       120 aaatatgtta ttagcatctt aagttaaatt gatttttat atctgcatta aggattacac       180
gactatattt gcgattgtgt gttggttaaa atataattta ggattgtctt taactacatt      240
taggattata tgactatatt tggttaaata taaatctag ctgtgattat tagtattcaa       300
aaataagtag cctaaccaat taaaacaacg gctattgggg caaattagaa catttagtg       360 tgtccaaaat ataatggtca ttaggtcata ttcctcctag cttcatcgca gcataattga      420
```

```
atgattgcct tatttagaag agcttttcca ctttcccaaa atctaggtgg gatcttttg      480 ttttgacctt cattttctt gtttaccatt tttagctaaa ttatttacga ttacaaaaga     540
tatcaaaagt tggatcataa tacaatttat agacttactg tagaaaattc gtatgtacaa    600
gtacaacaaa ttcttcataa taaattttga aaattctatt acaatgttg taagaaatag    660 aatttgaaat atatataaac taaggagaaa aaaaagaga acatgcattg ctctagtcag    720
agtggaccaa catcaacgag ataagataac ataaaaacca actcaccata actaaaaaca    780
tcccaagaga tccaacgatt catatcaaac acaaaaacat cgaacgatca gatttaaacc    840
atctctggta tctccaaaac acaaacactt ttttttttct tttgtctgaa tggaacaaaa    900
gcatgcgaca tctctgtgtc tttatcttct ctctcctctt cttgaaaaac tgaacctta     960 attctttctt cacatctcct ttagctttct gaagctgcta                         1000
```

<210> SEQ ID NO 167
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter YP0188

<400> SEQUENCE: 167

```
gattggtatg aaatttcgga gaccaacaaa aaaaacttta ttgagcttgg agtgaagcta     60
tatatatggg gcaagatcat aatatgttta tatcggcctt ttcgttaact gaaaataata    120
gttttgagaa atatatcaaa tggtaaacag acatcatctt tgaaaaatac catcaatgaa    180
gttaatattg ttattggcat atggtttacc catcttaatt ttaatgcaac caaacaaaca    240
agaaacaaaa actgtataag atacaaggtg ttttacgatt ttccgtctta aaaccgaaat    300 attttttgttc ctacgacttt aaacggactt tgcttaagtt gtgtgcatgt aagctcgtcg   360
tccctcgatt gtcatcaaca ttcaccaata tcagcctcta tcacgagt gaaggtggtg      420 attcggctta atgaaaacag agaaatattt caatatgatt cctattaaat tttaaatctt    480 tttctcaat ctctagattt tcattaaaag catcatgatt tttttccact atgttcatat     540
atctctatca cagtttagg tacattgtag aaattggata agatacgtca tacgtctaac     600
atgaatttgg tctagcaagg aaggtttgag ataataagtg aaaagaaaac acaagataat    660
aaattataat ttataaatgc tttatagtat tgaaaaataa gatgattttt ttttttttta    720
ataccggatt ggctgatcca cttatgatga ctcaaatgtt attaagtttc aagacaattt    780
atgatgacac aaatcacaat gagtcaatag tagccacgaa gccagaaaaa aaaatgtac    840 tacaaaaga taatgatagt acaaaatgat acgtcgtact gccacatgta cgacacaact    900
cgattaccaa aaagcagagc catccaacca taaaactcaa aacacacaga ttccactggc    960
gtgtgctctc ctcacttcac tcgtccttga aacttgaggt actga                   1005
```

<210> SEQ ID NO 168
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 168

```
taaatagtga cattggtaag aagaaaaaaa acactattaa atagtgaaaa aatggtttat     60
aactctctta attaacatta cttattattg ctagcaccta aaatctccca caaaatattt    120
```

```
gttgtaaaac acaaatttac aaaatgattt tgttttaaa ttagtaacac atgttcatat      180
atacgttaat aagaacatac cctatatgat tttatataaa aaaatttctt tgagacgtct      240
tattcttttt tctttaataa tatgcaattg tgagagtttg gatttgaatg gtagcattag      300
aagcaaactt gaaccaaaca tatttcatga agtcaaactt gaaccaatgt gatcactaat      360
cacagtgttc gcagtgtaag gcatcagaaa atagaagaag ggacatagct atgaatcata      420
taatcttgac acatgtttta taggttttag gtgtgtatgc taacaaaaaa tgagacagct      480
ttcttctaat agacttaata tttgggctaa atgtaccaca gttgtgaatt tcttacaaaa      540
atgggccgag ctacaaaaaa ctacaggccc actctcaact cttatcaaac gacagcgttt      600 tacttttta aaagcacaca cttttttgttt ggtgtcggtg acggtgagtt tcgtccgctc      660
ttcctttaaa ttgaagcaac ggttttgatc cgatcaaatc caacggtgct gattacacaa      720
agcccgagac gaaaacgttg actattaagt taggttttaa tctcagccgt taatctacaa      780
atcaacggtt ccctgtaaaa cgaatcttcc ttccttcttc acttccgcgt cttctctctc      840
aatcacctca aaaaaatcga tttcatcaaa atattcaccc gcccgaattt gactctccga      900
tcatcgtctc cgaatctaga tcgacgagat caaaaccccta gaaatctaaa tcggaatgag      960
aaattgattt tgatacgaat tagggatctg tgtgttgagg ac                      1002

<210> SEQ ID NO 169
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 169
agtcgattgg tacactctta atttaattag agtaagagat caacaaaaat atagaatttt       60
ctttatatcg aagtgctacg accttatata tatagaaaaa aaagcatagg tgaatctcta      120
aattgagatt gtgctgtagt aaacatatta agttttagt ttttttaaga aatgaatctt      180
tttgttgatt aattcaaact agtagtcatt aagattccgg agattccaat ttagaaaagt      240
caaagattca aagaacaagt ccaggtccac atgttgaatc cgattcatca tccactcatc      300
cttcatatct tcctccaccg tctccgccca aaaaatcaat aacaataaaa aatcctaaaa      360
aaacatattt gattttgaaa aaactttatc atatattata ttaattaaat agttatccga      420
tgactcatcc tatggtcagg gccttgctgt ctctgacgtc cttaattatc attatttta      480 aatttgtctc tctcagaaaa ttacgccaca atcttcctct ttcccttttc cgaaaacagc      540
taatatttgt ggacctaaac taaataacgt agcctctaga ttttatataa ttactaatac      600
tatatgctac tacttgttat tatttactcc aatcatatat gataccaatc aagaatcact      660
acataagtag aaaactttgc aatgagtcca ttaattaaaa ttaagaataa acttaaaatt      720
ttatggtatt ttaagattcc ctttggattg taatgacaag aaatcagcaa attagtcgta      780
actcgtaaga ataaacaaga tcaattttta cttttcttttac aaagattccg ttgtaatttt      840 agaaatttttt ttttgtcact gttttttat agattaattt atctgcatca atccgattaa      900
gaagtgtaca catgggcatc tatatatatc taacaggtaa aacgtgtatg tacatgcata      960
aggttttacg tgcttctata aatatatgtg gcagt                                995

<210> SEQ ID NO 170
<211> LENGTH: 1024
```

```
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 170
ccagtcgatt ggcgcctcgc atgcctatca tatttaaccg tcaataatgg atttggcggt     60
tttggtaggc cgggtcaacc ggattaaaag aaaacggttt ggagtccttc cttgcaattg    120
aattttcaca cattcgggtt ttgtgatttc tctgtcataa tgggcccggc acatatggtt    180
cataacccat gtgggcctat ggtataattt ttccaattaa aactattgtt aggtcgataa    240
aacaaaaaac aataaaaacg agtggaatac acataccaaa aagaatgtga tgaacattag    300
taattttatt ttgatggtta atgaaaaaca aaataaatgc atcttggcat cttccgttgg    360
aaagcgcaaa tagggcagat tttcagacag atatcactat gatgggggt gagagaaaga     420
aaacgaggcg tacctaatgt aacactactt aattagtcgt tagttatagg acttttttt     480
tgtttgggcc tagttatagg atcataaggt aaaaatgaag aatgaatatt agattagtag    540
gagctaatga tggagttaag tatgcacgtg taagaactgg gaagtgaaac ctcctgtatg    600
gtgaagaaac tatacaacaa agccctttgt tggtgtatac gtattaattt ttattctttt    660
atcacaagcg atacgtatct taagacataa taaatatata tcttactcat aataaatatc    720
ttaagatata tatacagtat acacctgtat atatataata aataggcata tagtagaaat    780
taatatgagt tgttgttgtt gcaaatatat aaatcaatca aaagatttaa aacccaccat    840
tcaatcttgg taagtaacga aaaaaaggg aagcaagaag aaccacagaa aaggggcta     900
acaactagac acgtagatct tcatctgccc gtccatctaa cctaccacac tctcatcttc    960
tttttcccgt gtcagtttgt tatataagct ctcactctcc ggtatatttc cccattgcac   1020
tgga                                                                1024

<210> SEQ ID NO 171
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 171
atctagctgt ggattccacc aaaattctgg cagggccatg atctaaaaac tgagactgcg     60
cgtgttgttt tgcagtgatt tgtatttcat atttgcacca tcctacacag tccacttggt    120
atcgtaacca aacataagga gaacctaatt acattattgt tttaatttcg tcaaactggt    180
ttttaccttt tagttacata gttgattctt catttgtttt agtagttatg gagcacaata    240
atgtgcaaca agaaagatc atagtggatt aatatgttga gaggtcagaa attcttggtt     300
aacaaaaaaa agttacaagg actgagattt tgggtgggag aaagccatag cttttaaaac    360
atgattgaac ttaaaagtga tgttatggtt tgaggggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
gatcggacga aaattgtaaa ctagtatagt ttcaaaaact agttgaacag gttatgtacc    600
ttaaacattt atttcaaact taaacactaa agaacatata tgaatagaag tttatataaa    660
ttactatata tctaccataa atctcttata attatgatgt cacgatgagg aagtgttgaa    720
```

| | |
|---|---|
| acgttaaaat gccaaaatat aagcatgcga cggaattttg gcagaagatt gtagagttgt | 780 |
| aatctgtcgc aatcattact cgtgctagca ttttcattt tcccttcatt tgtggataac | 840 |
| gcacgatata acattctaca caccaacaag attctataaa aacgcaaagg ttgtctccat | 900 |
| agaatatcgt c | 911 |

<210> SEQ ID NO 172
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 172

| | |
|---|---|
| aaacattaat atgtagtaac tatgggcgta tgctttactt tttaaaatgg gcctatgcta | 60 |
| taattgaatg acaaggatta aacaactaat aaaattgtag atgggttaag atgacttatt | 120 |
| tttttactta ccaatttata aatgggcttc gatgtactga aatatatcgc gcctattaac | 180 |
| gaggccattc aacgaatgtt ttaagggccc tatttcgaca ttttaaagaa cacctaggtc | 240 |
| atcattccag aaatggatat tataggattt agataatttc ccacgtttgg tttatttatc | 300 |
| tatttttga cgttgaccaa cataatcgtg cccaaccgtt tcacgcaacg aatttatata | 360 |
| cgaaatatat atatttttca aattaagata ccacaatcaa aacagctgtt gattaacaaa | 420 |
| gagatttttt tttttggtt ttgagttaca ataacgttag aggataaggt ttcttgcaac | 480 |
| gattaggaaa tcgtataaaa taaaatatgt tataattaag tgttttattt tataatgagt | 540 |
| attaatataa ataaaacctg caaaaggata gggatattga ataataaaga gaaacgaaag | 600 |
| agcaattta cttctttata attgaaatta tgtgaatgtt atgttacaa tgaatgattc | 660 |
| atcgttctat atattgaagt aaagaatgag tttattgtgc ttgcataatg acgttaactt | 720 |
| cacatataca cttattacat aacatttatc acatgtgcgt ctttttttt ttttactttg | 780 |
| taaaatttcc tcacttttaa gactttata acaattacta gtaaaataaa gttgcttggg | 840 |
| gctacaccct ttctccctcc aacaactcta tttatagata acattatatc aaaatcaaaa | 900 |
| catagtccct ttcttctata aaggtttttt cacaaccaaa tttccattat aaatcaaaaa | 960 |
| ataaaaactt aattagtttt tacagaagaa aagaaaaca | 999 |

<210> SEQ ID NO 173
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 173

| | |
|---|---|
| gggattatat atgatagacg attgtatttg cgggacattg agatgtttcc gaaaatagtc | 60 |
| atcaaatatc aaaccagaat ttgatgtgaa aacactaatt aaaacatata attgacaact | 120 |
| agactatatc atttgttaag ttgagcgttg aaagaaaatg aaagagtgta gactgtagta | 180 |
| cgtatgagtt tcccaaaaga tggtgctga atattattgg gaagagactt tggttggttc | 240 |
| ggttgaatga agatttttac ctgccatgtt gatagagaaa ggcaaataaa tgtaggggtc | 300 |
| gatgtctaac gtaaagactg gatcaaccaa gagtcctcct cctcgtcttc accaaaaaaa | 360 |
| aagagtcctc ctcgtggaaa cttatttctt ctccagccaa gatctcatct catctcttca | 420 |
| ctctatgaaa tataaaggaa tcttatggtt tttctaaaaa ctatagtacg tctatatacc | 480 |

```
aaaggaaaca atataaaatc agttaatctg ataaattttg agtaaataat aaagttaact    540
ttgtacttac ctatatcaaa ctaattcaca aaataaagta ataataacaa agaattttta    600
gtagatccac aatatacaca cacactatga gaaatcataa tagagaattt taatgatttt    660
gtctaactca tagcaacaag tcgctttggc cgagtggtta aggcgtgtgc ctgctaagta    720
catgggctct gcccgcgaga gttcgaatct ctcaggcgac gtttctttg ttttcggcca    780 taaggaaaa agcccaatta acacgtctcg cttataagcc cataaagcaa acaatgggct    840
gtctctgtct cactcacaca cgcgttttcc tacttttga ctatttttat aaccggcggg    900
tctgacttaa ttagggtttt ctttaataat cagacactct ctcactcgtt tcgtcaacat    960
tgaacacaga caaaaccgcg t                                              981

<210> SEQ ID NO 174
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

<400> SEQUENCE: 174
gaaaacaatc ataggttacg ctattatcat cgaaaggtat gtgatgcata ttcccattga     60
accagatttc catatatttt atttgtaaag tgataatgaa tcacaagatg attcaatatt    120
aaaaatgggt aactcacttt gacgtgtagt acgtggaaga atagttagct atcacgcata    180
catatatcta tgaataagtg tgtatgacat aagaaactaa aatatttacc taaagtccag    240
ttactcatac tgatttcatg catatatgta ttatttattt attttaata aagaagcgat    300 tggtgttttc atagaaatca tgatagattg ataggtattt cagttccaca aatctagatc    360
tgtgtgctat acatgcatgt attaattttt tccccttaaa tcatttcagt tgataatatt    420
gctctttgtt ccaactttag aaaaggtatg aaccaacctg acgattaaca agtaaacatt    480
aattaatctt tatatgagat aaaaccgagg atatatatga ttgtgttgct gtctattgat    540
gatgtgtcga tattatgctt gttgtaccaa tgctcgagcc gagcgtgatc gatgccttga    600
caaactatat atgtttcccg aattaattaa gttttgtatc ttaattagaa taacattttt    660
atacaatgta atttctcaag cagacaagat atgtatccta tattaattac tatatatgaa    720
ttgccgggca cctaccagga tgtttcaaat acgagagccc attagtttcc acgtaaatca    780
caatgacgcg acaaaatcta gaatcgtgtc aaaactctat caatacaata atatatattt    840
caagggcaat ttcgacttct cctcaactca atgattcaac gccatgaatc tctatataaa    900
ggctacaaca ccacaaagga tcatcagtca tcacaaccac attaactctt caccactatc    960
tctcaatctc tcgtttcatt tcttgacgcg tgaaaa                              996

<210> SEQ ID NO 175
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 175
taattttttt atttttggaa ctaacactta ttagtttagg tttccatcac ctatttaatt     60
cgtaattctt atacatgcat ataatagaga tacatatata caaatttatg atcattttg    120
```

```
cacaacatgt gatctcattc attagtatgc attatgcgaa aacctcgacg cgcaaaagac      180
acgtaatagc taataatgtt actcatttat aatgattgaa gcaagacgaa aacaacaaca      240
tatatatcaa attgtaaact agatatttct taaaagtgaa aaaaacaaa gaaatataaa       300 ggacaatttt gagtcagtct cttaatatta aacatatat acataaataa gcacaaacgt       360
ggttacctgt cttcatgcaa tgtggacttt agtttatcta atcaaaatca aataaaagg      420 tgtaatagtt ctcgtcattt ttcaaatttt aaaaatcaga accaagtgat tttgtttga      480 gtattgatcc attgttaaa caatttaaca cagtatatac gtctcttgag atgttgacat      540
gatgataaaa tacgagatcg tctcttggtt ttcgaatttt gaactttaat agttttctt       600 tttagggaaa ctttaatagt tgtttatcat aagattagtc acctaatggt tacgttgcag      660
taccgaacca attttttacc cttttttcta aatgtggtcg tggcataatt tccaaaagag      720
atccaaaacc cggtttgctc aactgataag ccggtcggtt ctggtttgaa aaacaagaaa      780
taatctgaaa gtgtgaaaca gcaacgtgtc tcggtgtttc atgagccacc tgccacctca      840
ttcacgtcgg tcattttgtc gtttcacggt tcacgctcta gacacgtgct ctgtcccac      900 catgactttc gctgccgact cgcttcgctt tgcaaactca acatgtgtg tatatgtaag      960 tttcatccta ataagcatct cttaccacat taattaaaaa                            1000
```

<210> SEQ ID NO 176
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 176

```
ttagttcatt gaaacgtcaa cttttactt gcaaccactt tgtaggacca ttaactgcaa       60
aataagaatt ctctaagctt cacaaggggt tcgtttggtg ctataaaaac attgttttaa      120
gaactggttt actggttcta taaatctata atccaaata tgaagtatgg caataataat       180
aacatgttag cacaaaaaat actcattaaa ttcctaccca aaaaaaatct ttatatgaaa      240
ctaaaactta tatacacaat aatagtgata caaagtaggt cttgatattc aactattcgg      300
gattttctgg tttcgagtaa ttcgtataaa aggtttaaga tctattatgt tcactgaaat      360
cttaactttg ttttgtttcc agttttaact agtagaaatt gaaattttta aaattgtta     420 cttacaataa aatttgaatc aatatcctta atcaaaggat cttaagacta gcacaattaa      480
aacatataac gtagaatatc tgaaataact cgaaaatatc tgaactaagt tagtagtttt      540
aaaatataat cccggtttgg accgggcagt atgtacttca atacttgtgg gttttgacga      600
ttttggatcg gattgggcgg gccagccaga ttgatctatt acaaatttca cctgtcaacg      660
ctaactccga acttaatcaa agattttgag ctaaggaaaa ctaatcagtg atcacccaaa      720
gaaaacattc gtgaataatt gtttgctttc catggcagca aaacaaatag gacccaaata      780
ggaatgtcaa aaaaagaaa gacacgaaac gaagtagtat aacgtaacac acaaaaataa      840
actagagata ttaaaaacac atgtccacac atggatacaa gagcatttaa ggagcagaag      900
gcacgtagtg gttagaaggt atgtgatata attaatcggc ccaaatagat tggtaagtag      960
tagccgtcta tatcatccat actcatcata acttcaacct                            1000
```

<210> SEQ ID NO 177
<211> LENGTH: 1000
<212> TYPE: DNA

<213> ORGANISM: Arabidopsis thaliana
<220> FEATURE:
<221> NAME/KEY: misc_feature
<223> OTHER INFORMATION: Ceres Promoter YP0374

<400> SEQUENCE: 177

| | | | | | |
|---|---|---|---|---|---|
| aagacacccg | taaatgttgt | catgtagaag | aaactagaaa | cgttaaacgc | atcaaatcaa | 60 |
| gaaattaaat | tgaaggtaat | ttttaacgcc | gcctttcaaa | tattcttcct | aggagaggct | 120 |
| acaagacgcg | tatttctttc | gaattctcca | aaccattacc | attttgatat | ataataccga | 180 |
| catgccgttg | ataaagtttg | tatgcaaatc | gttcattggg | tatgagcaaa | tgccatccat | 240 |
| tggttcttgt | aattaaatgg | tccaaaaata | gtttgttccc | actactagtt | actaatttgt | 300 |
| atcactctgc | aaaataatca | tgatataaac | gtatgtgcta | tttctaatta | aaactcaaaa | 360 |
| gtaatcaatg | tacaatgcag | agatgaccat | aaaagaacat | taaaacacta | cttccactaa | 420 |
| atctatgggg | tgccttggca | aggcaattga | ataaggagaa | tgcatcaaga | tgatatagaa | 480 |
| aatgctattc | agtttataac | attaatgttt | tggcggaaaa | ttttctatat | attagacctt | 540 |
| tctgtaaaaa | aaaaaaaatg | atgtagaaaa | tgctattatg | tttcaaaaat | ttcgcactag | 600 |
| tataatacgg | aacattgtag | tttacactgc | tcattaccat | gaaaaccaag | gcagtatata | 660 |
| ccaacattaa | taaactaaat | cgcgatttct | agcaccccca | ttaattaatt | ttactattat | 720 |
| acattctctt | tgcttctcga | aataataaac | ttctctatat | cattctacat | aataaataag | 780 |
| aaagaaatcg | acaagatcta | aatttagatc | tattcagctt | tttcgcctga | aagccaaaa | 840 |
| ttgtgaatag | aagaaagcag | tcgtcatctt | cccacgtttg | gacgaaataa | aacataacaa | 900 |
| taataaaata | ataaatcaaa | tatataaatc | cctaatttgt | ctttattact | ccacaatttt | 960 |
| ctatgtgtat | atatataccc | acctctctct | tgtgtatttg | | | 1000 |

<210> SEQ ID NO 178
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 178

| | | | | | |
|---|---|---|---|---|---|
| tataaaccat | tcctataaca | ccatatttaa | acataacaat | gaattgcttg | gatttcaaac | 60 |
| tttattaaat | ttggatttta | aattttaatt | tgattgaatt | ataccccctt | aattggataa | 120 |
| attcaaatat | gtcaactttt | tttttgtaag | attttttta | ggaaaaaaaa | attgattatt | 180 |
| cactaaaaag | atgacaggtt | acttataatt | taatatatgt | aaaccctaaa | agaagaaaa | 240 |
| tagtttctgt | tttcacttta | ggtcttatta | tctaaacttc | tttaagaaaa | tcgcaataaa | 300 |
| ttggtttgag | ttctaacttt | aaacacatta | atatttgtgt | gctatttaaa | aaataattta | 360 |
| caaaaaaaaa | aacaaattga | cagaaaatat | caggttttgt | aataagatat | ttcctgataa | 420 |
| atatttaggg | aatataacat | atcaaaagat | tcaaattctg | aaaatcaaga | atggtagaca | 480 |
| tgtgaaagtt | gtcatcaata | tggtccactt | ttctttgctc | tataacccaa | aattgaccct | 540 |
| gacagtcaac | ttgtacacgc | ggccaaacct | ttttataatc | atgctattta | tttccttcat | 600 |
| ttttattcta | tttgctatct | aactgatttt | tcattaacat | gataccagaa | atgaatttag | 660 |
| atggattaat | tcttttccat | ccacgacatc | tggaaacact | tatctcctaa | ttaaccttac | 720 |
| tttttttta | gtttgtgtgc | tccttcataa | aatctatatt | gtttaaaaca | aaggtcaata | 780 |
| aatataaata | tggataagta | taataaatct | ttattggata | tttctttttt | taaaaagaa | 840 |

| | |
|---|---|
| ataaatctttt tttggatatt ttcgtggcag catcataatg agagactacg tcgaaaccgc | 900 |
| tggcaaccac ttttgccgcg tttaatttct ttctgaggct tatataaata gatcaaaggg | 960 |
| gaaagtgaga tataatacag acaaaacaag agaaaaga | 998 |

```
<210> SEQ ID NO 179
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 179
```

| | |
|---|---|
| acaagtacca ttcactttt tacttttcaa tgtatacaat catcatgtga taaaaaaaaa | 60 |
| aatgtaacca atcaacacac tgagatacgg ccaaaaaatg gtaatacata aatgtttgta | 120 |
| ggttttgtaa tttaaatact ttagttaagt tatgatttta ttatttttgc ttatcactta | 180 |
| tacgaaatca tcaatctatt ggtatctctt aatcccgctt tttaatttcc accgcacacg | 240 |
| caaatcagca aatggttcca gccacgtgca tgtgaccaca tattgtggtc acagtactcg | 300 |
| tcctttttt ttcttttgta atcaataaat ttcaatccta aaacttcaca cattgagcac | 360 |
| gtcggcaacg ttagctccta aatcataacg agcaaaaaag ttcaaattag ggtatatgat | 420 |
| caattgatca tcactacatg tctacataat taatatgtat tcaaccggtc ggtttgttga | 480 |
| tactcatagt taagtatata tgtgctaatt agaattagga tgaatcagtt cttgcaaaca | 540 |
| actacggttt catataatat gggagtgtta tgtacaaaat gaaagaggat ggatcattct | 600 |
| gagatgttat gggctcccag tcaatcatgt tttgctcgca tatgctatct tttgagtctc | 660 |
| ttcctaaact catagaataa gcacgttggt tttttccacc gtcctcctcg tgaacaaaag | 720 |
| tacaattaca ttttagcaaa ttgaaaataa ccacgtggat ggaccatatt atatgtgatc | 780 |
| atattgcttg tcgtcttcgt tttcttttaa atgtttacac cactacttcc tgacacgtgt | 840 |
| ccctattcac atcatccttg ttatatcgtt ttacttataa aggatcacga acaccaaaac | 900 |
| atcaatgtgt acgtcttttg cataagaaga aacagagagc attatcaatt attaacaatt | 960 |
| acacaagaca gcgagattgt aaaagagtaa gagagagag | 999 |

```
<210> SEQ ID NO 180
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 180
```

| | |
|---|---|
| cacggtcaaa gtattgctaa catggtcatt acattgaaaa agaaaattaa ttgtctttac | 60 |
| tcatgtttat tctatacaaa taaaaatatt aaccaaccat cgcactaaca aaatagaaat | 120 |
| cttattctaa tcacttaatt gttgacaatt aaatcattga aaaatacact taaatgtcaa | 180 |
| atattcgttt tgcatacttt tcaatttaaa tacatttaaa gttcgacaag ttgcgtttac | 240 |
| tatcatagaa aactaaatct cctaccaaag cgaaatgaaa ctactaaagc gacaggcagg | 300 |
| ttacataacc taacaaatct ccacgtgtca attaccaaga gaaaaaaaga gaagataagc | 360 |
| ggaacacgtg gtagcacaaa aaagataatg tgatttaaat taaaaacaaa aacaaagac | 420 |
| acgtgacgac ctgacgctgc aacatcccac cttacaacgt aataaccact gaacataaga | 480 |

```
cacgtgtacg atcttgtctt tgttttctcg atgaaaacca cgtgggtgct caaagtcctt    540
gggtcagagt cttccatgat tccacgtgtc gttaatgcac caaacaaggg tactttcggt    600
attttggctt ccgcaaatta gacaaaacag ctttttgttt gattgatttt tctcttctct    660
ttttccatct aaattctctt tgggctctta atttcttttt gagtgttcgt tcgagatttg    720
tcggagattt tttcggtaaa tgttgaaatt ttgtgggatt tttttttatt tctttattaa    780 acttttttt attgaattta taaaagggga aggtcgtcat taatcgaaga aatgaaatct    840
tccaaaattt gatattttgc tgttttcttg ggatttgaat tgctctttat catcaagaat    900
ctgttaaaat ttctaatcta aaatctaagt tgagaaaaag agagatctct aatttaaccg    960
gaattaatat tctccgaccg aagttattat gttgcaggct                         1000

<210> SEQ ID NO 181
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 181
tttaaaaaat tggataaaac accgataaaa attcacattt gcaaatttta ttcagtcgga     60
atatatattt gaaacaagtt ttgaaatcca ttggacgatt aaaattcatt gttgagagga    120
taaatatgga tttgttcatc tgaaccatgt cgttgattag tgattgacta ccatgaaaaa    180
tatgttatga aaagtataac aacttttgat aaatcacatt tattaacaat aaatcaagac    240
aaaatatgtc aacaataata gtagtagaag atattaattc aaattcatcc gtaacaacaa    300
aaaatcatac cacaattaag tgtacagaaa aaccttttgg atatatttat tgtcgctttt    360
caatgatttt cgtgaaaagg atatatttgt gtaaaataag aaggatcttg acgggtgtaa    420
aaacatgcac aattcttaat ttagaccaat cagaagacaa cacgaacact tctttattat    480
aagctattaa acaaaatctt gcctattttg cttagaataa tatgaagagt gactcatcag    540
ggagtggaaa atatctcagg atttgctttt agctctaaca tgtcaaacta tctagatgcc    600
aacaacacaa agtgcaaatt cttttaatat gaaaacaaca ataatatttc taatagaaaa    660
ttaaaagggg aaataaaata ttttttttaaa atatacaaaa gaagaaggaa tccatcatca    720
aagttttata aaattgtaat ataatacaaa cttgtttgct tccttgtctc tccctctgtc    780
tctctcatct ctcctatctt ctccatatat acttcatctt cacacccaaa actccacaca    840
aaatatctct ccctctatct gcaaattttc caaagttgca tcctttcaat ttccactcct    900
ctctaatata attcacattt tcccactatt gctgattcat ttttttttgt gaattatttc    960
aaacccacat aaaaaaatct tgtttaaat ttaaaacca                            999

<210> SEQ ID NO 182
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 182
actcaacaat aggacaagcc aaaaaaattc caattattgt gttactctat tcttctaaat     60
ttgaacacta atagactatg acatatgagt atataatgtg aagtcttaag atattttcat    120
gtgggagatg aataggccaa gttggagtct gcaaacaaga agctcttgag ccacgacata    180
```

```
agccaagttg atgaccgtaa ttaatgaaac taaatgtgtg tggttatata ttagggaccc    240
atggccatat acacaatttt tgtttctgtc gatagcatgc gtttatatat atttctaaaa    300
aaactaacat atttactgga tttgagttcg aatattgaca ctaatataaa ctacgtacca    360
aactacatat gtttatctat atttgattga tcgaagaatt ctgaactgtt ttagaaaatt    420
tcaatacact taacttcatc ttacaacggt aaaagaaatc accactagac aaacaatgcc    480
tcataatgtc tcgaaccctc aaactcaaga gtatacattt tactagatta gagaatttga    540
tatcctcaag ttgccaaaga attggaagct tttgttacca aacttagaaa cagaagaagc    600
cacaaaaaaa gacaagggga gttaaagatt gaagtgatgc atttgtctaa gtgtgaaagg    660
tctcaagtct caactttgaa ccataataac attactcaca ctccttttt ttttctttt     720 ttttcccaaa gtacccttt taattccctc tataacccac tcactccatt ccctctttct    780
gtcactgatt caacacgtgg ccacactgat gggatccacc tttcctctta cccacctccc    840
ggtttatata aacccttcac aacacttcat cgctctcaaa ccaactctct cttctctctt    900
ctctcctctc ttctacaaga agaaaaaaaa cagagccttt acacatctca aaatcgaact    960
tactttaacc accaaatact gattgaacac acttgaaa                            998
```

<210> SEQ ID NO 183
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 183

```
catagtaaaa gtgaatttaa tcatactaag taaaataaga taaaacatgt tatttgaatt     60
tgaatatcgt gggatgcgta tttcggtatt tgattaaagg tctggaaacc ggagctccta    120
taacccgaat aaaaatgcat aacatgttct tccccaacga ggcgagcggg tcagggcact    180
agggtcattg caggcagctc ataaagtcat gatcatctag gagatcaaat tgtatgtcgg    240
ccttctcaaa attacctcta agaatctcaa acccaatcat agaacctcta aaagacaaa     300 gtcgtcgctt tagaatgggt tcggtttttg gaaccatatt tcacgtcaat ttaatgttta    360
gtataatttc tgaacaacag aattttggat ttatttgcac gtatacaaat atctaattaa    420
taaggacgac tcgtgactat ccttacatta agtttcactg tcgaaataac atagtacaat    480
acttgtcgtt aatttccacg tctcaagtct ataccgtcat ttacggagaa agaacatctc    540 tgttttcat ccaaactact attctcactt tgtctatata tttaaaatta agtaaaaaag     600
actcaatagt ccaataaaat gatgaccaaa tgagaagatg gttttgtgcc agattttagg    660
aaaagtgagt caaggtttca catctcaaat ttgactgcat aatcttcgcc attaacaacg    720
gcattatata tgtcaagcca attttccatg ttgcgtactt ttctattgag gtgaaaatat    780
gggtttgttg attaatcaaa gagtttgcct aactaatata actacgactt tttcagtgac    840
cattccatgt aaactctgct tagtgtttca tttgtcaaca atattgtcgt tactcattaa    900
atcaaggaaa aatatacaat tgtataattt tcttatattt taaattaat tttgatgtat     960 tacccctta taaataggct atcgctacaa caccaataac                           1000
```

<210> SEQ ID NO 184
<211> LENGTH: 1514
<212> TYPE: DNA
<213> ORGANISM: Arabidopsis thaliana

```
<220> FEATURE:
<221> NAME/KEY: misc_feature
<223> OTHER INFORMATION: Ceres Promoter p13879

<400> SEQUENCE: 184
tttcgatcct cttctttttt aggtttcttg atttgatgat cgccgccagt agagccgtcg    60
tcggaagttt cagagattaa accatcacc gtgtgagttg gtagcgaatt aacggaaagt   120
ctaagtcaag attttttaaa aagaaattta tgtgtgaaaa gaagccgttg tgtatattta   180
tataatttag aaaatgtttc atcattttaa ttaaaaaatt ataaatttgt agaagaaaga   240
agcatttttt atacataaat catttacctt ctttactgtg ttttcttca cttacttcat    300 ttttactttt ttacaaaaaa gtgaaaagta aattacgtaa ttggtaacat aaattcactt   360
taaatttgca tatgttttgt tttcttcgga actatatcg aaaagcaaac ggaaagaact    420
tcacaaaaaa ccctagctaa ctaaagacgc atgtgttctt cttattcttc atatatcctc   480
tgtttcttgt gttctgtttt gagtcttaca ttttcaatat ctgactctga ttactatatc   540
taaaagggaa catgaagaac ttgagaccat gttaaactgt acaatgcctt caaacatggc   600
taactaaaga tacattagat ggctttacag tgtgtaatgc ttattatctt taggttttt    660 aaatcccttg tattaagtta tttaccaaat tatgttcttg tactgcttat tggcttggtt   720
gttgtgtgct ttgtaaacaa cacctttggc tttatttcat cctttgtaaa cctactggtc   780
tttgttcagc tcctcttgga agtgagtttg tatgcctgga acgggtttta atggagtgtt   840
tatcgacaaa aaaaaaatgt agcttttgaa atcacagaga gtagttttat attcaaatta   900
catgcatgca actaagtagc aacaaagttg atatggccga gttggtctaa ggcgccagat   960
taaggttctg gtccgaaagg gcgtgggttc aaatcccact gtcaacattc tcttttctc   1020 aaattaatat ttttctgcct caatggttca ggcccaatta tactagacta ctatcgcgac  1080
taaaataggg actagccgaa ttgatccggc ccagtatcag ttgtgtatca ccacgttatt  1140
tcaaatttca aactaaggga taaagatgtc atttgacata tgagatattt ttttgctcca  1200
ctgagatatt tttctttgtc ccaagataaa atatcttttc tcgcatcgtc gtctttccat  1260
ttgcgcatta aaccaaaaag tgtcacgtga tatgtcccca accactacga attttaacta  1320
cagatttaac catggttaaa ccagaattca cgtaaaccga ctctaaacct agaaaatatc  1380
taaaccttgg ttaatatctc agccccctta taaataacga gacttcgtct acatcgttct  1440
acacatctca ctgctcacta ctctcactgt aatcccttag atcttctttt caaatttcac  1500
cattgcactg gatg                                                    1514

<210> SEQ ID NO 185
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 185
gtgggtaaaa gtatccttct ttgtgcattt ggtattttta agcatgtaat aagaaaaacc    60
aaaatagacg gctggtattt aataaaagga gactaatgta tgtatagtat atgatttgtg   120
tggaatataa taaagttgta aaatatagat gtgaagcgag tatctatctt ttgactttca   180
aaggtgatcg atcgtgttct ttgtgatagt tttggtcgtc ggtctacaag tcaacaacca   240
ccttgaagtt ttcgcgtctc ggtttcctct tcgcatctgg tatccaatag catacatata   300
```

| | |
|---|---:|
| ccagtgcgga aaatggcgaa gactagtggg cttgaaccat aaggtttggc cccaatacgg | 360 |
| attccaaaca acaagcctag cgcagtcttt tgggatgcat aagactaaac tgtcgcagtg | 420 |
| atagacgtaa gatatatcga cttgattgga atcgtctaag ctaataagtt taccttgacc | 480 |
| gtttatagtt gcgtcaacgt ccttatggag attgatgccc atcaaataaa cctgaaaatc | 540 |
| catcaccatg accaccataa actcccttgc tgccgctgct ttggcttgag caaggtgttt | 600 |
| ccttgtaaag ctccgatctt tggataaagt gttccacttt ttgcaagtag ctctgacccc | 660 |
| tctcagagat gtcaccggaa tcttagacag aacctcctct gccaaatcac ttggaagatc | 720 |
| ggacaatgtc atcattttg caggtaattt ctccttcgtt gctgctttgg cttgagcacg | 780 |
| gtgcttcttt gtaaagctcc gatctttgga taagagcgga tcggaatcct ctaggaggtg | 840 |
| ccagtccctt gacctattaa tttatagaag gttttagtgt atttttgttcc aatttcttct | 900 |
| ctaacttaac aaataacaac tgcctcatag tcatgggctt caaatttat cgcttggtgt | 960 |
| atttcgttat ttgcaaggcc ttggcccatt ttgagcccaa taactaaatc tagccttttc | 1020 |
| agaccggaca tgaacttcgc atattggcgt aactgtgcag ttttacccttt ttcggatcag | 1080 |
| acaagatcag atttagacca cccaacaata gtcagtcata tttgacaacc taagctagcc | 1140 |
| gacactacta aaaagcaaac aaaagaagaa ttctatgttg tcattttacc ggtggcaagt | 1200 |
| ggacccttct ataaaagagt aaagagacag cctgtgtgtg tataatctct aattatgttc | 1260 |
| accgacacaa tcacacaaac ccttctctaa tcacacaact tcttcatgat ttacgacatt | 1320 |
| aattatcatt aactctttaa attcacttta catgctcaaa aatatctaat ttgcagcatt | 1380 |
| aatttgagta ccgataacta ttattataat cgtcgtgatt cgcaatcttc ttcattagat | 1440 |
| gctgtcaagt tgtactcgca cgcggtggtc cagtgaagca atccaacgg tttaaaacct | 1500 |
| tcttacatttt ctagatctaa tctgaaccgt cagatatcta gatctcattg tctgaacaca | 1560 |
| gttagatgaa actgggaatg aatctggacg aaattacgat cttacaccaa cccctcgac | 1620 |
| gagctcgtat atataaagct tatacgctcc tccttcacct tcgtactact actaccacca | 1680 |
| catttcttta gctcaacctt cattactaat ctccttttaa ggtatgttca ctttctttcg | 1740 |
| attcatactt tctcaagatt cctgcatttc tgtagaattt gaaccaagtg tcgattttg | 1800 |
| tttgagagaa gtgttgattt atagatctgg ttattgaatc tagattccaa ttttttaattg | 1860 |
| attcgagttt gttatgtgtg tttatactac ttctcattga tcttgtttga tttctctgct | 1920 |
| ctgtattagg tttctttcgt gaatcagatc ggaa | 1954 |

<210> SEQ ID NO 186
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 186

| | |
|---|---:|
| gatcggcctt cttcaggtct tctctgtagc tctgttactt ctatcacagt tatcgggtat | 60 |
| ttgagaaaaa agagttagct aaaatgaatt tctccatata atcatggttt actacaggtt | 120 |
| tacttgattc gcgttagctt tatctgcatc caaagttttt tccatgatgt tatgtcatat | 180 |
| gtgataccgt tactatgttt ataactttat acagtctggt tcactggagt ttctgtgatt | 240 |
| atgttgagta catactcatt catcctttgg taactctcaa gtttaggttg tttgaattgc | 300 |
| ctctgttgtg atacttattg tctattgcat caatcttcta atgcaccacc ctagactatt | 360 |

```
tgaacaaaga gctgtttcat tcttaaacct ctgtgtctcc ttgctaaatg gtcatgcttt       420
aatgtcttca cctgtctttc tcttctatag atatgtagtc ttgctagata gttagttcta       480
cagctctctt ttgtagtctt gttagagagt tagttgagat attacctctt aaaagtatcc       540
ttgaacgctt tccggttatg accaatttgt tgtagctcct tgtaagtaga acttactggg       600
accagcgaga cagtttatgt gaatgttcat gcttaagtgt cgaacgtatc tatctctact       660
atagctctgt agtcttgtta gacagttagt tttatatctc cattttttg tagtcttgct        720 agttgagata ttacctcttc tcttcaaagt atccttgaac gctcaccggt tatgaaatct       780
ctacactata gctctgtagt cttgctagat agttagttct ttagctctct ttttgtagcc       840 tagttctttta gctctccttt tgtagccttg ctacagagta agatgggata ttacctcctt      900
gaacgctctc cggttatgac caatttgttg tagctccttg taagtagaac ttaggataga       960
gtgagtcaac tttaagaaag aacctagtat gtggcataac cagattgcag gctctgtctc      1020
ggctacagta acgtaactct atagctcttt gttttgttca gaaagaacca gtgattggat      1080
gattcgtcct tagaaactgg acctaacaac agtcattggc tttgaaatca gccacaaca       1140 atgcctatat gaaccgtcca tttcatttat ccgtttcaaa ccagcccatt acatttcgtc      1200
ccattgataa ccaaaagcgg ttcaatcaga ttatgtttta attttaccaa attctttatg      1260
aagtttaaat tatactcaca ttaaaaggat tattggataa tgtaaaaatt ctgaacaatt      1320
actgattttg gaaaattaac aaatattctt tgaaatagaa gaaaaagcct tttcttttt      1380 gacaacaaca tataaaatca tactcccatt aaaaagattt taatgtaaaa ttctgaatat      1440
aagatatttt ttacaacaac aaccaaaaat atttattttt ttcctttttt acagcaacaa      1500
gaaggaaaaa ctttttttt tgtcaagaaa aggggagatt atgtaaacag ataaaacagg       1560
gaaaataact aaccgaactc tcttaattaa catcttcaaa taaggaaaat tatgatccgc      1620
atatttagga agatcaatgc attaaaacaa cttgcacgtg gaaagagaga ctatacgctc      1680
cacacaagtt gcactaatgg tacctctcac aaaccaatca aaatactgaa taatgccaac      1740
gtgtacaaat tagggtttta cctcacaacc atcgaacatt ctcgaaacat tttaaacagc      1800
ctggcgccat agatctaaac tctcatcgac caattttga ccgtccgatg gaaactctag       1860
cctcaaccca aaactctata taagaaatc ttttccttcg ttattgctta ccaaatacaa       1920
accctagccg ccttattcgt cttcttcgtt ctctagtttt ttcctcagtc tctgttctta      1980
gatcccttgt agtttccaaa tcttccgata aggcct                                2016

<210> SEQ ID NO 187
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 187
acagttttct tttctcatct tacaacaagt ttccaggagg atagagacat aaacgaagct        60
cggattgtat cgttcttttt agcttttatt cacatccgaa agtcctgtag tttagattct       120
gttatcttgc ggttttgagt taatcagaaa cagagtaatc aatgtaatgt tgcaggctag       180
atctttcatc tttggaaatt tgtttttttc tcatgcaatt tctttagctt gaccatgagt       240
gactaaaaga tcaatcagta gcaatgattt gatttggcta agagacattt gtccacttgg       300
catcttgatt tggatggtta caacttgcaa gacccaattg gatacttgct atgacaactc       360
```

```
caactcaaga gtgtcgtgta actaagaacc ttgactaatt tgtaatttca atcccaagtc    420
atgttactat atgttttttt gtttgtatta ttttctctcc tacaattaag ctctttgacg    480
tacgtaatct ccggaaccaa ctcctatatc caccatttac tccacgttgt ctccaattat    540
tggacgttga aacttgacac aacgtaaacg tatctacgtg gttgattgta tgtacatatg    600
tacaaacgta cacctttctc ctctttcact tcatcacttg gcttgtgaat tcattaattc    660
ctgcgaa                                                              667
```

```
<210> SEQ ID NO 188
<211> LENGTH: 1836
<212> TYPE: DNA
<213> ORGANISM: Oryza sativa
<220> FEATURE:
<221> NAME/KEY: misc_feature
<223> OTHER INFORMATION: Ceres Promoter p530c10

<400> SEQUENCE: 188
```

```
gcctctcgac cacgagttta gcacttgtgc aacatatatg cgtgcgatga acatctactg     60
atgcgccatg cgaattttag cgttcgttca tgacgcttcc aacggcacag aggctgagca    120
gcagcatgca tgcatggctc ttgtgaaaac aaaaaaggtt actggtaaat gacatgctgc    180
tgtagctagc tagcagaatg caaggcccat gcatatgcaa tgctatgcga caagtacagt    240
accagcatgt atggtagcca gctaactaat ctatcagcag aggcagcaag ctcgtgcatg    300
gtgtgatgca cttctctcca gtaatctagt ggtaattttc acccaaagcg ttgctcatat    360
ggacagtaat tagtaatatt accaaggttc acaatcccgt tacctgacca aatactactc    420
acgaatggta tctctggttt tcgttaaaac cgttggtaaa ccagcaaaaa tagacaaaat    480
ttgtcaaaat tttaaatttt agtttttttt ttttaactta gccgggaaac cttgaagttt    540
gtgctgtcga gctgtcctgg gaaggacggt tttggttggg attgtgaacc ctggttactg    600
cacttcattt ttgaacagat attagtgcaa cagacaaatg ccaacgcatt ttttctgtt    660 taccggcaag ctgaagcttt tacgatcccc atacagccgt tgctgcaaac ctgccaagaa    720
agagcagcag aaacaggtgt cattttgtgg tggaaagcca agtaaagtaa acagaagatg    780
gaagatagtg aggaccaggg agtgaggcag gggacacatg gcccacgcct ccctgcacat    840
tttcgtgtat aaatacaggt ggatgcatcg ctctcccagc atccatcggt tctctgctct    900
gttcatccat agagtttcct cctcttctcc tttagtgcaa ggtagagaag agcatgtgtg    960
tgtgtgtgtg tgtgtgaact gtgaagtgca gagtgcttct gtagttctgt gttatgtcca   1020
tagtgatctt gttaggattg ttgctatgga tgcatgatgt tatggttgat ctctgaatta   1080
cagtagggac ttttctgaga tctctggatt agtgggggt gctaaatttt tttctggttg   1140
catcagcttg ggtttctggt attggtgtgg gttcttgctc tgaattttgg ttcagaatgt   1200
cgatttgttt gtgtttgttc tctgaagttg agagtagcta tgatccatcc agcacagaac   1260
tgcaggtcct gcctgccggc tgcatataca ggacatgcca ttttgcaagc tctgggctta   1320
tggtttctct tttggagttc ttcttcttgc atgatctgtg ttctctaaca aaggaagcaa   1380
gatttagcaa ctttattcag agacaagaaa aggatctggc aaccttttgt ttctgtttta   1440
tcctactcgt aaagattgtt atttaagcaa aaatttccca aaagttttaa atataatttc   1500
catgatgtgc cactctcatg tccttgaacc tggcactcat tatgggctcc tcagaagtgc   1560
tgtagctaat gtcactaatc ttttgtatct ttgttcatag tcttgtattt tatgatgctt   1620 atcccttgt gctttccatg tttgatgtcc aaatgtcatg gcaatgtttt tgacttctag   1680
```

```
tagggggtttt agtaccttttt tgttagataa gtacatccaa attctgttta tttattcaaa      1740
aatcattctg tttattcact gaaaacattt gtccattcaa tggactcata aactgtctgt      1800
gtttttcagg cttgaggatc catctagaag atagca                                 1836

<210> SEQ ID NO 189
<211> LENGTH: 3000
<212> TYPE: DNA
<213> ORGANISM: Oryza sativa
<220> FEATURE:
<221> NAME/KEY: misc_feature
<223> OTHER INFORMATION: Ceres Promoter pOsFIE2-2

<400> SEQUENCE: 189
gcttaacaca tgaactacca aaatatactg atcactttgt tctagtcata cataccttaa        60
gtcattttat tctgcagtgt ttggattgga gggagcattc tagcatccct tgggtcgttc       120
cagcaaatgt ggttctccaa agcagagtaa gcacaacaca gtattttagg ttatgtttcc       180
cctatctcgt cacggacagc tcacaagtta atgtgattta tctcactata gatacgaaga       240
acatggagta tcctacatcc aaaggaagtg cccatgaagt tgtggagcat cgctacgatt       300
tgtgaccaaa tttgggtgca tgtgggcaat cgtattacag ccaccctgtt gttgatctat       360
atcgactatt atccgacgat atttatcatt atattatgac tagttagttt gtagattttg       420
agagggcaac ataagaagca atccagctta acctgttatg ttcttgatgg tagattctag       480
ttcatgtgtt gaatctgttc tccctgctgt agaatgtatc gagttgctgc tctctactct       540
gtacttttag aataccttt caatcatttg gagtcagctg attgttgtac tacttatacg       600
ccacctgatt agtcatgtca acaattaaac ttgagcactg gttaagttaa gagtggcctg       660
attgtagttg ataatcacat tttattcgta gacattgtat gctggatctt tatcagccac       720
cgtcagatca tcctctgtaa taaatcttca tcagacgtgt gtgccaatcg caaggaacac       780
gaaatgcatc cgaaatgtta ctctgagtta atcaatacta taattcttgg tcaaattaat       840
tatttatatc tataaagttt aaattaaatt taggaaaatg aattcatgca aatcttgtgg       900
taagttgtca atttcataaa aaatccagct tactactccc tttttaggag tgtgttgtgg       960
ctgcacactt ctgcctttg atatatacgg ttctattctc ggtgtactcc tttattatta      1020
ttaaaacaat cccagttact tggtaagtgc taatcacgaa tcaaagtcaa cataacaaat      1080
catgtgcgta cagctataac tcgattacac aaacaacaaa attcatattt gaacataaat      1140
ccagttgtag catatctggt agtataaagt ttttttttg tatagaagag ttttaatttc      1200
tgtaagtttt ggaaagcatt taatcctaga aattgtagtg tagctcaact aaaaaataaa      1260
tgaacttgaa tcgaaattgg gttgtatcat aaatctttac cactcaaacg aatatttatc      1320
ctaaaccaca aatgactctt ttcatcaagg aatgttttgt tttcagcatt ttaaaaaaaa      1380
acttttctaa tatggttttc atgtttcgtt cttttgaaat ttaacatcta tttaatttgc      1440
acggctccat aaattcaacg gatacatatt ctgaataatt actaaggagg catatatcgg      1500
ctctcttaat acaaccgctt gtttctcaaa atttattttg agttttgtct acacattctc      1560
aaggacggta caaacacact atagatgttc acaattttttt ttttctaaag ttgattgatg      1620
gacaaatgtt tgaacatata aacatataag cactgaatat ttgcttatgc aggaggtatt      1680
tatatcaagt tcgatacttt actaccatag tccctaggac actaaaatgc cttcaatgat      1740
ctgatgaagc ctaagagaga atattgatca gtggagcgac ttgcaactac acatggcaca      1800
agtagactag acacggtata tattcatatt aacttgttaa aattttacta cttaacagtt      1860
```

| | |
|---|---|
| cacttgtggt gcatccatat caattcttac ttacacaata tttgtaaaaa caacctaaca | 1920 |
| ctataggatg acctagacaa cctttatgtc aatcacactt agaagatgat cgtctttta | 1980 |
| ataaataatg tgtactacac accatgctct ccatatagat caagatctac aaacccttcc | 2040 |
| acttataaac cttaccacca aaaactcatt aagttgcttc atttatctat gctattaaga | 2100 |
| aaaaaactta tttcgtttat gccatttcta gaaatggcta gtcacactat tcacaatatt | 2160 |
| atataataaa taaagtttc aaatattcat ccaccaaaaa tcatcaagtc gtgggactta | 2220 |
| tatgttaatt agagaagtcc ctttgggtgc aatcgatttt ggaaaccta aattttct | 2280 |
| atacatagaa gagagagatg tctagttgca attgcttttg cgatgtgcca accacccttc | 2340 |
| tagctttcat ccacgtctac ttaattgcca ttcttcttct tctttttctt cactattact | 2400 |
| acctcctatc ttagcgaatc ttcttcttct tcactattac tacctcccac cttagtgaat | 2460 |
| tcatcctcat tgttcacaat gacattgcta agttaactag gtatgctaag tacacaatta | 2520 |
| gaatataacc tagagccttt gtttccatca tacttaaaag atgacatttt tatatagata | 2580 |
| aagtgtgcta ctcacaaggc ttactatata tatgtatgat acacacaaac tccacaaccc | 2640 |
| aaaactcttt caagttgtgt ggcccatcta tgctattaaa aagcccattt agcccatcca | 2700 |
| acatgagaaa ccctagggtt ttttccctat aaaagatacc taggttattg ttgcttttcc | 2760 |
| accccgcccg ccgccgctcc ctattcctat ttaatcccat ctctcttcct catcaccgct | 2820 |
| ctcctctctc caggcaagag gtacgcactt tttgtttcgg atttgaaatc tttgcttcgt | 2880 |
| tttactatca ttggtcataa gttctttttt gaagatgttt gagaataagt ttatcattga | 2940 |
| gattatcgtc acttgtgata ggaagtacgc aacctcaagc cggacaagac gtgagcaaag | 3000 |

<210> SEQ ID NO 190
<211> LENGTH: 2023
<212> TYPE: DNA
<213> ORGANISM: Oryza sativa
<220> FEATURE:
<221> NAME/KEY: misc_feature
<223> OTHER INFORMATION: Ceres Promoter pOsMEA

<400> SEQUENCE: 190

| | |
|---|---|
| gagagcagaa catagtagcc gctgttttct gggggtgcaa tttgtgcaag atcgctatcc | 60 |
| ttatggacca tgcaagcacc aagcaatatt aagccaggtc caacagcggt cttggggaat | 120 |
| tcagaaatga gcttaaaaac ctccttgagc tggccagctc agccaaggag gtccatcatg | 180 |
| catgtgcatg ctcaatactt ggaattattg caaaatgatc ggtcattgac tggaagactt | 240 |
| tgcgcccttc ctcagccaac cttatgtggc tgcatgcata gagtaccaac aggaaggtag | 300 |
| cgtttgttgg aataaggttt gcatccagca tgtccttgta gagcttcaaa gcctcagcac | 360 |
| cttggcccat gaaggccata tccagctaat tgcattccat gagaccacat tcttgctatc | 420 |
| catactgttg aagtgaagat gctccgagct tcggaaatgc ttccacacta tgcatacatg | 480 |
| tcaatgagca ctgtcatgac ataaacattg gccccaagt cctcctcagc gataatccta | 540 |
| tgcagccact ttcccaggga caaagctcca agctgtgcac acgctgaaag agagctagaa | 600 |
| atgatgattg gatttggtca cacgctaagt accagcattt gctcaaagag ggcaattgcc | 660 |
| atctccgtcc agccattcta ggcatacct ggtattattg ctttccatga ttccgattcc | 720 |
| gtggtcttct atggcatcgc attgaaggcc ttccttgcag actccatatc atttaaccta | 780 |
| cagtacaata tggtaattgc tgtcgacact ggagaattcg cagtaaatcc agacttgaga | 840 |
| ggaccatgta agcattgatc aagcagttca ttcccaaaca gactatacgg gatcagtgcc | 900 |

```
agtgctcgag tttggcttca attccaaggc catcaaccca ataaacagat taactgatga    960
accaaccatg caattcgccg agcaaacata gattaagcat tgtaggcaac caaatctgga   1020
ttctccatca agtcaaagag acgccatgca gaattccaca tccccgctgt atacaccgag   1080
atcaaccggt cagaacatgc tcatactccg ccaaccctct cttcagaaca tgctcatact   1140
ccgccaaccc tctcttctct gcaagaggca tcctccccaa ttccccattg ttatatctgt   1200
tgctggtaag accgttgcca gcgtggttgt gtcagaccga acagactctg cactcgccat   1260
cctcacgaac gactccaggg cctccgaacc aggaagcccg gccggccatc agcgtgttcc   1320
acataacggt atccggcgac tgcacagtgt cgaacacctt gcgtgcgtgg tcacctctgg   1380
acagcatgaa gcgtacaggc tacagcttgg ccaatgcgga cgccacgaac gtgtcggcgg   1440
cgtaacccgc gcgtgcagcg cgccgcgcgc gggctgcgga gtcggttgga gacgacacgc   1500
cgccgccatg agagcaatga gcgaggtggc ggcgaaggcg aaggagaagt agtcgaggca   1560
agcggaagag aaggcggcag cggagaaagc gatcggggcg gcggaggagg tgggtgggag   1620
ggagggacgc gtagcggagg tcggaggagg agggagctga ggtttccggg gcggggtcg    1680 agagggtagt gtacggaggc gagggacacg gcgaggatct ggtcgaggta gcgcagtgtg   1740
aaggaaagcg cgatgaggcg gagggcgccg gcgaagagcg gcgcggcgga tagcgggagg   1800
aggcggcgcc ggcggggtct catccgattg gaaacagatt gggaaggggg aggggtagg    1860 aatacgtggc gtcggcagta ttaggtagag agagaaaccc tttccatcct ttgtctctta   1920
gccccgaagg agagagaaaa atcagaaaaa aaaaaccctc cgcgtgtggg ggaagcagag   1980
ctccggacgc tggcgccgct cgcgccaccg cacccgcacc gcc                     2023
```

<210> SEQ ID NO 191
<211> LENGTH: 2034
<212> TYPE: DNA
<213> ORGANISM: Oryza sativa
<220> FEATURE:
<221> NAME/KEY: misc_feature
<223> OTHER INFORMATION: Ceres Promoter pOsYp102

<400> SEQUENCE: 191

```
gaacgaccca aacgcgtaaa tggtggtact ggtttccctg ctttgccgag taccagcagc     60
cacgaagaac gttacacaat cgagtacaaa atctataaga gcaagtttaa tagcatagcc    120
aaatactacc tctaaatcat ctatagccaa tttaatagtt catttattca ataattactt    180
ataaacatat actacaatca ttaatatatg gtcttacttc ttatacacat aatattttgg    240
agtccgtgtt acagctggct ataaatataa gggattttgg ttggatgtgg tacatcctat    300
tataatgaat ctagacatga aacctgtcca aattcatcgt gctaggatac gccacatcta    360
accaaaatct cttatcttta gggatggaga gagtaataat taaatgaagc taggtagagt    420
ttcccggtca atacgcttgc gtgtgcttat aagagcatgg ccaacagttt cccgatactc    480
ttcccaatat cagttttgag gagttttgtt ggaaaaaatc gctccaacag tagacctaaa   540
tcacccctaa aagcttggcg tttccaaacc cgcatatttc gttctccact tgtagggaag    600
agactcggcg cccaatcctt caaccgcatg cacttcgcgc gcgctgtgtg aaaattttcc    660
taccaggttc ttctttgtgc gttcgtctac ctgtgagtca atccatcacg ccagcagcct    720
catcttcccc gcagctgtct gggaaagcag ccatggctcc cccaagcttc cccagcgtcg    780 acatttttttt ctcagcggca gcgccagacc catctccaac ccaattgggc ggaccttcgt    840
cggcgctccc ccagcaccac caccgactcg aatcggccgt cgcccctatt catctccaat    900
```

| | |
|---|---|
| cgtccctcga ccctaccgca tcctgcagca cagcctgtct ctcgcgtcag actggcgctg | 960 |
| cgctcccccc ggtaatgtgc aggcgacaaa ggccccatgc gatgcgacca gcagccggcg | 1020 |
| acaaccggag gtgcccagtc gctggccttc atcgaatcat cgtgcacctc ggtcggagtc | 1080 |
| gatttctgat tgttgctgct gctcaaatct ggagcttgct attgctgaga actgcttggt | 1140 |
| ggtggtactg gaaatttgtt gtttgctggc tgatgaaaac tgttgttctt tgctgctaaa | 1200 |
| aactgctgct tgctagtact gaaaagtact attgcagctg ctgaaatatc ttgctgcttg | 1260 |
| ctgctgaaaa cttcaagttg ttaacaccgt tcacactaaa aaagctgaaa ttttttttct | 1320 |
| gggctgaaaa ccccattgtt gatgattgca gaaccaatat ttttccatgt aaaatacagg | 1380 |
| agatcgtggt aataatcaag tgaaatatca ttttggggca aatactcaga tcgtacctga | 1440 |
| agccaatgga acattgttc aatgcttaaa ctgtcagtta tgatgtcaaa gagattgatc | 1500 |
| actgaatgtc ctgaaaggag ccgtgaggag gatgcagcat tgcagcgtgc gcgagcgtga | 1560 |
| gtggaggaga ggaatgacga ttctgttggt agttgtcgat gtggcctact ttttttgttt | 1620 |
| tgaggattaa attttgggaa tctcttggag ataaaaggta ttctcatacc ttaaatcctt | 1680 |
| tttagagatc taaaaaaaat gatttagggg attgaatttt gggtggctgt tggtgatgct | 1740 |
| ctaagttgca catcctgggg aaaaacctcc ctaatccatc agcaaaccga tcaaccaccc | 1800 |
| acgacaagtc gacgccaccg ttttttttt ctccctccta agtcctaacc ccacaaaaat | 1860 |
| cccgcgaact ttcgtctcac cacgcgccgc gtgcccccta caaataccaa acaacaccca | 1920 |
| ccacgtccac tcacaaacca cgcaggaaac ctcagaaaat caccgtacgc gacgcgggcc | 1980 |
| caagaaaacc ccgacagaaa ccgcgcagca gcaacaccac caccggcgtc ggag | 2034 |

<210> SEQ ID NO 192
<211> LENGTH: 1877
<212> TYPE: DNA
<213> ORGANISM: Oryza sativa
<220> FEATURE:
<221> NAME/KEY: misc_feature
<223> OTHER INFORMATION: Ceres Promoter pOsYp285

<400> SEQUENCE: 192

| | |
|---|---|
| ggcccgagtt aaacgatctt ccacgtgtca gcgaatccta gtcgttcgat gaatctgaat | 60 |
| ctgacttgtg gtggttggac ggccacgtgt taaaaaggg aaacgtccgc atcacccgat | 120 |
| gctgggacat ttgcaatttc gatccagctg tagattgacc agttgttact ctcttttttt | 180 |
| taacaccata caaacgtaat actccctctg tcccaaaata taagtatttt ttttaacctc | 240 |
| ggttcagtct tcgaggtgct actttgacca ataatattta taaaaataag atgttttaaa | 300 |
| taaagagagt tgcatattat gatagctcgt ttaatgataa acaaagtacc atcaaattta | 360 |
| catgattaat ctttttaatt tatttgctat taatagttaa aatttaaaaa gtttgacttc | 420 |
| acactgttct aaaaatactt atattttggg acggagggag tacacattag agcaggtaca | 480 |
| atagcagact agtagccagc tataaacata ttttaatgag ataaagatg agagagaaca | 540 |
| gcgggctaca gatctgtagc cagctgcagc acggactcca agacattgtg tgtgtatgac | 600 |
| aggtgggacc atatattaat agtacagtaa gtaactattg tatgaattgg ctattagatt | 660 |
| agctataggt gaattgtagc tagtagtggg ctatactatt gaacttactc ttatatctct | 720 |
| caatatctcc agaaaactag gacgatatat attgatatta acaaagtcat catagatatc | 780 |
| tcgctatcga catatatatt acctatcact gaaaaaataa ttaatcataa atgcaagcac | 840 |
| atatactacg ttcaacactg aatgtaggta gattggtaga cgggttccac cgcaagaaaa | 900 |

```
gcattgcacc agtgaagaaa gaaacatcgg aatttgtatg tagtttgttg tttgatgaat    960
tcttttgatt aaaaaaaact aaaatcagag ttgattcagt taatggtgtt gcctacgata   1020
tacttccata tcatgatatc actgtagact atgaatcata tctttaatta aaactaaatc   1080
aagaaattaa gtatgagacc tcaactcaat gaagaatttc tagttgaaaa acattcctag   1140
tgtgcgttcg gatggaggta gggatcttct ctccgttcat ataaaaccgg atggttcatt   1200
agaacatgat taattaagca acagttaatc taaaaataaa ttaatatttt ttaagaaatt   1260
tttgtataga gatcttttga aaaaaataca ttggttagaa agcatactaa taaaaagaga   1320
aaaataagaa catagtacta tagtagaaaa tgagaacttg gagtatttga gaggatggga   1380
aataagaaga ttaagaagat gcgtaaagtg aacggttaac gcatgattga ttaattaaat   1440
attaattatt ttaaatttgg aaaataaatt agtatgattt ttaagcaaca tatatatata   1500
tatatatata tatatagaaa aacatagttt tagaaaatat aagcgtgtaa aacgatatgc   1560
aggaacgaaa cgttgagcat tcaaaatttc aaattgaaca tatgaatcaa gagagaataa   1620
aaaaagaggc cttctaggct ggcatggaca attggacatg ttttcaacta gggtttcaag   1680
cttcgagcat ccacttttgt ccttgcaaac tttatacggc aaggcccgtg aatctagccc   1740
cccacaccac cccacccgcc cgcgccgcgc ggccgcctcg cctcccctcc cttctcctcc   1800
tctccgcccc cgccgccagg ccgtccacct ccgccgtctc ctcccccatt cgcacccaag   1860
gcgctggcgc ggaaggc                                                  1877

<210> SEQ ID NO 193
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0565

<400> SEQUENCE: 193
caccaaatat agtgttattt caatactaaa atggtgttat ggttggagat gccctaaaga     60
taaacatgac gagacacgag atttattaat ttcttgatca accataactt aataacttaa    120
tattaatttc acttaataat ttccaattaa gtgaatcttt acttcaccaa aagttcctaa    180
cgaactctta ttttctagca tcaatattac catgaactag catcaatact atcatgaaaa    240
attcctactt cctatccaac tcttaataac aatgctagtc ttaacaatat tcatcaaaaa    300
cttgatatag accttctaac ttagccacga ctagtatcgg tgaataccaa aattaatgta    360
ttcatgagaa cttgagattt ctctaatgta ttcttgttac taaacaagta acaacactca    420
agaaatatca tgatcaaata ttttactcat aaactccata tttcacattt tgaaaatttt    480
aaacagcaaa tcacattgaa ttttcgtggt aaaagtattt aaaattgaaa aatagcagct    540
cctgatttca atgtataaat ttatctttat atggtttatg tctccaactt atttttaaaaa   600
agagagaaag agcacccaaa aggtgaccgt ttgaaattcg aatttatttc cgtttgaaat    660
tcgaattcaa aaaaagtaaa ccgaaccgag tctcgttact gactgtcaca cattgtttcc    720
ctaaaagcta attaacccat acgtggcgta atataacagg tcagtgatca atactaaata    780
acagacatac acctttaaaa ttcgtgcacg ctccaaaaca aaatctacac ttcaaaatca    840
acggtcacga tcattcctca aatttcaaaa aattatttaa cctcacttcc ttcgctttgt    900
ttttaaaacc tctctctctt tctctttctc tttcgccatt aaaactctgt ttccttttc    960
agagattctc agagaagatt cattttaccc taagaaaaaa                         1000
```

<210> SEQ ID NO 194
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0015

<400> SEQUENCE: 194

| | | | | | |
|---|---|---|---|---|---|
| ttgagcctta | ttgttgttat | tgacttttag | ccaatagaaa | gagatggaaa | ttcaataatt | 60 |
| atccacaaaa | ttccaaatca | ttggtgtaca | aaaagatcta | aggctgttat | attttcaaaa | 120 |
| aagaaagaaa | agaaatgcaa | caaatatgga | ttaaactgtg | gtttgtaaat | tgagctttgc | 180 |
| atgaaaactt | tatcactatg | atttcactac | tccatattta | ttgactaaag | tggcactaat | 240 |
| gaatttctta | atcatgaaat | cttgtatcaa | aaagtactaa | aataaacatg | acattggcaa | 300 |
| ttaggaaaat | tctaaattag | aaattagtaa | aaatgaaagg | tgaaagggaa | agatgatgat | 360 |
| atgaattggt | tggtgaccag | gagaaatgta | tcccgatttt | tgcagacact | ttcagtgtcc | 420 |
| ccattcatat | aattatggcc | cacctcgtta | agattttca | ttcaccacca | taacaagatc | 480 |
| taagcttaga | tttcatgtaa | ttaaacatat | aatatacttg | ccaatactat | ctaataaagt | 540 |
| atacttaagc | aaaaattatt | actctagtgt | aaggcgatga | aatataagtt | tagttgaaaa | 600 |
| tttatgtcga | tataacaaag | tataatgaat | taagaccttg | gttttcgatt | aacaaactaa | 660 |
| ttaaacacta | gttttgccta | ataaaaccgg | gaatcgtatt | caaaaccgaa | cgacaaaaca | 720 |
| agggacaagt | tgagagacaa | aaccaaatca | gcatctttct | tccagaaatg | tcatgaccac | 780 |
| atgacgtcat | cttgacccctt | cttcattgtg | atatctgtgg | ataaagcgca | cgtgtttaat | 840 |
| tcacgaacct | tcgtagtaac | gaaaaatcca | caactttcat | atttttaat | tacccactaa | 900 |
| actaaaacaa | atttggaaaa | acatgaaaaa | ctttttcttt | ttttccaggt | tcgtgaacct | 960 |
| cgtaccctct | atataaacct | cttaaccacc | ttccacata | | | 999 |

<210> SEQ ID NO 195
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 195

| | | | | | |
|---|---|---|---|---|---|
| tgaattgagt | aaaatgtgtt | ttcaaacagt | taggtggtag | aaggtaaagg | taataacatc | 60 |
| atgatcttac | taaagaatt | gttgcatact | aactatcaat | attctcaaca | acataatata | 120 |
| atgttttttt | aggtaatttt | ccattttaat | tttttgtgat | taaacaatta | aacaactcga | 180 |
| atgatgatga | taaaaaaaaa | aaattaacaa | ctcgaataag | ttaaagtagc | aatacacatg | 240 |
| tcgttcaatt | caaccaataa | agtaagactt | atatttttaa | gaagttgact | aatagcttaa | 300 |
| taagttggaa | aacttgtgta | gtttcttaat | tcccacgtgc | agtaagaaat | aaaaatgaaa | 360 |
| aaaattatta | tatccttccc | actctgcgac | ttttcttta | ttttatcaaa | tattaaaaag | 420 |
| attcatatca | cagtttacac | attgaaatca | taaacgataa | ttatgtattt | tgtaataaaa | 480 |
| agttagttct | gaagctcata | ctttggatag | tcgctagtcg | ctaatatgct | ccttgtaata | 540 |
| attaaagtca | ctacgacgca | cgtcaaagcc | gatatttagg | gcttaattga | tgcgtgtttt | 600 |
| tcttttcata | taatagtaat | ataaattagt | actaataaag | tatgatggat | ggttgagaca | 660 |
| gaaaagaaaa | aagatgactg | tatggtcatc | attacaaaga | agaatgtatt | cttcatgttc | 720 |

```
ttaagaataa taaaatgtca cttgtaaatc aagttggtaa gcattttgag aactttgttc    780
gatgcaacgt atgatgattt atgtagacaa aagataaaac cgtatcttca actattgcca    840
agaaaagata aaacctaatc tagtcagtct ctcaacataa atacaaccca atagccaaac    900
tgtgtccaat tcggagagaa actaaactaa aacaaaacac aaaagcccaa cataagccca    960
ataaaaccca ttttataaac agaacattac taacactca                           999
```

```
<210> SEQ ID NO 196
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 196
```

```
atgatgaaca ttctacatat ataattatta tgtttaagca cttagacagc ataaattctt     60
tctaattata taaatctaac cttgttacat tgtacatcta taaattactt gaagaaataa    120
cgagttctat ttcttttttaa aaattaaaaa tactatacca tatctcagtg attaagttga   180
accaaaaggt acggaggaga aacaagcatt tgattcttcc ttattttatt ttattcatct    240
ctcactaatg atggtggaga aaaaaagaaa atacctaaca aacaaatata tattgtcata    300
caaaaatatt tctatatttt tagttaatta gtttatattc ctcactttttc agggcttata   360 taagaaagtg agcaaacaca aatcaaaatg cagcagcaaa tactatcatc acccatctcc    420
ttagttctat tttataattc ctcttctttt tgttcatagc tttgtaatta tagtcttatt    480
tctctttaag gctcaataag aggaggtact attactacac ttctctctac ttttacttgt    540
attttagcat taaaatccta aaatccgttt taaattcaaa aataaactta gagatgttta    600
atctcgattc ggttttttcgg ctttaggaga ataattatat gaaattagta tggatatctt   660
tactagtttc cattcaaatg attctgattt caatctaata ctctcactct ttaattaaac    720
tatatgtagt gtaatttcac actgttaaat ttctaccatg tcatgtatat tagagttgca    780
tagaaaattg taaacatcc atttgaattc gaatgaaaca aaatgtttta aaataaaatt     840
ttggttttta aaagaaaaat ctaaaactga attatatcgt ttaaccaagt tgtaaaagtc    900
ataaaacgta gtatcttgta aatcgctctt ccacggtcca aatagacttc tagtaataaa    960
caagtaaaac taattttggt ttcttactaa ttttcacaga                         1000
```

```
<210> SEQ ID NO 197
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 197
```

```
ttagctgaac caggaaattg atctcttata ccagtttccg ggtttagatt ggtttgatgg     60
cgatttgatt aaaccccga aattttatgt cgtagttgtg catagtatta ttattctttg    120
cggacaatag acgtatcggg accaagttct gtagcaaaat tgtataagct taagtttgat    180
gaaatttaaa ggtaatcact aaaacccaaa tgggacaata aaccggtgaa gatttagagt    240
ttttaatttt gactcatgaa tctggagaaa gagccctcgt taaaaggagt gaatcaatcc    300
ataggggaaa aagtttttgtc ttttttaaaaa ctaaagaacc aaaccttaat agaagcagct   360
```

```
caatgtgtga caactttcca ctggcactaa gataaagtga ctagcgatga gtgcaattat        420
tgaaatagta gatggtaaat attacataca agagtaaaaa tatctttatg tcaatgctta        480
attcagtgtt tctggttaac aagagaaact tctctaactt tcgtaattgg gtcttataaa        540
attttatgca attatgattt tacccttta  ctacttttca ttagctttca cgaatctatt        600
ttgacaagag aaatcattag aggtaaacat gcttttggt  caagggcctt aacagttcca        660
ccaatcaagc tcaaaagttg tacttaaccg acatcttctg tgaaaacata taattacatg        720
tacaaatcaa aactaccta  tgaaataat  agaaatattg cagttcattt ctaatttaac        780
ctcttcaact tttaaaacta tttacatttc tttatgtcat ttctagtcat tttgatgcaa        840
attgtaccat ttatggatta tcttcacaaa tttttaagtt ggtgaaaact ttttggtggg        900
tagttaaaac ttgaaataga aatttacttt accaaaataa actaatgaaa agtaatcact        960
ccactcccta taataagatt tccaacgttc ccactaagc                              999
```

<210> SEQ ID NO 198
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 198

```
tagttccatt acaatttcca aatgatttgt tacaaagcta caagattatt cgaaatagga         60
tttcatccat aagagagaat ggtgtggtcg acgctacaat gttgatttat tggttgtggt        120
ttgcatcttg gggatgtcaa atcctaagtt tcaagttctt gtaaaacgt  tttcaggttt        180 ctttaatata ttttaatatt aatgtaaaaa gaaaagatat agcttttgta caaaaaaatt        240
tgtttaatca ctatgtagga ggatgcgatc aaattcatgg aatgatgtat tattagcttt        300
tctatcctca ctctaaaaac aatactatag tgagttaaat aatttgatca tttcaatgta        360
gattaaaatt ttattaaaag aagaaaaatt taaaagccta taacaaaata aaaaaggagg        420
ctcgaggtat gatgggtgta gcagaagagc tggcaacagc tatcgactga gtgattacga        480
actcagtact cagtgttctc agctcacaca ctctttttt gttctctttc ttttggacag        540 cttttcatttt ctcttttctt ttttctattt tgtttcaaaa ttccatccat attaaaatag        600
gcctgatcat gagaataaag gaaatactaa tgatgagttt ctcaataatg caataagatg        660
caattattat gagctattta ctattgaaaa tgagcaaata aatgtcaaaa cacaatctgg        720
ttaagttaga gcaactccat tgtataggat tcatgtagtt tctaagaaaa caaatgtat         780 taatattta cttttacatc caaaaaacca acttatatga gtaatagaaa cgatcctaat        840
attaggaatt ttagagattt tctctcatct gtttcttaac ttttcaatat ttttattttt        900
taaaattgta tgagtttcta ctaagaaact actgctggag ttggtcttag cttcccaatg        960
cttctccacc tatatatatg catatctcct tcttaaaac                              999
```

<210> SEQ ID NO 199
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 199

```
aagcggcaat ttagtaagaa gtactcaaag tatcatttac caaaagtata tggttttggg         60
```

```
aagagttgtt agggatgtat tctttctaaa cagatgatat gacgatgttc ttgaaaacta      120
atgttaaaga cggaatctct ggcatcttca ctcgggagat atattaaacc gttgattgta      180
gttagccatg tacttagctt agtgcacaaa taatctgctg caagaaatct ttttctatta      240
taatatctct catttaaaca ttagaacata ttgtttaact tgttcttcta gaaataaaac      300
tgctaatttc ttatggtaaa ctatttttcct ttagattgca caatcgaact cgaaaatcta     360
gtggagacta tgtgactatg tttatatata tgaaacctaa atcaaattat cccaataatt      420
gggagacaca aagaaaaat tacgaaagaa acaggaaat caaatcaaaa gataaagaga        480
aggtaaaaaa aggcaagaag cactaatgtt taatatttat agttttctcc attaaagaaa     540
aagcgatgat gtgtgttctc atcttttgtg aaagtatata tattgctttt gcttttctca     600
aaagcaaaag actcatccaa caagaacaaa aaaaaaaact aaagctcaat ccaaaagacg     660
aagaatgcat tggatactac aacttctttt tcactttcct ttcaaattta caattatgat     720
tttcacaata cagtttattc aaaaataaat aaaaaaacga ggcatgaaaa taatgattat     780
cctcttcact tattaagcca ctcactataa gcagagcaac tccagaacat agtgagcccc     840
caaaacatta aagcatgatg atgtctaatg atgatgatct tcttcgttcc atttctctaa     900 attttttggga tttctgcgaa gaccccttctt ctctttctct tctctgaact tcaagattcg   960
tgtcggacaa attttttgttt ttattttttct gatgttaca                          999

<210> SEQ ID NO 200
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 200
atctataacg agttaacatg ttgccagttt gaatcaagaa gcttggatga tgaatgaatg       60
gatcggtttg tggtacaatt cttaaaattg tagtagagga gacagagaaa aaacatgata      120
agactttggt atttacaact tgacggagac aagacagtaa gccaaatctg tcacaaaaac      180
actcaaactc tttctcagt gttttgagtt taaagagaga cttattcact tcccctttcg      240
taacacttat ttgtctccca accaaacagt ttctgtcctt tcccttgtcc tcccacgtgc      300
atctttatat ctcatgactt ttcgtttcta gatcttgaat aatgtcttag tggattaggt      360
ttgttgtcgg taaattaggt gaccgttttt ttcttatatt tggaagatcg cgggatgaag      420
cagatactga gtttcagggc atacacacct aatttgaaaa tcattgttag tccaatttca      480
ctttaatctt gtttacaaaa aaattgatct gaaaatgttg atgggataag taaaaatgta     540
agttttgcta gtagtcatga tataataata gcaaaccag atcaattttg agcaaaagga      600
agaaacaaaa aacagatcga tcccacgagc aagactaagt gtaaagtggt tcccacaaga     660
gccatatgga tatggtcctt caacttttaa agcccattac ttcagtggtc gacccgacat      720
tacgccacga gtagtcacgc acgcacgact ccgttcacgt gacattcacg ttgatatttc      780 ccctctact ctcttctgct tggttgatct aaaaaacatg aagagaccaa cctaatttca       840
tattaatata tgatatagac ttcatactca acagtcactt tcgtaatcca atccatatc      900 ttacgaaatt agttcttaat aaaggttgtg gattaagtta taatattgtg ttaagagtta     960
agacacagca tataaccttg taccaacagt gctttattct taaatggaaa caaaacatat    1020
gtcaatgtca agcatacagc taaaatatca ttatctaata ttaagagtaa aacaagataa    1080
```

```
ttaaaaattg aaacaacacc atattttat agctttactt atcgtatttt tctagtcttc    1140
atggtaattg tgttgcttta ttttgtttat aaatgaattt ggttcgacca gatagtctaa    1200
tatcagtttt taaacactgg ttttaataaa atcatatgtc ggcaattcaa cctgttacgt    1260
tgtatgattg tatcctagtc aaataggga ggaggtacta gtcgtttcaa ttagtttacg     1320
taatcaatcc aaagaaacta taagctataa agatcctcaa tttgttggtt acaataaaaa    1380
caacagttgt caaatttat gtttataaaa agtaataact atgttccttc ccatatagag     1440
caaagtacct caggataggc aaaccgtact taatagccct tattcataat ttgatccaac    1500
tcttccccac aaaattgcaa ctgatgaagt caatacttgt atagtgagtc aagctataaa    1560
tgtctagtga tagttttgtc tcttaaaagg ttaacaaaag ttatgacaag ctgaaaaatc    1620
agagtttgct aggagtatta cttacagtta tcagtttaag tatcacatttt atagtattgt   1680 atacaatgat tcttaaattc caccttttcc gtgcgaaacc aaattttcta ttggaaacat    1740
agaatgtaaa caaaaatatg ggacgttgtc cgttccaaca ttaaccaaac ttgtctatta    1800
ctaatattcg tgttggtttg atgttggatg tctaaattcg ttgaatcatg tgtctcttga    1860
cgaaatatgc atcttcttat ttcttagtat agatgcactt tatcattctt ttagtacatg    1920 cttaatttttt tttttaaaa tatgttgatt gtcatattgc caaagtatg aattaaagac      1980 gcacatctaa cacaagttag cagccgtaaa tccttccata aatttatttt gcaagttttg    2040
ctcattatat aatgagcgga atttatgata taatcgtttg taataatgtt atgttttgat    2100
caaaatttga aattaaaagt aggtgagaac ttgttataca gtgtagataa ggtggatctt    2160
gaatataaaa ataaaattta taagatgtat ttaaagcaga aaagcataaa actttagata    2220
aaataatgta aaaatgtgtt agcatcaatg ttgggatatt ggccgacccg aacttaatca    2280
atgtcggaag ccattacttc tctcccaaaa gacctttttc cttcggagaa ctaggaactt    2340
cctcactacc tttcgcttaa cgtgaaagcc ataaatttca tatattcata aaaatcagaa    2400
aatctaaaac tgtttagtat cacctgtttt tggtatagac tattggtttt gtgttacttc    2460
ctaaactata tgatttcgta cttcattgga tcttatagag atgaatattc gtaaaaagat    2520
aagttatctg gtgaaacgtt acttcagtca tgttgggtct agatttacat actactatga    2580 aacatttaa gataataatt atcctagcca actatatgtt ctatattatg ggccaagaag      2640
atatagaact aaaagttcag aatttaacga tataaattac tagtatattc taatacttga    2700
atgattactg ttttagttgt ttagaataaa tagtagcgtg ttggttaaga taccatctat    2760
ccacatctat atttgtgtgg gttacataaa atgtacataa tattatatac atatatatgt    2820 atattttga taaagccata tattactcct tgacctctgc ccccatttcc ttttactata     2880
aataggaata ctcatgatcc tctaattcag caatcaacac caacgaacac aacctttccc    2940
aaagccaata ataaaagaac aaaagctttt agtttcatca agacgaagc tgccttagaa     3000
```

<210> SEQ ID NO 201
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 201

```
agaagtattc acgcaccaag gttatatttg tagtgacata ttctacaatt atcacatttt      60
tctcttatgt ttcgtagtcg cagatggtca atttttctta taataatttg tccttgaaca    120
```

```
caccaaactt tagaaacgat gatatatacc gtattgtcac gctcacaatg aaacaaacgc    180
gatgaatcgt catcaccagc taaaagccta aacaccatc ttagttttca ctcagataaa    240
aagattattt gtttccaacc tttctattga attgattagc agtgatgacg taattagtga    300
tagtttatag taaaacaaat ggaagtggta ataaatttac acaacaaaat atggtaagaa    360
tctataaaat aagaggttaa gagatctcat gttatattaa atgattgaaa gaaaacaaa    420 ctattggttg atttccatat gtaatagtaa gttgtgatga aagtgatgac gtaattagtt    480
gtatttatag taaacaaat taaaatggta aggtaaattt ccacaacaaa acttggtaaa    540
aatcttaaaa aaaaaaaaag aggtttagag atcgcatgcg tgtcatcaaa ggttcttttt    600
cactttaggt ctgagtagtg ttagactttg attggtgcac gtaagtgttt cgtatcgcga    660
tttaggagaa gtacgtttta cacgtggaca caatcaacgg tcaagatttc gtcgtccaga    720
tagaggagcg atacgtcacg ccattcaaca atctcctctt cttcattcct tcattttgat    780
tttgagtttt gatctgcccg ttcaaaagtc tcggtcatct gcccgtaaat ataaagatga    840
ttatatttat ttatatcttc tggtgaaaga agctaatata aagcttccat ggctaatctt    900
gtttaagctt ctcttcttct tctctctcct gtgtctcgtt cactagtttt ttttcggggg    960
agagtgatgg agtgtgtttg ttgaatagtt ttgacgatca                        1000

<210> SEQ ID NO 202
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 202
caaagtattt gacaagccat atggttttgg atcaaaaagt cggtccaaaa ttaatgtttt     60
atgtgcaaga accgacccat tgtacacacg tgttaacatc ttcaagactt tcatctctat    120
ttttcttttg gtcattaaga tacccattga tccgaatctg ttacattccc acctactttt    180
ttaattttta ctatccactc caaattaaac acaaccgatg attttaataa ttggaagctt    240
tttaaaatat ttctccacgt gcctctttgt gtttgtctat ata                     283

<210> SEQ ID NO 203
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0623

<400> SEQUENCE: 203
aaagttattg acattttgaa aggaccgtaa atattaccaa aaaactgacg gagttaggat     60
cggccacgta gaaagggaca agagagaaac agtcacggac tcggccagac taagtatggg    120
cctgtctgaa tccaaactca gctaagttcc aaaagcataa agagagatgt gtaatgaaat    180
gaacgtattc tagaaacgaa agcaatgtta tgctttgttt ttgagccaca tgttttttggg    240 agatggagag aatcttttt acgtttttaa cctaacccac ttggcacttg gccaaaaaag    300
tgagaagaaa ctgtggcgaa tgagtaggcc acgccatgga cttttgttcct tgtccttcaa    360 aagttaaatt tatgttatgc gtggggacaa tctaagcaac gtggttcctt taaatatcgc    420
agcttcctct tttacacttt tggagcctac gtgttttgtt ttggaccggc caaatacacg    480
```

-continued

```
agtcagtcag tttagaaata atttggatgt ccaaaaatct tggagatcca aataaaataa    540
ttagcatgtt ttagttcata agaatatgaa atgtagataa actgtctata ttaattttc     600 catagaattg gctttttatc gaggtgatgt acttaatgac tttgttgatt actactcgta    660
taacaataaa gaatatgata ctatgtgaga cttataatga atttggtgtg tgttaattaa    720
tccagttgaa acagtttaat aacaaatcag aataaaaatt gtagtaagaa aatttgaacg    780
ctgatccttc aacctagata gtgaacctt caaatactat atgattcacg tgtaatgttt     840
ttgaccgttg gttattttg tgtgaactat attaacttat caatatcgaa aggctaaata     900
agtaaataac taaagaaag ttcaggaaac aactcgacct aatgacctat catttctgat     960
cacccgtcct ataaatacat acgtaagatc attcgttact                         1000
```

<210> SEQ ID NO 204
<211> LENGTH: 33
<212> TYPE: PRT
<213> ORGANISM: Artificial Sequence
<220> FEATURE:
<223> OTHER INFORMATION: Truncated version of Ceres CLONE ID no.
      100021733
<220> FEATURE:
<221> NAME/KEY: misc_feature
<223> OTHER INFORMATION: Ceres CLONE ID no. 100021733_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 204

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 205
<211> LENGTH: 33
<212> TYPE: PRT
<213> ORGANISM: Artificial Sequence
<220> FEATURE:
<223> OTHER INFORMATION: Truncated version of Ceres CLONE ID no. 1036726
<220> FEATURE:
<221> NAME/KEY: misc_feature
<223> OTHER INFORMATION: Ceres CLONE ID no. 1036726_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 205

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

```
<210> SEQ ID NO 206
<211> LENGTH: 33
<212> TYPE: PRT
<213> ORGANISM: Artificial Sequence
<220> FEATURE:
<223> OTHER INFORMATION: Truncated version of Ceres CLONE ID no. 1482731
<220> FEATURE:
<221> NAME/KEY: misc_feature
<223> OTHER INFORMATION: Ceres CLONE ID no. 1482731_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 206

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys

<210> SEQ ID NO 207
<211> LENGTH: 80
<212> TYPE: PRT
<213> ORGANISM: Artificial Sequence
<220> FEATURE:
<223> OTHER INFORMATION: Truncated version of Ceres CLONE ID no. 1554560
<220> FEATURE:
<221> NAME/KEY: misc_feature
<223> OTHER INFORMATION: Ceres CLONE ID no. 1554560_T
<220> FEATURE:
<221> NAME/KEY: misc_feature
<222> LOCATION: (17)..(78)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 207

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

<210> SEQ ID NO 208
<211> LENGTH: 77
<212> TYPE: PRT
<213> ORGANISM: Artificial Sequence
<220> FEATURE:
<223> OTHER INFORMATION: Truncated version of Ceres CLONE ID no. 1802327
<220> FEATURE:
<221> NAME/KEY: misc_feature
<223> OTHER INFORMATION: Ceres CLONE ID no. 1802327_T
<220> FEATURE:
<221> NAME/KEY: misc_feature
```

```
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 208

Met Ala Leu Ala Glu Gly Asn Val Ile Phe Gly Glu Gln Glu Ala
1               5                   10                  15

Leu Val Leu Lys Ser Trp Ala Leu Met Lys Lys Asp Ser Ala Asp Leu
                20                  25                  30

Gly Leu Arg Phe Phe Leu Lys Ile Phe Glu Ile Ala Pro Ser Ala Lys
                35                  40                  45

Gln Met Phe Ser Phe Leu Arg Asp Ser Asp Val Pro Leu Glu Lys Asn
            50                  55                  60

Pro Lys Leu Lys Asn His Ala Met Ser Val Phe Val Met
65                  70                  75

<210> SEQ ID NO 209
<211> LENGTH: 77
<212> TYPE: PRT
<213> ORGANISM: Artificial Sequence
<220> FEATURE:
<223> OTHER INFORMATION: Truncated version of Ceres CLONE ID no. 1876458
<220> FEATURE:
<221> NAME/KEY: misc_feature
<223> OTHER INFORMATION: Ceres CLONE ID no. 1876458_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 209

Met Ala Leu Ala Glu Gly Asn Val Ile Phe Gly Glu Gln Glu Ala
1               5                   10                  15

Leu Val Leu Lys Ser Trp Ala Leu Met Lys Lys Asp Ser Ala Asp Leu
                20                  25                  30

Gly Leu Arg Phe Phe Leu Lys Ile Phe Glu Ile Ala Pro Ser Ala Lys
                35                  40                  45

Gln Met Phe Ser Phe Leu Arg Asp Ser Asp Val Pro Leu Glu Lys Asn
            50                  55                  60

Pro Lys Leu Lys Thr His Ala Met Ser Val Phe Val Met
65                  70                  75

<210> SEQ ID NO 210
<211> LENGTH: 79
<212> TYPE: PRT
<213> ORGANISM: Artificial Sequence
<220> FEATURE:
<223> OTHER INFORMATION: Truncated version of Ceres CLONE ID no. 1879148
<220> FEATURE:
<221> NAME/KEY: misc_feature
<223> OTHER INFORMATION: Ceres CLONE ID no. 1879148_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
```

-continued

<223> OTHER INFORMATION: Functional homolog of Ceres Clone ID no. 30469
      given in SEQ ID NO: 7

<400> SEQUENCE: 210

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 211
<211> LENGTH: 33
<212> TYPE: PRT
<213> ORGANISM: Artificial Sequence
<220> FEATURE:
<223> OTHER INFORMATION: Truncated version of Ceres CLONE ID no. 1884696
<220> FEATURE:
<221> NAME/KEY: misc_feature
<223> OTHER INFORMATION: Ceres CLONE ID no. 1884696_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 211

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 212
<211> LENGTH: 76
<212> TYPE: PRT
<213> ORGANISM: Artificial Sequence
<220> FEATURE:
<223> OTHER INFORMATION: Truncated version of Ceres CLONE ID no. 1916866
<220> FEATURE:
<221> NAME/KEY: misc_feature
<223> OTHER INFORMATION: Ceres CLONE ID no. 1916866_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 212

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys

```
                    35                  40                  45
Leu Phe Ser Phe Leu Arg Asp Ser Asn Val Pro Leu Glu Gln Asn Thr
                50                  55                  60
Lys Leu Lys Pro His Ala Met Ser Val Phe Val Met
65                  70                  75

<210> SEQ ID NO 213
<211> LENGTH: 33
<212> TYPE: PRT
<213> ORGANISM: Artificial Sequence
<220> FEATURE:
<223> OTHER INFORMATION: Truncated version of Ceres CLONE ID no. 1950105
<220> FEATURE:
<221> NAME/KEY: misc_feature
<223> OTHER INFORMATION: Ceres CLONE ID no. 1950105_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 213

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
                20                  25                  30

Lys

<210> SEQ ID NO 214
<211> LENGTH: 79
<212> TYPE: PRT
<213> ORGANISM: Artificial Sequence
<220> FEATURE:
<223> OTHER INFORMATION: Truncated version of Ceres CLONE ID no. 1990746
<220> FEATURE:
<221> NAME/KEY: misc_feature
<223> OTHER INFORMATION: Ceres CLONE ID no. 1990746_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 214

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
                20                  25                  30

Asp Leu Gly Leu Arg Phe Phe Leu Lys Ile Phe Glu Ile Ala Pro Ser
                35                  40                  45

Ala Lys Gln Met Phe Ser Phe Leu Arg Asp Ser Asp Val Pro Leu Glu
                50                  55                  60

Lys Asn Pro Lys Leu Lys Thr His Ala Met Ser Val Phe Val Met
65                  70                  75

<210> SEQ ID NO 215
<211> LENGTH: 79
<212> TYPE: PRT
```

```
<213> ORGANISM: Artificial Sequence
<220> FEATURE:
<223> OTHER INFORMATION: Truncated version of Ceres CLONE ID no. 2033803
<220> FEATURE:
<221> NAME/KEY: misc_feature
<223> OTHER INFORMATION: Ceres CLONE ID no. 2033803_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 215

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 216
<211> LENGTH: 33
<212> TYPE: PRT
<213> ORGANISM: Artificial Sequence
<220> FEATURE:
<223> OTHER INFORMATION: Truncated version of Ceres CLONE ID no. 2034916
<220> FEATURE:
<221> NAME/KEY: misc_feature
<223> OTHER INFORMATION: Ceres CLONE ID no. 2034916_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 216

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 217
<211> LENGTH: 33
<212> TYPE: PRT
<213> ORGANISM: Artificial Sequence
<220> FEATURE:
<223> OTHER INFORMATION: Truncated version of Ceres CLONE ID no. 513071
<220> FEATURE:
<221> NAME/KEY: misc_feature
<223> OTHER INFORMATION: Ceres CLONE ID no. 513071_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
```

```
<221> NAME/KEY: misc_feature
<223> OTHER INFORMATION: Functional homolog of Ceres Clone ID no. 2403
      given in SEQ ID NO: 40

<400> SEQUENCE: 217

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys

<210> SEQ ID NO 218
<211> LENGTH: 33
<212> TYPE: PRT
<213> ORGANISM: Artificial Sequence
<220> FEATURE:
<223> OTHER INFORMATION: Truncated version of Ceres CLONE ID no. 522921
<220> FEATURE:
<223> OTHER INFORMATION: Ceres CLONE ID no. 522921_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 218

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 219
<211> LENGTH: 76
<212> TYPE: PRT
<213> ORGANISM: Artificial Sequence
<220> FEATURE:
<223> OTHER INFORMATION: Truncated version of Ceres CLONE ID no. 546001
<220> FEATURE:
<221> NAME/KEY: misc_feature
<223> OTHER INFORMATION: Ceres CLONE ID no. 546001_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 219

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met
65                  70                  75
```

<210> SEQ ID NO 220
<211> LENGTH: 76
<212> TYPE: PRT
<213> ORGANISM: Artificial Sequence
<220> FEATURE:
<223> OTHER INFORMATION: Truncated version of Ceres CLONE ID no. 651581
<220> FEATURE:
<221> NAME/KEY: misc_feature
<223> OTHER INFORMATION: Ceres CLONE ID no. 651581_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 220

Met Glu Ser Glu Gly Lys Ile Val Phe Thr Glu Glu Gln Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 221
<211> LENGTH: 77
<212> TYPE: PRT
<213> ORGANISM: Artificial Sequence
<220> FEATURE:
<223> OTHER INFORMATION: Truncated version of Ceres CLONE ID no. 839727
<220> FEATURE:
<221> NAME/KEY: misc_feature
<223> OTHER INFORMATION: Ceres CLONE ID no. 839727_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 221

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met
65                  70                  75

<210> SEQ ID NO 222
<211> LENGTH: 76
<212> TYPE: PRT

-continued

```
<213> ORGANISM: Artificial Sequence
<220> FEATURE:
<223> OTHER INFORMATION: Truncated version of Public GI ID no. 11095158
<220> FEATURE:
<221> NAME/KEY: misc_feature
<223> OTHER INFORMATION: Public GI ID no. 11095158_T
<220> FEATURE:
<221> NAME/KEY: misc_feature
<222> LOCATION: (13)..(76)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 222

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met
65                  70                  75

<210> SEQ ID NO 223
<211> LENGTH: 71
<212> TYPE: PRT
<213> ORGANISM: Artificial Sequence
<220> FEATURE:
<223> OTHER INFORMATION: Truncated version of Public GI ID no. 12963875
<220> FEATURE:
<221> NAME/KEY: misc_feature
<223> OTHER INFORMATION: Public GI ID no. 12963875_T
<220> FEATURE:
<221> NAME/KEY: misc_feature
<222> LOCATION: (8)..(69)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 223

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met
65                  70

<210> SEQ ID NO 224
<211> LENGTH: 84
<212> TYPE: PRT
<213> ORGANISM: Artificial Sequence
<220> FEATURE:
<223> OTHER INFORMATION: Truncated version of Public GI ID no. 14701800
<220> FEATURE:
<221> NAME/KEY: misc_feature
```

<223> OTHER INFORMATION: Public GI ID no. 14701800_T
<220> FEATURE:
<221> NAME/KEY: misc_feature
<222> LOCATION: (21)..(82)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 224

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met

<210> SEQ ID NO 225
<211> LENGTH: 76
<212> TYPE: PRT
<213> ORGANISM: Artificial Sequence
<220> FEATURE:
<223> OTHER INFORMATION: Truncated version of Public GI ID no. 15226675
<220> FEATURE:
<221> NAME/KEY: misc_feature
<223> OTHER INFORMATION: Public GI ID no. 15226675_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 225

Met Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 226
<211> LENGTH: 76
<212> TYPE: PRT
<213> ORGANISM: Artificial Sequence
<220> FEATURE:
<223> OTHER INFORMATION: Truncated version of Public GI ID no. 15824736
<220> FEATURE:
<221> NAME/KEY: misc_feature
<223> OTHER INFORMATION: Public GI ID no. 15824736_T

```
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 226

Met Ala Thr Tyr Glu Gly Lys Val Phe Thr Glu Glu Gln Glu Ala Leu
1               5                   10                  15

Val Val Lys Ser Trp Thr Val Met Lys Lys Lys Thr Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 227
<211> LENGTH: 76
<212> TYPE: PRT
<213> ORGANISM: Artificial Sequence
<220> FEATURE:
<223> OTHER INFORMATION: Truncated version of Public GI ID no. 30909306
<220> FEATURE:
<221> NAME/KEY: misc_feature
<223> OTHER INFORMATION: Public GI ID no. 30909306_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 227

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 228
<211> LENGTH: 73
<212> TYPE: PRT
<213> ORGANISM: Artificial Sequence
<220> FEATURE:
<223> OTHER INFORMATION: Truncated version of Public GI ID no. 37903656
<220> FEATURE:
<221> NAME/KEY: misc_feature
<223> OTHER INFORMATION: Public GI ID no. 37903656_T
<220> FEATURE:
<221> NAME/KEY: misc_feature
<222> LOCATION: (10)..(71)
<223> OTHER INFORMATION: Pfam Name: Globin
      Pfam Description: Globin
```

```
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 228

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met
65                  70

<210> SEQ ID NO 229
<211> LENGTH: 76
<212> TYPE: PRT
<213> ORGANISM: Artificial Sequence
<220> FEATURE:
<223> OTHER INFORMATION: Truncated version of Public GI ID no. 62548111
<220> FEATURE:
<221> NAME/KEY: misc_feature
<223> OTHER INFORMATION: Public GI ID no. 62548111_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 229

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75
```